US008017375B2

(12) United States Patent
Feldman et al.

(10) Patent No.: US 8,017,375 B2
(45) Date of Patent: Sep. 13, 2011

(54) YEAST ORGANISM PRODUCING ISOBUTANOL AT A HIGH YIELD

(75) Inventors: Reid M. Renny Feldman, Highlands Ranch, CO (US); Uvini Gunawardena, Irvine, CA (US); Jun Urano, Aurora, CO (US); Peter Meinhold, Denver, CO (US); Aristos A. Aristidou, Highlands Ranch, CO (US); Catherine Asleson Dundon, Englewood, CO (US); Christopher Smith, Englewood, CO (US)

(73) Assignee: Gevo, Inc., Englewood, CO (US)

( * ) Notice: Subject to any disclaimer, the term of this patent is extended or adjusted under 35 U.S.C. 154(b) by 359 days.

(21) Appl. No.: 12/343,375

(22) Filed: Dec. 23, 2008

(65) Prior Publication Data

US 2009/0226991 A1    Sep. 10, 2009

Related U.S. Application Data

(60) Provisional application No. 61/016,483, filed on Dec. 23, 2007.

(51) Int. Cl.
 C12P 7/04    (2006.01)
 C12P 7/16    (2006.01)
 C12N 1/15    (2006.01)
 C12N 1/16    (2006.01)
 C12N 15/00   (2006.01)
 C12N 9/88    (2006.01)

(52) U.S. Cl. ............. 435/254.2; 435/254.21; 435/157; 435/160; 435/320.1; 435/232

(58) Field of Classification Search ............. 435/254.2, 435/254.21, 320.1, 157
See application file for complete search history.

(56) References Cited

U.S. PATENT DOCUMENTS

| | | | |
|---|---|---|---|
| 7,109,010 B2 | 9/2006 | Rajgarhia et al. | |
| 2004/0029256 A1 | 2/2004 | Rajgarhia et al. | |
| 2004/0146996 A1 | 7/2004 | Yocum et al. | |
| 2007/0092957 A1 | 4/2007 | Donaldson et al. | |
| 2009/0305363 A1 | 12/2009 | Anthony et al. | |

FOREIGN PATENT DOCUMENTS

| | | |
|---|---|---|
| WO | WO 99/14335 A1 | 3/1999 |
| WO | WO 03/102152 A2 | 12/2003 |
| WO | WO 2004/099425 A2 | 11/2004 |
| WO | WO 2006/102342 A2 | 9/2006 |
| WO | WO 2007/032792 A2 | 3/2007 |
| WO | WO 2007/061590 A1 | 5/2007 |
| WO | WO 2008/042338 A2 | 4/2008 |
| WO | WO 2008/052991 A2 | 5/2008 |
| WO | WO 2008/063650 A2 | 5/2008 |
| WO | WO 2008/080124 A2 | 7/2008 |
| WO | WO 2008/098277 A2 | 8/2008 |
| WO | WO 2008/121701 A1 | 10/2008 |
| WO | WO 2008/130372 A2 | 10/2008 |
| WO | WO 2009/103533 A1 | 8/2009 |

OTHER PUBLICATIONS

Langkjaer et al., Nature 421:848-852, 2003.*
Merico et al., FEBS Journal 274:976-989, 2007.*
Zhou et al., Cell Mol Life Sci 63(19-20):2260-2290, 2006.*
Kozak, M., Gene 234:187-208, 1999.*
Adachi, E. et al. (1998) Modification of Metabolic Pathways of *Saccharomyces cerevisive* by the Expression of Lactate Dehydrogenase and Deletion of Pyruvate Decarboxylase Genes for the Lactic Acid Fermentation at Low pH Value, *Journal of Fermentation and Bioengineering* 86(3):284-9.
Atsumi, S, et al. (2008) "Non-fermentative pathways for synthesis of branched-chain higher alcohols as biofuels," *Nature* 451 (7174):86-9.
Nevoigt, E and Stahl, U. (1996) "Reduced pyruvate decarboxylase and increased glycerol-3-phosphate debydrogenase [NAD+] levels enhance glycerol production in *Saccharomyces cerevisiae*," *Yeast* 12(13):1331-7.
Overkamp, KM, et al. (2002) "Metabolic Engineering of Glycerol Production in *Saccharomyces cerevisiae*," *Applied and Environmental Microbiology* 68(6):2814-21.
Porro D, et al. (1995) "Development of Metabolically Engineered *Saccharomyces cerevisiae* Cells for the Production of Lactic Acid," *Biotechnol Prog* 11:294-8.
Porro, D, et al. (1999) "Replacement of a Metabolic Pathway for Large-Scale Production of Lactic Acid from Engineered Yeasts," *Applied and Environmental Microbiology* 65(9), 4211-5.
Pronk, J.T., et al. (1996) "Pyruvate Metabolism in *Saccharomyces cerevisiae*," *Yeast* 12:1607-1633.
Salani, F and Bianchi, M. (2006) "Production of glucoamylase in pyruvate decarboxylase deletion mutants of the yeast *Kluyveromyces lactis*," *Applied Microbiology and Biotechnology* 69(5):564-72.
van Maris, AJA, et al. (2004) "Directed Evolution of Pyruvate Decarboxylase-Negative *Saccharomyces cerevisiae*, Yielding a $C_2$-Independent, Glucose-Tolerant, and Pyruvate-Hyperproducing Yeast," *Applied and Environmental Microbiology* 70(1):159-66.
Wang, Q, et al. (2005) "Metabolic engineering of *Torulopsis glabrata* for improved pyruvate production," *Enzyme and Microbial Technology* 36(5-6):832-9.
Yonehara, T and Mirata, R. (1994) "Fermentative Production of Pyruvic Acid by Yeast," *Baiosaiensu to Indasutori* 52(7):567-70.

(Continued)

*Primary Examiner* — Delia Ramirez
(74) *Attorney, Agent, or Firm* — Cooley LLP

(57) ABSTRACT

There is disclosed a method of producing isobutanol. In an embodiment, the method includes providing a microorganism transformed with an isobutanol producing pathway containing at least one exogenous gene. The microorganism is selected to produce isobutanol from a carbon source at a yield of at least 10 percent theoretical. The method includes cultivating the microorganism in a culture medium containing a feedstock providing the carbon source, until isobutanol is produced. The method includes recovering the isobutanol. In one embodiment, the microorganism is a yeast with a Crabtree-negative phenotype. In another embodiment, the microorganism is a yeast microorganism with a Crabtree-positive phenotype. There is disclosed a microorganism for producing isobutanol. In an embodiment, the microorganism includes an isobutanol producing pathway containing at least one exogenous gene, and is selected to produce a recoverable quantity of isobutanol from a carbon source at a yield of at least 10 percent theoretical.

7 Claims, 34 Drawing Sheets

OTHER PUBLICATIONS

Zelle, RM, et al. (2008) "Malic Acid Production by *Saccharomyces cerevisiae*: Engineering of Pyruvate Carboxylation, Oxaloacetate Reduction, and Malate Export," *Applied and Environmental Microbiology* 74(9):2766-77.

International Search Report and Written Opinion mailed Jul. 23, 2009 in the International (PCT) Application No. PCT/US08/88235, 10 pages.

De La Plaza, et al., "Biochemical and molecular characterization of α-ketoisovalerate decarboxylase, an enzyme involved in the formation of aldehydes from amino acids by *Lactococcus lactis*," *FEMS Microbiology Letters* 238: 367-374 (Aug. 2004).

Fernandez De Palencia, et al., "Diversity of amino acid converting enzymes in wild lactic acid bacteria," *Enzyme and Microbiol Technology* 38: 88-93 (Jan. 2006).

Hansen, et al., "Brewer's yeast: genetic structure and targets for improvement," *Topics in Current Genetics*, vol. 2., J.H. de Winde (Ed.): Functional Genetics of Industrial Yeasts (2003).

Smit, "Formation of amino acid derived cheese flavour compounds," Thesis Wageningen University, The Netherlands, 2004.

Smit, et al., "Identification, cloning, and characterization of a *Lactococcus lactis* branched-chain α-keto acid decarboxylase involved in flavor formation," *Applied and Environmental Microbiology* 71(1): 303-311 (Jan. 2005).

Baburina, et al., "Reactivity at the substrate activation site of yeast pyruvate decarboxylase: inhibition by distortion of domain interactions," *Biochemistry* 37: 1245-55 (1998).

Butler, et al., "Identification of an upstream activation site in the pyruvate decarboxylase structual gene (PDC1) of *Saccharomyces cerevisiae*," *Current Genetics* 14: 405-12 (1988).

Eberhardt, et al., "Autoregulation of yeast pyruvate decarboxylase gene expression requires the enzyme but not its catalytic activity," *Eur. J. Biochem.* 262: 191-201 (1999).

Joseph, et al., "Function of a conserved loop of the β-domain, not involved in thiamin diphosphate binding, in catalysis and substrate activation in yeast pyruvate decarboxylase," *Biochemistry* 45: 13517-27 (2006).

Kellermann, et al., "Analysis of the primary structure and promoter function of a pyruvate decarboxylase gene (*PDC1*) from *Saccharomyces cerevisiae*," *Nuc. Acids Res.* 14(22): 8963-77(1986).

Kellermann, et al., "The glucose- and ethanol-dependent regulation of *PDC1* from *Saccharomyces cerevisiae* are controlled by two distinct promoter regions," *Current Genetics* 14: 137-44 (1988).

Kutter, et al., "Covalently bound substrate at the regulatory site triggers allosteric enzyme activation," *Nature Precedings*: hdl:10101/npre.2008.1639.1 (Posted Feb. 27, 2008, Available Online Feb. 28, 2008); Available from Nature Precedings <http://hdl.handle.net/10101/npre.2008.1639.1>.

Li, et al., "Role of glutamate 91 in information transfer during substrate activation of yeast pyruvate decarboxylase," *Biochemistry* 38: 9992-10003 (1999).

Li, et al., "Effects of substitution of tryptophan 412 in the substrate activation pathway of yeast pyruvate decarboxylase," *Biochemistry* 38: 10004-10012 (1999).

Sergienko, et al., "Catalytic acid-base groups in yeast pyruvate decarboxylase. 2. Insights into the specific roles of D28 and E477 from the rates and stereospecificity of formation of carboligase side products," *Biochemistry* 40: 7369-7381 (2001).

Serienko, et al., "Catalytic acid-base groups in yeast pyruvate decarboxylase. 3. A steady-state kinetic model consistent with the behavior of both wild-type and variant enzymes at all relevant pH values," *Biochemistry* 40: 7382-7403 (2001).

Serienko, et al., "Yeast pyruvate decarboxylase tetramers can dissociate into dimers along two interfaces. Hybrids of low-activity D28A (or D28N) and E477Q variants, with substitution of adjacent active center acidic groups from different subunits, display restored activity," *Biochemistry* 41: 6164-6169 (2002).

* cited by examiner

YEAST ORGANISM PRODUCING ISOBUTANOL AT A HIGH YIELD

CROSS-REFERENCE TO RELATED APPLICATIONS

This application claims priority to U.S. Provisional Application Ser. No. 61/016,483 filed Dec. 23, 2007. Accordingly, this application incorporates by reference in its entirety all subject matter of the above-referenced application to the extent such subject matter is not inconsistent herewith.

TECHNICAL FIELD

Metabolically engineered microorganisms and methods of producing such organisms are provided. Also provided are methods of producing metabolites that are biofuels by contacting a suitable substrate with metabolically engineered microorganisms and enzymatic preparations there from.

BACKGROUND

Biofuels have a long history ranging back to the beginning of the 20th century. As early as 1900, Rudolf Diesel demonstrated at the World Exhibition in Paris, France, an engine running on peanut oil. Soon thereafter, Henry Ford demonstrated his Model T running on ethanol derived from corn. Petroleum-derived fuels displaced biofuels in the 1930s and 1940s due to increased supply, and efficiency at a lower cost.

Market fluctuations in the 1970s coupled to the decrease in US oil production led to an increase in crude oil prices and a renewed interest in biofuels. Today, many interest groups, including policy makers, industry planners, aware citizens, and the financial community, are interested in substituting petroleum-derived fuels with biomass-derived biofuels. The leading motivations for developing biofuels are of economical, political, and environmental nature.

One is the threat of 'peak oil', the point at which the consumption rate of crude oil exceeds the supply rate, thus leading to significantly increased fuel cost results in an increased demand for alternative fuels. In addition, instability in the Middle East and other oil-rich regions has increased the demand for domestically produced biofuels. Also, environmental concerns relating to the possibility of carbon dioxide related climate change is an important social and ethical driving force which is starting to result in government regulations and policies such as caps on carbon dioxide emissions from automobiles, taxes on carbon dioxide emissions, and tax incentives for the use of biofuels.

Ethanol is the most abundant fermentatively produced fuel today but has several drawbacks when compared to gasoline. Butanol, in comparison, has several advantages over ethanol as a fuel: it can be made from the same feedstocks as ethanol but, unlike ethanol, it is compatible with gasoline at any ratio and can also be used as a pure fuel in existing combustion engines without modifications. Unlike ethanol, butanol does not absorb water and can thus be stored and distributed in the existing petrochemical infrastructure. Due to its higher energy content which is close to that of gasoline, the fuel economy (miles per gallon) is better than that of ethanol. Also, butanol-gasoline blends have lower vapor pressure than ethanol-gasoline blends, which is important in reducing evaporative hydrocarbon emissions.

Isobutanol has the same advantages as butanol with the additional advantage of having a higher octane number due to its branched carbon chain. Isobutanol is also useful as a commodity chemical and is also a precursor to MTBE. Isobutanol can be produced in microorganisms expressing a heterologous metabolic pathway, but these microorganisms are not of commercial relevance due to their inherent low performance characteristics, which include low productivity, low titer, low yield, and the requirement for oxygen during the fermentation process.

SUMMARY OF THE INVENTION

In one embodiment, a method of producing isobutanol is provided. The method includes providing a recombinant microorganism comprising an isobutanol producing metabolic pathway, the microorganism selected to produce the isobutanol from a carbon source at a yield of at least 5 percent theoretical. The method further includes cultivating the microorganism in a culture medium containing a feedstock providing the carbon source, until a recoverable quantity of the isobutanol is produced and recovering the isobutanol. In some aspects the microorganism is selected to produce isobutanol at a yield of greater than about 10 percent, 20 percent or 50 percent theoretical.

In another embodiment, a method provided herein includes a recombinant microorganism engineered to include reduced pyruvate decarboxylase (PDC) activity as compared to a parental microorganism. In one aspect, the recombinant microorganism includes a mutation in at least one pyruvate decarboxylase (PDC) gene resulting in a reduction of pyruvate decarboxylase activity of a polypeptide encoded by said gene. In another aspect, the recombinant microorganism includes a partial deletion of a pyruvate decarboxylase (PDC) gene resulting in a reduction of pyruvate decarboxylase activity of a polypeptide encoded by the gene. In another aspect, the recombinant microorganism comprises a complete deletion of a pyruvate decarboxylase (PDC) gene resulting in a reduction of pyruvate decarboxylase activity of a polypeptide encoded by the gene. In yet another aspect, the recombinant microorganism includes a modification of the regulatory region associated with at least one pyruvate decarboxylase (PDC) gene resulting in a reduction of pyruvate decarboxylase activity of a polypeptide encoded by said gene. In another aspect, the recombinant microorganism comprises a modification of the transcriptional regulator resulting in a reduction of pyruvate decarboxylase gene transcription. In another aspect, the recombinant microorganism comprises mutations in all pyruvate decarboxylase (PDC) genes resulting in a reduction of pyruvate decarboxylase activity of a polypeptide encoded by the gene.

In another embodiment, methods provided herein utilize recombinant microorganisms that have been further engineered to express a heterologous metabolic pathway for conversion of pyruvate to isobutanol. In one aspect, the recombinant microorganism is further engineered to increase the activity of a native metabolic pathway for conversion of pyruvate to isobutanol. In another aspect, the recombinant microorganism is further engineered to include at least one enzyme encoded by a heterologous gene and at least one enzyme encoded by a native gene. In yet another aspect, the recombinant microorganism is selected to include a native metabolic pathway for conversion of pyruvate to isobutanol.

In one embodiment, a method provided herein includes a yeast recombinant microorganism of the *Saccharomyces* clade.

In another embodiment, a method provided herein includes a recombinant organism that is a *Saccharomyces* sensu stricto yeast microorganism. In one aspect, a *Saccharomyces* sensu stricto yeast microorganism is selected from one of the species: *S. cerevisiae, S. cerevisiae, S. kudriavzevii, S. mikatae, S. bayanus, S. uvarum, S. carocanis* or hybrids thereof.

In another embodiment, a method provided herein includes a Crabtree-positive recombinant yeast microorganism. In one aspect, a Crabtree-positive yeast microorganism is selected from one of the genera: *Saccharomyces, Kluyveromyces, Zygosaccharomyces, Debaryomyces, Pichia* or *Schizosaccharomyces*. In other aspects, a Crabtree-positive yeast microorganism is selected from *Saccharomyces cerevisiae, Saccharomyces uvarum, Saccharomyces bayanus, Saccharomyces paradoxus, Saccharomyces castelli, Saccharomyces kluyveri, Kluyveromyces thermotolerans, Candida glabrata, Z. bailli, Z. rouxii, Debaryomyces hansenii, Pichia pastorius, Schizosaccharomyces pombe,* or *Saccharomyces uvarum*.

In another embodiment, a method provided herein includes a post-WGD (whole genome duplication) yeast microorganism. In one aspect, a post-WGD yeast is selected from one of the genera *Saccharomyces* or *Candida*. In another aspect, a post-WGD yeast is selected from *Saccharomyces cerevisiae, Saccharomyces uvarum, Saccharomyces bayanus, Saccharomyces paradoxus, Saccharomyces castelli,* and *Candida glabrata*.

In another embodiment, a method of producing isobutanol is provided. The method includes providing a recombinant microorganism that includes an isobutanol producing metabolic pathway and is selected to produce the isobutanol from a carbon source. The recombinant further includes a reduction in pyruvate decarboxylase (PDC) activity as compared to a parental microorganism. The method includes cultivating the microorganism in a culture medium containing a feedstock providing the carbon source until a recoverable quantity of the isobutanol is produced and recovering the isobutanol. In some aspects, the microorganism is a yeast of the *Saccharomyces* clade. In other aspects, the microorganism is engineered to grow on glucose independently of C2-compounds at a growth rate substantially equivalent to the growth rate of a parental microorganism without altered PDC activity. In one aspect, the microorganism is a *Saccharomyces* sensu stricto yeast. In other aspects, the microorganism is engineered to grow on glucose independently of C2-compounds at a growth rate substantially equivalent to the growth rate of a parental microorganism without altered PDC activity.

In other aspects, the microorganism is a Crabtree-negative yeast microorganism selected from one of the genera: *Kluyveromyces, Pichia, Hansenula,* or *Candida*. In other aspects, the Crabtree-negative yeast microorganism is selected from *Kluyveromyces lactis, Kluyveromyces marxianus, Pichia anomala, Pichia stipitis, Hanensula. anomala, Candida utilis,* or *Kluyveromyces waltii*. In other aspects, a the Crabtree-negative yeast microorganism is selected from *Tricosporon pullulans, Rhodotorula lignophila,* or *Myxozyma vanderwaltii, Candida ethanolica, Debaromyces carsonii, Pichia castillae.*

In another aspect, the microorganism is a Crabtree-positive yeast microorganism. In some aspects, the microorganism is engineered to grow on glucose independently of C2-compounds at a growth rate substantially equivalent to the growth rate of a parental microorganism without altered PDC activity. A Crabtree-positive yeast microorganism may be selected from one of the genera: *Saccharomyces, Kluyveromyces, Zygosaccharomyces, Debaryomyces, Pichia* or *Schizosaccharomyces*. In other aspects, the Crabtree-positive yeast microorganism is selected from *Saccharomyces cerevisiae, Saccharomyces uvarum, Saccharomyces bayanus, Saccharomyces paradoxus, Saccharomyces castelli, Saccharomyces kluyveri, Kluyveromyces thermotolerans, Candida glabrata, Z. bailli, Z. rouxii, Debaryomyces hansenii, Pichia pastorius, Schizosaccharomyces pombe,* or *Saccharomyces uvarum*. In other aspects, the microorganism is engineered to grow on glucose independently of C2-compounds at a growth rate substantially equivalent to the growth rate of a parental microorganism without altered PDC activity.

In other aspects, the microorganism is a post-WGD (whole genome duplication) yeast selected from one of the genera *Saccharomyces* or *Candida*. In other aspects, the post-WGD yeast is selected from *Saccharomyces cerevisiae, Saccharomyces uvarum, Saccharomyces bayanus, Saccharomyces paradoxus, Saccharomyces castelli,* and *Candida glabrata*. In other aspects, the microorganism is engineered to grow on glucose independently of C2-compounds at a growth rate substantially equivalent to the growth rate of a parental microorganism without altered PDC activity.

In another aspect, the microorganism is a pre-WGD (whole genome duplication) yeast selected from one of the genera *Saccharomyces, Kluyveromyces, Candida, Pichia, Debaryomyces, Hansenula, Pachysolen, Yarrowia* or *Schizosaccharomyces*. In other aspects, the pre-WGD yeast is selected from *Saccharomyces kluyveri, Kluyveromyces thermotolerans, Kluyveromyces marxianus, Kluyveromyces waltii, Kluyveromyces lactis, Candida tropicalis, Pichia pastoris, Pichia anomala, Pichia stipitis, Debaryomyces hansenii, H. anomala, Pachysolen tannophilis, Yarrowia lipolytica,* and *Schizosaccharomyces pomb.*

In other aspects, a method provided herein includes a microorganism that is a non-fermenting yeast microorganism selected from one of the genera: *Tricosporon, Rhodotorula,* or *Myxozyma.*

In another embodiment, recombinant microorganisms are provided. The microorganism includes an isobutanol producing metabolic pathway and is selected to produce the isobutanol from a carbon source. The microorganism also includes a reduction in pyruvate decarboxylase (PDC) activity as compared to a parental microorganism. In various aspects, a microorganism provided herein includes Crabtree-negative yeast microorganisms, microorganisms of the *Saccharomyces* clade, *Saccharomyces* sensu stricto yeast microorganisms, Crabtree-positive yeast microorganisms, post-WGD (whole genome duplication) yeast microorganism, pre-WGD (whole genome duplication) yeast microorganisms, and non-fermenting yeast microorganisms.

In some embodiments, a microorganism provided herein has been engineered to grow on glucose independently of C2-compounds at a growth rate substantially equivalent to the growth rate of a parental microorganism without altered PDC activity.

BRIEF DESCRIPTION OF DRAWINGS

Illustrative embodiments of the invention are illustrated in the drawings, in which.

DETAILED DESCRIPTION

Figure 1:
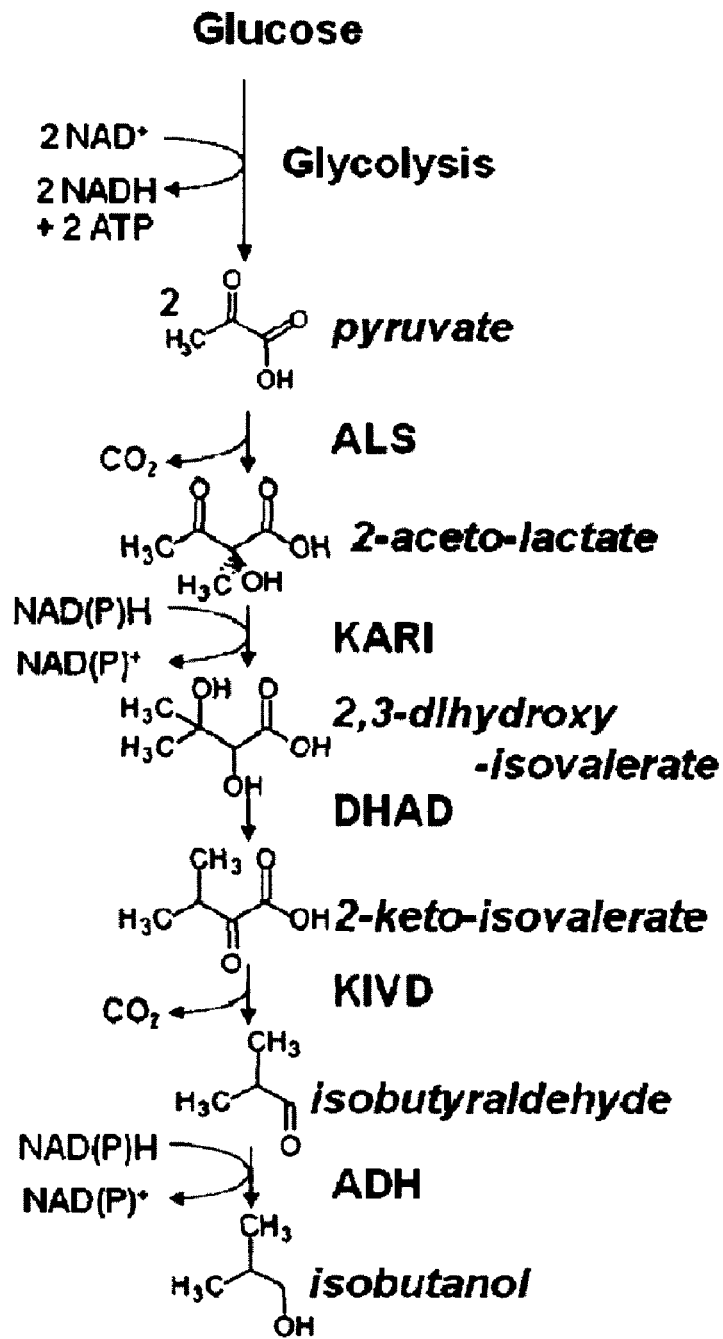
FIG. 1 illustrates an exemplary embodiment of an isobutanol pathway.

As used herein and in the appended claims, the singular forms "a," "and," and "the" include plural referents unless the context clearly dictates otherwise. Thus, for example, reference to "a polynucleotide" includes a plurality of such polynucleotides and reference to "the microorganism" includes reference to one or more microorganisms, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

Any publications discussed above and throughout the text are provided solely for their disclosure prior to the filing date of the present application. Nothing herein is to be construed as an admission that the inventors are not entitled to antedate such disclosure by virtue of prior disclosure.

The term "microorganism" includes prokaryotic and eukaryotic microbial species from the Domains Archaea, Bacteria and Eucarya, the latter including yeast and filamentous fungi, protozoa, algae, or higher Protista. The terms "microbial cells" and "microbes" are used interchangeably with the term microorganism.

"Bacteria", or "eubacteria", refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) *Proteobacteria*, e.g., Purple photosynthetic+non-photosynthetic Gram-negative bacteria (includes most "common" Gram-negative bacteria); (3) *Cyanobacteria*, e.g., oxygenic phototrophs; (4) *Spirochetes* and related species; (5) *Planctomyces*; (6) *Bacteroides, Flavobacteria*; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho* thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

The term "genus" is defined as a taxonomic group of related species according to the Taxonomic Outline of Bacteria and Archaea (Garrity, G. M., Lilburn, T. G., Cole, J. R., Harrison, S. H., Euzeby, J., and Tindall, B. J. (2007) The Taxonomic Outline of Bacteria and Archaea. TOBA Release 7.7, March 2007. Michigan State University Board of Trustees.

The term "species" is defined as a collection of closely related organisms with greater than 97% 16S ribosomal RNA sequence homology and greater than 70% genomic hybridization and sufficiently different from all other organisms so as to be recognized as a distinct unit.

The term "recombinant microorganism" and "recombinant host cell" are used interchangeably herein and refer to microorganisms that have been genetically modified to express or over-express endogenous polynucleotides, or to express heterologous polynucleotides, such as those included in a vector, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by PCR or by northern hybridization (see Sambrook et al., Molecular Cloning: A Laboratory Manual, Cold Spring Harbor Laboratory Press (1989)).

Protein encoded by a selected sequence can be quantitated by various methods, e.g., by ELISA, by assaying for the biological activity of the protein, or by employing assays that are independent of such activity, such as western blotting or radioimmunoassay, using antibodies that are recognize and bind reacting the protein. See Sambrook et al., 1989, supra. The polynucleotide generally encodes a target enzyme involved in a metabolic pathway for producing a desired metabolite. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

The term "wild-type microorganism" describes a cell that occurs in nature, i.e. a cell that has not been genetically modified. A wild-type microorganism can be genetically modified to express or overexpress a first target enzyme. This microorganism can act as a parental microorganism in the generation of a microorganism modified to express or overexpress a second target enzyme. In turn, the microorganism modified to express or overexpress a first and a second target enzyme can be modified to express or overexpress a third target enzyme.

Accordingly, a "parental microorganism" functions as a reference cell for successive genetic modification events. Each modification event can be accomplished by introducing a nucleic acid molecule in to the reference cell. The introduction facilitates the expression or overexpression of a target enzyme. It is understood that the term "facilitates" encompasses the activation of endogenous polynucleotides encoding a target enzyme through genetic modification of e.g., a promoter sequence in a parental microorganism. It is further understood that the term "facilitates" encompasses the introduction of heterologous polynucleotides encoding a target enzyme in to a parental microorganism The term "engineer" refers to any manipulation of a microorganism that result in a detectable change in the microorganism, wherein the manipulation includes but is not limited to inserting a polynucleotide and/or polypeptide heterologous to the microorganism and mutating a polynucleotide and/or polypeptide native to the microorganism. The term "metabolically engineered" or "metabolic engineering" involves rational pathway design and assembly of biosynthetic genes, genes associated with operons, and control elements of such polynucleotides, for the production of a desired metabolite. "Metabolically engineered" can further include optimization of metabolic flux by regulation and optimization of transcription, translation, protein stability and protein functionality using genetic engineering and appropriate culture condition including the reduction of, disruption, or knocking out of, a competing metabolic pathway that competes with an intermediate leading to a desired pathway.

The terms "metabolically engineered microorganism" and "modified microorganism" are used interchangeably herein and refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "mutation" as used herein indicates any modification of a nucleic acid and/or polypeptide which results in an altered nucleic acid or polypeptide. Mutations include, for example, point mutations, deletions, or insertions of single or multiple residues in a polynucleotide, which includes alterations arising within a protein-encoding region of a gene as well as alterations in regions outside of a protein-encoding sequence, such as, but not limited to, regulatory or promoter sequences. A genetic alteration may be a mutation of any type. For instance, the mutation may constitute a point mutation, a frame-shift mutation, an insertion, or a deletion of part or all of a gene. In addition, in some embodiments of the modified microorganism, a portion of the microorganism genome has been replaced with a heterologous polynucleotide. In some embodiments, the mutations are naturally-occurring. In other embodiments, the mutations are the results of artificial selection pressure. In still other embodiments, the mutations in the microorganism genome are the result of genetic engineering.

The term "biosynthetic pathway", also referred to as "metabolic pathway", refers to a set of anabolic or catabolic biochemical reactions for converting one chemical species into another. Gene products belong to the same "metabolic pathway" if they, in parallel or in series, act on the same substrate, produce the same product, or act on or produce a metabolic intermediate (i.e., metabolite) between the same substrate and metabolite end product.

The term "heterologous" as used herein with reference to molecules and in particular enzymes and polynucleotides, indicates molecules that are expressed in an organism other than the organism from which they originated or are found in nature, independently of the level of expression that can be lower, equal or higher than the level of expression of the molecule in the native microorganism.

On the other hand, the term "native" or "endogenous" as used herein with reference to molecules, and in particular enzymes and polynucleotides, indicates molecules that are expressed in the organism in which they originated or are found in nature, independently of the level of expression that can be lower equal or higher than the level of expression of the molecule in the native microorganism. It is understood that expression of native enzymes or polynucleotides may be modified in recombinant microorganisms.

The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a biofuel in a fermentation process. However, a feedstock may contain nutrients other than a carbon source.

The term "substrate" or "suitable substrate" refers to any substance or compound that is converted or meant to be converted into another compound by the action of an enzyme. The term includes not only a single compound, but also combinations of compounds, such as solutions, mixtures and other materials which contain at least one substrate, or derivatives thereof. Further, the term "substrate" encompasses not only compounds that provide a carbon source suitable for use as a starting material, such as any biomass derived sugar, but also intermediate and end product metabolites used in a pathway associated with a metabolically engineered microorganism as described herein.

The term "fermentation" or "fermentation process" is defined as a process in which a microorganism is cultivated in a culture medium containing raw materials, such as feedstock and nutrients, wherein the microorganism converts raw materials, such as a feedstock, into products.

The term "cell dry weight" or "CDW" refers to the weight of the microorganism after the water contained in the microorganism has been removed using methods known to one skilled in the art. CDW is reported in grams.

The term "biofuel" refers to a fuel in which all carbon contained within the fuel is derived from biomass and is biochemically converted, at least in part, in to a fuel by a microorganism. A biofuel is further defined as a non-ethanol compound which contains less than 0.5 oxygen atoms per carbon atom. A biofuel is a fuel in its own right, but may be blended with petroleum-derived fuels to generate a fuel. A biofuel may be used as a replacement for petrochemically-derived gasoline, diesel fuel, or jet fuel.

The term "volumetric productivity" or "production rate" is defined as the amount of product formed per volume of medium per unit of time. Volumetric productivity is reported in gram per liter per hour (g/L/h).

The term "yield" is defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product. For example, the theoretical yield for one typical conversion of glucose to isobutanol is 0.41 g/g. As such, a yield of isobutanol from glucose of 0.39 g/g would be expressed as 95% of theoretical or 95% theoretical yield.

The term "titer" is defined as the strength of a solution or the concentration of a substance in solution. For example, the titer of a biofuel in a fermentation broth is described as g of biofuel in solution per liter of fermentation broth (g/L).

A "facultative anaerobic organism" or a "facultative anaerobic microorganism" is defined as an organism that can grow in either the presence or in the absence of oxygen.

A "strictly anaerobic organism" or a "strictly anaerobic microorganism" is defined as an organism that cannot grow in the presence of oxygen and which does not survive exposure to any concentration of oxygen.

An "anaerobic organism" or an "anaerobic microorganism" is defined as an organism that cannot grow in the presence of oxygen.

"Aerobic conditions" are defined as conditions under which the oxygen concentration in the fermentation medium is sufficiently high for an aerobic or facultative anaerobic microorganism to use as a terminal electron acceptor.

In contrast, "Anaerobic conditions" are defined as conditions under which the oxygen concentration in the fermentation medium is too low for the microorganism to use as a terminal electron acceptor. Anaerobic conditions may be achieved by sparging a fermentation medium with an inert gas such as nitrogen until oxygen is no longer available to the microorganism as a terminal electron acceptor. Alternatively, anaerobic conditions may be achieved by the microorganism consuming the available oxygen of the fermentation until oxygen is unavailable to the microorganism as a terminal electron acceptor.

"Aerobic metabolism" refers to a biochemical process in which oxygen is used as a terminal electron acceptor to make energy, typically in the form of ATP, from carbohydrates. Aerobic metabolism occurs e.g. via glycolysis and the TCA cycle, wherein a single glucose molecule is metabolized completely into carbon dioxide in the presence of oxygen.

In contrast, "anaerobic metabolism" refers to a biochemical process in which oxygen is not the final acceptor of electrons contained in NADH. Anaerobic metabolism can be divided into anaerobic respiration, in which compounds other than oxygen serve as the terminal electron acceptor, and substrate level phosphorylation, in which the electrons from NADH are utilized to generate a reduced product via a "fermentative pathway."

In "fermentative pathways", NAD(P)H donates its electrons to a molecule produced by the same metabolic pathway that produced the electrons carried in NAD(P)H. For example, in one of the fermentative pathways of certain yeast strains, NAD(P)H generated through glycolysis transfers its electrons to pyruvate, yielding ethanol. Fermentative pathways are usually active under anaerobic conditions but may also occur under aerobic conditions, under conditions where NADH is not fully oxidized via the respiratory chain. For example, above certain glucose concentrations, Crabtree positive yeasts produce large amounts of ethanol under aerobic conditions.

The term "byproduct" means an undesired product related to the production of a biofuel or biofuel precursor. Byproducts are generally disposed as waste, adding cost to a production process.

The term "non-fermenting yeast" is a yeast species that fails to demonstrate an anaerobic metabolism in which the electrons from NADH are utilized to generate a reduced product via a fermentative pathway such as the production of ethanol and $CO_2$ from glucose. Non-fermentative yeast can be identified by the "Durham Tube Test" (J. A. Barnett, R. W. Payne, and D. Yarrow. 2000. Yeasts Characteristics and Identification. $3^{rd}$ edition. p. 28-29. Cambridge University Press, Cambridge, UK.) or the by monitoring the production of fermentation productions such as ethanol and $CO_2$.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotidic oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "operon" refers to two or more genes which are transcribed as a single transcriptional unit from a common promoter. In some embodiments, the genes comprising the operon are contiguous genes. It is understood that transcription of an entire operon can be modified (i.e., increased, decreased, or eliminated) by modifying the common promoter. Alternatively, any gene or combination of genes in an operon can be modified to alter the function or activity of the encoded polypeptide. The modification can result in an increase in the activity of the encoded polypeptide. Further, the modification can impart new activities on the encoded polypeptide. Exemplary new activities include the use of alternative substrates and/or the ability to function in alternative environmental conditions.

A "vector" is any means by which a nucleic acid can be propagated and/or transferred between organisms, cells, or cellular components. Vectors include viruses, bacteriophage, pro-viruses, plasmids, phagemids, transposons, and artificial chromosomes such as YACs (yeast artificial chromosomes), BACs (bacterial artificial chromosomes), and PLACs (plant artificial chromosomes), and the like, that are "episomes," that is, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not episomal in nature, or it can be an organism which comprises one or more of the above polynucleotide constructs such as an *agrobacterium* or a bacterium.

"Transformation" refers to the process by which a vector is introduced into a host cell. Transformation (or transduction, or transfection), can be achieved by any one of a number of means including chemical transformation (e.g. lithium acetate transformation), electroporation, microinjection, biolistics (or particle bombardment-mediated delivery), or *agrobacterium* mediated transformation.

The term "enzyme" as used herein refers to any substance that catalyzes or promotes one or more chemical or biochemical reactions, which usually includes enzymes totally or partially composed of a polypeptide, but can include enzymes composed of a different molecule including polynucleotides.

The term "protein" or "polypeptide" as used herein indicates an organic polymer composed of two or more amino acidic monomers and/or analogs thereof. As used herein, the term "amino acid" or "amino acidic monomer" refers to any natural and/or synthetic amino acids including glycine and both D or L optical isomers. The term "amino acid analog" refers to an amino acid in which one or more individual atoms have been replaced, either with a different atom, or with a different functional group. Accordingly, the term polypeptide includes amino acidic polymer of any length including full length proteins, and peptides as well as analogs and fragments thereof. A polypeptide of three or more amino acids is also called a protein oligomer or oligopeptide The term "homolog", used with respect to an original enzyme or gene of a first family or species, refers to distinct enzymes or genes of a second family or species which are determined by functional, structural or genomic analyses to be an enzyme or gene of the second family or species which corresponds to the original enzyme or gene of the first family or species. Most often, homologs will have functional, structural or genomic similarities. Techniques are known by which homologs of an enzyme or gene can readily be cloned using genetic probes and PCR. Identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. (Thus, the term "homologous proteins" is defined to mean that the two proteins have similar amino acid sequences).

The term "analog" or "analogous" refers to nucleic acid or protein sequences or protein structures that are related to one another in function only and are not from common descent or do not share a common ancestral sequence. Analogs may differ in sequence but may share a similar structure, due to convergent evolution. For example, two enzymes are analogs or analogous if the enzymes catalyze the same reaction of conversion of a substrate to a product, are unrelated in sequence, and irrespective of whether the two enzymes are related in structure.

The Microorganism in General

Native producers of 1-butanol, such as *Clostridium acetobutylicum*, are known, but these organisms also generate byproducts such as acetone, ethanol, and butyrate during fermentations. Furthermore, these microorganisms are relatively difficult to manipulate, with significantly fewer tools available than in more commonly used production hosts such as *S. cerevisiae* or *E. coli*. Additionally, the physiology and metabolic regulation of these native producers are much less well understood, impeding rapid progress towards high-efficiency production. Furthermore, no native microorganisms have been identified that can metabolize glucose into isobutanol in industrially relevant quantities.

The production of isobutanol and other fusel alcohols by various yeast species, including *Saccharomyces cerevisiae* is of special interest to the distillers of alcoholic beverages, for whom fusel alcohols constitute often undesirable off-notes. Production of isobutanol in wild-type yeasts has been documented on various growth media, ranging from grape must from winemaking (Romano, et al., Metabolic diversity of *Saccharomyces cerevisiae* strains from spontaneously fermented grape musts, World Journal of Microbiology and Biotechnology. 19:311-315, 2003), in which 12-219 mg/L isobutanol were produced, to supplemented minimal media (Oliviera, et al. (2005) World Journal of Microbiology and Biotechnology 21:1569-1576), producing 16-34 mg/L isobutanol. Work from Dickinson, et al. (J Biol. Chem. 272(43): 26871-8, 1997) has identified the enzymatic steps utilized in an endogenous *S. cerevisiae* pathway converting branch-chain amino acids (e.g., valine or leucine) to isobutanol.

Recombinant microorganisms provided herein can express a plurality of heterologous and/or native target enzymes involved in pathways for the production isobutanol from a suitable carbon source.

Accordingly, metabolically "engineered" or "modified" microorganisms are produced via the introduction of genetic material into a host or parental microorganism of choice and/or by modification of the expression of native genes, thereby modifying or altering the cellular physiology and biochemistry of the microorganism. Through the introduction of genetic material and/or the modification of the expression of native genes the parental microorganism acquires new properties, e.g. the ability to produce a new, or greater quantities of, an intracellular metabolite. As described herein, the introduction of genetic material into and/or the modification of the expression of native genes in a parental microorganism results in a new or modified ability to produce isobutanol. The genetic material introduced into and/or the genes modified for expression in the parental microorganism contains gene(s), or parts of genes, coding for one or more of the enzymes involved in a biosynthetic pathway for the production of isobutanol and may also include additional elements for the expression and/or regulation of expression of these genes, e.g. promoter sequences.

In addition to the introduction of a genetic material into a host or parental microorganism, an engineered or modified microorganism can also include alteration, disruption, deletion or knocking-out of a gene or polynucleotide to alter the cellular physiology and biochemistry of the microorganism. Through the alteration, disruption, deletion or knocking-out of a gene or polynucleotide the microorganism acquires new or improved properties (e.g., the ability to produce a new metabolite or greater quantities of an intracellular metabolite, improve the flux of a metabolite down a desired pathway, and/or reduce the production of byproducts).

Recombinant microorganisms provided herein may also produce metabolites in quantities not available in the parental microorganism. A "metabolite" refers to any substance produced by metabolism or a substance necessary for or taking part in a particular metabolic process. A metabolite can be an organic compound that is a starting material (e.g., glucose or pyruvate), an intermediate (e.g., 2-ketoisovalerate), or an end product (e.g., isobutanol) of metabolism. Metabolites can be used to construct more complex molecules, or they can be broken down into simpler ones. Intermediate metabolites may be synthesized from other metabolites, perhaps used to make more complex substances, or broken down into simpler compounds, often with the release of chemical energy.

Exemplary metabolites include glucose, pyruvate, and isobutanol. The metabolite isobutanol can be produced by a recombinant microorganism metabolically engineered to express or over-express a metabolic pathway that converts pyruvate to isobutanol. An exemplary metabolic pathway that converts pyruvate to isobutanol may be comprised of an acetohydroxy acid synthase (ALS), a ketolacid reductoisomerase (KARI), a dihyroxy-acid dehydratase (DHAD), a 2-keto-acid decarboxylase (KIVD), and an alcohol dehydrogenase (ADH).

Accordingly, provided herein are recombinant microorganisms that produce isobutanol and in some aspects may include the elevated expression of target enzymes such as ALS, KARI, DHAD, KIVD, and ADH The disclosure identifies specific genes useful in the methods, compositions and organisms of the disclosure; however it will be recognized that absolute identity to such genes is not necessary. For example, changes in a particular gene or polynucleotide comprising a sequence encoding a polypeptide or enzyme can be performed and screened for activity. Typically such changes comprise conservative mutation and silent mutations. Such modified or mutated polynucleotides and polypeptides can be screened for expression of a functional enzyme using methods known in the art.

Due to the inherent degeneracy of the genetic code, other polynucleotides which encode substantially the same or functionally equivalent polypeptides can also be used to clone and express the polynucleotides encoding such enzymes.

As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons. Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, typical stop codons for *S. cerevisiae* and mammals are UAA and UGA, respectively. The typical stop codon for monocotyledonous plants is UGA, whereas insects and *E. coli* commonly use UAA as the stop codon (Dalphin et al. (1996) Nucl. Acids Res. 24: 216-218). Methodology for optimizing a nucleotide sequence for expression in a plant is provided, for example, in U.S. Pat. No. 6,015,891, and the references cited therein.

Those of skill in the art will recognize that, due to the degenerate nature of the genetic code, a variety of DNA compounds differing in their nucleotide sequences can be used to encode a given enzyme of the disclosure. The native DNA sequence encoding the biosynthetic enzymes described above are referenced herein merely to illustrate an embodiment of the disclosure, and the disclosure includes DNA compounds of any sequence that encode the amino acid sequences of the polypeptides and proteins of the enzymes utilized in the methods of the disclosure. In similar fashion, a polypeptide can typically tolerate one or more amino acid substitutions, deletions, and insertions in its amino acid sequence without loss or significant loss of a desired activity. The disclosure includes such polypeptides with different amino acid sequences than the specific proteins described herein so long as they modified or variant polypeptides have the enzymatic anabolic or catabolic activity of the reference polypeptide. Furthermore, the amino acid sequences encoded by the DNA sequences shown herein merely illustrate embodiments of the disclosure.

In addition, homologs of enzymes useful for generating metabolites are encompassed by the microorganisms and methods provided herein.

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 30%, typically at least 40%, more typically at least 50%, even more typically at least 60%, and even more typically at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

When "homologous" is used in reference to proteins or peptides, it is recognized that residue positions that are not identical often differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of homology may be adjusted upwards to correct for the conservative nature of the substitution. Means for making this adjustment are well known to those of skill in the art (see, e.g., Pearson W. R. Using the FASTA program to search protein and DNA sequence databases, Methods in Molecular Biology, 1994, 25:365-89, hereby incorporated herein by reference).

The following six groups each contain amino acids that are conservative substitutions for one another: 1) Serine (S), Threonine (T); 2) Aspartic Acid (D), Glutamic Acid (E); 3) Asparagine (N), Glutamine (Q); 4) Arginine (R), Lysine (K); 5) Isoleucine (I), Leucine (L), Methionine (M), Alanine (A), Valine (V), and 6) Phenylalanine (F), Tyrosine (Y), Tryptophan (W).

Sequence homology for polypeptides, which is also referred to as percent sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutant protein thereof. See, e.g., GCG Version 6.1.

A typical algorithm used comparing a molecule sequence to a database containing a large number of sequences from different organisms is the computer program BLAST (Altschul, S. F., et al. (1990) "Basic local alignment search tool." J. Mol. Biol. 215:403-410; Gish, W. and States, D. J. (1993) "Identification of protein coding regions by database similarity search." Nature Genet. 3:266-272; Madden, T. L., et al. (1996) "Applications of network BLAST server" Meth. Enzymol. 266:131-141; Altschul, S. F., et al. (1997) "Gapped BLAST and PSI-BLAST: a new generation of protein database search programs." Nucleic Acids Res. 25:3389-3402; Zhang, J. and Madden, T. L. (1997) "PowerBLAST: A new network BLAST application for interactive or automated sequence analysis and annotation." Genome Res. 7:649-656), especially blastp or tblastn (Altschul, S. F., et al. (1997) "Gapped BLAST and PSI-BLAST: a new generation of protein database search programs." Nucleic Acids Res. 25:3389-3402). Typical parameters for BLASTp are: Expectation value: 10 (default); Filter: seg (default); Cost to open a gap: 11 (default); Cost to extend a gap: 1 (default); Max. alignments: 100 (default); Word size: 11 (default); No. of descriptions: 100 (default); Penalty Matrix: BLOWSUM62.

When searching a database containing sequences from a large number of different organisms, it is typical to compare amino acid sequences. Database searching using amino acid sequences can be measured by algorithms other than blastp known in the art. For instance, polypeptide sequences can be compared using FASTA, a program in GCG Version 6.1. FASTA provides alignments and percent sequence identity of the regions of the best overlap between the query and search sequences (Pearson, W. R. (1990) "Rapid and Sensitive Sequence Comparison with FASTP and FASTA" Meth. Enzymol. 183:63-98). For example, a percent sequence identity between amino acid sequences can be determined using FASTA with its default parameters (a word size of 2 and the PAM250 scoring matrix), as provided in GCG Version 6.1, hereby incorporated herein by reference.

The disclosure provides metabolically engineered microorganisms comprising a biochemical pathway for the production of isobutanol from a suitable substrate at a high yield. A metabolically engineered microorganism of the disclosure comprises one or more recombinant polynucleotides within the genome of the organism or external to the genome within the organism. The microorganism can comprise a reduction, disruption or knockout of a gene found in the wild-type organism and/or introduction of a heterologous polynucleotide and/or expression or overexpression of an endogenous polynucleotide.

In one aspect, the disclosure provides a recombinant microorganism comprising elevated expression of at least one target enzyme as compared to a parental microorganism or encodes an enzyme not found in the parental organism. In another or further aspect, the microorganism comprises a reduction, disruption or knockout of at least one gene encoding an enzyme that competes with a metabolite necessary for the production of isobutanol. The recombinant microorganism produces at least one metabolite involved in a biosynthetic pathway for the production of isobutanol. In general, the recombinant microorganisms comprises at least one recombinant metabolic pathway that comprises a target enzyme and may further include a reduction in activity or expression of an enzyme in a competitive biosynthetic pathway. The pathway acts to modify a substrate or metabolic intermediate in the production of isobutanol. The target enzyme is encoded by, and expressed from, a polynucleotide derived from a suitable biological source. In some embodiments, the polynucleotide comprises a gene derived from a prokaryotic or eukaryotic source and recombinantly engineered into the microorganism of the disclosure. In other embodiments, the polynucleotide comprises a gene that is native to the host organism.

It is understood that a range of microorganisms can be modified to include a recombinant metabolic pathway suitable for the production of isobutanol. In various embodiments, microorganisms may be selected from yeast microorganisms. Yeast microorganisms for the production of isobutanol may be selected based on certain characteristics:

One characteristic may include the property that the microorganism is selected to convert various carbon sources into isobutanol. Accordingly, in one embodiment, the recombinant microorganism herein disclosed can convert a variety of carbon sources to products, including but not limited to glucose, galactose, mannose, xylose, arabinose, lactose, sucrose, and mixtures thereof.

Another characteristic may include the property that the wild-type or parental microorganism is non-fermenting. In other words, it cannot metabolize a carbon source anaerobically while the yeast is able to metabolize a carbon source in the presence of oxygen. Non-fermenting yeast refers to both naturally occurring yeasts as well as genetically modified yeast. During anaerobic fermentation with fermentative yeast, the main pathway to oxidize the NADH from glycolysis is through the production of ethanol. Ethanol is produced by alcohol dehydrogenase (ADH) via the reduction of acetaldehyde, which is generated from pyruvate by pyruvate decarboxylase (PDC). Thus, in one embodiment, a fermentative yeast can be engineered to be non-fermentative by the reduction or elimination of the native PDC activity. Thus, most of the pyruvate produced by glycolysis is not consumed by PDC and is available for the isobutanol pathway. Deletion of this pathway increases the pyruvate and the reducing equivalents available for the isobutanol pathway. Fermentative pathways contribute to low yield and low productivity of isobutanol. Accordingly, deletion of PDC may increase yield and productivity of isobutanol.

A third characteristic may include the property that the biocatalyst is selected to convert various carbon sources into isobutanol.

In one embodiment, the yeast microorganisms may be selected from the "*Saccharomyces* Yeast Clade", defined as an ascomycetous yeast taxonomic class by Kurtzman and Robnett in 1998 ("Identification and phylogeny of ascomycetous yeast from analysis of nuclear large subunit (26S) ribosomal DNA partial sequences." Antonie van Leeuwenhoek 73: 331-371, FIG. 2). They were able to determine the relatedness of approximately 500 yeast species by comparing the nucleotide sequence of the D1/D2 domain at the 5' end of the gene encoding the large ribosomal subunit 26S. In pair-wise comparisons of the D1/D2 nucleotide sequences of *S. cerevisiae* and of the two most distant yeast from this *Saccharomyces* yeast Glade, *K. lactis* and *K. marxianus*, share greater than 80% identity.

The term "*Saccharomyces* sensu stricto" taxonomy group is a cluster of yeast species that are highly related to *S. cerevisiae* (Rainieri, S. et al 2003. *Saccharomyces* Sensu Stricto Systematics, Genetic Diversity and Evolution. J. Biosci Bioengin 96(1)1-9. *Saccharomyces* sensu stricto yeast species include but are not limited to *S. cerevisiae, S. cerevisiae, S. kudriavzevii, S. mikatae, S. bayanus, S. uvarum, S. carocanis* and hybrids derived from these species (Masneuf et al. 1998. New Hybrids between *Saccharomyces* Sensu Stricto Yeast Species Found Among Wine and Cider Production Strains. *Yeast* 7(1)61-72).

An ancient whole genome duplication (WGD) event occurred during the evolution of the hemiascomycete yeast and was discovered using comparative genomic tools (Kellis et al 2004 "Proof and evolutionary analysis of ancient genome duplication in the yeast *S. cerevisiae.*" *Nature* 428: 617-624. Dujon et al 2004 "Genome evolution in yeasts." *Nature* 430:35-44. Langkjaer et al 2003 "Yeast genome duplication was followed by asynchronous differentiation of duplicated genes." *Nature* 428:848-852. Wolfe and Shields 1997 "Molecular evidence for an ancient duplication of the entire yeast genome." *Nature* 387:708-713.) Using this major evolutionary event, yeast can be divided into species that diverged from a common ancestor following the WGD event (termed "post-WGD yeast" herein) and species that diverged from the yeast lineage prior to the WGD event (termed "pre-WGD yeast" herein).

Accordingly, in one embodiment, the yeast microorganism may be selected from a post-WGD yeast genus, including but not limited to *Saccharomyces* and *Candida*. The favored post-WGD yeast species include: *S. cerevisiae, S. uvarum, S. bayanus, S. paradoxus, S. castelli,* and *C. glabrata*.

In another embodiment, the yeast microorganism may be selected from a pre-whole genome duplication (pre-WGD) yeast genus including but not limited to *Saccharomyces, Kluyveromyces, Candida, Pichia, Issatchenkia, Debaryomyces, Hansenula, Yarrowia* and, *Schizosaccharomyces*. Representative pre-WGD yeast species include: *S. kluyveri, K. thermotolerans, K. marxianus, K. waltii, K. lactis, C. tropicalis, P. pastoris, P. anomala, P. stipitis, I. orientalis, I. occidentalis, I. scutulata, D. hansenii, H. anomala, Y. lipolytica,* and *S. pombe*.

A yeast microorganism may be either Crabtree-negative or Crabtree-positive. A yeast cell having a Crabtree-negative phenotype is any yeast cell that does not exhibit the Crabtree effect. The term "Crabtree-negative" refers to both naturally occurring and genetically modified organisms. Briefly, the Crabtree effect is defined as the inhibition of oxygen consumption by a microorganism when cultured under aerobic conditions due to the presence of a high concentration of glucose (e.g., 50 g-glucose L-1). In other words, a yeast cell having a Crabtree-positive phenotype continues to ferment irrespective of oxygen availability due to the presence of glucose, while a yeast cell having a Crabtree-negative phenotype does not exhibit glucose mediated inhibition of oxygen consumption.

Accordingly, in one embodiment the yeast microorganism may be selected from yeast with a Crabtree-negative phenotype including but not limited to the following genera: *Kluyveromyces, Pichia, Issatchenkia, Hansenula,* and *Candida*. Crabtree-negative species include but are not limited to: *K. lactis, K. marxianus, P. anomala, P. stipitis, I. orientalis, I. occidentalis, I. scutulata, H. anomala,* and *C. utilis*.

In another embodiment, the yeast microorganism may be selected from a yeast with a Crabtree-positive phenotype, including but not limited to *Saccharomyces, Kluyveromyces, Zygosaccharomyces, Debaryomyces, Pichia* and *Schizosaccharomyces*. Crabtree-positive yeast species include but are not limited to: *S. cerevisiae, S. uvarum, S. bayanus, S. paradoxus, S. castelli, S. kluyveri, K. thermotolerans, C. glabrata, Z. bailli, Z. rouxii, D. hansenii, P. pastorius,* and *S. pombe*.

In one embodiment, a yeast microorganism is engineered to convert a carbon source, such as glucose, to pyruvate by glycolysis and the pyruvate is converted to isobutanol via an engineered isobutanol pathway (PCT/US2006/041602, PCT/US2008/053514). Alternative pathways for the production of isobutanol have been described in International Patent Application No PCT/US2006/041602 and in Dickinson et al., *Journal of Biological Chemistry* 273:25751-15756 (1998).

Accordingly, the engineered isobutanol pathway to convert pyruvate to isobutanol can be comprised of the following reactions:

1. 2 pyruvate→acetolactate+$CO_2$
2. acetolactate+NADPH→2,3-dihydroxyisovalerate+$NADP^+$
3. 2,3-dihydroxyisovalerate→alpha-ketoisovalerate
4. alpha-ketoisovalerate→isobutyraldehyde+$CO_2$
5. isobutyraldehyde+NADPH→isobutanol+$NADP^+$ These reactions are carried out by the enzymes 1) Acetolactate Synthase (ALS, EC4.1.3.18), 2) Keto-acid Reducto-Isomerase (KARI, EC1.1.1.86), 3) Dihydroxy-acid dehydratase (DHAD, EC4.2.1.9), 4) Keto-isovalerate decarboxylase (KIVD, EC4.1.1.1), and 5) an Alcohol dehydrogenase (ADH, EC1.1.1.1 or 1.1.1.2).

In another embodiment, the yeast microorganism is engineered to overexpress these enzymes. For example, these enzymes can be encoded by native genes. For example, ALS can be encoded by the alsS gene of *B. subtilis*, alsS of *L. lactis*, or the ilvK gene of *K. pneumonia*. For example, KARI can be encoded by the ilvC genes of *E. coli, C. glutamicum, M. maripaludis,* or *Piromyces* sp E2. For example, DHAD can be encoded by the ilvD genes of *E. coli* or *C. glutamicum*. KIVD can be encoded by the kivD gene of *L. lactis*. ADH can be encoded by ADH2, ADH6, or ADH7 of *S. cerevisiae*.

The yeast microorganism of the invention may be engineered to have increased ability to convert pyruvate to isobutanol. In one embodiment, the yeast microorganism may be engineered to have increased ability to convert pyruvate to isobutyraldehyde. In another embodiment, the yeast microorganism may be engineered to have increased ability to convert pyruvate to keto-isovalerate. In another embodiment, the yeast microorganism may be engineered to have increased ability to convert pyruvate to 2,3-dihydroxyisovalerate. In another embodiment, the yeast microorganism may be engineered to have increased ability to convert pyruvate to acetolactate.

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis, which are known to those of ordinary skill in the art. Such action allows those of ordinary skill in the art to optimize the enzymes for expression and activity in yeast.

In addition, genes encoding these enzymes can be identified from other fungal and bacterial species and can be expressed for the modulation of this pathway. A variety of organisms could serve as sources for these enzymes, including, but not limited to, *Saccharomyces* spp., including *S. cerevisiae* and *S. uvarum*, *Kluyveromyces* spp., including *K. thermotolerans*, *K. lactis*, and *K. marxianus*, *Pichia* spp., *Hansenula* spp., including *H. polymorpha*, *Candida* spp., *Trichosporon* spp., *Yamadazyma* spp., including *Y. spp. stipitis*, *Torulaspora pretoriensis*, *Schizosaccharomyces* spp., including *S. pombe*, *Cryptococcus* spp., *Aspergillus* spp., *Neurospora* spp., or *Ustilago* spp. Sources of genes from anaerobic fungi include, but not limited to, *Piromyces* spp., *Orpinomyces* spp., or *Neocallimastix* spp. Sources of prokaryotic enzymes that are useful include, but not limited to, *Escherichia. coli*, *Zymomonas mobilis*, *Staphylococcus aureus*, *Bacillus* spp., *Clostridium* spp., *Corynebacterium* spp., *Pseudomonas* spp., *Lactococcus* spp., *Enterobacter* spp., and *Salmonella* spp.

Methods in General
Identification of PDC in a Yeast Microorganism

Any method can be used to identify genes that encode for enzymes with pyruvate decarboxylase (PDC) activity. PDC catalyzes the decarboxylation of pyruvate to form acetaldehyde. Generally, homologous or similar PDC genes and/or homologous or similar PDC enzymes can be identified by functional, structural, and/or genetic analysis. In most cases, homologous or similar PDC genes and/or homologous or similar PDC enzymes will have functional, structural, or genetic similarities. Techniques known to those skilled in the art may be suitable to identify homologous genes and homologous enzymes. Generally, analogous genes and/or analogous enzymes can be identified by functional analysis and will have functional similarities. Techniques known to those skilled in the art may be suitable to identify analogous genes and analogous enzymes. For example, to identify homologous or analogous genes, proteins, or enzymes, techniques may include, but not limited to, cloning a PDC gene by PCR using primers based on a published sequence of a gene/enzyme or by degenerate PCR using degenerate primers designed to amplify a conserved region among PDC genes. Further, one skilled in the art can use techniques to identify homologous or analogous genes, proteins, or enzymes with functional homology or similarity. Techniques include examining a cell or cell culture for the catalytic activity of an enzyme through in vitro enzyme assays for said activity, then isolating the enzyme with said activity through purification, determining the protein sequence of the enzyme through techniques such as Edman degradation, design of PCR primers to the likely nucleic acid sequence, amplification of said DNA sequence through PCR, and cloning of said nucleic acid sequence. To identify homologous or similar genes and/or homologous or similar enzymes, analogous genes and/or analogous enzymes or proteins, techniques also include comparison of data concerning a candidate gene or enzyme with databases such as BRENDA, KEGG, or MetaCYC. The candidate gene or enzyme may be identified within the above mentioned databases in accordance with the teachings herein. Furthermore, PDC activity can be determined phenotypically. For example, ethanol production under fermentative conditions can be assessed. A lack of ethanol production may be indicative of a yeast microorganism with no PDC activity.

Genetic Insertions and Deletions

Any method can be used to introduce a nucleic acid molecule into yeast and many such methods are well known. For example, transformation and electroporation are common methods for introducing nucleic acid into yeast cells. See, e.g., Gietz et al., *Nucleic Acids Res.* 27:69-74 (1992); Ito et al., *J. Bacteriol.* 153:163-168 (1983); and Becker and Guarente, *Methods in Enzymology* 194:182-187 (1991).

In an embodiment, the integration of a gene of interest into a DNA fragment or target gene of a yeast microorganism occurs according to the principle of homologous recombination. According to this embodiment, an integration cassette containing a module comprising at least one yeast marker gene and/or the gene to be integrated (internal module) is flanked on either side by DNA fragments homologous to those of the ends of the targeted integration site (recombinogenic sequences). After transforming the yeast with the cassette by appropriate methods, a homologous recombination between the recombinogenic sequences may result in the internal module replacing the chromosomal region in between the two sites of the genome corresponding to the recombinogenic sequences of the integration cassette. (Orr-Weaver et al., *Proc Natl Acad Sci USA* 78:6354-6358 (1981))

In an embodiment, the integration cassette for integration of a gene of interest into a yeast microorganism includes the heterologous gene under the control of an appropriate promoter and terminator together with the selectable marker flanked by recombinogenic sequences for integration of a heterologous gene into the yeast chromosome. In an embodiment, the heterologous gene includes an appropriate native gene desired to increase the copy number of a native gene(s). The selectable marker gene can be any marker gene used in yeast, including but not limited to, HIS3, TRP1, LEU2, URA3, bar, ble, hph, and kan. The recombinogenic sequences can be chosen at will, depending on the desired integration site suitable for the desired application.

In another embodiment, integration of a gene into the chromosome of the yeast microorganism may occur via random integration (Kooistra, R., Hooykaas, P. J. J., Steensma, H. Y. 2004. *Yeast* 21: 781-792).

Additionally, in an embodiment, certain introduced marker genes are removed from the genome using techniques well known to those skilled in the art. For example, URA3 marker loss can be obtained by plating URA3 containing cells in FOA (5-fluoro-orotic acid) containing medium and selecting for FOA resistant colonies (Boeke, J. et al, 1984, *Mol. Gen. Genet,* 197, 345-47).

The exogenous nucleic acid molecule contained within a yeast cell of the disclosure can be maintained within that cell in any form. For example, exogenous nucleic acid molecules can be integrated into the genome of the cell or maintained in an episomal state that can stably be passed on ("inherited") to daughter cells. Such extra-chromosomal genetic elements (such as plasmids, etc.) can additionally contain selection markers that ensure the presence of such genetic elements in daughter cells. Moreover, the yeast cells can be stably or transiently transformed. In addition, the yeast cells described herein can contain a single copy, or multiple copies of a particular exogenous nucleic acid molecule as described above.

Reduction of Enzymatic Activity

Yeast microorganisms within the scope of the invention may have reduced enzymatic activity such as reduced pyruvate decarboxylase activity. The term "reduced" as used herein with respect to a particular enzymatic activity refers to a lower level of enzymatic activity than that measured in a comparable yeast cell of the same species. The term reduced also refers to the elimination of enzymatic activity than that measured in a comparable yeast cell of the same species. Thus, yeast cells lacking pyruvate decarboxylase activity are considered to have reduced pyruvate decarboxylase activity since most, if not all, comparable yeast strains have at least some pyruvate decarboxylase activity. Such reduced enzymatic activities can be the result of lower enzyme concentration, lower specific activity of an enzyme, or a combination thereof. Many different methods can be used to make yeast having reduced enzymatic activity. For example, a yeast cell can be engineered to have a disrupted enzyme-encoding locus using common mutagenesis or knock-out technology. See, e.g., Methods in Yeast Genetics (1997 edition), Adams, Gottschling, Kaiser, and Stems, Cold Spring Harbor Press (1998). In addition, certain point-mutation(s) can be introduced which results in an enzyme with reduced activity.

Alternatively, antisense technology can be used to reduce enzymatic activity. For example, yeast can be engineered to contain a cDNA that encodes an antisense molecule that prevents an enzyme from being made. The term "antisense molecule" as used herein encompasses any nucleic acid molecule that contains sequences that correspond to the coding strand of an endogenous polypeptide. An antisense molecule also can have flanking sequences (e.g., regulatory sequences). Thus antisense molecules can be ribozymes or antisense oligonucleotides. A ribozyme can have any general structure including, without limitation, hairpin, hammerhead, or axhead structures, provided the molecule cleaves RNA.

Yeast having a reduced enzymatic activity can be identified using many methods. For example, yeast having reduced pyruvate decarboxylase activity can be easily identified using common methods, which may include, for example, measuring ethanol formation via gas chromatography.

Overexpression of Heterologous Genes

Methods for overexpressing a polypeptide from a native or heterologous nucleic acid molecule are well known. Such methods include, without limitation, constructing a nucleic acid sequence such that a regulatory element promotes the expression of a nucleic acid sequence that encodes the desired polypeptide. Typically, regulatory elements are DNA sequences that regulate the expression of other DNA sequences at the level of transcription. Thus, regulatory elements include, without limitation, promoters, enhancers, and the like. For example, the exogenous genes can be under the control of an inducible promoter or a constitutive promoter. Moreover, methods for expressing a polypeptide from an exogenous nucleic acid molecule in yeast are well known. For example, nucleic acid constructs that are used for the expression of exogenous polypeptides within *Kluyveromyces* and *Saccharomyces* are well known (see, e.g., U.S. Pat. Nos. 4,859,596 and 4,943,529, for *Kluyveromyces* and, e.g., Gellissen et al., Gene 190(1):87-97 (1997) for *Saccharomyces*). Yeast plasmids have a selectable marker and an origin of replication. In addition certain plasmids may also contain a centromeric sequence. These centromeric plasmids are generally a single or low copy plasmid. Plasmids without a centromeric sequence and utilizing either a 2 micron (*S. cerevisiae*) or 1.6 micron (*K. lactis*) replication origin are high copy plasmids. The selectable marker can be either prototrophic, such as HIS3, TRP1, LEU2, URA3 or ADE2, or antibiotic resistance, such as, bar, ble, hph, or kan.

In another embodiment, heterologous control elements can be used to activate or repress expression of endogenous genes. Additionally, when expression is to be repressed or eliminated, the gene for the relevant enzyme, protein or RNA can be eliminated by known deletion techniques.

As described herein, any yeast within the scope of the disclosure can be identified by selection techniques specific to the particular enzyme being expressed, over-expressed or repressed. Methods of identifying the strains with the desired phenotype are well known to those skilled in the art. Such methods include, without limitation, PCR, RT-PCR, and nucleic acid hybridization techniques such as Northern and Southern analysis, altered growth capabilities on a particular substrate or in the presence of a particular substrate, a chemical compound, a selection agent and the like. In some cases, immunohistochemistry and biochemical techniques can be used to determine if a cell contains a particular nucleic acid by detecting the expression of the encoded polypeptide. For example, an antibody having specificity for an encoded enzyme can be used to determine whether or not a particular yeast cell contains that encoded enzyme. Further, biochemical techniques can be used to determine if a cell contains a particular nucleic acid molecule encoding an enzymatic polypeptide by detecting a product produced as a result of the expression of the enzymatic polypeptide. For example, transforming a cell with a vector encoding acetolactate synthase and detecting increased acetolactate concentrations compared to a cell without the vector indicates that the vector is both present and that the gene product is active. Methods for detecting specific enzymatic activities or the presence of particular products are well known to those skilled in the art. For example, the presence of acetolactate can be determined as described by Hugenholtz and Starrenburg, *Appl. Microbiol. Biotechnol.* 38:17-22 (1992).

Increase of Enzymatic Activity

Yeast microorganisms of the invention may be further engineered to have increased activity of enzymes. The term "increased" as used herein with respect to a particular enzymatic activity refers to a higher level of enzymatic activity than that measured in a comparable yeast cell of the same species. For example, overexpression of a specific enzyme can lead to an increased level of activity in the cells for that enzyme. Increased activities for enzymes involved in glycolysis or the isobutanol pathway would result in increased productivity and yield of isobutanol.

Methods to increase enzymatic activity are known to those skilled in the art. Such techniques may include increasing the expression of the enzyme by increased copy number and/or use of a strong promoter, introduction of mutations to relieve negative regulation of the enzyme, introduction of specific mutations to increase specific activity and/or decrease the Km for the substrate, or by directed evolution. See, e.g., Methods in Molecular Biology (vol. 231), ed. Arnold and Georgiou, Humana Press (2003).

Carbon Source

The biocatalyst herein disclosed can convert various carbon sources into isobutanol. The term "carbon source" generally refers to a substance suitable to be used as a source of carbon for prokaryotic or eukaryotic cell growth. Carbon sources include, but are not limited to, biomass hydrolysates, starch, sucrose, cellulose, hemicellulose, xylose, and lignin, as well as monomeric components of these substrates. Carbon sources can comprise various organic compounds in various forms, including, but not limited to polymers, carbohydrates, acids, alcohols, aldehydes, ketones, amino acids, peptides, etc. These include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis. In some embodiments, carbon sources may be selected from biomass hydrolysates and glucose.

The term "C2-compound" as used as a carbon source for engineered yeast microorganisms with mutations in all pyruvate decarboxylase (PDC) genes resulting in a reduction of pyruvate decarboxylase activity of said genes refers to organic compounds comprised of two carbon atoms, including but not limited to ethanol and acetate The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a biofuel in a fermentation process. However, a feedstock may contain nutrients other than a carbon source.

The term "traditional carbohydrates" refers to sugars and starches generated from specialized plants, such as sugar cane, corn, and wheat. Frequently, these specialized plants concentrate sugars and starches in portions of the plant, such as grains, that are harvested and processed to extract the sugars and starches. Traditional carbohydrates are used as food and also to a lesser extent as carbon sources for fermentation processes to generate biofuels, such as and chemicals The term "biomass" as used herein refers primarily to the stems, leaves, and starch-containing portions of green plants, and is mainly comprised of starch, lignin, cellulose, hemicellulose, and/or pectin. Biomass can be decomposed by either chemical or enzymatic treatment to the monomeric sugars and phenols of which it is composed (Wyman, C. E. 2003 Biotechnological Progress 19:254-62). This resulting material, called biomass hydrolysate, is neutralized and treated to remove trace amounts of organic material that may adversely affect the biocatalyst, and is then used as a feed stock for fermentations using a biocatalyst.

The term "starch" as used herein refers to a polymer of glucose readily hydrolyzed by digestive enzymes. Starch is usually concentrated in specialized portions of plants, such as potatoes, corn kernels, rice grains, wheat grains, and sugar cane stems.

The term "lignin" as used herein refers to a polymer material, mainly composed of linked phenolic monomeric compounds, such as p-coumaryl alcohol, coniferyl alcohol, and sinapyl alcohol, which forms the basis of structural rigidity in plants and is frequently referred to as the woody portion of plants. Lignin is also considered to be the non-carbohydrate portion of the cell wall of plants.

The term "cellulose" as used herein refers is a long-chain polymer polysaccharide carbohydrate of beta-glucose of formula $(C_6H_{10}O_5)_n$, usually found in plant cell walls in combination with lignin and any hemicellulose.

The term "hemicellulose" refers to a class of plant cell-wall polysaccharides that can be any of several heteropolymers. These include xylane, xyloglucan, arabinoxylan, arabinogalactan, glucuronoxylan, glucomannan and galactomannan. Monomeric components of hemicellulose include, but are not limited to: D-galactose, L-galactose, D-mannose, L-rhamnose, L-fucose, D-xylose, L-arabinose, and D-glucuronic acid. This class of polysaccharides is found in almost all cell walls along with cellulose. Hemicellulose is lower in weight than cellulose and cannot be extracted by hot water or chelating agents, but can be extracted by aqueous alkali. Polymeric chains of hemicellulose bind pectin and cellulose in a network of cross-linked fibers forming the cell walls of most plant cells.

Microorganism Characterized by Producing Isobutanol at High Yield

For a biocatalyst to produce isobutanol most economically, it is desired to produce a high yield. Preferably, the only product produced is isobutanol. Extra products lead to a reduction in product yield and an increase in capital and operating costs, particularly if the extra products have little or no value. Extra products also require additional capital and operating costs to separate these products from isobutanol.

The microorganism may convert one or more carbon sources derived from biomass into isobutanol with a yield of greater than 5% of theoretical. In one embodiment, the yield is greater than 10%. In one embodiment, the yield is greater than 50% of theoretical. In one embodiment, the yield is greater than 60% of theoretical. In another embodiment, the yield is greater than 70% of theoretical. In yet another embodiment, the yield is greater than 80% of theoretical. In yet another embodiment, the yield is greater than 85% of theoretical. In yet another embodiment, the yield is greater than 90% of theoretical. In yet another embodiment, the yield is greater than 95% of theoretical. In still another embodiment, the yield is greater than 97.5% of theoretical.

More specifically, the microorganism converts glucose, which can be derived from biomass into isobutanol with a yield of greater than 5% of theoretical. In one embodiment, the yield is greater than 10% of theoretical. In one embodiment, the yield is greater than 50% of theoretical. In one embodiment the yield is greater than 60% of theoretical. In another embodiment, the yield is greater than 70% of theoretical. In yet another embodiment, the yield is greater than 80% of theoretical. In yet another embodiment, the yield is greater than 85% of theoretical. In yet another embodiment the yield is greater than 90% of theoretical. In yet another embodiment, the yield is greater than 95% of theoretical. In still another embodiment, the yield is greater than 97.5% of theoretical Microorganism Characterized by Production of Isobutanol from Pyruvate Via an Overexpressed Isobutanol Pathway and a Pdc-Minus Phenotype In yeast, the conversion of pyruvate to acetaldehyde is a major drain on the pyruvate pool (FIG. 2A), and, hence, a major source of competition with the isobutanol pathway. This reaction is catalyzed by the pyruvate decarboxylase (PDC) enzyme. Reduction of this enzymatic activity in the yeast microorganism results in an increased availability of pyruvate and reducing equivalents to the isobutanol pathway and may improve isobutanol production and yield in a yeast microorganism that expresses a pyruvate-dependent isobutanol pathway (FIG. 2B).

Reduction of PDC activity can be accomplished by 1) mutation or deletion of a positive transcriptional regulator for the structural genes encoding for PDC or 2) mutation or deletion of all PDC genes in a given organism. The term "transcriptional regulator" can specify a protein or nucleic acid that works in trans to increase or to decrease the transcription of a different locus in the genome. For example, in *S. cerevisiae*, the PDC2 gene, which encodes for a positive transcriptional regulator of PDC1,5,6 genes can be deleted; a

*S. cerevisiae* in which the PDC2 gene is deleted is reported to have only ~10% of wildtype PDC activity (Hohmann, *Mol Gen Genet,* 241:657-666 (1993)). Alternatively, for example, all structural genes for PDC (e.g. in *S. cerevisiae*, PDC1, PDC5, and PDC6, or in *K. lactis*, PDC1) are deleted.

Crabtree-positive yeast strains such as *Saccharomyces. cerevisiae* strain that contains disruptions in all three of the PDC alleles no longer produce ethanol by fermentation. However, a downstream product of the reaction catalyzed by PDC, acetyl-CoA, is needed for anabolic production of necessary molecules. Therefore, the Pdc-mutant is unable to grow solely on glucose, and requires a two-carbon carbon source, either ethanol or acetate, to synthesize acetyl-CoA. (Flikweert M T, de Swaaf M, van Dijken J P, Pronk J T. FEMS Microbiol Lett. 1999 May 1; 174(1):73-9. PMID:10234824 and van Maris A J, Geertman J M, Vermeulen A, Groothuizen M K, Winkler A A, Piper M D, van Dijken J P, Pronk J T. Appl Environ Microbiol. 2004 January; 70(1):159-66. PMID: 14711638).

Thus, in an embodiment, such a Crabtree-positive yeast strain may be evolved to generate variants of the PDC mutant yeast that do not have the requirement for a two-carbon molecule and has a growth rate similar to wild type on glucose. Any method, including chemostat evolution or serial dilution may be utilized to generate variants of strains with deletion of three PDC alleles that can grow on glucose as the sole carbon source at a rate similar to wild type (van Maris et al., Directed Evolution of Pyruvate Decarboxylase-Negative *Saccharomyces cerevisiae*, Yielding a C2-Independent, Glucose-Tolerant, and Pyruvate-Hyperproducing Yeast, Applied and Environmental Microbiology, 2004, 70(1), 159-166).

Method of Using Microorganism for High-Yield Isobutanol Fermentation

In a method to produce isobutanol from a carbon source at high yield, the yeast microorganism is cultured in an appropriate culture medium containing a carbon source.

Another exemplary embodiment provides a method for producing isobutanol comprising a recombinant yeast microorganism of the invention in a suitable culture medium containing a carbon source that can be converted to isobutanol by the yeast microorganism of the invention.

In certain embodiments, the method further includes isolating isobutanol from the culture medium. For example, isobutanol may be isolated from the culture medium by any method known to those skilled in the art, such as distillation, pervaporation, or liquid-liquid extraction.

EXAMPLES

General Methods

Sample preparation: Samples (2 mL) from the fermentation broth were stored at −20° C. for later substrate and product analysis. Prior to analysis, samples were thawed and then centrifuged at 14,000×g for 10 min. The supernatant was filtered through a 0.2 μm filter. Analysis of substrates and products was performed using authentic standards (>99%, obtained from Sigma-Aldrich), and a 5-point calibration curve (with 1-pentanol as an internal standard for analysis by gas chromatography).

Determination of optical density and cell dry weight: The optical density of the yeast cultures was determined at 600 nm using a DU 800 spectrophotometer (Beckman-Coulter, Fullerton, Calif., USA). Samples were diluted as necessary to yield an optical density of between 0.1 and 0.8. The cell dry weight was determined by centrifuging 50 mL of culture prior to decanting the supernatant. The cell pellet was washed once with 50 mL of milliQ $H_2O$, centrifuged and the pellet was washed again with 25 mL of milliQ $H_2O$. The cell pellet was then dried at 80° C. for at least 72 hours. The cell dry weight was calculated by subtracting the weight of the centrifuge tube from the weight of the centrifuge tube containing the dried cell pellet.

Gas Chromatography: Analysis of ethanol and isobutanol was performed on a HP 5890 gas chromatograph fitted with a DB-FFAP column (Agilent Technologies; 30 m length, 0.32 mm ID, 0.25 μM film thickness) or equivalent connected to a flame ionization detector (FID). The temperature program was as follows: 200° C. for the injector, 300° C. for the detector, 100° C. oven for 1 minute, 70° C./minute gradient to 235° C., and then hold for 2.5 min.

High Performance Liquid Chromatography: Analysis of glucose and organic acids was performed on a HP-1100 High Performance Liquid Chromatography system equipped with a Aminex HPX-87H Ion Exclusion column (Bio-Rad, 300× 7.8 mm) or equivalent and an $H^+$ cation guard column (Bio-Rad) or equivalent. Organic acids were detected using an HP-1100 UV detector (210 nm, 8 nm 360 nm reference) while glucose was detected using an HP-1100 refractive index detector. The column temperature was 60° C. This method was Isocratic with 0.008N sulfuric acid in water as mobile phase. Flow was set at 0.6 mL/min. Injection size was 20 μL and the run time was 30 minutes.

Anaerobic batch fermentations: Anaerobic batch cultivations were performed at 30° C. in stoppered 100 mL serum bottles. A total of 20 mL of synthetic medium with an initial glucose concentration of 20 g-glucose $L^{-1}$ was used (Kaiser et al., Methods in Yeast Genetics, a Cold Spring Harbor Laboratory Manual (1994)). 2 mL samples are taken at 24 and 48 hours. The fermentation is ended after 48 hours or when all glucose is consumed. Samples are processed and analyzed by Gas Chromatography and/or High Performance Liquid Chromatography as described above.

Yeast transformations—*K. lactis*: Transformations were performed by electroporation according to Kooistra et al., Yeast 21:781-792 (2004).

Lithium Acetate transformations of *S. cerevisiae* strains were transformed by the Lithium Acetate method (Gietz et al., *Nucleic Acids Res.* 27:69-74 (1992). Cells were collected from overnight cultures grown in 50 mL of defined (SC) ethanol media at an $OD_{600}$ of approximately 0.8 to 1.0 by centrifugation at 2700 rcf for 2 minutes at room temperature. The cell pellet was resuspended in 50 mL sterile water, collected by centrifugation (2700 rcf; 2 min; room temp.), and resuspended in 25 mL sterile water. The cells were collected by centrifugation (2700 rcf; 2 min; room temp.) and resuspended in 1 mL 100 mM lithium acetate. The cell suspension was transferred to a sterile 1.5 mL tube and collected by centrifugation at full speed for 10 seconds. The cells were resuspended in 100 mM lithium acetate with a volume four times the volume of the cell pellet (e.g. 400 μL for 100 μL cell pellet). To the prepared DNA Mix (72 μl 50% PEG, 10 μl 1M Lithium Acetate, 3 μl boiled salmon sperm DNA, and 5 μl of each plasmid), 15 μl of the cell suspension was added and mixed by vortexing with five short pulses. The cell/DNA suspensions were incubated at 30° C. for 30 minutes and at 42° C. for 22 minutes. The cells were collected by centrifugation for 10 seconds at full speed and resuspended in 100 μl SOS (1M Sorbitol, 0.34% (w/v) Yeast Extract, 0.68% (w/v) Peptone, 6.5 mM CaCl). The cell suspensions were top spread over appropriate selective agar plates.

Yeast colony PCR: Yeast cells were taken from agar medium and transferred to 30 μl 0.2% SDS and heated for 4 mins at 90° C. The cells were spun down and 1 µl of the supernatant was used for PCR using standard Taq (NEB).

Molecular biology: Standard molecular biology methods for cloning and plasmid construction were generally used, unless otherwise noted (Sambrook & Russell).

Media:

YP: contains 1% (w/v) yeast extract, 2% (w/v) peptone. YPD is YP containing 2% (w/v) glucose, YPE is YP containing 2% (w/v) Ethanol.

SC+Complete: 20 g/L glucose, 14 g/L Sigma™ Synthetic Dropout Media supplement (includes amino acids and nutrients excluding histidine, tryptophan, uracil, and leucine), and 6.7 g/L Difco™ Yeast Nitrogen Base. 0.076 g/L histidine, 0.076 g/L tryptophan, 0.380 g/L leucine, and 0.076 g/L uracil.

SC-HWUL: 20 g/L glucose, 14 g/L Sigma™ Synthetic Dropout Media supplement (includes amino acids and nutrients excluding histidine, tryptophan, uracil, and leucine), and 6.7 g/L Difco™ Yeast Nitrogen Base SC-WLU: 20 g/L glucose, 14 g/L Sigma™ Synthetic Dropout Media supplement (includes amino acids and nutrients excluding histidine, tryptophan, uracil, and leucine), 6.7 g/L Difco™ Yeast Nitrogen Base without amino acids, and 0.076 g/L histidine.

SC-HWU: 20 g/L glucose, 14 g/L Sigma™ Synthetic Dropout Media supplement (includes amino acids and nutrients excluding histidine, tryptophan, uracil, and leucine), 6.7 g/L Difco™ Yeast Nitrogen Base without amino acids, and 0.380 g/L leucine.

SC-Ethanol-HWU: 2% (w/v) ethanol, 14 g/L Sigma™ Synthetic Dropout Media supplement (includes amino acids and nutrients excluding histidine, tryptophan, uracil, and leucine), 6.7 g/L Difco™ Yeast Nitrogen Base, and 0.380 g/L leucine.

Solid versions of the above described media contain 2% (w/v) agar.

Strains, Plasmids and Primer Sequences

Table 1 details the genotype of strains disclosed herein:

| GEVO No. | Genotype and/or Reference |
|---|---|
| GEVO1187 | S. cerevisiae CEN.PK MAT a ho his3-leu2 trp1 ura3 PDC1 PDC5 PDC6 |
| GEVO1188 | S. cerevisiae CEN.PK MAT alpha ho his3-leu2 trp1 ura3 PDC1 PDC5 PDC6 |
| GEVO1287[1] | K. lactis MATα uraA1 trp1 leur2 lysA1 ade1 lac4-8 [pKD1] (ATCC #87365) |
| GEVO1537[2] | S. cerevisiae HO/HO pdc1::Tn5ble/pdc1::Tn5ble pdc5::Tn5ble/pdc5::Tn5ble pdc6::APT1/pdc6::APT1 HIS3/HIS, LEU2/LEU2, URA3/URA3, TRP1/TRP1 |
| Gevo1538 | S. cerevisiae MAT a/α, HIS3, LEU2, TRP1, URA3, pdc1::ble/pdc1::ble, pdc5::ble/pdc5::ble, pdc6::apt1(kanR)/pdc6::apt1(kanR), HO/HO |
| GEVO1581 | S. cerevisiae MAT a/alpha, his3/his3, trp1/trp1, ura3/ura3, LEU2/LEU2, pdc1::ble/pdc1::ble, pdc5::ble/pdc5::ble, pdc6::apt1(kanR)/pdc6::apt1(kanR), HO/HO |
| Gevo1715 | S. cerevisiae MAT a, leu2, ura3, pdc1::ble, pdc5::ble, pdc6::apt1(kanR), ho |
| GEVO1584 | S. cerevisiae MAT a, his3, trp1, ura3, leu2, pdc1::ble, pdc5::ble, pdc6::apt1(kanR), ho- |
| GEVO1742 | K. lactis MATα uraA1 trp1 leur2 lysA1 ade1 lac4-8 [pKD1] Klpdc1Δ::pGV1537 (G418$^R$)] |
| GEVO1794 | K. lactis MATalpha uraA1 trp1 leu2 lysA1 ade1 lac4-8 [pKD1] pdc1::kan {Ll-kivd; Sc-Adh7:KmURA3 integrated} |
| GEVO1818 | K. lactis MATalpha uraA1 trp1 leu2 lysA1 ade1 lac4-8 [pKD1] pdc1::kan {Ec-ilvC-deltaN; Ec-ilvD-deltaN(codon opt for K. lactis):Sc-LEU2 integrated} {Ll-kivd; Sc-Adh7:KmURA3 integrated} |
| GEVO1829 | K. lactis MATalpha uraA1 trp1 leu2 lysA1 ade1 lac4-8 [pKD1] pdc1::kan {Ec-ilvC-deltaN; Ec-ilvD-deltaN(codon opt for K. lactis):Sc-LEU2 integrated} {Ll-kivd; Sc-Adh7:KmURA3 integrated} {ScCUP1-1 promoter:Bs alsS, TRP1 random integrated} |
| Gevo1863 | S. cerevisiae MAT a, his3, trp1, ura3, leu2, pdc1::ble, pdc5::ble, pdc6::apt1(kanR), ho-, chemostat-evolved to be C2-independent. |

[1] same as ATCC200826
[2] The strains Gevo1537 and Gevo1538 were originally designated GG570 (derived from strain T2-3D) and was obtained from Paul van Heusden from the University of Leiden, the Netherlands. For complete references for both strains, see: Flikweert, M. T. et al., (1996) Yeast 12: 247-257.

Table 2 outlines the plasmids disclosed herein:

| GEVO No. | FIG. | Genotype or Reference |
|---|---|---|
| pGV1056 | 21 | bla(amp$^r$) S.c. TDH3 promoter - polylinker - CYC1 terminator CEN6/ARSH4 HIS3 pUC ori |
| pGV1062 | 22 | bla(amp$^r$) S.c. TDH3 promoter - polylinker - CYC1 terminator CEN6/ARSH4 URA3 pUC ori |
| pGV1102 | 23 | bla(amp$^r$) S.c. TEF1 promoter - HA tag - polylinker - CYC1 terminator 2micron URA3 pUC ori |
| pGV1103 | 24 | bla(amp$^r$) S.c. TDH3 promoter - myc tag - polylinker - CYC1 terminator 2micron HIS3 pUC ori |
| pGV1104 | 25 | bla(amp$^r$) S.c. TDH3 promoter - myc tag - polylinker - CYC1 terminator 2micron TRP1 pUC ori |
| pGV1106 | 26 | bla(amp$^r$) S.c. TDH3 promoter - myc tag - polylinker - CYC1 terminator 2micron URA3 pUC ori |
| pGV1254 | 14 | bla(amp$^r$) S.c. TEF1 promoter - HA-L.l. KIVD - S.c. TDH3 promoter - myc - S.c. ADH2 - CYC1 terminator 2micron URA3 pUC ori |
| pGV1295 | 15 | bla(amp$^r$) S.c. TDH3 promoter - myc - ilvC - CYC1 terminator 2micron TRP1 pUC ori |
| pGV1390 | 16 | bla(amp$^r$) S.c. CUP1-1 promoter - L.l. alsS - CYC1 terminator 2micron HIS3 pUC ori |

-continued

| GEVO No. | FIG. | Genotype or Reference |
|---|---|---|
| pGV1438 | 17 | bla(amp′) S.c. TDH3 promoter - myc - ilvD - CYC1 terminator 2micron LEU2 pUC ori |
| pGV1503 | 6 | bla(amp′) S.c. TEF1 promoter - KanR pUC ori |
| pGV1537 | 7 | bla(amp′) S.c. TEF1 promoter - KanR pUC ori K. lactis PDC1 5′ region- PmlI - K. lactis PDC1 3′ region |
| pGV1429 | 8 | bla(amp′) S.c. TDH3 promoter - myc tag - polylinker - CYC1 terminator 1.6 micron TRP1 pUC ori |
| pGV1430 | 9 | bla(amp′) S.c. TDH3 promoter - myc tag - polylinker - CYC1 terminator 1.6 micron LEU2 pUC ori |
| pGV1431 | 10 | bla(amp′) S.c. TDH3 promoter - myc tag - polylinker - CYC1 terminator 1.6 micron K.m. URA3 pUC ori |
| pGV1472 | 11 | bla(amp′) S.c. TEF1 promoter - AU1(x2)-L.l. alsS - CYC1 terminator 1.6 micron LEU2 pUC ori |
| pGV1473 | 12 | bla(amp′) S.c. TEF1 promoter - AU1(x2)-E.c. ilvD - S.c. TDH3 promoter - myc - E.c. ilvC - CYC1 terminator 1.6micron TRP1 pUC ori |
| pGV1475 | 13 | bla(amp′) S.c. TEF1 promoter - HA - L.l. KIVD - S.c. TDH3 promoter - myc - S.c. ADH7 - CYC1 terminator 1.6 micron K.m. URA3 pUC ori |
| pGV1590 | 18 | bla(amp′) S.c. TEF1 promoter - L.l. KIVD - S.c. TDH3 promoter - S.c. ADH7 - CYC1 terminator 1.6 micron K.m. URA3 pUC ori |
| pGV1726 | 19 | bla(amp′) S.c. CUP1-1 promoter - B.s. alsS - CYC1 terminator TRP1 pUC ori |
| pGV1727 | 20 | bla(amp′) S.c. TEF1 promoter - E.c. ilvD deltaN - S.c. TDH3 promoter - E.c. ilvC deltaN - CYC1 terminator LEU2 pUC ori |
| pGV1649 | 27 | bla(amp′) S.c. CUP1-1 promoter - B.s. alsS - CYC1 terminator 2micron TRP1 pUC ori |
| pGV1664 | 28 | bla(amp′) S.c. TEF1 promoter - L.l. KIVD - S.c. TDH3 promoter - S.c. ADH7 - CYC1 terminator 2micron URA3 pUC ori |
| pGV1672 | 29 | bla(amp′) S.c. CUP1-1 promoter - polylinker - CYC1 terminator CEN6/ARSH4 TRP1 pUC ori |
| pGV1673 | 30 | bla(amp′) S.c. CUP1-1 promoter - B.s. alsS - CYC1 terminator CEN6/ARSH4 TRP1 pUC ori |
| pGV1677 | 31 | bla(amp′) S.c. TEF1 promoter - E.c. ilvD deltaN - S.c. TDH3 promoter - E.c. ilvC deltaN - CYC1 terminator 2micron HIS3 pUC ori |
| pGV1679 | 32 | bla(amp′) S.c. TEF1 promoter - E.c. ilvD deltaN - S.c. TDH3 promoter - E.c. ilvC deltaN - CYC1 terminator CEN6/ARSH4 HIS3 pUC ori |
| pGV1683 | 33 | bla(amp′) S.c. TEF1 promoter - L.l. KIVD - S.c. TDH3 promoter - S.c. ADH7 - CYC1 terminator CEN6/ARSH4 URA3 pUC ori |

| No. | Name | SEQ ID NO: | Sequence |
|---|---|---|---|
| 489 | MAT common | 30 | AGTCACATCAAGATCGTTTATGG |
| 490 | MAT alpha | 31 | GCACGGAATATGGGACTACTTCG |
| 491 | MAT a | 32 | ACTCCACTTCAAGTAAGAGTTTG |
| 838 | pGV1423-seq1 (838) | 33 | TATTGTCTCATGAGCGGATAC |
| 965 | KIPDC1 -616 FOR | 34 | ACAACGAGTGTCATGGGGAGAGGAAGAGG |
| 966 | KIPDC1 +2528 REV | 35 | GATCTTCGGCTGGGTCATGTGAGGCGG |
| 995 | KIPDC1 internal | 36 | ACGCTGAACACGTTGGTGTCTTGC |
| 996 | KIPDC1 internal | 37 | AACCCTTAGCAGCATCGGCAACC |
| 1010 | KI-PDC1-prom-seq-c | 38 | TATTCATGGGCCAATACTACG |
| 1006 | KI-PDC1-prom-3c | 39 | GTAGAAGACGTCACCTGGTAGACCAAAGATG |
| 1009 | KI-PDC1-term-5c | 40 | CATCGTGACGTCGCTCAATTGACTGCTGCTAC |
| 1016 | KI-PDC1-prom-5-v2 (1016) | 41 | ACTAAGCGACACGTGCGGTTTCTGTGGTATAG |
| 1017 | KI-PDC1-term-3c-v2 (1017) | 42 | GAAACCGCACGTGTCGCTTAGTTTACATTTCTTTCC |
| 1019 | TEF1prom-5c (1019) | 43 | TTTGAAGTGGTACGGCGATG |
| 1321 | Bs-alsS-Q-A5 (1321) | 44 | AATCATATCGAACACGATGC |

-continued

| No. | Name | SEQ ID NO: | Sequence |
|---|---|---|---|
| 1324 | Bs-alsS-Q-B3 (1324) | 45 | AGCTGGTCTGGTGATTCTAC |
| 1325 | Ec-ilvC-dN-Q-A5 (1325) | 46 | TATCACCGTAGTGATGGTTG |
| 1328 | Ec-ilvC-dN-Q-B3 (1328) | 47 | GTCAGCAGTTTCTTATCATCG |
| 1330 | Ec-ilvD-dN-co-KI-Q-A3 (1330) | 48 | GCGAAACTTACTTGACGTTC |
| 1331 | Ec-ilvD-dN-co-KI-Q-B5 (1331) | 49 | ACTTTGGACGATGATAGAGC |
| 1334 | Ll-kivd-co-Ec-Q-A3 (1334) | 50 | GCGTTAGATGGTACGAAATC |
| 1335 | Ll-kivd-co-Ec-Q-B5 (1335) | 51 | CTTCTAACACTAGCGACCAG |
| 1338 | Sc-ADH7-Q-A3 (1338) | 52 | AAAGATGATGAGCAAACGAC |
| 1339 | Sc-ADH7-Q-B5 (1339) | 53 | CGAGCAATACTGTACCAATG |
| 1375 | HO +1300 F | 54 | TCACGGATGATTTCCAGGGT |
| 1376 | HO +1761 R | 55 | CACCTGCGTTGTTACCACAA |

Example 1

Construction and Confirmation of PDC Deletion in K. lactis

The purpose of this Example is to describe how a PDC-deletion variant of a member of the Saccharomyces clade, Crabtree-negative yeast, pre-WGD yeast K. lactis was constructed and confirmed.

Figure 6:
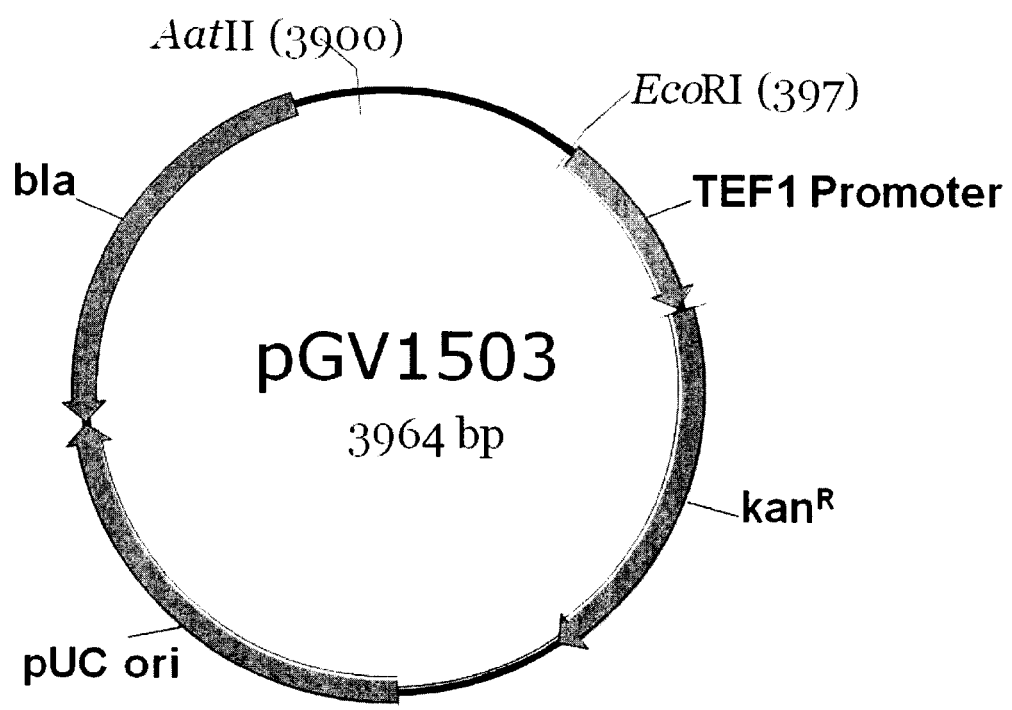
FIG. 6 illustrates a schematic map of plasmid pGV1503.
Figure 7:
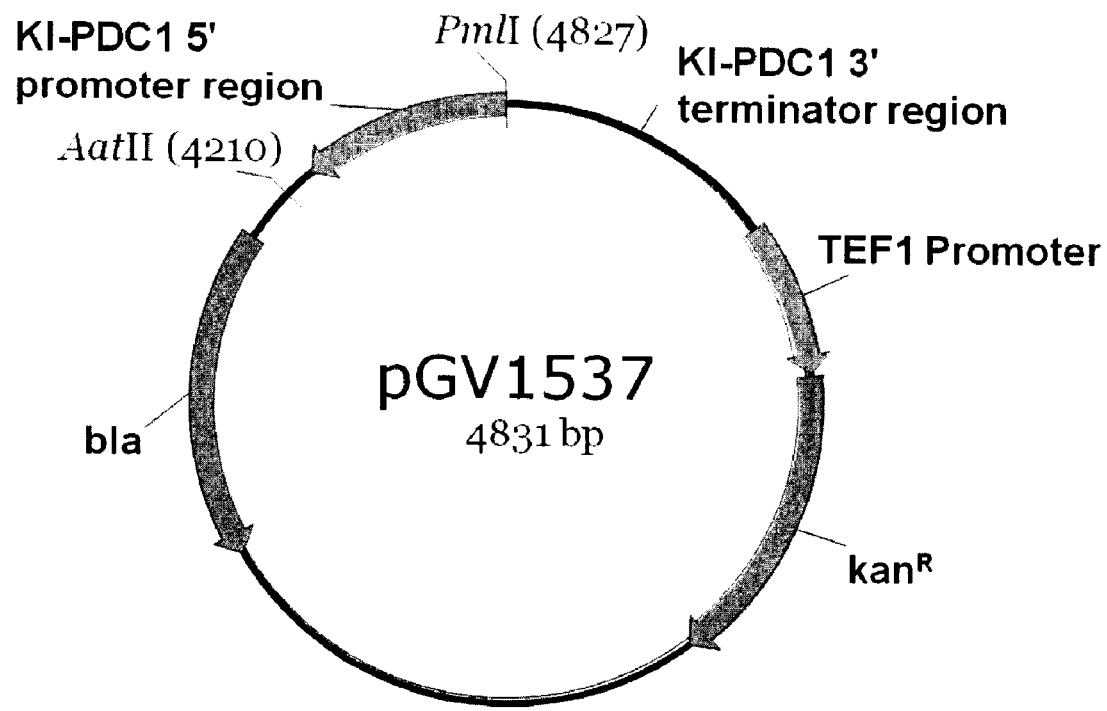
FIG. 7 illustrates a schematic map of plasmid pGV1537.

Construction of plasmid pGV1537: Plasmid pGV1537 (SEQ ID NO: 1) was constructed by the following series of steps. All PCR reactions carried out to generate pGV1537 used KOD polymerase (Novagen, Inc., Gibbstown, N.J.) and standard reaction conditions according to the manufacturer. A first round of two PCR reactions was carried out, wherein one PCR reaction contained primers 1006 and 1016 and used approximately 100 ng of genomic DNA from K. lactis strain GEVO1287 as a template. The other first-round PCR reaction contained primers 1017 and 1009 and approximately 100 ng of genomic DNA from K. lactis strain GEVO1287 as a template. The two resulting PCR products (approximately 530 bp and 630 bp in size, respectively) were gel purified using a Zymo Research Gel DNA Extraction kit (Zymo Research, Orange, Calif.) according to manufacturer's instructions and eluted into 10 µL of water. Two (2) microliters of each eluted PCR product were then used as a template for a final round of KOD polymerase-catalyzed PCR, which also included primers 1006 plus 1009. The resulting product was purified (Zymo Research DNA Clean & Concentrate kit, Zymo Research, Orange, Calif.), digested to completion with the enzymes MfeI and AatII, and the resulting product gel purified and eluted as described above. This DNA was ligated into the vector pGV1503 (FIG. 6), which had been digested with EcoRI plus AatII, treated with calf alkaline phosphatase, and gel purified as described above. Colonies arising from transformation of the ligated DNA were screened by restriction digest analysis and confirmed by DNA sequencing reactions using primers 838, 1010, and 1019. Correct recombinant DNA resulting from the ligation and subsequent analysis was named pGV1537 (FIG. 7).

Construction of a K. lactis Klpdc1Δ strain: Strain GEVO1287 was transformed with PmlI-digested, linearized plasmid pGV1537. Transformation was carried out by electroporation with approximately 300 ng of linearized pGV1537, essentially as described by Kooistra et al. (Kooistra, R., Hooykaas, P. J. J., and Steensman, H. Y. (2004) "Efficient gene targeting in Kluyveromyces lactis". Yeast 21:781-792). Transformed cells were selected by plating onto YPD plates containing 0.2 mg/mL geneticin (G418). Colonies arising from the transformation were further selected by patching colonies onto YPD plates and then replica plating onto YPD containing 5 µM (final concentration) of the respiratory inhibitor Antimycin A, as Pdc– variants of K. lactis are unable to grow on glucose in the presence of Antimycin A (Bianchi, M., et al., (1996). "The 'petite negative yeast Kluyveromyces lactis has a single gene expressing pyruvate decarboxylase activity". Molecular Microbiology 19(1):27-36) and can therefore be identified by this method. Of the 83 G418-resistant colonies patched onto YPD+Antimycin A, six colonies (~7%) were unable to grow and were therefore identified as candidate Klpdc1::pGV1537 disruption strains.

Confirmation of a K. lactis Klpdc1Δ strain by colony PCR: Candidate Klpdc1::pGV1537 disruption strains were confirmed by colony PCR analysis. To do so, genomic DNA from candidate lines was obtained by the following method. A small amount (equivalent to a matchhead) of yeast cells were resuspended in 50 µL of 0.2% SDS and heated to 95° C. for 6 minutes. The suspension was pelleted by centrifugation (30 sec, 16,000×g) and 1 µL of the supernatant was used as template in 50 µL PCR reactions. In addition to standard components, the reactions contained Triton X-100 at a final concentration of 1.5% and DMSO at a final concentration of 5%. The various primer sets used, and the expected amplicon sizes expected, are indicated in Table EX1-1. By these analyses, a correct Klpdc1Δ::pGV1537 strain was identified and was named GEVO1742.

TABLE EX1-1

Primer pairs and expected amplicon sizes predicted for colony PCR screening of candidate Klpdc1Δ::pGV1537 cells.

| Primer Pair | Expected product size for Klpdc1Δ::pGV1537 | Expected product size for KlPDC1+ |
|---|---|---|
| 965 & 838 | 796 bp | (none) |
| 1019 & 966 | 947 bp | (none) |
| 995 & 996 | (none) | 765 bp |

Confirmation of GEVO1742 Klpdc1Δ::pGV1537 by fermentation: Strains of *K. lactis* lacking KlPdc1p (Klpdc1Δ) have been shown to produce significantly lower levels of ethanol when grown on glucose (Bianchi, M., et al., (1996). "The 'petite negative yeast *Kluyveromyces lactis* has a single gene expressing pyruvate decarboxylase activity". Molecular Microbiology 19(1):27-36). To confirm this phenotype, fermentations with strains GEVO1287 and GEVO1742 were carried out. Briefly, a saturated overnight (3 mL) culture of each strain grown in YPD was inoculated into 25 mL of YPD at a starting $OD_{600}$ of 0.1 and grown aerobically in a loosely-capped flask in a shaker for 24 hours at 30° C., 250 rpm. Following growth, 2 mL of culture were collected, the cells pelleted by centrifugation (5 minutes, 14,000×g) and the supernatant subjected to analysis by gas chromatography and liquid chromatography. A summary of the data from these analyses is summarized in Table EX1-2. The strongly diminished production of ethanol and the increased accumulation of pyruvate in the fermentation medium are characteristic of *K. lactis* strains in which PDC1 has been deleted. Thus, these observations confirm the molecular genetic conclusions that strain GEVO1742 is in fact Klpdc1Δ.

TABLE EX1-2

Ethanol and pyruvate produced and glucose consumed in aerobic fermentations of GEVO1287 and GEVO1742.

| STRAIN | Ethanol produced (g/L) | Pyruvate produced (g/L) | Glucose consumed (g/L) |
|---|---|---|---|
| GEVO1287 | 8.129 | (not detected) | 17.56 |
| GEVO1742 | 0.386 | 1.99 | 5.25 |

Example 2

Construction and Confirmation of PDC Deletion in *S. cerevisiae*

The purpose of this Example is to describe how a PDC deletion variant of a member of the *Saccharomyces* sensu stricto yeast group, the *Saccharomyces* yeast clade, a Crabtree-positive yeast, and a post-WGD yeast, *S. cerevisiae* was constructed and confirmed.

Strains GEVO1537 and GEVO1538 were incubated in 1% potassium acetate for 3-4 days which induces sporulation. The resulting haploid spores were recovered by random spore analysis. Briefly, a culture of sporulating cells was examined microscopically to ensure that a sufficient fraction of cells had sporulated (>10%). Five (5) mL of a culture of sporulated cells were collected by centrifugation (5 minutes at 3000×g) and washed once in 1 mL of water. The cells were resuspended in 5 mL water to which was added 0.5 mL of a 1 mg/mL solution (freshly made) of Zymolyase-T (in water) as well as 10 μL of β-mercaptoethanol. The cell suspension was incubated overnight at 30° C. in a shaker at 50 rpm. Five mL of 1.5% Triton X-100 were added and the mixture was incubated on ice for 15 minutes. The solution was sonicated three times for 30 seconds per cycle at 50% power, with 2 minutes rest on ice in between sonication cycles. The suspension was centrifuged (1200×g, 5 minutes) and washed twice with 5 mL of water. The final cell pellet was resuspended in 1 mL water and cells were plated to YP+2% EtOH.

Following this procedure, the separate individual spores, were plated onto solid medium to obtain colonies, all of genotype HO pdc1::Tn5ble pdc5::Tn5ble pdc6:APT1 HIS3 LEU2 TRP1 URA3 and of unknown mating type. Some fraction of the cells were (homozygous) diploid due to the HO+ gene status and resultant mating type switching and re-mating to form diploids.

The genotype of the mating type locus of the putative Pdc-minus colonies was confirmed by PCR using Taq DNA polymerase (New England BioLabs, Ipswich, Mass.) under standard conditions using primers specific for the MAT a locus (primers #489 and #491) or MAT α locus (primers #490 and #491). Colonies that generated a single PCR product with one of the two possible primer sets primer set and no product when tested with the other were putative haploid Pdc-minus strains. To confirm the mating type, such strains were crossed to Gevo1187 and Gevo1188 (CEN.PK). Resulting diploid progeny were selected on medium containing glucose (to select for the presence of PDC+ genes introduced by CEN.PK background) and also lacking at least one of the following nutrients: histidine, leucine, tryptophan, or uracil (to select for the appropriate prototrophy as provided by the wild-type allele of the corresponding gene from the Gevo1537 or GEVO1538 background.

Diploid cells were sporulated and germinated on agar plates containing YP+2% ethanol (to permit growth of Pdc-minus isolates). To identify Pdc-minus candidates, viable colonies were streaked on to YPD agar plates and colonies that were inviable on glucose were isolated. Inability to grow on glucose confirms that these candidates are pdc1::ble and pdc5::ble. The pdc6::apt1 was confirmed their ability to grow on YP+Ethanol plates containing the antibiotic G418. The genotype of the mating type locus of the putative Pdc-minus colonies was confirmed by PCR using Taq DNA polymerase (New England BioLabs, Ipswich, Mass.) under standard conditions using primers specific for the MAT a locus (primers #489 and #491) or MAT α locus (primers #490 and #491). The presence of a product from both sets of PCR reactions indicated that both mating type alleles were present in the population, as a consequence of mating type allele switching by an active HO−encoded enzyme. The presence of a PCR product for one set of MAT locus-specific primers but not the other indicated that the strain lacks this activity and was therefore ho−. Based upon these analyses, six candidates colonies were identified as ho− strains and one candidate #4 was HO.

These Pdc-minus strains were streaked to SC+Ethanol plates lacking one of: leucine, histidine, tryptophan, or uracil, to determine presence of auxotrophic mutations within these strains. One Pdc-minus strain, GEVO1581, was auxotrophic for histidine, uracil, and tryptophan, and thus carried three of the makers (his3, ura3, and trp1). Another Pdc-minus strain, GEVO1715, was auxotrophic for uracil and leucine and thus carried the two markers, ura3 and leu2.

GEVO1581 and GEVO1715 were screened by RFLP analysis to verify the presence of the ho allele. A 447 bp portion of the HO locus was amplified by PCR that contained the codon that is altered in the ho allele (H475L) using primers 1375 and 1376. This mutation introduces an AluI restriction site, and consequently, digestion with AluI (New England BioLabs, Ipswich, Mass.) yielded either a 447 bp fragment (HO) or a 122 bp fragment plus a 325 bp fragment (ho). Based upon RFLP analysis, GEVO1581 was HO and GEVO1715 was ho.

To obtain a Pdc-minus strain with all four auxotrophic markers, GEVO1715 was crossed to and diploids generated as described above. The resulting diploid was sporulated and Pdc-minus candidates were isolated by plating onto YP+Ethanol containing both Phleomycin and G418. These candidates were then streaked onto YPD agar plates and tested for their inviability on glucose. Those that did not grow on glucose were isolated as this phenotype, in addition to their resistance to Phleomycin and G418 confirms that these candidates are pdc1::ble, pdc5::ble and pdc6::apt1. These isolates were streaked to SC+Ethanol plates lacking one of: leucine, histidine, tryptophan, or uracil, to determine presence of auxotrophic mutations within these strains. One of these Pdc-minus strains, GEVO1584, was auxotrophic for histidine, uracil, tryptophan and leucine and thus carried all four markers, his3, ura3, trp1, and leu2. GEVO1584 was also confirmed to be MATa and ho by colony PCR and RFLP analysis, respectively, as described above.

TABLE EX2-1

Summary table of S. cerevisiae Pdc-minus strains obtained

| GEVO No. | GENOTYPE | STRAIN SOURCE |
|---|---|---|
| 1537 | MAT a/α, HIS3, LEU2, TRP1, URA3, pdc1::ble/pdc1::ble, pdc5::ble/pdc5::ble, pdc6::apt1(kanR)/pdc6::apt1(kanR), HO/HO | Strain GG570 from Paul van Heusden, Univ. of Leiden, Netherlands |
| 1538 | MAT a/α, HIS3, LEU2, TRP1, URA3, pdc1::ble/pdc1::ble, pdc5::ble/pdc5::ble, pdc6::apt1(kanR)/pdc6::apt1(kanR), HO/HO | Strain GG570 from Paul van Heusden, Univ. of Leiden, Netherlands |
| 1581 | MAT a/α, his3/his3, trp1/trp1, ura3/ura3, LEU2/LEU2, pdc1::ble/pdc1::ble, pdc5::ble/pdc5::ble, pdc6::apt1(kanR)/pdc6::apt1(kanR), HO/HO | candidate #4 GEVO1537 × GEVO1187 |
| 1584 | MAT a, his3, trp1, ura3, leu2, pdc1::ble, pdc5::ble, pdc6::apt1(kanR), ho | candidate #201 GEVO1715 × GEVO1188 |
| 1715 | MAT a, leu2, ura3, pdc1::ble, pdc5::ble, pdc6::apt1(kanR), ho | candidate #104 GEVO1187 × GEVO1537 |

Example 3

Other Pdc-Minus S. cerevisiae Strains

S. cerevisiae engineered to be deficient in PDC activity have been previously described: (Flikweert, M. T., van der Zanden, L., Janssen, W. M. T. M, Steensma, H. Y., van Dijken J. P., Pronk J. T. (1996) Yeast 12(3):247-57). Such strains may be obtained from these sources.

Example 4

Chemostat Evolution of S. cerevisiae PDC Triple-Mutant

This example demonstrates that a PDC deletion variant of a member Saccharomyces sensu stricto yeast group, the Saccharomyces clade yeast, Crabtree-positive, post-WGD yeast, S. cerevisiae, can be evolved so that it does not have the requirement for a two-carbon molecule and has a growth rate similar to the parental strain on glucose.

A DasGip fermentor vessel was sterilized and filled with 200 ml of YNB (Yeast Nitrogen Base; containing per liter of distilled water: 6.7 g YNB without amino acids from Difco, the following were added per liter of medium: 0.076 g histidine, 0.076 g tryptophan, 0.380 g leucine, and/or 0.076 g uracil; medium was adjusted pH to 5 by adding a few drops of HCL or KOH) and contained 2% w/v ethanol. The vessel was installed and all probes were calibrated according to DasGip instructions. The vessel was also attached to an off-gas analyzer of the DasGip system, as well as to a mass spectrometer. Online measurements of oxygen, carbon dioxide, isobutanol, and ethanol were taken throughout the experiment. The two probes that were inside the vessel measured pH and dissolved oxygen levels at all times. A medium inlet and an outlet were also set up on the vessel. The outlet tube was placed at a height just above the 200 ml level, and the pump rate was set to maximum. This arrangement helped maintain the volume in the vessel at 200 ml. Air was sparged into the fermentor at 12 standard liters per hour (slph) at all times. The temperature of the vessel was held constant at 31.8° C. and the agitation rate was kept at 300 rpm. The off-gas was analyzed for $CO_2$, $O_2$, ethanol and isobutanol concentrations. The amount of carbon dioxide ($X_{CO2}$) and oxygen ($X_{O2}$) levels in the off-gas were used to assess the metabolic state of the cells. An increase in $X_{CO2}$ levels and decrease in $X_{O2}$ levels indicated an increase in growth rate and glucose consumption rate. The ethanol levels were monitored to ensure that there was no contamination, either from other yeast cells or from potential revertants of the mutant strain since the S. cerevisiae PDC triple-mutant (GEVO1584) does not produce ethanol. The minimum pH in the vessel was set to 5, and a base control was set up to pump in potassium hydroxide into the vessel when the pH dropped below 5.

GEVO1584 was inoculated into 10 ml of YNB medium with 2% w/v ethanol as the carbon source. The culture was incubated at 30° C. overnight with shaking. The overnight culture was used to inoculate the DasGip vessel. Initially, the vessel was run in batch mode, to build up a high cell density. When about 3 g CDW/L of cell biomass was reached, the vessel was switched to chemostat mode and the dilution of the culture began. The medium pumped into the vessel was YNB with 7.125 g/L glucose and 0.375 g/L of acetate (5% carbon equivalent). The initial dilution rate was set to 0.1 $h^{-1}$, but as the cell density started dropping, the dilution rate was decreased to 0.025 $h^{-1}$ to avoid washout. GEVO1584 was mating type a. A PCR check for the mating type of the chemostat population several days into the experiment indicated that the strain still present was mating type a.

Figure 3:
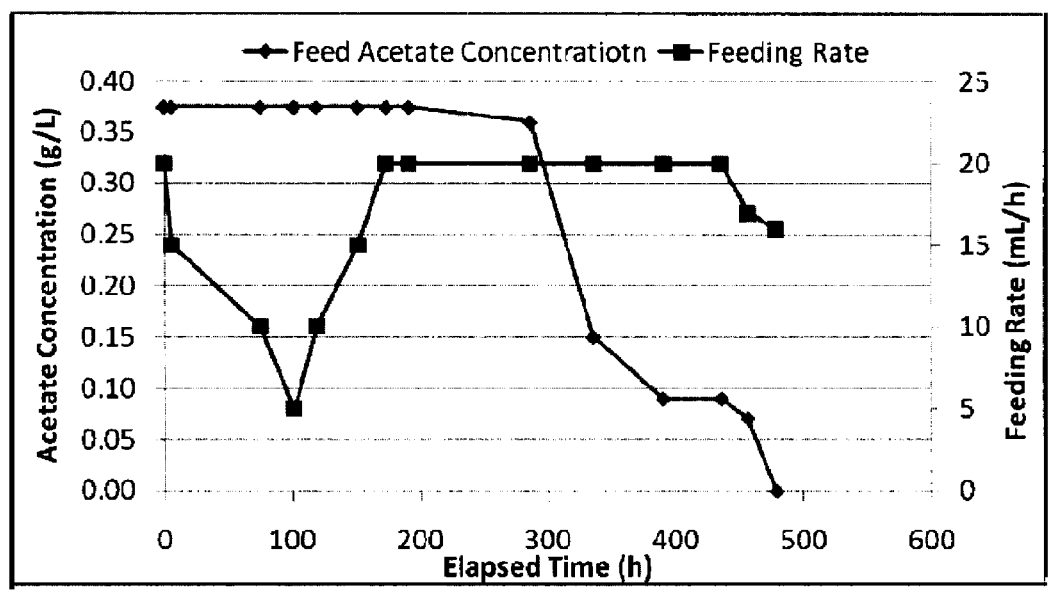
FIG. 3 illustrates the Carbon source composition and feeding rate over time during chemostat evolution of the *S. cerevisiae* Pdc-minus strain GEVO1584. This graph shows how the acetate was decreased over a period of 480 hours from 0.375 g/L to 0 g/L. It also shows the total feeding rate. Higher feeding rate meant that growth rate was higher. Since the chemostat contained 200 ml of culture, dilution rate can be calculated by dividing the feeding rate by 200 ml.

The culture in the chemostat was stabilized and the dilution rate increased to 0.1 $h^{-1}$. After steady state was reached at the 0.1 $h^{-1}$ dilution rate, the concentration of acetate was slowly decreased. This was achieved by using a two pump system, effectively producing a gradient pumping scheme. Initially pump A was pumping YNB with 7.125 g/L glucose, and 0.6 g/L of acetate at a rate of 12.5 mL/h and pump C was pumping YNB with only 7.125 g/L glucose at a rate of 7.5 mL/h. The combined acetate going into the vessel was 0.375 g/L. Then, over a period of 3 weeks, the rate of pump A was slowly decreased and the rate of pump C was increased by the same amount so that the combined rate of feeding was always 20 mL/h. When the rate of pump A dropped below 3 mL/h the culture started to slowly wash out. To avoid complete washout the dilution rate was decreased to 0.075 h$^{-1}$ from 0.1 h$^{-1}$ (FIG. 3). At this dilution rate, the rate of pump A was finally reduced to 0, and the evolved strain was able to grow on glucose only. Over the period of about five weeks, a sample was occasionally removed, either from the vessel directly or from the effluent line. Samples were analyzed for glucose, acetate, and pyruvate using HPLC, and were plated on YNB with glucose, YNB with ethanol, and YNB (w/o uracil) plus glucose or ethanol as negative control. Strains isolated from the chemostat did not grow on the YNB plates without uracil. OD$_{600}$ was taken regularly to make sure the chemostat did not wash out. Freezer stocks of samples of the culture were made regularly for future characterization of the strains.

Figure 4:
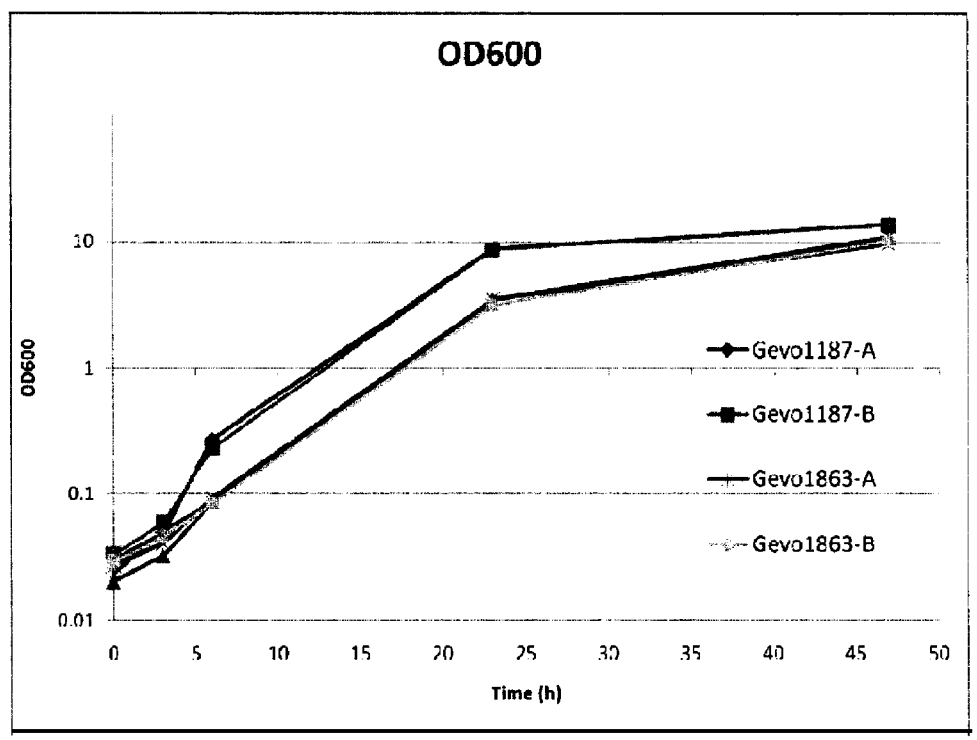
FIG. 4 illustrates growth of evolved Pdc-minus mutant strain GEVO1863 in YPD compared to the parental strain, GEVO1187.
Figure 5:
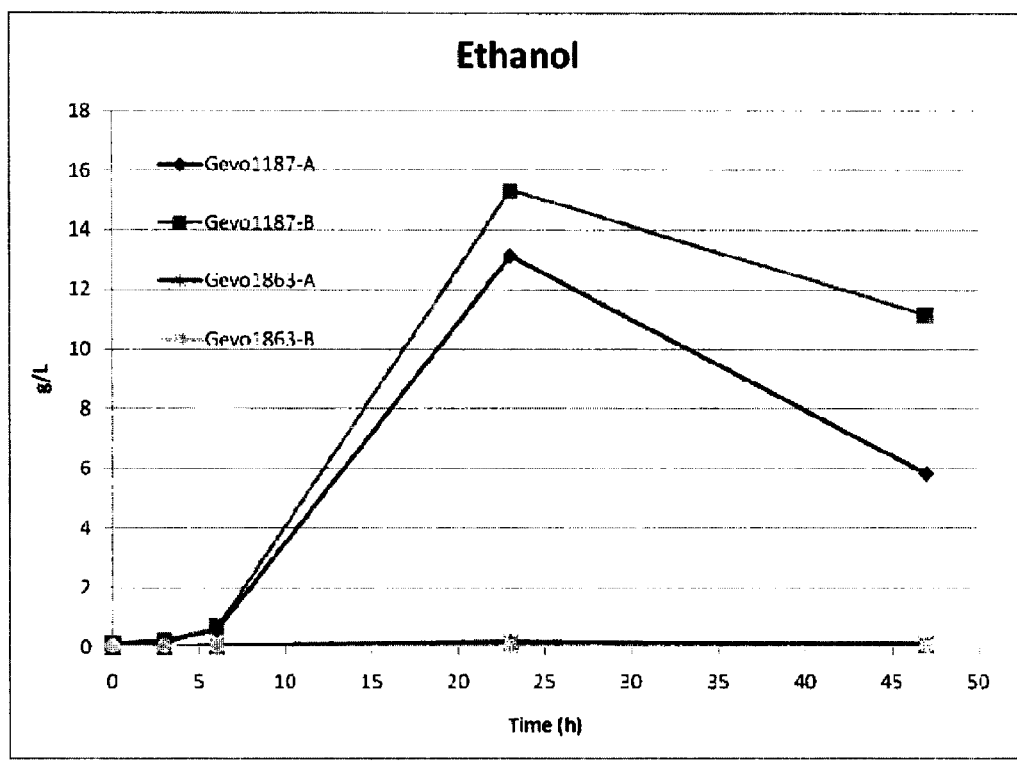
FIG. 5 illustrates that the evolved PCD mutant, GEVO1863, does not produce ethanol in YPD medium, unlike the parental strain GEVO1187.

To characterize growth of the evolved strains YNB, YPD (yeast extract, peptone, dextrose), and YPE (yeast extract, peptone, ethanol) were used with various concentrations of glucose or ethanol. The growth characterization was performed in either snap-cap test tubes or 48-well plates (7.5 ml). The snap-cap test tubes were not closed completely so that air would vent in/out of the tubes, and the 48-well plates were covered with an air permeable membrane to allow for oxygen transfer. To check for contaminations, YPD or YPE agar plates were used with the antibiotics G418 and Phleomycin. The PDC triple mutant strain (GEVO1584) has both G418 and Phleomycin resistance markers, so the progeny of that strain were able to grow on the antibiotics. Single colonies isolated from each chemostat sample were studied for growth rates. A single colony isolated from the 35-day chemostat population was selected because of high growth rates on glucose as a sole carbon source, was resistant to both G418 and Phleomycin, and grew without the need for ethanol or acetate. The single colony was further evolved through 24 successive serial transfers in test tubes on YPD at 30° C., 250 rpm shaking. The resulting strain, GEVO1863, grew similarly to the wild-type yeast parent on glucose (FIG. 4), did not produce ethanol (FIG. 5), and did not require ethanol or acetate for growth.

Example 5

Isobutanol Production in Pdc-Plus *K. lactis*

This example demonstrates isobutanol production in a member of the *Saccharomyces* clade, Crabtree-negative, pre-WGD yeast, *K. lactis*.

Figure 8:
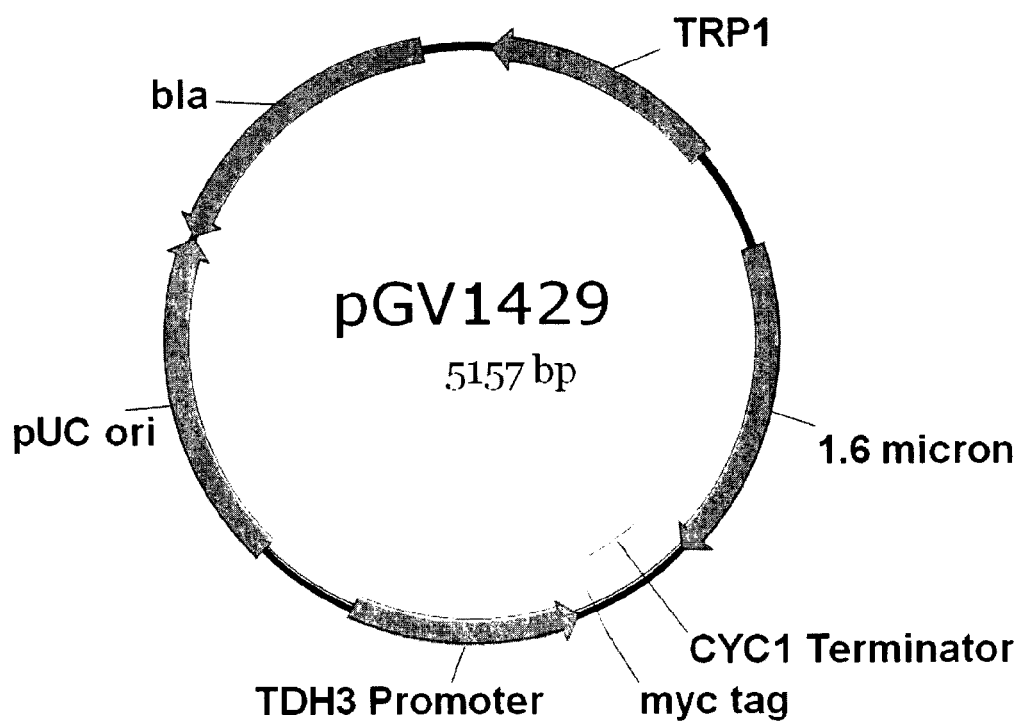
FIG. 8 illustrates a schematic map of plasmid pGV1429.
Figure 9:
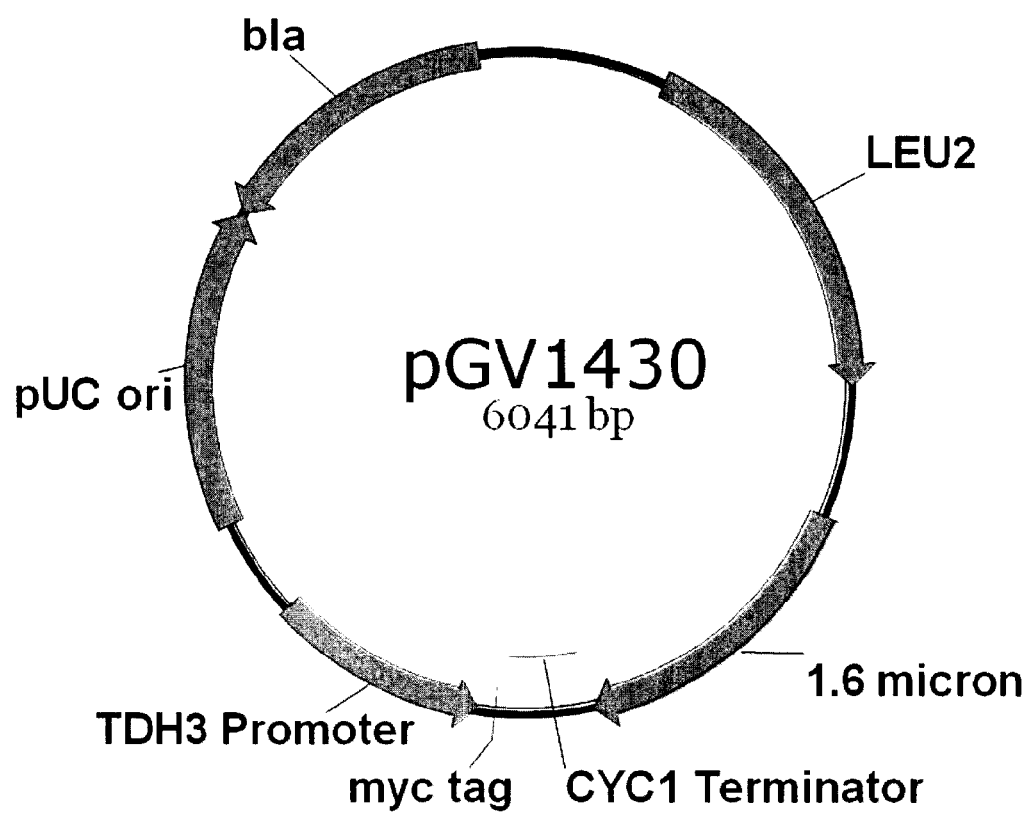
FIG. 9 illustrates a schematic map of plasmid pGV1430.
Figure 10:
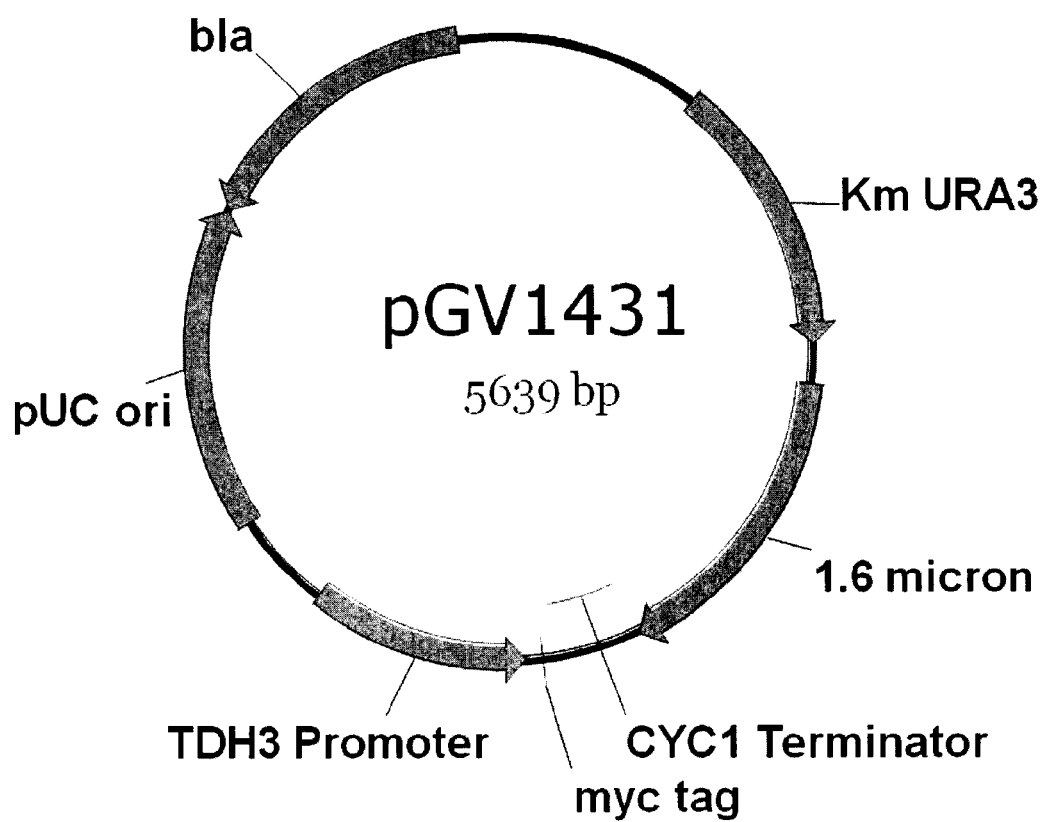
FIG. 10 illustrates a schematic map of plasmid pGV1431.
Figure 11:
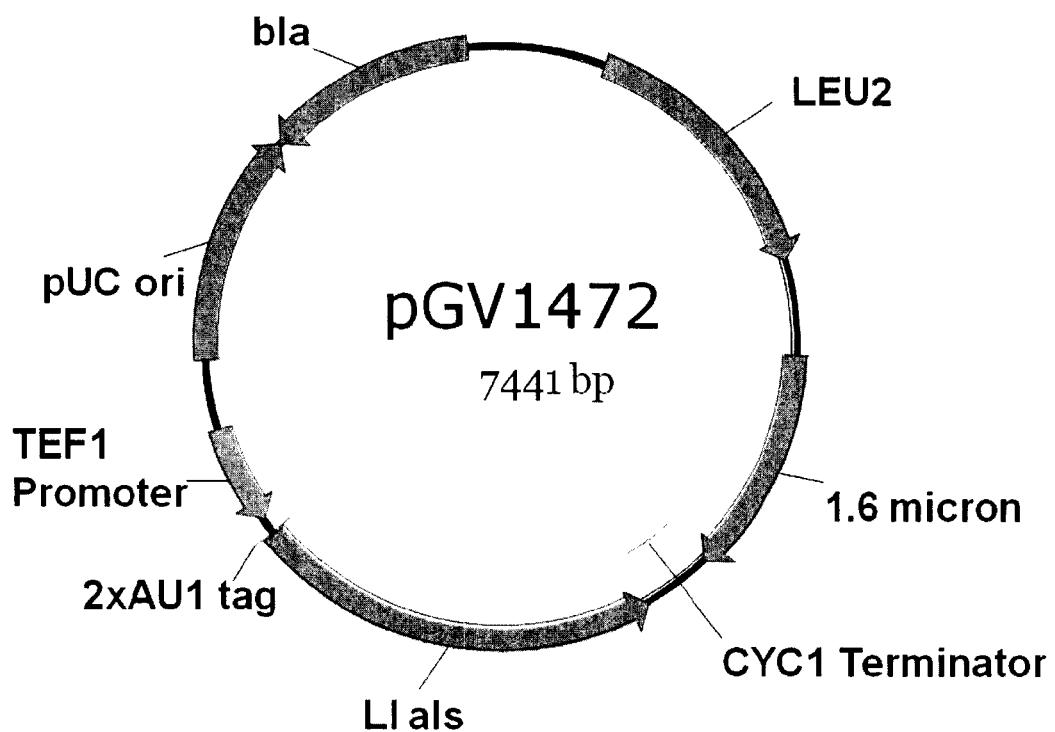
FIG. 11 illustrates a schematic map of plasmid pGV1472.
Figure 12:
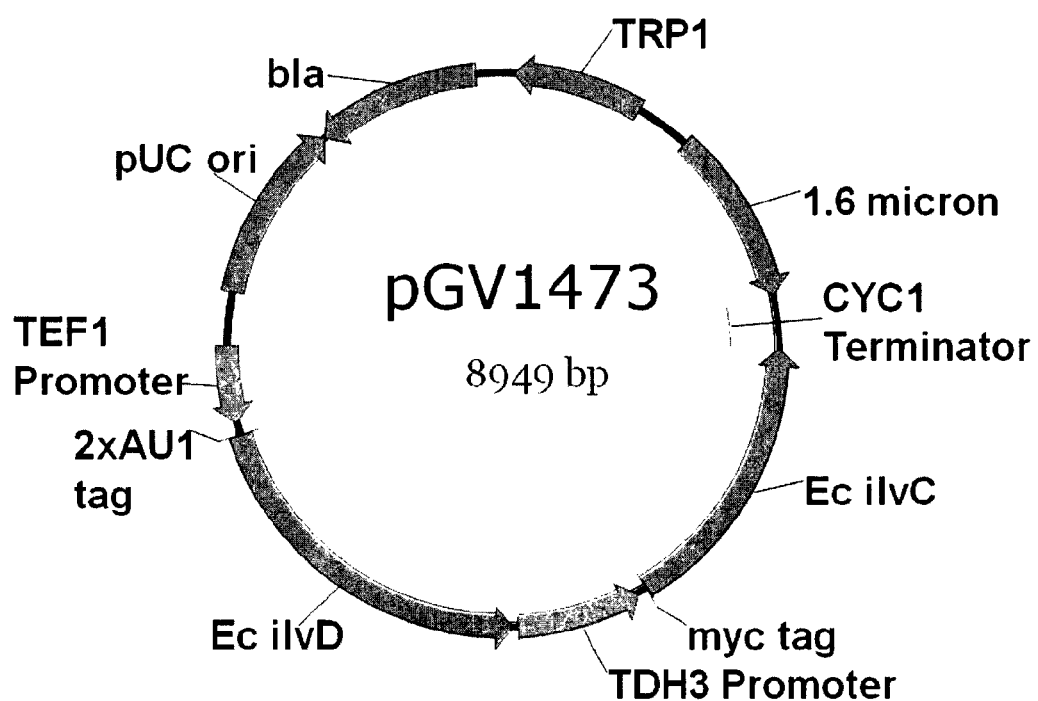
FIG. 12 illustrates a schematic map of plasmid pGV1473.
Figure 13:
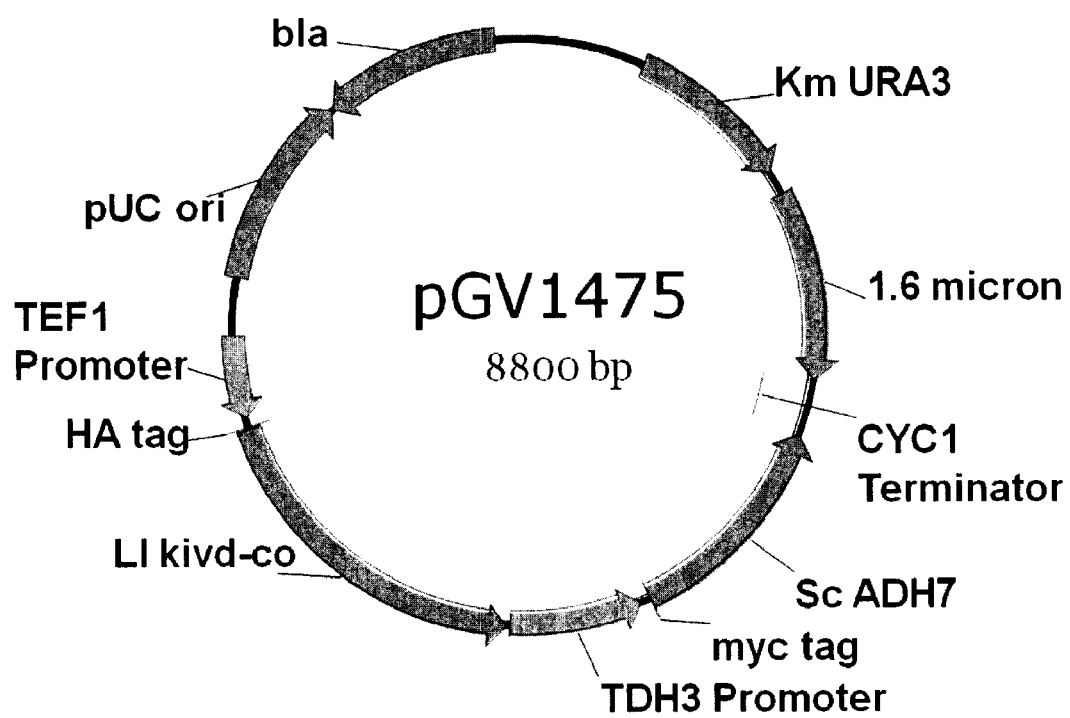
FIG. 13 illustrates a schematic map of plasmid pGV1475.

The isobutanol production pathway was cloned in a *K. lactis* vector-based expression system: a SacI-MluI fragment containing the TEF1 promoter. *Lactococcus lactis* alsS and part of the CYC1 terminator sequence was cloned into the same sites of the *K. lactis* expression plasmid, pGV1430 (FIG. 9), to generate pGV1472 (FIG. 11, SEQ ID NO: 2). A SacI-MluI fragment containing the TEF1 promoter, *E. coli* ilvD, TDH3 promoter, *E. coli* ilvC, and part of the CYC1 terminator was cloned into the same sites of the *K. lactis* expression plasmid, pGV1429 (FIG. 8), to generate pGV1473 (FIG. 12, SEQ ID NO: 3). A BssHII-NotI fragment containing the TEF1 promoter, *L. lactis* kivD, TDH3 promoter and *S. cerevisiae* ADH7. ScAdh7 was cloned into the *K. lactis* expression plasmid, pGV1431 (FIG. 10), to obtain pGV1475 (FIG. 13, SEQ ID NO: 4).

The *K. lactis* strain GEVO1287 was transformed with the above plasmids, pGV1472, pGV1473, and pGV1475 (Table EX5-1) to express the isobutanol pathway. As a control, *K. lactis* GEVO1287 was also transformed with empty vectors pGV1430, pGV1429, and pGV1431 (Table EX5-1)

TABLE EX5-1

| | | | | | | | | | |
|---|---|---|---|---|---|---|---|---|---|
| | | | *K. lactis* clones expression isobutanol pathway | | | | | | |
| clone | Host | Plasmid 1 | Plasmid 2 | Plasmid 3 | ALS | KARI | DHAD | KIVD | ADH |
| iB165 | GEVO1287 | pGV1430 | pGV1429 | pGV1431 | — | — | — | — | — |
| iB173 | GEVO1287 | pGV1472 | pGV1473 | pGV1475 | Ptef1-Ll.alsS | Ec.ilvC | Ec.ilvD | Ll.Kivd | Sc.Adh7 |

Transformed cells were grown overnight and transferred to 100 mL fermentation bottles using 20 mL SC-WLU medium. Two mL samples were taken at 24 and 48 hours for GC analysis. At each time point, 2 mL of a 20% glucose was added after removing samples for GC analysis. At 48 hours the fermentation was ended. GC samples were processed as described. Results are shown in Table EX5-2 Up to 0.25 g/L isobutanol was produced in *K. lactis* transformed with an isobutanol pathway whereas the control strain without the pathway only produced 0.022 g/L in 48 hours.

TABLE EX5-2

| | | | |
|---|---|---|---|
| | *K. lactis* fermentation results | | |
| clone | Isobutanol titer (mg/L) | Isobutanol yield (% theoretical) | Ethanol (g/L) |
| iB165 | 0.022 | 0.13 | 11.4 |
| iB173 | 0.25 | 1.5 | 12.6 |

To determine if isobutanol titers can be increased by using a rich complex media, fermentations were performed as described above with iB165 (vector only control) and iB173 using YPD instead of SC-WLU medium. In addition, fermentations were also carried out in 250 mL screw-cap flasks (microaerobic conditions) and in 125 mL metal-cap flasks (aerobic conditions). Samples were taken at 24, 48, and 72 and the isobutanol levels obtained are shown in Table EX5-3.

TABLE EX5-3

| | | | | |
|---|---|---|---|---|
| | *K. lactis* fermentation results using YPD | | | |
| clone | Condition | Isobutanol titer (mg/L) | Isobutanol yield (% theoretical) | Ethanol (g/L) |
| iB165 | Anaerobic | 66 | 0.4 | 27.4 |
| iB165 | Microaerobic | 117 | 0.7 | 24.5 |
| iB165 | Aerobic | 104 | 0.6 | 11.7 |
| iB173 | Anaerobic | 297 | 1.8 | 25.8 |
| iB173 | Microaerobic | 436 | 2.6 | 23.4 |
| iB173 | Aerobic | 452 | 2.7 | 13.4 |

Example 6

Isobutanol Production in Pdc Plus *S. cerevisiae*

This example demonstrates isobutanol production in a member of *Saccharomyces* sensu stricto group, *Saccharomyces* clade, Crabtree-positive, post-WGD yeast, *S. cerevisiae*.

Figure 14:
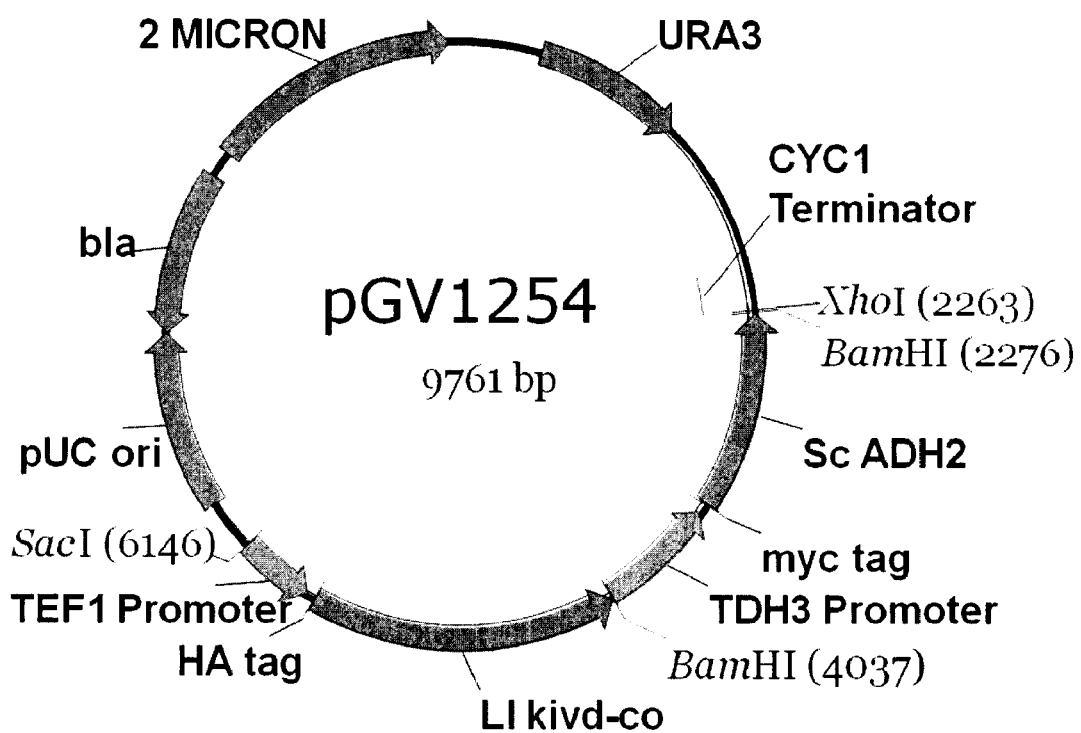
FIG. 14 illustrates a schematic map of plasmid pGV1254.
Figure 15:
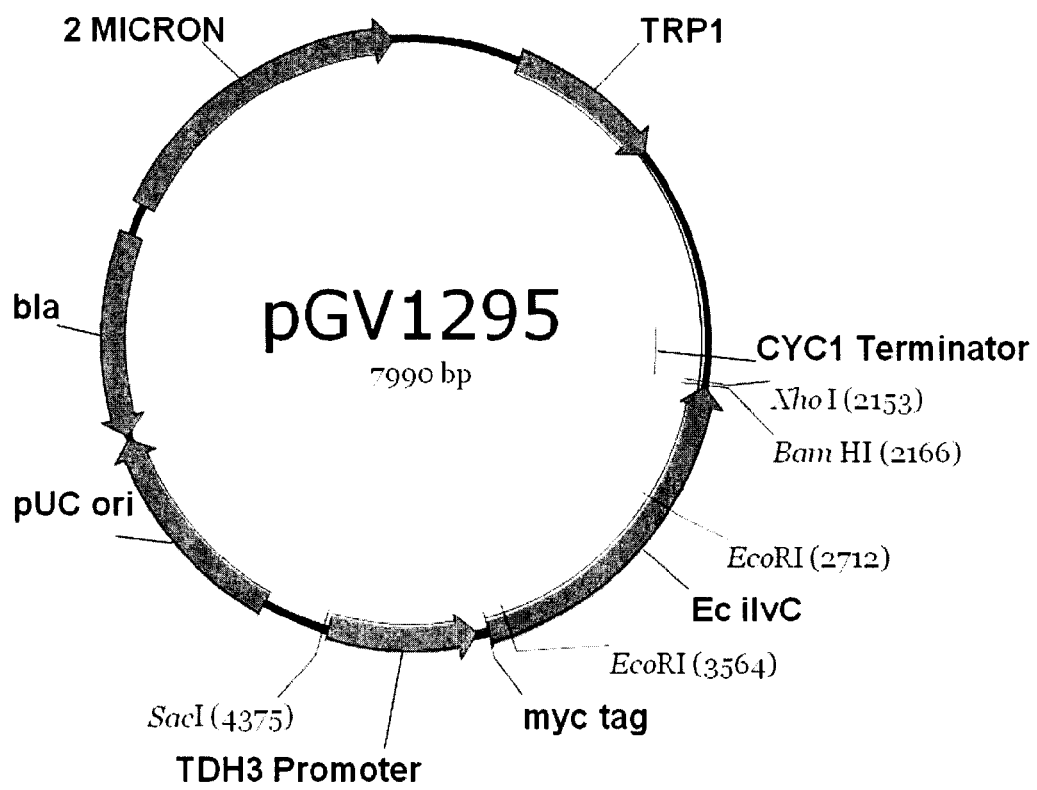
FIG. 15 illustrates a schematic map of plasmid pGV1295.
Figure 16:
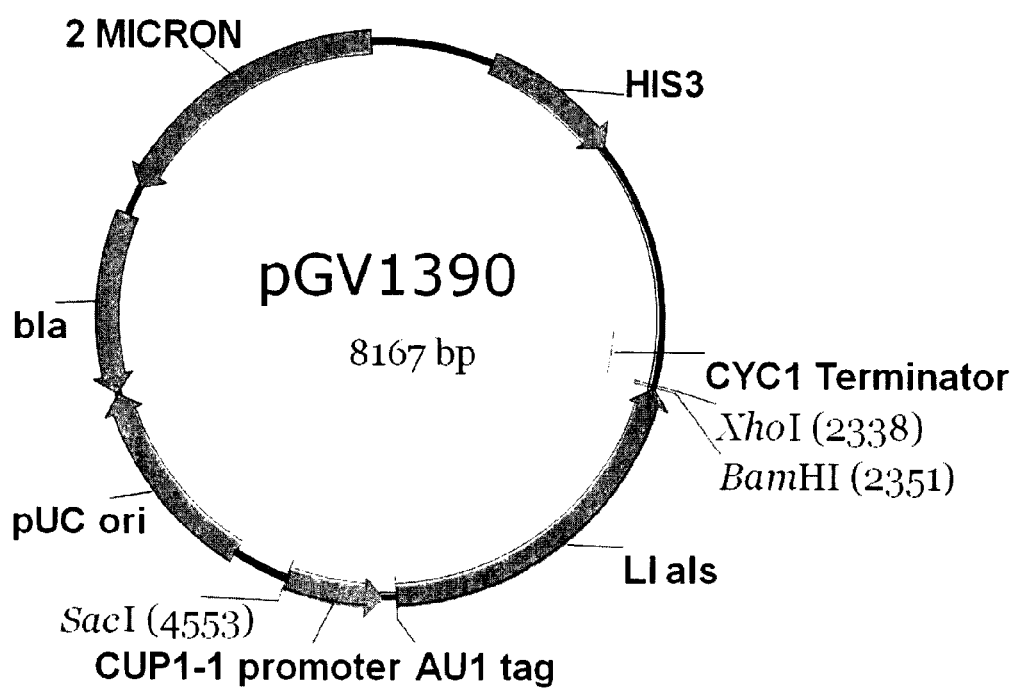
FIG. 16 illustrates a schematic map of plasmid pGV1390.
Figure 17:
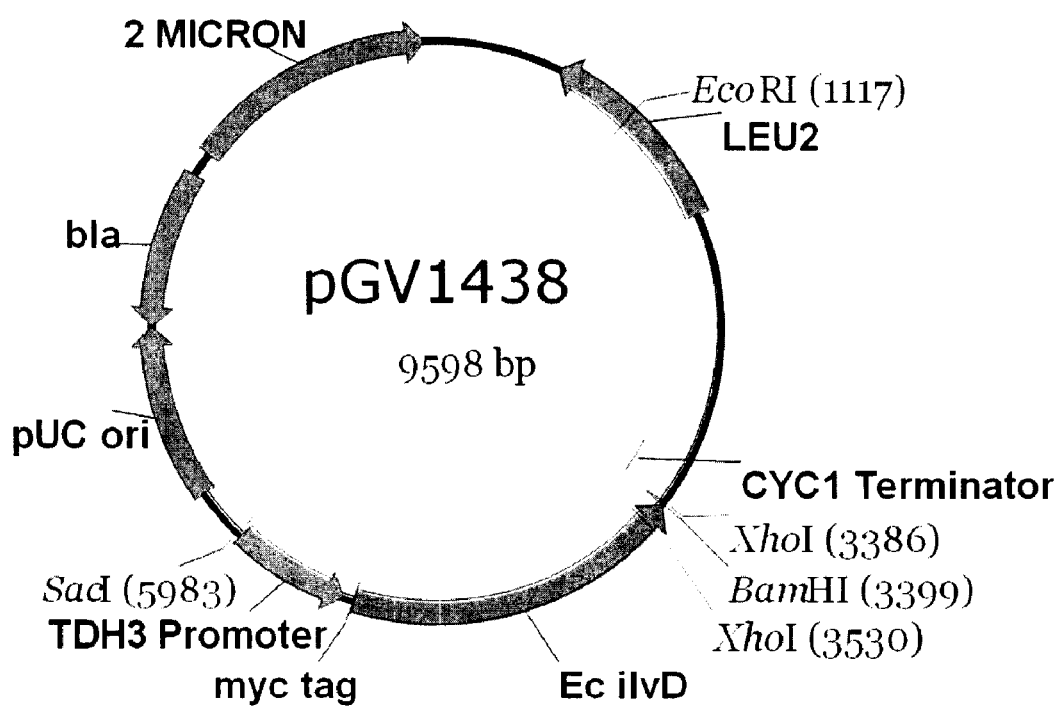
FIG. 17 illustrates a schematic map of plasmid pGV1438.

Various plasmids carrying the isobutanol production pathway were constructed for expression of this metabolic pathway in a Pdc-plus variant of *S. cerevisiae*, GEVO1187. Plasmids pGV1254 (FIG. 14; SEQ ID NO: 10), pGV1295 (FIG. 15; SEQ ID NO: 11) pGV1390 (FIG. 16; SEQ ID NO: 12), and pGV1438 (FIG. 17; SEQ ID NO: 13) were high copy *S. cerevisiae* plasmids that together expressed the five genes of the isobutanol pathway (TABLE EX6-1). pGV1390 was generated by cloning a SalI-BamHI fragment containing the *L. lactis* alsS (SEQ ID NO: 5) into the high copy *S. cerevisiae* expression plasmid, pGV1387, where the *L. lactis* alsS would be expressed under the CUP1 promoter. pGV1295 was generated by cloning a SalI-BamHI fragment containing the *E. coli* ilvC (SEQ ID NO: 6) into the high copy *S. cerevisiae* expression plasmid, pGV1266, where the *E. coli* ilvC would be expressed using the TDH3 promoter. pGV1438 was generated by cloning a SalI-BamHI fragment containing the *E. coli* ilvD (SEQ ID NO: 7) into the high copy *S. cerevisiae* expression plasmid, pGV1267, where the *E. coli* ilvD would be expressed using the TDH3 promoter. pGV1254 was made by cloning an EcoRI (filled in by Klenow polymerase treatment)—XhoI fragment containing the TDH3 promoter and *S. cerevisiae* ADH2 from pGV1241 into the BamHI (filled in by Klenow) and XhoI sites of pGV1186. pGV1186 was made by cloning a SalI-BamHI fragment containing the *L. lactis* kivD (SEQ ID NO: 8) into a high copy *S. cerevisiae* expression plasmid, pGV1102, where the *L. lactis* kivD would be expressed using the TEF1 promoter. pGV1241 was made by cloning a SalI-BamHI fragment containing the *S. cerevisiae* ADH2 (SEQ ID NO: 9) into a high copy *S. cerevisiae* expression plasmid, pGV1106, where the *S. cerevisiae* ADH2 would be expressed using the TDH3 promoter.

Figure 21:
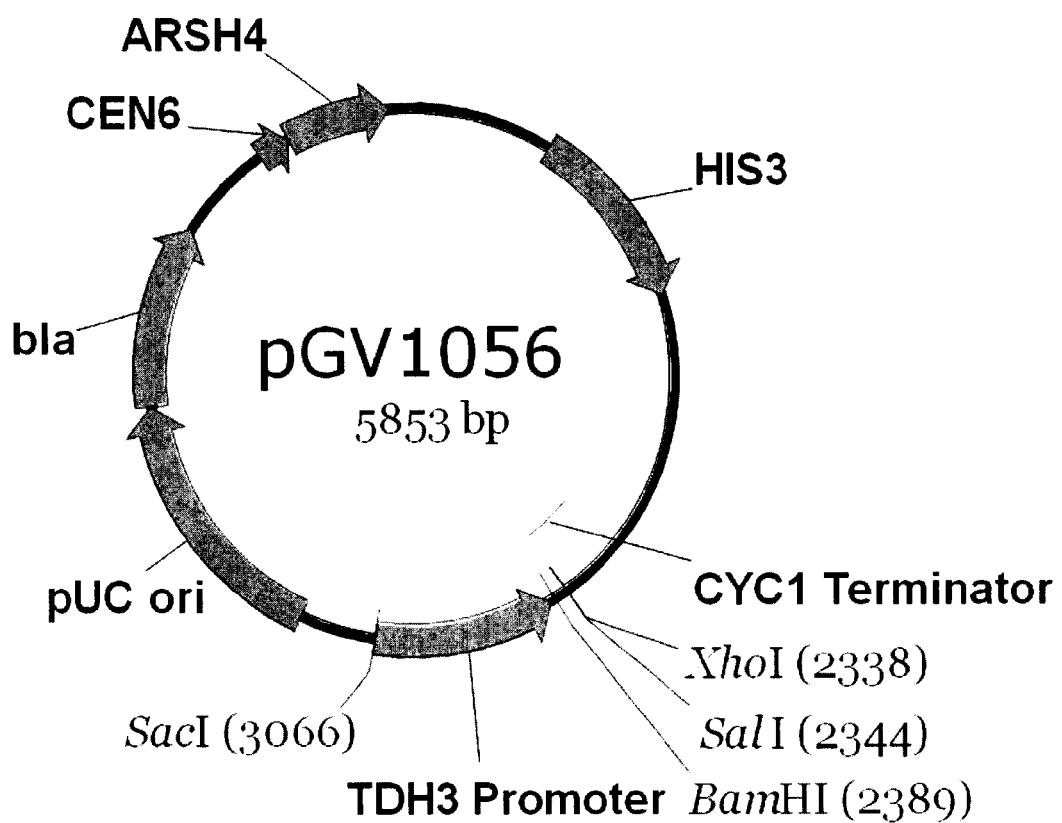
FIG. 21 illustrates a schematic map of plasmid pGV1056.

GEVO1187 was transformed with plasmids as shown in Table EX6-1. As a defective isobutanol pathway control, cells were transformed with pGV1056 (FIG. 21, empty vector control) instead of pGV1390. The transformants were plated onto appropriate selection plates. Single colonies from the transformation were isolated and tested for isobutanol production by fermentation.

TABLE EX6-1

| pGV# | Promoter | Gene | Plasmid type | Plasmid marker |
|---|---|---|---|---|
| pGV1254 | Sc TEF1 | *L. lactis* kivD | High copy | Sc URA3 |
| pGV1295 | Sc TDH3 | *E. coli* ilvC | High copy | Sc TRP1 |
| pGV1390 | Sc CUP1 | *L. lactis* alsS | High copy | Sc HIS3 |
| pGV1438 | Sc TDH3 | *E. coli* ilvD | High copy | Sc LEU1 |

The cells were grown overnight and anaerobic batch fermentations were carried out as described in General Methods. SC-HWUL was used as the media. 2 mL samples were taken at 24, 48 and 72 hours for GC At each time point, the cultures were fed 2 mL of a 40% glucose solution. The fermentation was ended after 72 hours. Samples were processed and analyzed as described. The results are shown in Table EX6-2. As shown, isobutanol was produced in GEVO1187 transformed with the isobutanol-pathway containing plasmids.

TABLE EX6-2

Isobutanol production in *S. cerevisiae*, GEVO1187, after 72 hours

| | | Isobutanol | | Ethanol | |
|---|---|---|---|---|---|
| Strain | Plasmids | Titer [gL$^{-1}$] | Yield [%] | Titer [gL$^{-1}$] | Yield [%] |
| GEVO1187 | pGV1254, pGV1438, pGV1390, pGV1438 | 0.13 | 0.31 | 31 | 60 |
| GEVO1187 | pGV1056, pGV1295, pGV1438, pGV1254 | 0.04 | 0.10 | 42 | 82 |

This example demonstrates isobutanol production in a Pdc-minus member of the *Saccharomyces* clade, Crabtree-negative, pre-WGD yeast, *K. lactis*.

Figure 18:
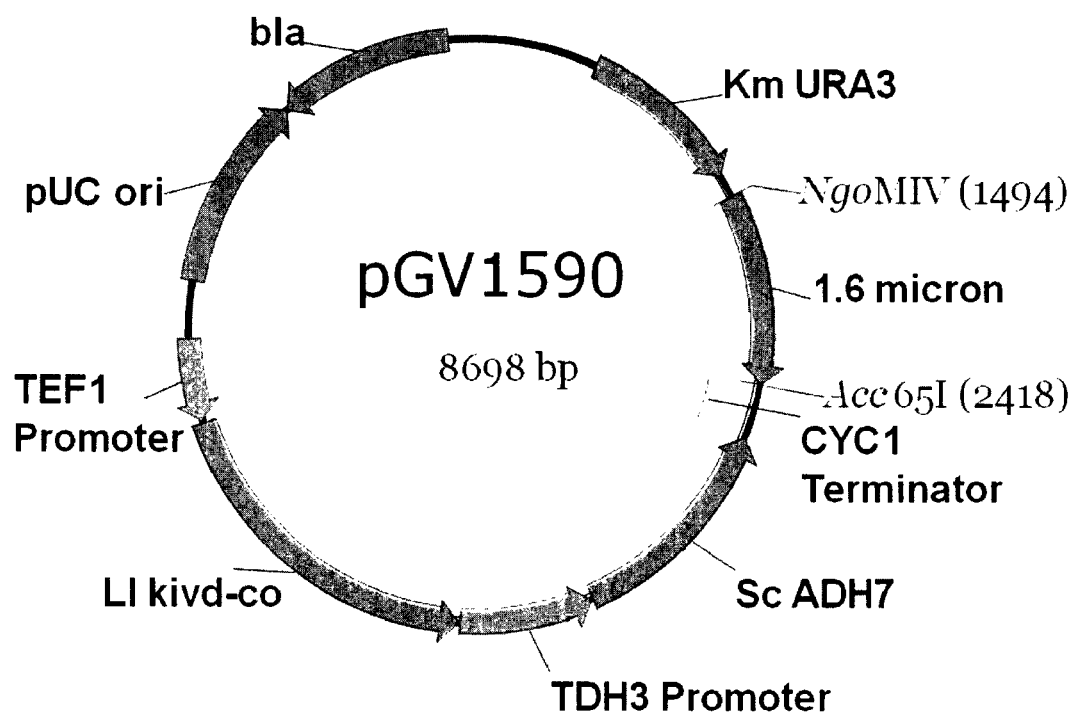
FIG. 18 illustrates a schematic map of plasmid pGV1590.
Figure 19:
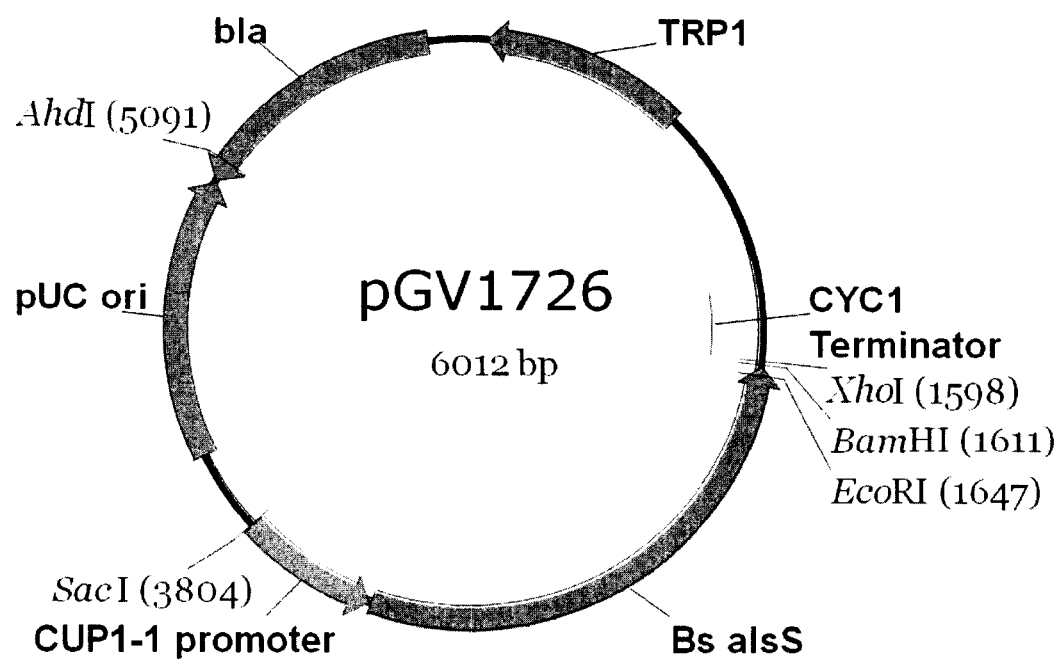
FIG. 19 illustrates a schematic map of plasmid pGV1726.
Figure 20:
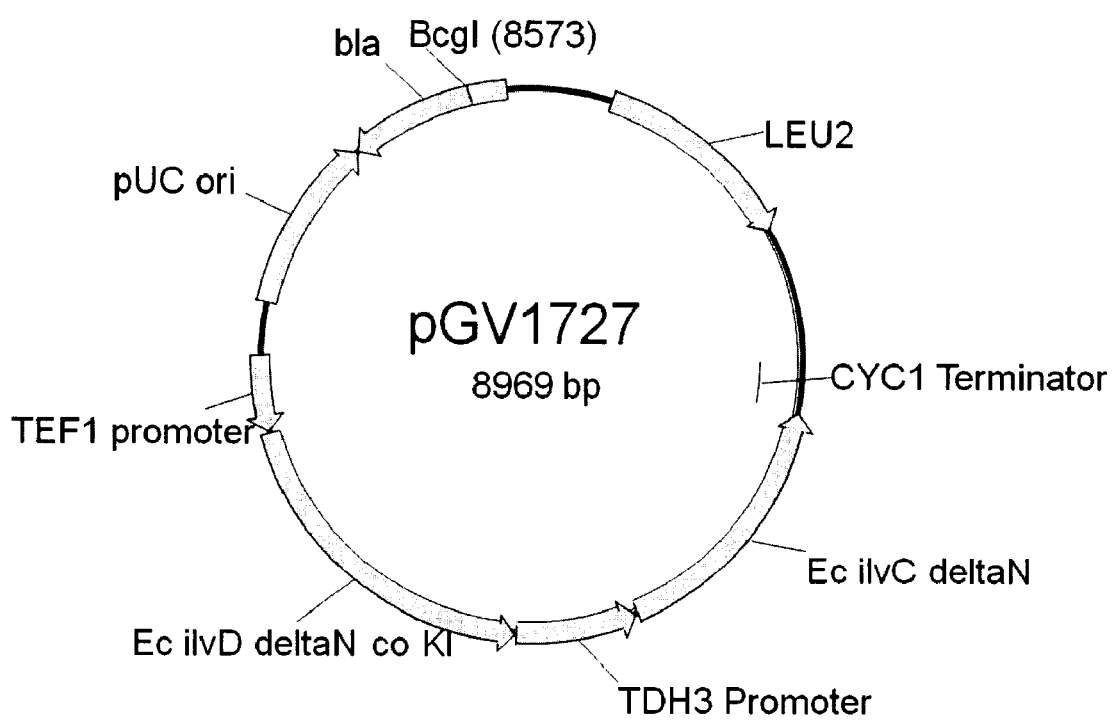
FIG. 20 illustrates a schematic map of plasmid pGV1727.

Description of plasmids pGV1590 pGV1726 pGV1727: pGV1590 (FIG. 18, SEQ ID NO: 14) is a *K. lactis* expression plasmid used to express *L. lactis* kivD (under TEF1 promoter) and *S. cerevisiae* ADH7 (under TDH3 promoter). This plasmid also carries the *K. marxianus* URA3 gene and the 1.6 micron replication origin that allow for DNA replication in *K. lactis*. pGV1726 (FIG. 19, SEQ ID NO: 15) is a yeast integration plasmid carrying the TRP1 marker and expressing *B. subtilis* alsS using the CUP1 promoter. pGV1727 (FIG. 20, SEQ ID NO: 16) is a yeast integration plasmid carrying the LEU2 marker and expressing *E. coli* ilvD under the TEF1 promoter and *E. coli* ilvC under the TDH3 promoter. Neither pGV1726 or pGV1727 carry a yeast replication origin.

Construction of GEVO1829, a *K. lactis* strain with pathway integrated: The isobutanol pathway was introduced into the Pdc-minus *K. lactis* strain GEVO1742 by random integrations of the pathway genes. GEVO1742 was transformed with the Acc65I-NgoMIV fragment of pGV1590 containing the *L. lactis* kivd and *S. cerevisiae* ADH7 but without the yeast replication origin, to generate GEVO1794. The presence of both *L. lactis* kivd and *S. cerevisiae* ADH7 was confirmed by colony PCR using primer sets 1334+1335 and 1338+1339, respectively. GEVO1794 was transformed with pGV1727, a yeast integration plasmid carrying *E. coli* ilvD (under the TEF1 promoter) and *E. coli* ilvC (under TDH3 promoter), that had been linearized by digesting with BcgI. The resulting strain, GEVO1818, was confirmed by colony PCR for the presence of *E. coli* ilvD and *E. coli* ilvC using primer sets 1330+1331 and 1325+1328, respectively. GEVO1818 was then transformed with pGV1726, a yeast integration plasmid carrying *B. subtilis* alsS (under the CUP1 promoter), that had been linearized by digesting with AhdI to generate GEVO1829. The presence of *B. subtilis* alsS was confirmed by colony PCR using primers 1321+1324.

Aerobic fermentations were carried out to test isobutanol production by the Pdc-minus strain carrying the isobutanol pathway, GEVO1829. The Pdc-minus strain without the isobutanol pathway, GEVO1742, was used as a control. These strains were cultured in YPD overnight at 30° C., 250 rpm, then diluted into 20 mL fresh YPD in a 125 mL flask and grown at 30° C., 250 rpm. 2 mL samples were taken at 24 and 48 hours, cells pelleted for 5 minutes at 14,000×g and the supernatant was analyzed for isobutanol by GC. In addition glucose concentrations were analyzed by LC. The results are shown in Table EX7-1. At 48 hours, the OD of the GEVO1742 strain had reached over 8.5 while the OD of the GEVO1829 was less than 5. GEVO1829 consumed around 15.7 g/L glucose while GEVO1742 consumed roughly 7.7 g/L glucose. GEVO1829 produced 0.17 g/L isobutanol while GEVO1742 did not produce any isobutanol above media background.

TABLE EX7-1

K. lactis fermentation results

| Clone | Isobutanol titer (mg/L) | Isobutanol yield (% theoretical) | Ethanol (mg/L) |
|---|---|---|---|
| GEVO1742 | 0 | 0 | 17 |
| GEVO1829 | 170 | 2.6 | 53 |

Example 8A

Isobutanol Production in Pdc-Minus *S. cerevisiae* GEVO1581

This example demonstrates isobutanol production in a Pdc-minus member of the *Saccharomyces* sensu stricto group, *Saccharomyces* clade yeast, Crabtree-positive yeast, post-WGD yeast, *S. cerevisiae*.

Figure 24:
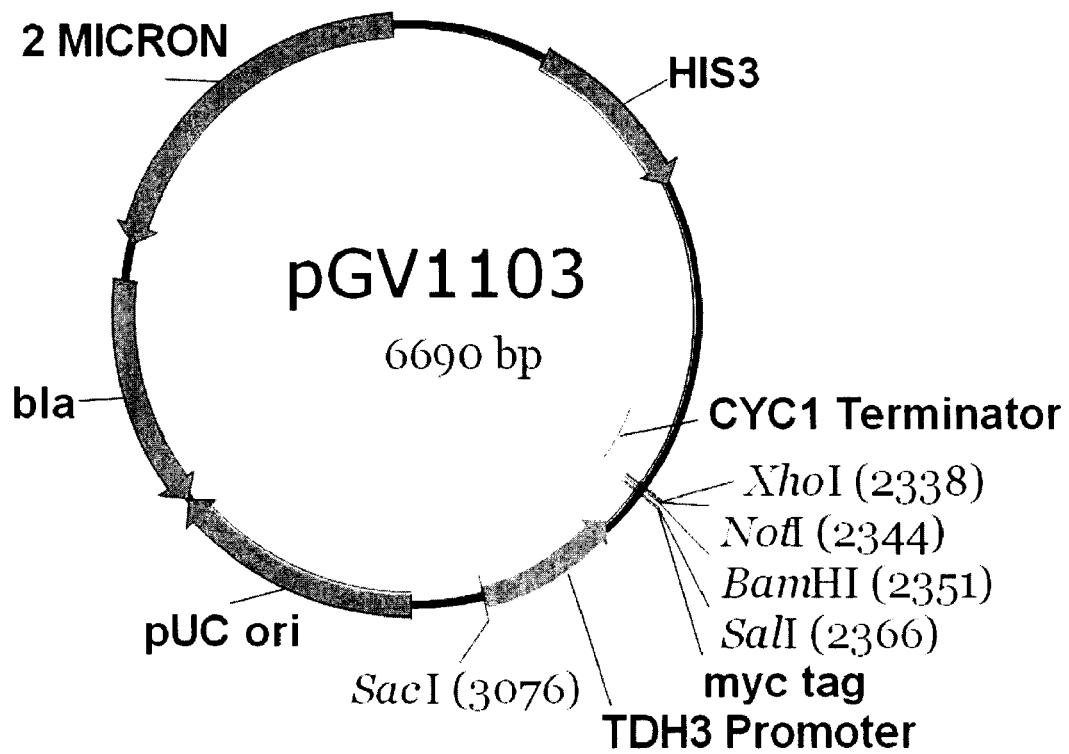
FIG. 24 illustrates a schematic map of plasmid pGV1103.
Figure 25:
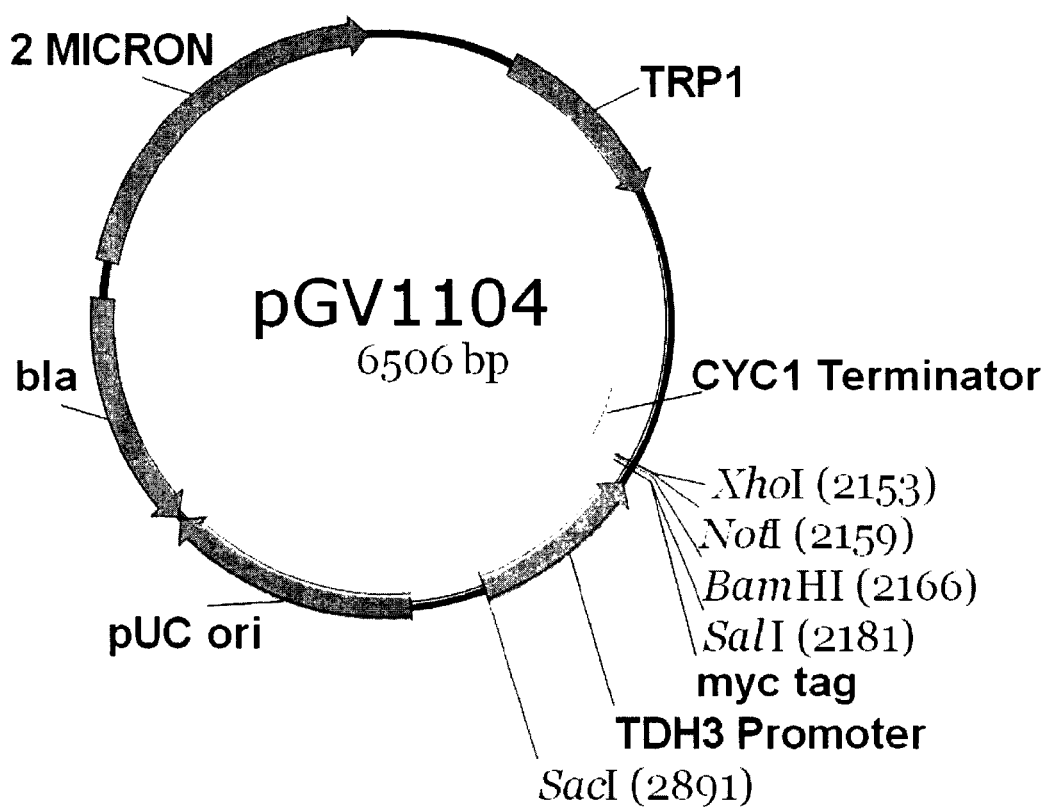
FIG. 25 illustrates a schematic map of plasmid pGV1104.
Figure 26:
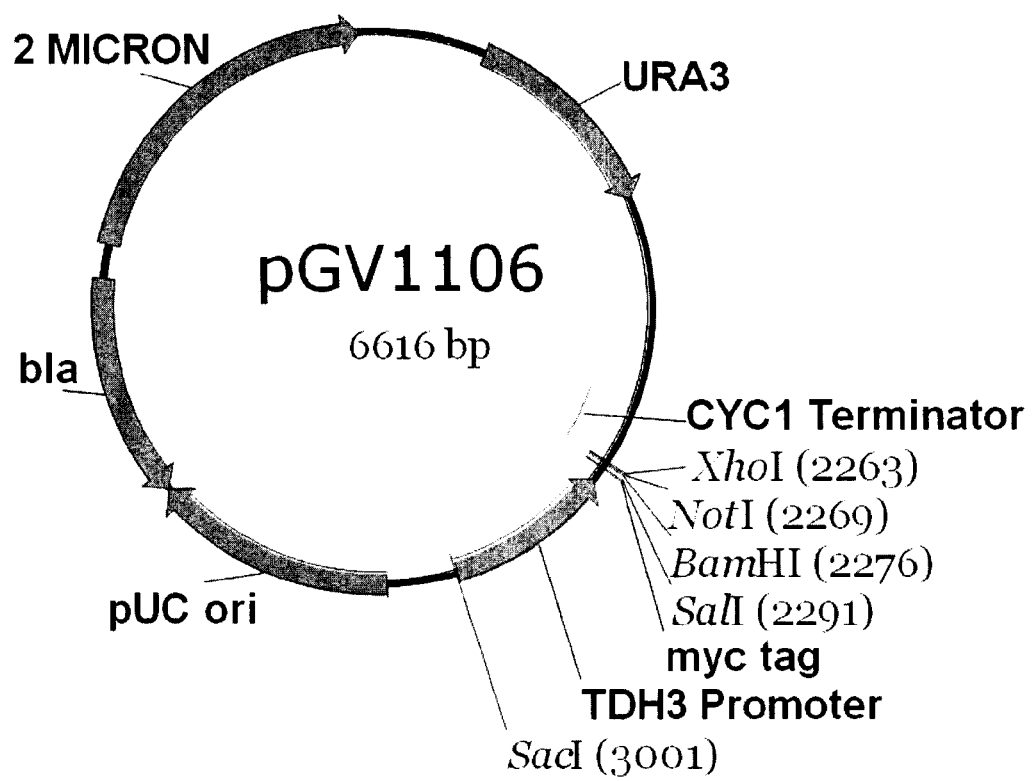
FIG. 26 illustrates a schematic map of plasmid pGV1106.
Figure 27:
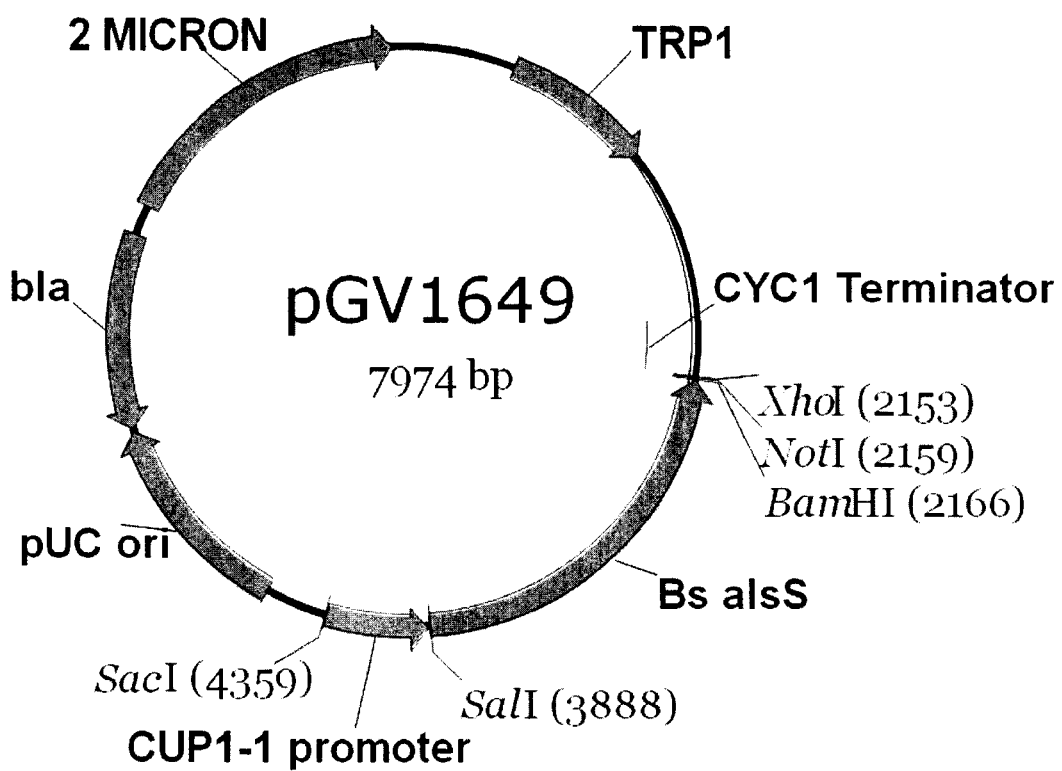
FIG. 27 illustrates a schematic map of plasmid pGV1649.
Figure 28:
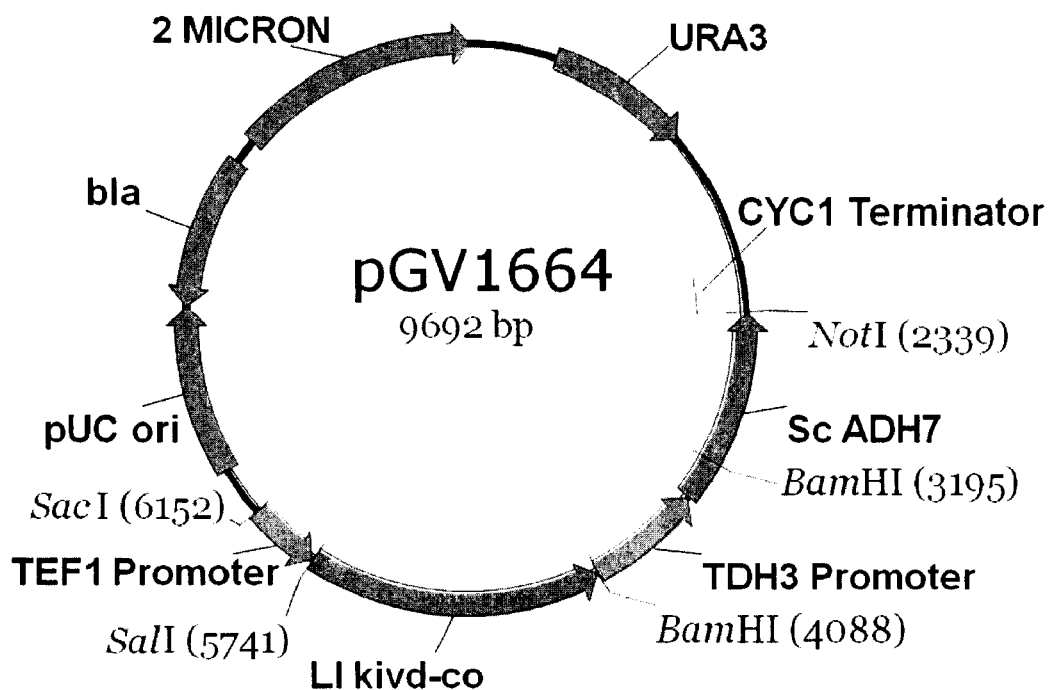
FIG. 28 illustrates a schematic map of plasmid pGV1664.
Figure 30:
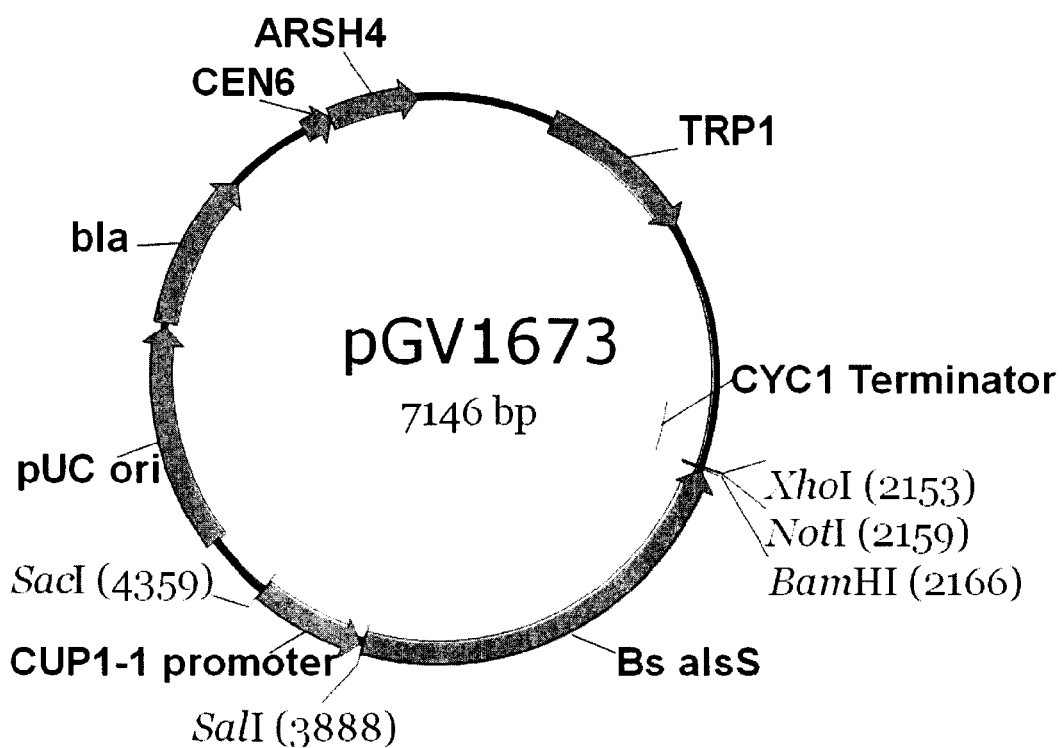
FIG. 30 illustrates a schematic map of plasmid pGV1673.
Figure 31:
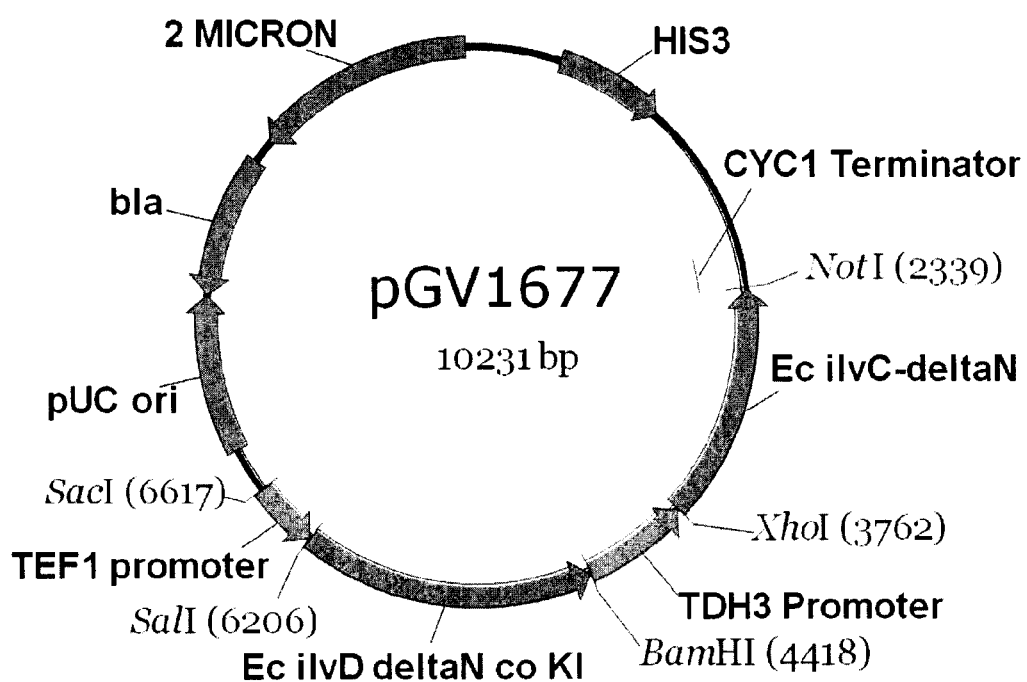
FIG. 31 illustrates a schematic map of plasmid pGV1677.

Strain GEVO1581 with the three genes encoding PDC activity deleted (pdc1Δ, pdc5Δ, and pdc6Δ) was used to produce isobutanol. Isobutanol pathway enzymes were encoded by genes cloned into three plasmids. pGV1103 (FIG. 24, SEQ ID NO: 20), pGV1104 (FIG. 25, SEQ ID NO: 21) and pGV1106 (FIG. 26, SEQ ID NO: 22) were empty high copy expression vectors that carry as marker genes, URA3, HIS3 and TRP1, respectively. The *B. subtilis* alsS gene, express using the CUP1 promoter, was encoded on either a low copy CEN plasmid, pGV1673 (FIG. 30, SEQ ID NO: 26) or a high copy plasmid, pGV1649 (FIG. 27, SEQ ID NO: 23). Both of these plasmids used TRP1 as a marker gene. *E. coli* ilvD (expressed using the TEF1 promoter) and *E. coli* ilvC (expressed using the TDH3 promoter) were expressed off of the high copy plasmid pGV1677 (FIG. 31, SEQ ID NO: 27). This plasmid utilized HIS3 as a marker gene. *L. lactis* kivd (expressed using the TEF1 promoter) and *S. cerevisiae* ADH7 (expressed using the TDH3 promoter) were expressed off of the high copy plasmid pGV1664 (FIG. 28, SEQ ID NO: 24). This plasmid utilized URA3 as a marker gene. Combination of these plasmids (Table EX8-1) to reconstitute the isobutanol pathway were introduced into GEVO1581 by lithium acetate transformation (described in General Methods).

TABLE EX8-1

Plasmids transformed into GEVO1581

| Fermentation # | Strain | Plasmids | Notes |
|---|---|---|---|
| iB250 | GEVO1581 | pGV1103, pGV1104, pGV1106 | Vector Control |
| iB251 | GEVO1581 | pGV1677, pGV1649, pGV1664 | iBuOH Pathway, alsS on 2 micron plasmid |
| iB252 | GEVO1581 | pGV1677, pGV1673, pGV1664 | iBuOH Pathway, alsS on CEN plasmid |

Fermentation experiments were carried out with GEVO1581 transformed with plasmids according to Table EX8-1 to determine the amount of isobutanol produced (titer) and the percentage of isobutanol to consumed glucose (yield).

Fermentations with Transformants of GEVO1581: Using cells grown in 3 mL defined (SC-Ethanol) medium, 20 mL cultures were inoculated with transformants of GEVO1581 (3 independent colonies per transformation set) to an $OD_{600}$ of approximately 0.1. The cultures were incubated at 30° C. at 250 RPM in 125 mL metal cap flasks until they reached an $OD_{600}$ of approximately 1. Glucose was added to a final concentration of 5% and a 2 mL aliquot was removed from each sample (T=0 sample). The $OD_{600}$ of each sample was measured, the cells in each sample were pelleted by centrifugation (14,000×g, 5 min), and the supernatant from each sample was stored at −20° C. The remaining cultures were incubated at 30° C. at 125 RPM for another 48 hours. Samples (2 mL) were removed after 24 and 48 hours and prepared as just described. The samples were thawed, and prepared as described in General Methods. Three individual transformants were used for each set of plasmids during the fermentations. The amount of glucose consumed and the amount of pyruvate, glycerol, ethanol, and isobutanol produced after 48 hours are listed in Table EX8A-2.

TABLE EX8A-2

48 hour time point data are shown as an average of three replicates

| | Glucose consumed (g/L) | Isobutanol (mg/L) | Yield (% theoretical) |
|---|---|---|---|
| iB250 | 3.6 ± .7 | 4.7 ± 0.00 | 0.31 ± 0.04 |
| iB251 | 2.8 ± 1.6 | 122 ± 41 | 11.0 ± 5.0 |
| iB252 | 1.2 ± .5 | 62 ± 11 | 12.8 ± 2.8 |

Again using cells grown in 3 mL defined (SC-Ethanol) medium, 20 mL cultures were inoculated with transformants of GEVO1581 to an $OD_{600}$ of approximately 0.1. The cultures were incubated at 30° C. at 250 RPM in 125 mL metal cap flasks until they reached an $OD_{600}$ of approximately 1. Biomass was pelleted and resuspended in 20 ml media with 2% glucose as the sole carbon source and a 2 mL aliquot was removed from each sample (T=0 sample). The $OD_{600}$ of each sample was measured and each sample was stored at −20° C. The remaining cultures were incubated at 30° C. at 125 RPM for another 48 hours. Samples mL) were removed after 24 and 48 hours and stored at −20° C. The samples were thawed, and prepared as described in General Methods. The amounts of ethanol and isobutanol produced after 48 hours are listed in Table EX8A-3.

TABLE EX8A-3

48 hour time point data for fermentation in glucose, shown as an average of three replicates

| | Isobutanol (mg/L) | Isobutanol yield (% theoretical) | Ethanol (mg/L)l | Ethanol yield (% theoretical) |
|---|---|---|---|---|
| iB250 | 0 | 0 | 0 | 0 |
| iB251 | 210 | 3.5 | 110 | 1.8 |

Example 8B

Isobutanol Production in Pdc-Minus *S. cerevisiae* GEVO1584

This example demonstrates isobutanol production in a Pdc-minus member of the *Saccharomyces* sensu stricto group, *Saccharomyces* clade, Crabtree-positive yeast, WGD yeast, *S. cerevisiae*.

GEVO1581 is a diploid strain, thus, a second backcross of a Pdc-minus yeast into the CEN.PK background was performed, yielding a Pdc-minus haploid strain GEVO1584 with the required auxotrophic markers for plasmid propagation.

Figure 22:
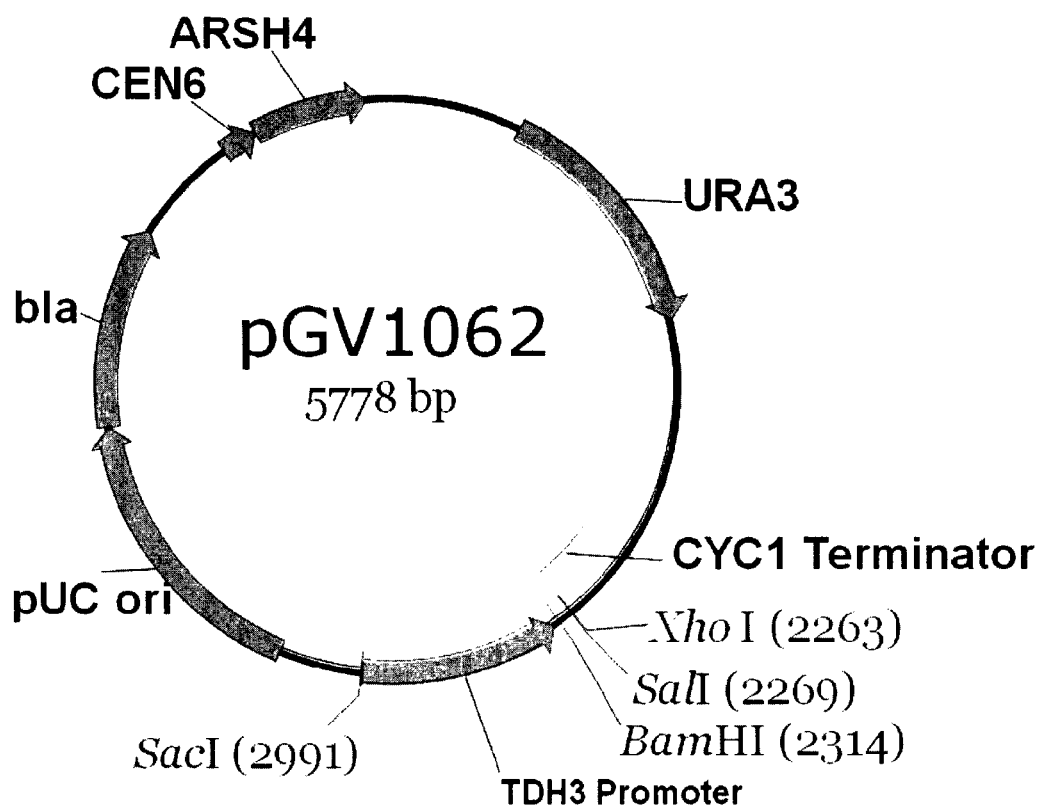
FIG. 22 illustrates a schematic map of plasmid pGV1062.
Figure 23:
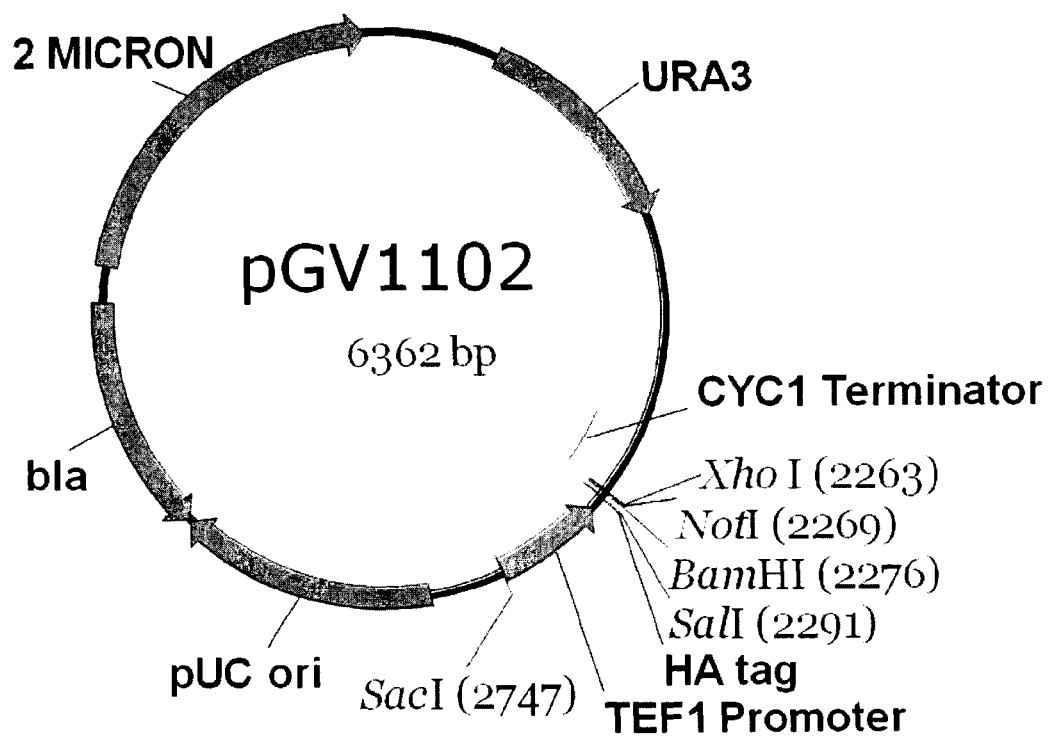
FIG. 23 illustrates a schematic map of plasmid pGV1102.
Figure 29:
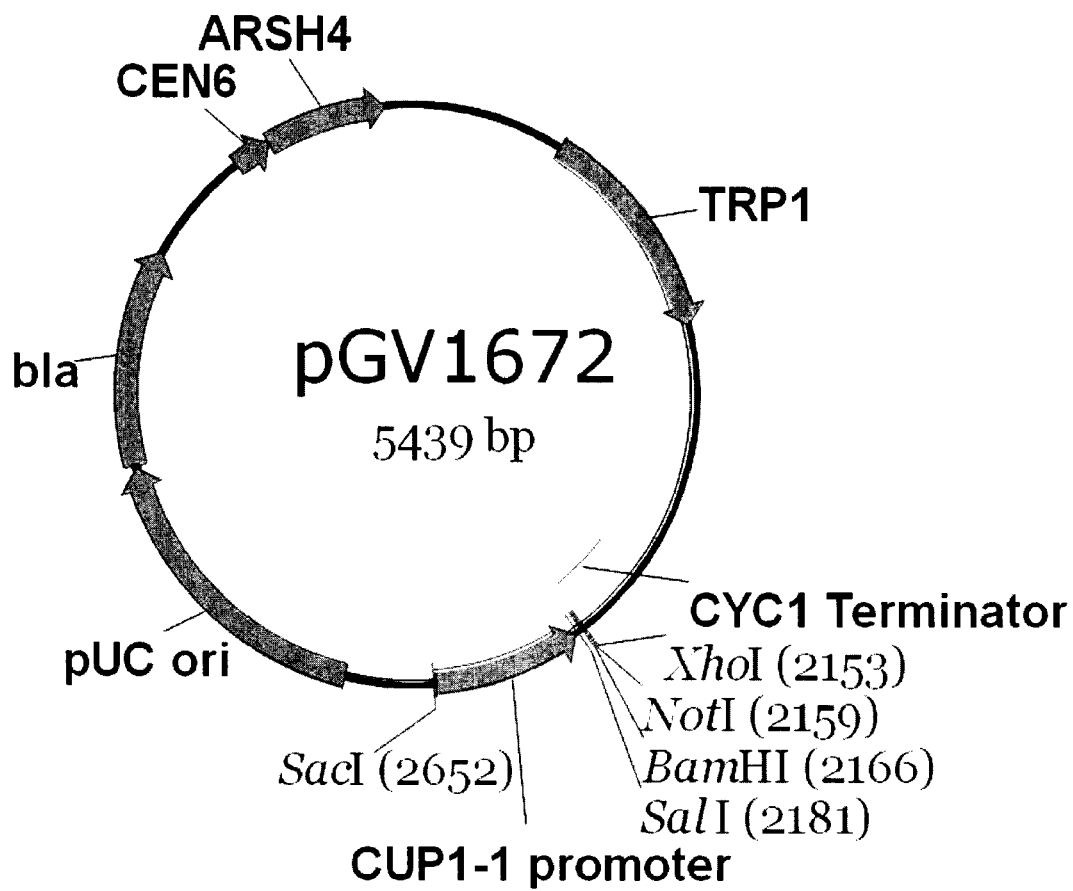
FIG. 29 illustrates a schematic map of plasmid pGV1672.
Figure 32:
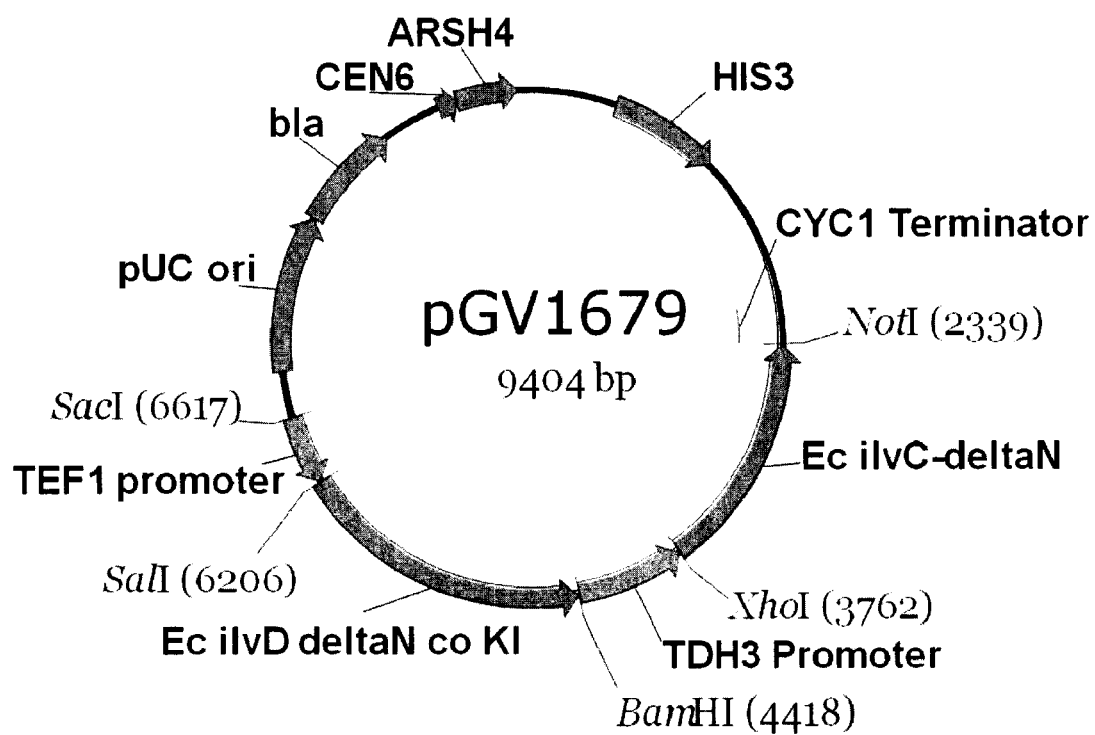
FIG. 32 illustrates a schematic map of plasmid pGV1679.
Figure 33:
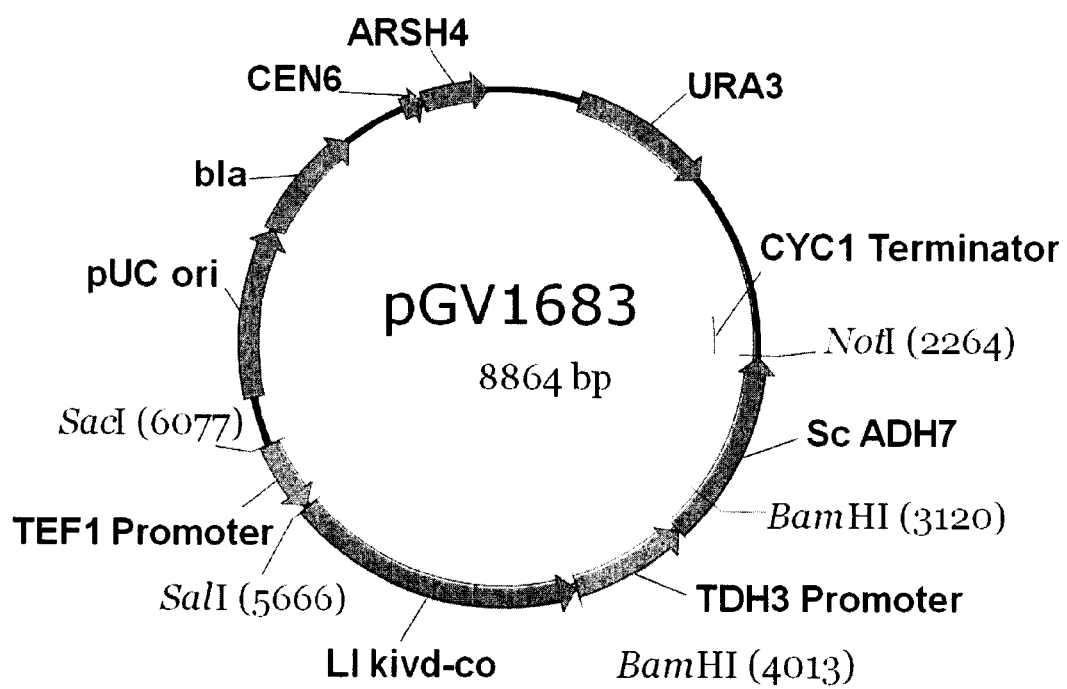
FIG. 33 illustrates a schematic map of plasmid pGV1683.

Transformations of GEVO1584: The following combinations of plasmids were transformed into GEVO1584 (Table EX8B-1) using lithium acetate transformation (described in General Methods) followed by selection on appropriate minimal media. pGV1672 (FIG. 29, SEQ ID NO: 25), pGV1056 (FIG. 21, SEQ ID NO: 17), and pGV1062 (FIG. 22, SEQ ID NO: 18) were empty low copy CEN expression vectors that carry as marker genes, TRP1, HIS3, and URA3. pGV1103 (FIG. 24, SEQ ID NO: 20), pGV1104 (FIG. 25 SEQ ID NO: 21) and pGV1102 (FIG. 23, SEQ ID NO: 19) were empty high copy expression vectors that carry as marker genes, URA3, HIS3 and TRP1, respectively. The isobutanol pathway was expressed off of low copy CEN plasmids pGV1673 (FIG. 30, SEQ ID NO: 26), pGV1679 (FIG. 32, SEQ ID NO: 28) and pGV1683 (FIG. 33, SEQ ID NO: 29). pGV1673 carried the *B. subtilis* alsS under the CUP1 promoter and utilized the TRP1 marker gene. pGV1679 carried the *E. coli* ilvD and *E. coli* ilvC genes expressed using the TEF1 and TDH3 promoters, respectively, and utilized the HIS3 marker gene. pGV1683 carried the *L. lactis* kivd and the *S. cerevisiae* ADH7 genes expressed using the TEF1 and TDH3 promoters, respectively, and utilized the URA3 marker gene. The isobutanol pathway was also expressed off of high copy plasmids pGV1649 (FIG. 27, SEQ ID NO: 23), pGV1677 (FIG. 31, SEQ ID NO: 27) and pGV1664 (FIG. 28, SEQ ID NO: 24). pGV1649 carried the *B. subtilis* alsS under the CUP1 promoter and utilized the TRP1 marker gene. pGV1677 carried the *E. coli* ilvD and *E. coli* ilvC genes expressed using the TEF1 and TDH3 promoters, respectively, and utilized the HIS3 marker gene. pGV1664 carried the *L. lactis* kivd and the *S. cerevisiae* ADH7 genes expressed using the TEF1 and TDH3 promoters, respectively, and utilized the URA3 marker gene.

TABLE EX8B-1

| Fermentation # | Strain | Plasmids | Notes |
| --- | --- | --- | --- |
| iB300 | GEVO1584 | pGV1672, pGV1056, pGV1062 | Vector Control (CEN plasmids) |
| iB301 | GEVO1584 | pGV1673, pGV1679, pGV1683 | Isobutanol pathway (CEN plasmids) |
| iB302 | GEVO1584 | pGV1103, pGV1104, pGV1102 | Vector Control (2μ plasmids) |
| iB303 | GEVO1584 | pGV1677, pGV1649, pGV1664 | Isobutanol pathway (2μ plasmids) |

Fermentations with Transformants of GEVO1584: Using cells grown in 3 mL defined (SC) media containing ethanol (SC+Ethanol-HWU), 200 mL cultures were inoculated with transformants of GEVO1584 and incubated in SC+Ethanol-HWU at 30° C. at 250 RPM in 500 mL shake flasks for 72 hours. The $OD_{600}$ values measured after 72 hours ranged from 1.4 to 3.5. The cultures were diluted 1:10 into fresh 250 mL SC+Ethanol-HWU media and incubated at 30° C. at 250 RPM in 500 mL shake for 24 hours. The cells were collected by centrifugation at 3000 RPM for 3 minutes and resuspended in 20 mL SC+Glucose-HWU media in 125 mL metal cap flasks. 250 μL of 100% ethanol was added to each culture to bring the concentration of ethanol to 1%. A 2 mL aliquot was removed, the $OD_{600}$ was measured using 100 μL, and the remaining aliquot was centrifuged to pellet cells (14,000×g, 5 min) and the supernatants were stored at −20° C. The cultures were incubated at 125 rpm at 30° C. A 2 mL aliquot was removed from each culture after 24 and 48 hours of incubation, and the $OD_{600}$ was measured as before (see Table 3, t=24 and t=48) and the sample centrifuged and stored as described above. The samples were thawed, and the samples were prepared and analyzed via GC and HPLC as described in General Methods. Results are shown in Table EX8B-2

TABLE EX8B-2

| | 48 hour time point data are shown as an average of three replicates | | | | |
| --- | --- | --- | --- | --- | --- |
| Fermentation # | | Isobutanol Titer (g/L) | Glucose Consumed (g/L) | Ethanol Consumed (g/L) | Yield (% theor.)] |
| iB300 | Vector Control (CEN plasmids) | 0.012 ± 0.003 | 9.75 ± 4.17 | 2.47 ± 0.30 | 0.30% |
| iB301 | Isobutanol pathway (CEN plasmids) | 0.392 ± 0.087 | 9.31 ± 5.03 | 0.95 ± 0.64 | 10.27% |
| iB302 | Vector Control (2μ plasmids) | 0.013 ± 0.006 | 8.61 ± 4.51 | 0.64 ± 0.17 | 0.37% |
| iB303 | Isobutanol pathway (2μ plasmids) | 0.248 ± 0.032 | 9.51 ± 1.25 | 0.77 ± 0.59 | 6.36% |

Figure 2A:
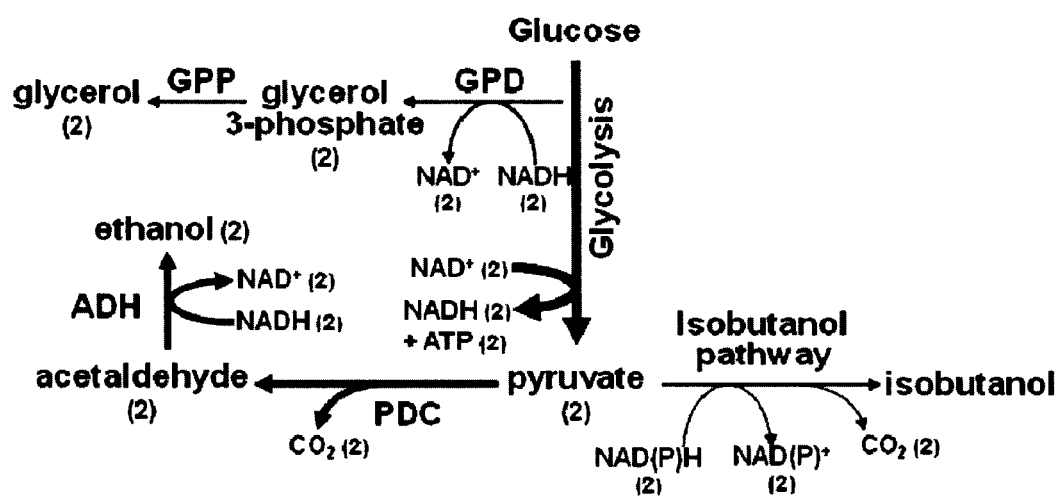
FIG. 2A illustrates production of pyruvate via glycolysis, together with an isobutanol pathway which converts pyruvate to isobutanol and a PDC pathway which converts pyruvate to acetaldehyde and carbon dioxide.
Figure 2B:
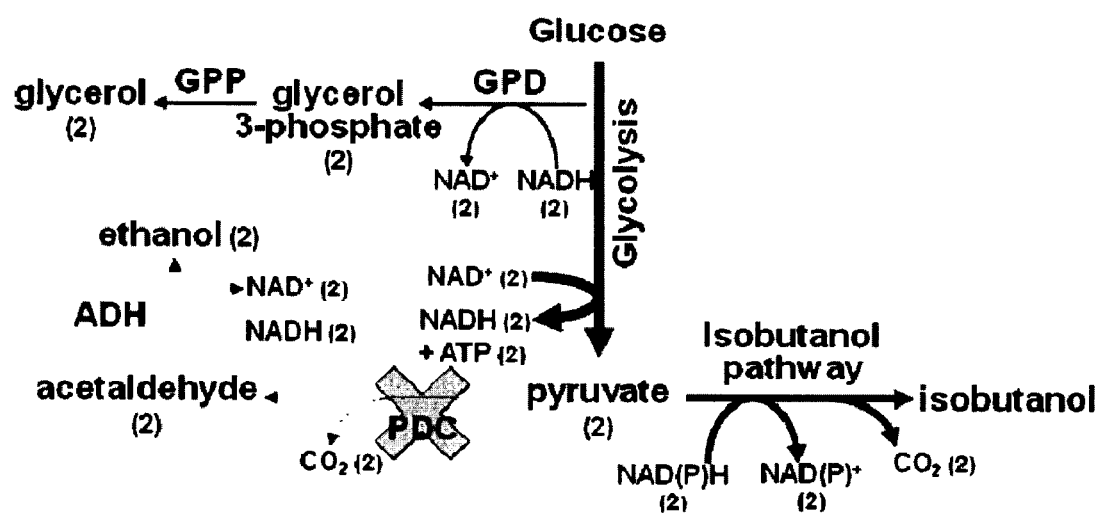
FIG. 2B illustrates an isobutanol pathway receiving additional pyruvate to form isobutanol at higher yield due to the deletion or reduction of the PDC pathway.

All Pdc-minus yeast (GEVO1584) consumed approximately 10 g/L of glucose and less than 2 g/L of ethanol after 48 hours incubation (FIG. 2A and FIG. 2B). All strains accumulated ~1.5 g/L pyruvate, except for those carrying the isobutanol pathway on 2μ plasmids (<0.5 g/L). The accumulation of pyruvate and failure of the yeast to produce ethanol from glucose is confirmation that all lacked PDC activity. After 48 hours, the Pdc-minus yeast with the isobutanol pathway encoded on 2μ plasmids generated 0.248±0.032 g/L isobutanol at a theoretical yield of 6.36% of the consumed glucose (Table EX8B-2). The CEN plasmid isobutanol pathway strain generated 0.392±0.087 g/L isobutanol at a yield of 10.27% (Table EX8B-2). Isobutanol titers were well above the equivalent vector control strains.

What is claimed is:

1. A recombinant yeast microorganism for producing isobutanol, the recombinant yeast microorganism comprising an isobutanol producing metabolic pathway, wherein said isobutanol producing metabolic pathway comprises the following substrate to product conversions:
   (i) pyruvate to acetolactate;
   (ii) acetolactate to 2,3-dihydroxyisovalerate;
   (iii) 2,3-dihydroxyisovalerate to α-ketoisovalerate;
   (iv) α-ketoisovalerate to isobutyraldehyde; and
   (v) isobutyraldehyde to isobutanol;
wherein said recombinant yeast microorganism expresses:
   (a) an acetolactate synthase to catalyze the conversion of pyruvate to acetolactate;
   (b) a ketol-acid reductoisomerase to catalyze the conversion of acetolactate to 2,3-dihydroxyisovalerate;
   (c) a dihydroxy acid dehydratase to catalyze the conversion of 2,3-dihydroxyisovalerate to α-ketoisovalerate;
   (d) an α-ketoisovalerate decarboxylase from *Lactococcus lactis* to catalyze the conversion of α-ketoisovalerate to isobutyraldehyde; and
   (e) an alcohol dehydrogenase to catalyze the conversion of isobutyraldehyde to isobutanol;
wherein the recombinant yeast microorganism has been engineered to disrupt, mutate, or delete one or more endogenous pyruvate decarboxylase (PDC) genes, wherein said recombinant yeast microorganism has reduced endogenous PDC activity as compared to the corresponding yeast microorganism that has not been engineered to have reduce endogenous PDC activity, and wherein said recombinant yeast microorganism produces:
   (A) isobutanol at a yield which is at least 10% of the theoretical yield of isobutanol from glucose; and/or
   (B) ethanol at a yield which is 1.8% or less of the theoretical yield of ethanol from glucose.

2. The recombinant yeast microorganism of claim 1, wherein the recombinant yeast microorganism is further engineered or selected to grow on glucose independently of C2-compounds at a growth rate substantially equivalent to the growth rate of the corresponding yeast microorganism that has not been engineered to have reduced endogenous PDC activity.

3. The recombinant yeast microorganism of claim 1, wherein the recombinant yeast microorganism is a yeast of the *Saccharomyces* clade.

4. The recombinant yeast microorganism of claim 1, wherein the recombinant yeast microorganism is a non-fermenting yeast microorganism.

5. The recombinant yeast microorganism of claim 1, wherein said one or more endogenous PDC genes is selected from the group consisting of PDC1, PDC2, PDC5, and PDC6.

6. The recombinant yeast microorganism of claim 1, wherein said α-ketoisovalerate decarboxylase is encoded by a gene that has been codon optimized for expression in yeast.

7. A method of producing isobutanol, comprising:
   (a) providing the recombinant yeast microorganism according to claim 1;
   (b) cultivating the recombinant yeast microorganism in a culture medium containing a feedstock providing the carbon source, until the isobutanol is produced; and
   (c) recovering the isobutanol.

* * * * *

(12) INTER PARTES REEXAMINATION CERTIFICATE (935th)
United States Patent
Feldman et al.

(10) Number: US 8,017,375 C1
(45) Certificate Issued: Aug. 15, 2014

(54) YEAST ORGANISM PRODUCING ISOBUTANOL AT A HIGH YIELD

(75) Inventors: Reid M. Renny Feldman, Highlands Ranch, CO (US); Uvini Gunawardena, Irvine, CA (US); Jun Urano, Aurora, CO (US); Peter Meinhold, Denver, CO (US); Aristos A. Aristidou, Highlands Ranch, CO (US); Catherine Asleson Dundon, Englewood, CO (US); Christopher Smith, Englewood, CO (US)

(73) Assignee: Gevo, Inc., Englewood, CO (US)

Reexamination Request:
No. 95/002,158, Sep. 7, 2012

Reexamination Certificate for:
Patent No.: 8,017,375
Issued: Sep. 13, 2011
Appl. No.: 12/343,375
Filed: Dec. 23, 2008

Related U.S. Application Data

(60) Provisional application No. 61/016,483, filed on Dec. 23, 2007.

(51) Int. Cl.
*C12P 7/04* (2006.01)
*C12P 7/16* (2006.01)
*C12N 1/15* (2006.01)
*C12N 1/16* (2006.01)
*C12N 15/00* (2006.01)
*C12N 9/88* (2006.01)

(52) U.S. Cl.
USPC ........ 435/254.2; 435/157; 435/160; 435/232; 435/254.21; 435/320.1

(58) Field of Classification Search
None
See application file for complete search history.

(56) References Cited

To view the complete listing of prior art documents cited during the proceeding for Reexamination Control Number 95/002,158, please refer to the USPTO's public Patent Application Information Retrieval (PAIR) system under the Display References tab.

*Primary Examiner* — Jerry D Johnson

(57) ABSTRACT

There is disclosed a method of producing isobutanol. In an embodiment, the method includes providing a microorganism transformed with an isobutanol producing pathway containing at least one exogenous gene. The microorganism is selected to produce isobutanol from a carbon source at a yield of at least 10 percent theoretical. The method includes cultivating the microorganism in a culture medium containing a feedstock providing the carbon source, until isobutanol is produced. The method includes recovering the isobutanol. In one embodiment, the microorganism is a yeast with a Crabtree-negative phenotype. In another embodiment, the microorganism is a yeast microorganism with a Crabtree-positive phenotype. There is disclosed a microorganism for producing isobutanol. In an embodiment, the microorganism includes an isobutanol producing pathway containing at least one exogenous gene, and is selected to produce a recoverable quantity of isobutanol from a carbon source at a yield of at least 10 percent theoretical.

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-7 are cancelled.

* * * * *

SEQUENCE LISTING

<160> NUMBER OF SEQ ID NOS: 55

<210> SEQ ID NO 1
<211> LENGTH: 4831
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
gcttagttta catttctttc ccaagtttaa ttcaatttct tcaacaaaga tttagagagt      60
atacttgcgc cgtcatcata ctggctgcct ttccgtttca tcaataaata tatgtattct     120
ctaattaatt ttatgctcat aatatatcgg ttgcacgaga tggtcattcc gatggtttca     180
gactctagtt aaaagaagaa gctagatgct gataatattg atttcggatg ttactgattg     240
aatattttga gctattataa taatatcaac aaagaaaatt ttaacgtggg ttgattctta     300
ggtttaaaaa gacccatcgt atatctcacc aaatatcggt accgtattcg aaggataagg     360
actaacgact taatctctaa cttgtggtaa ctaaatttag tcctttatct acaatttctc     420
tatagagcat tcaacaaaga ttgtggtttt tatctatcaa gtattattcc attactatta     480
atgtacttat aaaattctgt atatgaagag tatcaagaaa actgtgactt ctccacatca     540
gtatagtaaa gccaacaaag gggatacctt tgcagttgta gcaactattg gcgtaaacgt     600
ttcaaatggg gtaaagaaa gaataaaga gtatatcgtt catatatatc atttagaaat     660
caaatcacta aaattcgatt agttcttagc gttggtagca gcagtcaatt cgagctcata     720
gcttcaaaat gtttctactc cttttttact cttccagatt ttctcggact ccgcgcatcg     780
ccgtaccact tcaaaacacc caagcacagc atactaaatt tcccctcttt cttcctctag     840
ggtgtcgtta attcccgta ctaaaggttt ggaaaagaaa aaagagaccg cctcgtttct     900
ttttcttcgt cgaaaaggc aataaaaatt tttatcacgt ttcttttct tgaaaatttt     960 tttttgatt tttttctctt tcgatgacct cccattgata tttaagttaa taaacggtct    1020
tcaatttctc aagtttcagt ttcatttttc ttgttctatt acaactttt ttacttcttg    1080 ctcattagaa agaaagcata gcaatctaat ctaagttttc tagtatgatt gaacaagatg    1140
gattgcacgc aggttctccg gccgcttggg tggagaggct attcggctat gactgggcac    1200
aacagacaat cggctgctct gatgccgccg tgttccggct gtcagcgcag gggcgcccgg    1260 ttcttttgt caagaccgac ctgtccggtg ccctgaatga actgcaggac gaggcagcgc    1320
ggctatcgtg gctggccacg acgggcgttc cttgcgcagc tgtgctcgac gttgtcactg    1380
aagcgggaag ggactggctg ctattgggcg aagtgccggg gcaggatctc ctgtcatctc    1440
accttgctcc tgccgagaaa gtatccatca tggctgatgc aatgcggcgg ctgcatacgc    1500
ttgatccggc tacctgccca ttcgaccacc aagcgaaaca tcgcatcgag cgagcacgta    1560
ctcggatgga agccggtctt gtcgatcagg atgatctgga cgaagagcat caggggctcg    1620
cgccagccga actgttcgcc aggctcaagg cgcgcatgcc cgacggcgag gatctcgtcg    1680
tgacccatgg cgatgcctgc ttgccgaata tcatggtgga aaatggccgc ttttctggat    1740
tcatcgactg tggccggctg ggtgtggcgg accgctatca ggacatagcg ttggctaccc    1800
gtgatattgc tgaagagctt ggcggcgaat gggctgaccg cttcctcgtg ctttacggta    1860
tcgccgctcc cgattcgcag cgcatcgcct ctatcgcct tcttgacgag ttcttctgaa    1920
ccggtagagt tctccgagaa caagcagagg ttcgagtgta ctcggatcag aagttacaag    1980
```

```
ttgatcgttt atatataaac tatacagaga tgttagagtg taatggcatt gcgtaagctt    2040
ggcgtaatca tggtcatagc tgtttcctgt gtgaaattgt tatccgctca caattccaca    2100
caacatacga gccggaagca taaagtgtaa agcctgggGT gcctaatgag tgagctaact    2160
cacattaatt gcgttgcgct cactgcccgc tttccagtcg ggaaacctgt cgtgccagct    2220
gcattaatga atcggccaac gcgcggggag aggcggtttg cgtattgggc gctcttccgc    2280
ttcctcgctc actgactcgc tgcgctcggt cgttcggctg cggcgagcgg tatcagctca    2340
ctcaaaggcg gtaatacggt tatccacaga atcaggggat aacgcaggaa agaacatgtg    2400
agcaaaaggc cagcaaaagg ccaggaaccg taaaaaggcc gcgttgctgg cgttttttcca   2460
taggctccgc cccctgacg agcatcacaa aaatcgacgc tcaagtcaga ggtggcgaaa     2520
cccgacagga ctataaagat accaggcgtt tcccctgga agctccctcg tgcgctctcc     2580
tgttccgacc ctgccgctta ccggatacct gtccgccttt ctcccttcgg aagcgtggc     2640
gctttctcat agctcacgct gtaggtatct cagttcggtg taggtcgttc gctccaagct    2700
gggctgtgtg cacgaacccc ccgttcagcc cgaccgctgc gccttatccg gtaactatcg    2760
tcttgagtcc aacccggtaa gacacgactt atcgccactg gcagcagcca ctggtaacag    2820
gattagcaga gcgaggtatg taggcggtgc tacagagttc ttgaagtggt ggcctaacta    2880
cggctacact agaaggacag tatttggtat ctgcgctctg ctgaagccag ttaccttcgg    2940
aaaaagagtt ggtagctctt gatccggcaa acaaaccacc gctggtagcg gtggttttttt   3000
tgtttgcaag cagcagatta cgcgcagaaa aaaggatct caagaagatc ctttgatctt     3060
ttctacgggg tctgacgctc agtggaacga aaactcacgt taagggattt tggtcatgag    3120
attatcaaaa aggatcttca cctagatcct tttaaattaa aatgaagttt taaatcaat    3180
ctaaagtata tatgagtaaa cttggtctga cagttaccaa tgcttaatca gtgaggcacc   3240
tatctcagcg atctgtctat ttcgttcatc catagttgcc tgactccccg tcgtgtagat   3300
aactacgata cgggagggct taccatctgg ccccagtgct gcaatgatac cgcgagaccc   3360
acgctcaccg gctccagatt tatcagcaat aaaccagcca gccggaaggg ccgagcgcag   3420
aagtggtcct gcaactttat ccgcctccat ccagtctatt aattgttgcc gggaagctag   3480
agtaagtagt tcgccagtta atagtttgcg caacgttgtt gccattgcta caggcatcgt   3540
ggtgtcacgc tcgtcgtttg gtatggcttc attcagctcc ggttcccaac gatcaaggcg   3600
agttacatga tcccccatgt tgtgcaaaaa agcggttagc tccttcggtc ctccgatcgt   3660
tgtcagaagt aagttggccg cagtgttatc actcatggtt atggcagcac tgcataattc   3720
tcttactgtc atgccatccg taagatgctt ttctgtgact ggtgagtact caaccaagtc   3780
attctgagaa tagtgtatgc ggcgaccgag ttgctcttgc ccggcgtcaa tacgggataa   3840
taccgcgcca catagcagaa ctttaaaagt gctcatcatt ggaaaacgtt cttcggggcg   3900
aaaactctca aggatcttac cgctgttgag atccagttcg atgtaaccca ctcgtgcacc   3960
caactgatct tcagcatctt ttactttcac cagcgtttct gggtgagcaa aaacaggaag   4020
gcaaaatgcc gcaaaaaagg gaataagggc gacacggaaa tgttgaatac tcatactctt   4080
ccttttcaa tattattgaa gcatttatca gggttattgt ctcatgagcg gatacatatt    4140
tgaatgtatt tagaaaaata aacaaatagg ggttccgcgc acatttcccc gaaaagtgcc   4200
acctgacgtc acctggtaga ccaaagatgg tttgaacttc gacttgcttt aatctttcga   4260
acaagtaacg acctaatgta atttcagaca ttgtaattta agtggttttt gagttgtagt   4320
tttatcctta atattaatag ttaatactat aatatgtttg gctttagtgg atggtttttg   4380
```

```
aggtaatcaa aagtatataa ttaagattat gattaagaca tgatgggaaa ctctagccat      4440
tacagataat catgcccatg tatttatact ttatctgagt taactaaaaa aaatagaaag      4500
gtcatattca ccacccagcc agccctgcct ctcacctcac tctcccccct taatggataa      4560
ttgacacaag tggtactact attccaacct taagatattc atgggccaat actacgtata      4620
caccttaaaa ggttgaatct tttcacaaat attgcataat ctatcccatg gttctacata      4680
gcaaatacag aatatgcaaa atacaggaca cgcacaaggg ccagcaatgg ttagctaatt      4740
tgaataattt ccaataccat gaaattatcc cacctttttac cttggttgac tctcatttcc    4800
gattttctat accacagaaa ccgcacgtgt c                                    4831

<210> SEQ ID NO 2
<211> LENGTH: 7441
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
ccagttaact gtgggaatac tcaggtatcg taagatgcaa gagttcgaat ctcttagcaa        60
ccattatttt tttcctcaac ataacgagaa cacacagggg cgctatcgca cagaatcaaa      120
ttcgatgact ggaaattttt tgttaatttc agaggtcgcc tgacgcatat acctttttca      180
actgaaaaat tgggagaaaa aggaaaggtg agagcgccgg aaccggcttt tcatatagaa      240
tagagaagcg ttcatgacta aatgcttgca tcacaatact tgaagttgac aatattattt      300
aaggacctat tgttttttcc aataggtggt tagcaatcgt cttacttct aacttttctt       360 accttttaca tttcagcaat atatatat atatttcaag gatataccat tctaatgtct        420
gcccctaaga agatcgtcgt tttgccaggt gaccacgttg gtcaagaaat cacagccgaa      480
gccattaagg ttcttaaagc tatttctgat gttcgttcca atgtcaagtt cgatttcgaa      540
aatcatttaa ttggtggtgc tgctatcgat gctacaggtg ttccacttcc agatgaggcg      600
ctggaagcct ccaagaaggc tgatgccgtt ttgttaggtg ctgtgggtgg tcctaaatgg      660
ggtaccggta gtgttagacc tgaacaaggt ttactaaaaa tccgtaaaga acttcaattg      720
tacgccaact taagaccatg taactttgca tccgactctc ttttagactt atctccaatc      780
aagccacaat ttgctaaagg tactgacttc gttgttgtca gagaattagt gggaggtatt      840
tactttggta agagaaagga agacgatggt gatggtgtcg cttgggatag tgaacaatac      900
accgttccag aagtgcaaag aatcacaaga atggccgctt tcatggccct acaacatgag      960
ccaccattgc ctatttggtc cttggataaa gctaatgttt tggcctcttc aagattatgg     1020
agaaaaactg tggaggaaac catcaagaac gaattcccta cattgaaggt tcaacatcaa     1080
ttgattgatt ctgccgccat gatcctagtt aagaacccaa cccacctaaa tggtattata     1140
atcaccagca acatgtttgg tgatatcatc tccgatgaag cctccgttat cccaggttcc     1200 ttgggttttgt tgccatctgc gtccttggcc tctttgccag acaagaacac cgcatttggt     1260
ttgtacgaac catgccacgg ttctgctcca gatttgccaa agaataaggt caaccctatc     1320
gccactatct tgtctgctgc aatgatgttg aaattgtcat tgaacttgcc tgaagaaggt     1380
aaggccattg aagatgcagt taaaaaggtt ttggatgcag gtatcagaac tggtgattta     1440
ggtggttcca acagtaccac cgaagtcggt gatgctgtcg ccgaagaagt taagaaaatc     1500
cttgcttaaa aagattctct ttttttatga tatttgtaca taaactttat aaatgaaatt     1560
```

```
cataatagaa acgacacgaa attacaaaat ggaatatgtt cataggggtag acgaaactat    1620 atacgcaatc tacatacatt tatcaagaag gagaaaaagg aggatgtaaa ggaatacagg    1680
taagcaaatt gatactaatg gctcaacgtg ataaggaaaa agaattgcac tttaacatta    1740
atattgacaa ggaggagggc accacacaaa aagttaggtg taacagaaaa tcatgaaact    1800
atgattccta atttatatat tggaggattt tctctaaaaa aaaaaaaata caacaaataa    1860
aaaacactca atgacctgac catttgatgg agttgccggc gatcacagcg acggtggtg     1920 gcatgatggg gcttgcgatg ctatgtttgt ttgttttgtg atgatgtata ttattattga    1980
aaaacgatat cagacatttg tctgataatg cttcattatc agacaaatgt ctgatatcgt    2040
ttggagaaaa agaaaaggaa aacaaactaa atatctacta tataccactg tattttatac    2100
taatgacttt ctacgcctag tgtcaccctc tcgtgtaccc attgaccctg tatcggcgcg    2160
ttgcctcgcg ttcctgtacc atatattttt gtttatttag gtattaaaat ttactttcct    2220
catacaaata ttaaattcac caaacttctc aaaaactaat tattcgtagt tacaaactct    2280
attttacaat cacgtttatt caaccattct acatccaata accaaaatgc ccatgtacct    2340
ctcagcgaag tccaacggta ctgtccaata ttctcattaa atagtctttc atctatatat    2400
cagaaggtaa ttataattag agatttcgaa tcattaccgt gccgattcgc acgctgcaac    2460
ggcatgcatc actaatgaaa agcatacgac gcctgcgtct gacatgcact cattctgaag    2520
aagattctgg gcgcgtttcg ttctcgtttt cctctgtata ttgtactctg gtggacaatt    2580
tgaacataac gtcttttcacc tcgccattct caataatggg ttccaattct atccaggtag    2640
cggttaattg acggtgctta agccgtatgc tcactctaac gctaccgttg tccaaacaac    2700 ggacccettt gtgacgggtg taagacccat catgaagtaa aacatctcta acggtatgga    2760
aaagagtggt acggtcaagt ttcctggcac gagtcaattt tccctcttcg tgtagatcgg    2820
taccggccgc aaattaaagc cttcgagcgt cccaaaacct tctcaagcaa ggttttcagt    2880
ataatgttac atgcgtacac gcgtctgtac agaaaaaaaa gaaaaatttg aaatataaat    2940
aacgttctta atactaacat aactataaaa aaataaatag ggacctagac ttcaggttgt    3000
ctaactcctt cctttcggt tagagcggat gtgggggggag ggcgtgaatg taagcgtgac    3060
ataactaatt acatgactcg agcggccgcg gatcctcaat aaaactcttc aggcaataat    3120
ttttctgcta atttaatgtt atcagaatag tccaaggaa cgtcaattac tactggtcca     3180
gtagtatctg ggattgattt aagaatttca gcaagttctt ctttgctgtg tgcacggtaa    3240
ccttttgctc ccattgcttc agcatatttt acgtaatcaa catagccaaa atcaacggct    3300
gctgaacgac catatttcat ttcttcttgg aatttaacca tatcataatg gccgtcattc    3360
cagataattt gaacgattgg aagattcaaa cgtacagctg tttccaactc ttgccctgtg    3420
aaaaggaagc ctccatcacc agagtgtgaa taaactttt tacctgggcg caacaatgcg    3480
gctgtaattg cccaaggaag tgcaactcca agtgtttgca ttccgtttga gaagaggaga    3540
tgacgtggtt cgtatgattt gaaatgacgt gccatccaaa tgtagagtga acctacgtca    3600
acggttactg tttcatcatc tttaacgatt tcttggaaag tgctgaccaa atcaagaggg    3660
tgcattctac cttcttcagt attttcagta tcaaattcgt gttgctcagc aacttcatga    3720
aggccatcga gataatcttt tgttccttt ggattttgt atccacgaac agctggtaaa      3780
agattatcca atgttgctgc gatatcacca attaattcac gttctggttg gtagtaagta    3840
tcaatttcag caatggcatt atcaataacg ataattcgac tatcaatttc tgcattccag    3900
ttacgagctt catattcaat tgggtcataa ccaacagcaa taacaaggtc agaacgtttc    3960
```

-continued

```
agaagcatat ctcctggttg attgcggaaa agaccgatac gtccataaaa agtatgttct    4020
aaatcatgtg aaataacccc tgcaccttgg aatgtttcaa cgacaggaat attaacatga    4080
gttaatagat tacgcaatga tgaagcgact ttagcatctg aagcaccagc tccaaccaaa    4140
attactggca atacagcatt tttaattgct tgtgctaaat aattaatgtc atcaatagag    4200
gcattcccca ttttagggtc tgaaagtggt tgaatggcct tgattgatac ttcggcatcc    4260
gttacatctt gggggattga taagaaagtt gcacctggat gtcctgattt tgcaatacga    4320
taagcgttgg caattgattc agaaagtgta tcagggtcaa gaacttctgc tgaatatttt    4380
gttgctgatt gcatcattcc agcattatcc attgattggt gcgcacgttt aagacggtca    4440
cttcgtttaa cttgtccacc gatagccaaa atagcatcac cttctgaagt cgcggtcaaa    4500
agcggagtcg caaggtttga tacaccaggc ccactcgtaa caactactac accaggttcg    4560
ccagtcaaac gaccaacagc ttgagccatg aaagcagctc cttgctcatg acgagtcacg    4620
accatttgag ggccttcttc attttctaat aaatcaaaaa cccggtcaat ttttgctcct    4680
ggaatcccaa atacatactt cactttatgg ttaatcaaac tatcgacaac caagttcgcc    4740
ccaaattgtt tctcagacat gtcgacaccg atatacctgt atgtgtcacc accaatgtat    4800
ctataagtat ccatgctagt tctagaaaac ttagattaga ttgctatgct ttcttttctaa    4860 tgagcaagaa gtaaaaaaag ttgtaataga acaagaaaaa tgaaactgaa acttgagaaa    4920
ttgaagaccg tttattaact taaatatcaa tgggaggtca tcgaaagaga aaaaaatcaa    4980 aaaaaaatt tcaagaaaa agaaacgtga taaaatttt tattgccttt ttcgacgaag        5040 aaaagaaac gaggcggtct cttttttctt ttccaaacct ttagtacggg taattaacga    5100
caccctagag gaagaaagag gggaaattta gtatgctgtg cttgggtgtt ttgaagtggt    5160
acggcgatgc gcggagtccg agaaaatctg gaagagtaaa aaaggagtag aaacattttg    5220
aagctatgag ctccagcttt tgttcccttt agtgagggtt aattgcgcgc ttggcgtaat    5280
catggtcata gctgtttcct gtgtgaaatt gttatccgct cacaattcca cacaacatag    5340
gagccggaag cataaagtgt aaagcctggg gtgcctaatg agtgaggtaa ctcacattaa    5400
ttgcgttgcg ctcactgccc gctttccagt cgggaaacct gtcgtgccag ctgcattaat    5460
gaatcggcca acgcgcgggg agaggcggtt tgcgtattgg gcgctcttcc gcttcctcgc    5520
tcactgactc gctgcgctcg tcgttcggc tgcggcgagc ggtatcagct cactcaaagg    5580
cggtaatacg gttatccaca gaatcagggg ataacgcagg aaagaacatg tgagcaaaag    5640
gccagcaaaa ggccaggaac cgtaaaaagg ccgcgttgct ggcgtttttc cataggctcc    5700
gcccccctga cgagcatcac aaaaatcgac gctcaagtca ggtggcga aacccgacag     5760 gactataaag ataccaggcg tttccccctg gaagctccct cgtgcgctct cctgttccga    5820
ccctgccgct taccggatac ctgtccgcct ttctcccttc gggaagcgtg gcgctttctc    5880
atagctcacg ctgtaggtat ctcagttcgg tgtaggtcgt tcgctccaag ctgggctgtg    5940
tgcacgaacc ccccgttcag cccgaccgct gcgccttatc cggtaactat cgtcttgagt    6000
ccaacccggt aagacacgac ttatcgccac tggcagcagc cactggtaac aggattagca    6060
gagcgaggta tgtaggcggt gctacagagt tcttgaagtg gtggcctaac tacggctaca    6120
ctagaaggac agtatttggt atctgcgctc tgctgaagcc agttaccttc ggaaaaagag    6180
ttggtagctc ttgatccggc aaacaaacca ccgctggtag cggtggtttt tttgtttgca    6240
agcagcagat tacgcgcaga aaaaaaggat ctcaagaaga tcctttgatc ttttctacgg    6300
ggtctgacgc tcagtggaac gaaaactcac gttaagggat tttggtcatg agattatcaa    6360
```

```
aaaggatctt cacctagatc cttttaaatt aaaaatgaag ttttaaatca atctaaagta    6420
tatatgagta aacttggtct gacagttacc aatgcttaat cagtgaggca cctatctcag    6480
cgatctgtct atttcgttca tccatagttg cctgactccc cgtcgtgtag ataactacga    6540
tacgggaggg cttaccatct ggccccagtg ctgcaatgat accgcgagac ccacgctcac    6600
cggctccaga tttatcagca ataaaccagc cagccggaag ggccgagcgc agaagtggtc    6660
ctgcaacttt atccgcctcc atccagtcta ttaattgttg ccgggaagct agagtaagta    6720
gttcgccagt taatagtttg cgcaacgttg ttgccattgc tacaggcatc gtggtgtcac    6780
gctcgtcgtt tggtatggct tcattcagct ccggttccca acgatcaagg cgagttacat    6840
gatcccccat gttgtgcaaa aaagcggtta gctccttcgg tcctccgatc gttgtcagaa    6900
gtaagttggc cgcagtgtta tcactcatgg ttatggcagc actgcataat tctcttactg    6960
tcatgccatc cgtaagatgc ttttctgtga ctggtgagta ctcaaccaag tcattctgag    7020
aatagtgtat gcggcgaccg agttgctctt gcccggcgtc aatacgggat aataccgcgc    7080
cacatagcag aactttaaaa gtgctcatca ttggaaaacg ttcttcgggg cgaaaactct    7140
caaggatctt accgctgttg agatccagtt cgatgtaacc cactcgtgca cccaactgat    7200
cttcagcatc ttttactttc accagcgttt ctgggtgagc aaaaacagga aggcaaaatg    7260
ccgcaaaaaa gggaataagg gcgacacgga aatgttgaat actcatactc ttcctttttc    7320
aatattattg aagcatttat cagggttatt gtctcatgag cggatacata tttgaatgta    7380
tttagaaaaa taaacaaata ggggttccgc gcacatttcc ccgaaaagtg ccacctgacg    7440
t                                                                   7441
```

<210> SEQ ID NO 3
<211> LENGTH: 8949
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
caggcaagtg cacaaacaat acttaaataa atactactca gtaataacct atttcttagc      60 attttttgacg aaatttgcta ttttgttaga gtcttttaca ccatttgtct ccacacctcc    120
gcttacatca acaccaataa cgccatttaa tctaagcgca tcaccaacat tttctggcgt    180
cagtccacca gctaacataa aatgtaagct ttcggggctc tcttgccttc caacccagtc    240
agaaatcgag ttccaatcca aaagttcacc tgtcccacct gcttctgaat caaacaaggg    300
aataaacgaa tgaggtttct gtgaagctgc actgagtagt atgttgcagt cttttggaaa    360
tacgagtctt ttaataactg gcaaaccgag gaactcttgg tattcttgcc acgactcatc    420
tccatgcagt tggacgatat caatgccgta atcattgacc agagccaaaa catcctcctt    480
aggttgatta cgaaacacgc caaccaagta tttcggagtg cctgaactat ttttatatgc    540
ttttacaaga cttgaaattt tccttgcaat aaccgggtca attgttctct ttctattggg    600
cacacatata atacccagca agtcagcatc ggaatctaga gcacattctg cggcctctgt    660
gctctgcaag ccgcaaactt tcaccaatgg accagaacta cctgtgaaat taataacaga    720
catactccaa gctgcctttg tgtgcttaat cacgtatact cacgtgctca atagtcacca    780
atgccctccc tcttggccct ctcctttttct ttttcgacc gaattaattc ttaatcggca    840 aaaaagaaa agctccggat caagattgta cgtaaggtga caagctatttt ttcaataaag    900 aatatcttcc actactgcca tctggcgtca taactgcaaa gtacacatat attacgatgc    960
```

```
tgtctattaa atgcttccta tattatatat atagtaatgt cgttgacgtc gccggcgatc    1020
acagcggacg gtggtggcat gatggggctt gcgatgctat gtttgtttgt tttgtgatga    1080
tgtatattat tattgaaaaa cgatatcaga catttgtctg ataatgcttc attatcagac    1140
aaatgtctga tatcgtttgg agaaaaagaa aaggaaaaca aactaaatat ctactatata    1200
ccactgtatt ttatactaat gactttctac gcctagtgtc accctctcgt gtacccattg    1260
accctgtatc ggcgcgttgc ctcgcgttcc tgtaccatat attttttgttt atttaggtat    1320 taaaatttac tttcctcata caaatattaa attcaccaaa cttctcaaaa actaattatt    1380
cgtagttaca aactctattt tacaatcacg tttattcaac cattctacat ccataaacca    1440
aaatgcccat gtacctctca gcgaagtcca acggtactgt ccaatattct cattaaaatag   1500 tctttcatct atatatcaga aggtaattat aattagagat ttcgaatcat taccgtgccg    1560
attcgcacgc tgcaacggca tgcatcacta atgaaaagca tacgacgcct gcgtctgaca    1620
tgcactcatt ctgaagaaga ttctgggcgc gtttcgttct cgtttttcctc tgtatattgt   1680 actctggtgg acaatttgaa cataacgtct ttcacctcgc cattctcaat aatgggttcc    1740
aattctatcc aggtagcggt taattgacgg tgcttaagcc gtatgctcac tctaacgcta    1800
ccgttgtcca acaacggac cccttttgtga cgggtgtaag acccatcatg aagtaaaaca    1860
tctctaacgg tatggaaaag agtggtacgg tcaagtttcc tggcacgagt caattttccc    1920
tcttcgtgta gatcggtacc ggccgcaaat taaagccttc gagcgtccca aaaccttctc    1980
aagcaaggtt ttcagtataa tgttacatgc gtacacgcgt ctgtacagaa aaaaagaaa     2040 aatttgaaat ataataacg ttcttaatac taacataact ataaaaaaat aaatagggac    2100
ctagacttca ggttgtctaa ctccttcctt ttcggttaga gcggatgtgg ggggaggcg     2160 tgaatgtaag cgtgacataa ctaattacat gactcgagcg gccgcggatc cttaacccgc    2220
aacagcaata cgtttcatat ctgtcatata gccgcgcagt ttcttaccta cctgctcaat    2280
cgcatggctg cgaatcgctt cgttcacatc acgcagttgc ccgttatcta ccgcgccttc    2340
cggaatagct ttacccaggt cgcccggttg cagctctgcc ataaacggtt tcagcaacgg    2400
cacacaagcg taagagaaca gatagttacc gtactcagcg gtatcagaga taaccacgtt    2460
catttcgtac agacgcttac gggcgatggt gttggcaatc agcggcagct cgtgcagtga    2520
ttcataatat gcagactctt caatgatgcc ggaatcgacc atggtttcga acgccagttc    2580
aacgcccgct ttcaccatcg caatcatcag tacgccttta tcgaagtact cctgctcgcc    2640 gatttttgcct tcatactgcg gcgcggtttc aaacgcggtt ttgccggtct cttcacgcca    2700
ggtcagcagt ttcttatcat cgttggccca gtccgccatc ataccggaag agaattcgcc    2760
ggagatgatg tcgtccatat gtttctggaa caggggtgcc atgatctctt tcagctgttc    2820
agaaagcgca taagcacgca gtttcgccgg gttagagaga cggtccatca tcagggtgat    2880
gccgccctgt ttcagtgctt cggtgatggt ttcccaaccg aactgaatca gttttttctgc    2940 gtatgctgga tcggtacctt cttccaccag cttgtcgaag cacagcagag agccagcctg    3000
caacataccg cacaggatgg tttgctcgcc catcaggtca gatttcactt ccgcaacgaa    3060
ggacgattcc agcacaccg cacggtgacc accggttgca gccgcccagg ctttggcaat    3120
cgccatgcct tcgcctttcg gatcgttttc cgggtgaacg gcaatcagcg tcggtacgcc    3180
gaacccacgt ttgtactctt cacgcacttc ggtgcctggg catttcggcg caaccatcac    3240
tacggtgata tctttacgga tctgctcgcc cacttcgacg atgttgaaac cgtgcgagta    3300
gcccagcgcc gcgccgtctt tcatcagtgg ctgtacggtg cgcactacat cagagtgctg    3360
```

```
cttgtccggc gtcaggttaa tcaccagatc cgcctgtggg atcagttctt cgtaagtacc   3420
cactttaaaa ccatttttcgg tcgctttacg ccaggacgcg cgcttctcgg caatcgcttc   3480
tttacgcaga gcgtaggaga tatcgagacc agaatcacgc atgttcaggc cctggttcag   3540
accctgtgcg ccacagccga cgatgactac tttttttaccc tgaaggtagc tcgcgccatc   3600
ggcgaattca tcgcggccca taaagcgaca tttgcccagc tgtgccagct gctggcgcag   3660
attcagtgta ttgaagtagt tagccatgtc gacaccatct tcttctgaga tgagttttttg   3720 ttccatgcta gttctagaat ccgtcgaaac taagttctgg tgttttaaaa ctaaaaaaaa   3780
gactaactat aaaagtagaa tttaagaagt ttaagaaata gatttacaga attacaatca   3840
atacctaccg tctttatata cttattagtc aagtagggga ataatttcag ggaactggtt   3900 tcaaccttttt ttttcagctt tttccaaatc agagagagca gaaggtaata gaaggtgtaa   3960
gaaaatgaga tagatacatg cgtgggtcaa ttgccttgtg tcatcattta ctccaggcag   4020
gttgcatcac tccattgagg ttgtgcccgt ttttgcctg tttgtgcccc tgttctctgt   4080
agttgcgcta agagaatgga cctatgaact gatggttggt gaagaaaaca atattttggt   4140
gctgggattc ttttttttttc tggatgccag cttaaaaagc gggctccatt atatttagtg   4200
gatgccagga ataaactgtt cacccagaca cctacgatgt tatatattct gtgtaacccg   4260
ccccctattt tgggcatgta cgggttacag cagaattaaa aggctaattt tttgactaaa   4320
taaagttagg aaaatcacta ctattaatta tttacgtatt ctttgaaatg gcgagtattg   4380
ataatgataa actgagctag atctgggccg cggatcctta accccccagt ttcgatttat   4440
cgcgcaccgc gcctttgtcg gcgctggttg ccaggctggc ataagcacgc agggcaaagg   4500
agacctgacg ttcacgattt ttcggcgtcc aggctttgtc acctcgagcg tcctgcgctt   4560
cacgacgcgc cgccagttcg gcatcgctta cctgtaactg aatgccacgg ttcgggatgt   4620
cgatagcgat caggtcacca tcttcaatca ggccaatgct gccgccgctt gccgcttccg   4680
gtgagacgtg gccgatggaa agaccagagg tgccaccaga gaaacgaccg tcggtgatca   4740
gcgcacaggc tttgccgaga cccattgatt tcaggaagct ggttgggtag agcatttcct   4800
gcatccccgg accgcctttc gggccttcat agcgaattac taccacatct ccggcgacaa   4860
ctttaccgcc gagaatcgct tctaccgcat cgtcctggct ttcgtacact ttcgccgggc   4920
cggtgaattt gaggatgctg tcatcgacgc ctgccgtttt cacgatgcag ccgttttccg   4980
caaagttacc gtagagcacc gccaggccgc cgtctttgct gtaggcgtgt tccagcgagc   5040
ggatacagcc attggcgcga tcgtcgtcca gcgtatccca acggcaatct tgcgagaatg   5100
cctgtgtggt acgaatgcct gcaggacctg cgcggaacat attttttacc gcgtcatcct   5160
gggtcagcat aacgtcgtat tgttccagcg tttgcggcaa cgtcaggcca agtacgtttt   5220
tcacatcacg gttcagtaac cccgcgcgat ccagttcgcc gagaataccg ataacaccac   5280
cagcacggtg aacatcttcc atatggtatt tctgggtgct cggcgcaact ttacacagct   5340
gtggaacctt gcgggaaagc ttatcgatat cactcatggt gaagtcgatt tccgcttcct   5400
gcgccgccgc cagcaggtga agtacggtgt tagtcgatcc acccatcgcg atatccagcg   5460
tcatggcgtt ttcaaacgcc gccttactgg cgatattacg cggcagtgca ctttcgtcgt   5520
tttgctcgta ataacgtttg gtcaattcaa caatgcgttt accagcatta aggaacagct   5580
gcttacggtc ggcgtggggtt gccagcagcg agccgttgcc cggctgcgac aggcccagcg   5640
cttcggtcag gcagttcatt gagttagcgg taaacatccc ggagcaggaa ccgcaggtcg   5700
gacacgcgga acgttcaacc tgatcgctct gggagtcaga tactttcggg tctgcgccct   5760
```

```
ggatcatcgc atcaaccaga tcgagcttga tgatctgatc ggaaagtttg gtttccccgg    5820
cctccatcgg gccgccggaa acaaagatca ccggaatatt caggcgcagg gaagccatca    5880
gcatccccgg ggtgattttg tcgcagttag agatgcagac catggcgtcg gcgcagtggg    5940
cgttgaccat atactcaacg gaatcagcga tcagttcgcg agatggcagt gaataaagca    6000 tcccccgtg gcccatggca atcccatcat ccaccgcaat ggtgttgaac tctttggcaa     6060
cgccgccagc cgcttcaatt tgttcggcga ccagtttacc gagatcgcgc agatggacgt    6120
gacccggtac aaattgggtg aacgagttca caaccgcgat aatcggctta ccgaaatcgg    6180
cgtcggtcat tccggtggcg cgccacagcg cacgagcacc cgccatatta cgaccatgag    6240
tggtggtggc ggaacggtac ttaggcatgt cgacaccgat atacctgtat gtgtcaccac    6300
caatgtatct ataagtatcc atgctagttc tagaaaactt agattagatt gctatgcttt    6360
ctttctaatg agcaagaagt aaaaaaagtt gtaatagaac aagaaaaatg aaactgaaac    6420
ttgagaaatt gaagaccgtt tattaactta aatatcaatg ggaggtcatc gaaagagaaa    6480
aaaatcaaaa aaaaaatttt caagaaaaag aaacgtgata aaaattttta ttgccttttt    6540
cgacgaagaa aaagaaacga ggcggtctct tttttctttt ccaaaccttt agtacgggta    6600
attaacgaca ccctagagga agaaagaggg gaaatttagt atgctgtgct tgggtgtttt    6660
gaagtggtac ggcgatgcgc ggagtccgag aaaatctgga agagtaaaaa aggagtagaa    6720
acattttgaa gctatgagct ccagcttttg ttcccttag tgagggttaa ttgcgcgctt     6780
ggcgtaatca tggtcatagc tgtttcctgt gtgaaattgt tatccgctca caattccaca    6840
caacatagga gccggaagca taaagtgtaa agcctggggt gcctaatgag tgaggtaact    6900
cacattaatt gcgttgcgct cactgcccgc tttccagtcg ggaaacctgt cgtgccagct    6960
gcattaatga atcggccaac gcgcgggag aggcggtttg cgtattgggc gctcttccgc      7020
ttcctcgctc actgactcgc tgcgctcggt cgttcggctg cggcgagcgg tatcagctca    7080
ctcaaaggcg gtaatacggt tatccacaga atcagggga taacgcagga agaacatgtg     7140
agcaaaaggc cagcaaaagg ccaggaaccg taaaaaggcc gcgttgctgg cgttttcca    7200 taggctccgc cccctgacg agcatcacaa aaatcgacgc tcaagtcaga ggtggcgaaa     7260
cccgacagga ctataaagat accaggcgtt ccccctgga agctccctcg tgcgctctcc     7320
tgttccgacc ctgccgctta ccggatacct gtccgccttt ctcccttcgg aagcgtggc     7380 gctttctcat agctcacgct gtaggtatct cagttcggtg taggtcgttc gctccaagct    7440
gggctgtgtg cacgaacccc ccgttcagcc cgaccgctgc gccttatccg gtaactatcg    7500
tcttgagtcc aacccggtaa gacacgactt atcgccactg gcagcagcca ctggtaacag    7560
gattagcaga gcgaggtatg taggcggtgc tacagagttc ttgaagtggt ggcctaacta    7620
cggctacact agaaggacag tatttggtat ctgcgctctg ctgaagccag ttaccttcgg    7680
aaaaagagtt ggtagctctt gatccggcaa acaaaccacc gctggtagcg gtggtttttt    7740
tgtttgcaag cagcagatta cgcgcagaaa aaaaggatct caagaagatc ctttgatctt    7800
ttctacgggg tctgacgctc agtggaacga aaactcacgt taagggattt tggtcatgag    7860
attatcaaaa aggatcttca cctagatcct tttaaattaa aaatgaagtt ttaaatcaat    7920
ctaaagtata tatgagtaaa cttggtctga cagttaccaa tgcttaatca gtgaggcacc    7980
tatctcagcg atctgtctat ttcgttcatc catagttgcc tgactccccg tcgtgtagat    8040
aactacgata cgggagggct taccatctgg ccccagtgct gcaatgatac cgcgagaccc    8100
acgctcaccg gctccagatt tatcagcaat aaaccagcca gccggaaggg ccgagcgcag    8160
```

```
aagtggtcct gcaactttat ccgcctccat ccagtctatt aattgttgcc gggaagctag      8220
agtaagtagt tcgccagtta atagtttgcg caacgttgtt gccattgcta caggcatcgt      8280
ggtgtcacgc tcgtcgtttg gtatggcttc attcagctcc ggttcccaac gatcaaggcg      8340
agttacatga tcccccatgt tgtgcaaaaa agcggttagc tccttcggtc ctccgatcgt      8400
tgtcagaagt aagttggccg cagtgttatc actcatggtt atggcagcac tgcataattc      8460
tcttactgtc atgccatccg taagatgctt ttctgtgact ggtgagtact caaccaagtc      8520
attctgagaa tagtgtatgc ggcgaccgag ttgctcttgc ccggcgtcaa tacgggataa      8580
taccgcgcca catagcagaa ctttaaaagt gctcatcatt ggaaaacgtt cttcggggcg      8640
aaaactctca aggatcttac cgctgttgag atccagttcg atgtaaccca ctcgtgcacc      8700
caactgatct tcagcatctt ttactttcac cagcgtttct gggtgagcaa aaacaggaag      8760
gcaaaatgcc gcaaaaaagg gaataagggc gacacggaaa tgttgaatac tcatactctt      8820
cctttttcaa tattattgaa gcatttatca gggttattgt ctcatgagcg gatacatatt      8880
tgaatgtatt tagaaaaata aacaataggg gttccgcgc acatttcccc gaaaagtgcc      8940
acctgacgt                                                             8949
```

<210> SEQ ID NO 4
<211> LENGTH: 8800
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
ctgattggaa agaccattct gctttacttt tagagcatct tggtcttctg agctcattat       60
acctcaatca aaactgaaat taggtgcctg tcacggctct ttttttactg tacctgtgac      120
ttcctttctt atttccaagg atgctcatca caatacgctt ctagatctat tatgcattat      180
aattaatagt tgtagctaca aaaggtaaaa gaaagtccgg ggcaggcaac aatagaaatc      240
ggcaaaaaaa actacagaaa tactaagagc ttcttcccca ttcagtcatc gcatttcgaa      300
acaagagggg aatggctctg gctagggaac taaccaccat cgcctgactc tatgcactaa      360
ccacgtgact acatatatgt gatcgttttt aacattttc aaaggctgtg tgtctggctg      420
tttccattaa ttttcactga ttaagcagtc atattgaatc tgagctcatc accaacaaga      480
aatactaccg taaagtgta aaagttcgtt taaatcattt gtaaactgga acagcaagag      540
gaagtatcat cagctagccc cataaactaa tcaaggagg atgtctacta agagttactc      600
ggaaagagca gctgctcata gaagtccagt tgctgccaag cttttaaact tgatggaaga      660
gaagaagtca aacttatgtg cttctcttga tgttcgtaaa acagcagagt tgttaagatt      720
agttgaggtt ttgggtccat atatctgtct attgaagaca catgtagata tcttggagga      780
tttcagcttt gagaatacca ttgtgccgtt gaagcaatta gcagagaaac acaagttttt      840
gatatttgaa gacaggaagt ttgccgacat tgggaacact gttaaattac aatacacgtc      900
tggtgtatac cgtatcgccg aatggtctga tatcaccaat gcacacggtg tgactggtgc      960
gggcattgtt gctggtttga agcaaggtgc cgaggaagtt acgaaagaac ctagaggggtt     1020 gttaatgctt gccgagttat cgtccaaggg gtctctagcg cacggtgaat acactcgtgg     1080
gaccgtggaa attgccaaga gtgataagga ctttgttatt ggatttattg ctcaaaacga     1140
tatgggtgga agagaagagg gctacgattg gttgatcatg acgccaggtg ttggtcttga     1200
```

```
tgacaaaggt gatgctttgg gacaacaata cagaactgtg gatgaagttg ttgccggtgg    1260
atcagacatc attattgttg gtagaggtct tttcgcaaag ggaagagatc ctgtagtgga    1320
aggtgagaga tacagaaagg cgggatggga cgcttacttg aagagagtag gcagatccgc    1380
ttaagagttc tccgagaaca agcagaggtt cgagtgtact cggatcagaa gttacaagtt    1440
gatcgtttat atataaacta tacagagatg ttagagtgta atggcattgc gtgccggcga    1500
tcacagcgga cggtggtggc atgatggggc ttgcgatgct atgtttgttt gttttgtgat    1560
gatgtatatt attattgaaa aacgatatca gacatttgtc tgataatgct tcattatcag    1620
acaaatgtct gatatcgttt ggagaaaaag aaaaggaaaa caaactaaat atctactata    1680
taccactgta ttttatacta atgactttct acgcctagtg tcaccctctc gtgtacccat    1740
tgaccctgta tcggcgcgtt gcctcgcgtt cctgtaccat atattttgt ttatttaggt     1800 attaaatttt actttcctca tacaaatatt aaattcacca aacttctcaa aaactaatta    1860
ttcgtagtta caaactctat tttacaatca cgtttattca accattctac atccaataac    1920
caaaatgccc atgtacctct cagcgaagtc caacggtact gtccaatatt ctcattaaat    1980 agtcttttcat ctatatatca gaaggtaatt ataattagag atttcgaatc attaccgtgc   2040
cgattcgcac gctgcaacgg catgcatcac taatgaaaag catacgacgc ctgcgtctga    2100
catgcactca ttctgaagaa gattctgggc gcgtttcgtt ctcgttttcc tctgtatatt    2160
gtactctggt ggacaatttg aacataacgt cttttcacctc gccattctca ataatgggtt    2220
ccaattctat ccaggtagcg gttaattgac ggtgcttaag ccgtatgctc actctaacgc    2280
taccgttgtc caaacaacgg acccctttgt gacgggtgta agaccatca tgaagtaaaa     2340 catctctaac ggtatggaaa agagtggtac ggtcaagttt cctggcacga gtcaattttc    2400
cctcttcgtg tagatcggta ccggccgcaa attaaagcct tcgagcgtcc caaaaccttc    2460
tcaagcaagg ttttcagtat aatgttacat gcgtacacgc gtctgtacag aaaaaaaaga    2520
aaaatttgaa atataaataa cgttcttaat actaacataa ctataaaaaa ataaataggg    2580
acctagactt caggttgtct aactccttcc ttttcggtta gagcggatgt ggggggaggg    2640
cgtgaatgta agcgtgacat aactaattac atgactcgag cggccgccta tttatggaat    2700
ttcttatcat aatcgaccaa agtaaatctg tatttgacgt ctccgctttc catccttgta    2760
aaggcatggc tgacgccttc ttcgctgatc ggaagttttt ccacccatat tttgacattc    2820
ttttcggaaa ctaatttcaa tagttgttcg atttccttcc tagatccgat agcactgctt    2880
gagattgata ctcccattag gcccaacggt tttaaaacaa gcttttcatt aacttcagga    2940
gcagcaattg aaacgatgga gcctccaatc ttcataatct taacgatact gtcaaaatta    3000
actttcgaca aagatgatga gcaaacgaca agaaggtcca aagcgttaga gtattgttct    3060
gtccagcctt tatcctccaa catagcaata tagtgatcag caccgagttt catagaatcc    3120
tcccgcttgg agtggcctcg cgaaaacgca taaacctcgg ctcccatagc tttagccaac    3180
agaatcccca tatgcccaat accaccgatg ccaacaatac ctaccctctt acctggacca    3240
cagccatttc ttagtagtgg agagaaaact gtaataccac cacacaataa tggagcggct    3300
agcggacttg gaatattttc tggtattga atagcaaagt gttcatgaag cctcacgtgg     3360
gaggcaaagc ctccttgtga aatgtagccg tccttgtaag gagtccacat agtcaaaacg    3420
tggtcattgg tacagtattg ctcgttgtca cttttgcaac gttcacactc aaaacacgcc    3480
aaggcttggg caccaacacc aacacggtca ccgattttta ccccagtgtg gcacttggat    3540
ccaaccttca ccacgcggcc aattattca tgtccaagga tttgattttc tgggactgga    3600
```

```
ccccaattac caacggctat atgaaaatca gatccgcaga taccacaggc ttcaatttca   3660
acatcaacgt catgatcgcc aaagggtttt gggtcaaaac tcactaattt aggatgcttc   3720
caatcctttg cgttggaaat accgatgccc tgaaattttt ctgggtaaag catgtcgaca   3780
ccatcttctt ctgagatgag ttttttgttcc atgctagttc tagaatccgt cgaaactaag   3840
ttctggtgtt ttaaaactaa aaaaaagact aactataaaa gtagaattta agaagtttaa   3900
gaaatagatt tacagaatta caatcaatac ctaccgtctt tatatactta ttagtcaagt   3960
aggggaataa tttcagggaa ctggtttcaa ccttttttt cagcttttc caaatcagag     4020
agagcagaag gtaatagaag gtgtaagaaa atgagataga tacatgcgtg ggtcaattgc   4080
cttgtgtcat catttactcc aggcaggttg catcactcca ttgaggttgt gcccgttttt   4140
tgcctgtttg tgcccctgtt ctctgtagtt gcgctaagag aatggaccta tgaactgatg   4200
gttggtgaag aaaacaatat tttggtgctg ggattctttt tttttctgga tgccagctta   4260
aaaagcgggc tccattatat ttagtggatg ccaggaataa actgttcacc cagacaccta   4320
cgatgttata tattctgtgt aacccgcccc ctattttggg catgtacggg ttacagcaga   4380
attaaaaggc taattttttg actaaataaa gttaggaaaa tcactactat taattattta   4440
cgtattcttt gaaatggcga gtattgataa tgataaactg aggatcctta ggatttattc   4500
tgttcagcaa acagcttgcc cattttcttc agtaccttcg gtgcgccttc tttcgccagg   4560
atcagttcga tccagtacat acggttcgga tcggcctggg cctctttcat cacgctcaca   4620
aattcgtttt cggtacgcac aattttagac acaacacggt cctcagttgc gccgaaggac   4680
tccggcagtt tagagtagtt ccacataggg atatcgttgt aagactggtt cggaccgtgg   4740
atctcacgct caacggtgta gccgtcattg ttaataatga agcaaatcgg gttgatcttt   4800
tcacgaattg ccagacccag ttcctgtacg gtcagctgca gggaaccgtc accgatgaac   4860
agcagatgac gagattcttt atcagcgatc tgagagccca gcgctgccgg gaaagtatag   4920
ccaatgctac cccacagcgg ctgaccgata aaatggcttt tggatttcag aaagatagaa   4980
gacgcgccga aaaagctcgt accttgttcc gccacgatgg tttcattgct ctgggtcagg   5040
ttctccacgg cctgccacag gcgatcctgg gacagcagtg cgttagatgg tacgaaatct   5100
tcttgctttt tgtcaatgta tttgccttta tactcgattt cggacaggtc cagcagagag   5160
ctgatcaggc tttcgaagtc gaagttctgg atacgctcgt tgaagatttt accctcgtcg   5220
atgttcaggc taatcatttt gttttcgttc agatggtgag tgaatgcacc ggtagaagag   5280
tcggtcagtt taacgcccag catcaggatg aagtccgcag attcaacaaa ttctttcagg   5340
ttcggttcgc tcagagtacc gttgtagatg cccaggaaag acggcagagc ctcgtcaaca   5400
gaggacttgc cgaagttcag ggtggtaatc ggcagtttgg ttttgctgat gaattgggtc   5460
acggtcttct ccagaccaaa agaaatgatt tcgtggccgg tgatcacgat tggtttcttt   5520
gcgttttca gagactcctg gattttgttc aggatttcct ggtcgctagt gttagaagtg    5580
gagttttctt tcttcagcgg caggctcggt ttttccgctt tagctgccgc aacatccaca   5640
ggcaggttga tgtaaactgg tttgcgttct ttcagcagcg cagacagaac gcggtcgatt   5700
tccacagtag cgttctctgc agtcagcagc gtacgtgccg cagtcacagg ttcatgcatt   5760
ttcatgaagt gtttgaaatc gccgtcagcc agagtgtggt ggacgaattt accttcgttc   5820
tgaactttgc tcgttgggct gcctacgatc tccaccaccg gcaggttttc ggcgtaggag   5880
cccgccagac cgttgacggc gctcagttcg ccaacaccga aagtggtcag aaatgccgcg   5940
gctttcttgg tacgtgcata accatctgcc atgtagcttg cgttcagttc gttagcgtta   6000
```

```
cccacccatt tcatgtcttt atgagagatg atctgatcca ggaactgcag attgtaatca    6060
cccggaacgc cgaagatttc ttcgataccc agttcatgca gacggtccag cagataatca    6120
ccaacagtat acatgtcgac acccgcatag tcaggaacat cgtatgggta catgctagtt    6180
ctagaaaact tagattagat tgctatgctt tctttctaat gagcaagaag taaaaaaagt    6240
tgtaatagaa caagaaaaat gaaactgaaa cttgagaaat tgaagaccgt ttattaactt    6300
aaatatcaat gggaggtcat cgaaagagaa aaaatcaaa aaaaaatttt tcaagaaaaa    6360
gaaacgtgat aaaaatttt attgccttt tcgacgaaga aaagaaacg aggcggtctc    6420
tttttctt tccaaacctt tagtacgggt aattaacgac accctagagg aagaaagagg    6480
ggaaatttag tatgctgtgc ttgggtgttt tgaagtggta cggcgatgcg cggagtccga    6540
gaaaatctgg aagagtaaaa aaggagtaga acattttga agctatgagc tccagctttt    6600
gttcccttta gtgagggtta attgcgcgct tggcgtaatc atggtcatag ctgtttcctg    6660
tgtgaaattg ttatccgctc acaattccac acaacatagg agccgaagc ataaagtgta    6720
aagcctgggg tgcctaatga gtgaggtaac tcacattaat tgcgttgcgc tcactgcccg    6780
ctttccagtc gggaaacctg tcgtgccagc tgcattaatg aatcggccaa cgcgcgggga    6840
gaggcggttt gcgtattggg cgctcttccg cttcctcgct cactgactcg ctgcgctcgg    6900
tcgttcggct gcggcgagcg gtatcagctc actcaaaggc ggtaatacgg ttatccacag    6960
aatcagggga taacgcagga aagaacatgt gagcaaaagg ccagcaaaag gccaggaacc    7020
gtaaaaaggc cgcgttgctg gcgttttcc ataggctccg cccccctgac gagcatcaca    7080
aaaatcgacg ctcaagtcag aggtggcgaa acccgacagg actataaaga taccaggcgt    7140
ttccccctgg aagctccctc gtgcgctctc ctgttccgac cctgccgctt accggatacc    7200
tgtccgcctt tctcccttcg ggaagcgtgg cgctttctca tagctcacgc tgtaggtatc    7260
tcagttcggt gtaggtcgtt cgctccaagc tgggctgtgt gcacgaaccc cccgttcagc    7320
ccgaccgctg cgccttatcc ggtaactatc gtcttgagtc aacccggta agacacgact    7380
tatcgccact ggcagcagcc actggtaaca ggattagcag agcgaggtat gtaggcggtg    7440
ctacagagtt cttgaagtgg tggcctaact acggctacac tagaaggaca gtatttggta    7500
tctgcgctct gctgaagcca gttaccttcg gaaaaagagt tggtagctct tgatccggca    7560
aacaaaccac cgctggtagc ggtggttttt tgtttgcaa gcagcagatt acgcgcagaa    7620
aaaaaggatc tcaagaagat cctttgatct tttctacggg gtctgacgct cagtggaacg    7680
aaaactcacg ttaagggatt ttggtcatga gattatcaaa aaggatcttc acctagatcc    7740
ttttaaatta aaaatgaagt tttaaatcaa tctaaagtat atatgagtaa acttggtctg    7800
acagttacca atgcttaatc agtgaggcac ctatctcagc gatctgtcta tttcgttcat    7860
ccatagttgc ctgactcccc gtcgtgtaga taactacgat acgggagggc ttaccatctg    7920
gccccagtgc tgcaatgata ccgcgagacc cacgctcacc ggctccagat ttatcagcaa    7980
taaaccagcc agccggaagg gccgagcgca gaagtggtcc tgcaacttta tccgcctcca    8040
tccagtctat taattgttgc cgggaagcta gagtaagtag ttcgccagtt aatagtttgc    8100
gcaacgttgt tgccattgct acaggcatcg tggtgtcacg ctcgtcgttt ggtatggctt    8160
cattcagctc cggttcccaa cgatcaaggc gagttacatg atccccatg ttgtgcaaaa    8220
aagcggttag ctccttcggt cctccgatcg ttgtcagaag taagttggcc gcagtgttat    8280
cactcatggt tatggcagca ctgcataatt ctcttactgt catgccatcc gtaagatgct    8340
tttctgtgac tggtgagtac tcaaccaagt cattctgaga atagtgtatg cggcgaccga    8400
```

-continued

| | |
|---|---|
| gttgctcttg cccggcgtca atacgggata ataccgcgcc acatagcaga actttaaaag | 8460 |
| tgctcatcat tggaaaacgt tcttcggggc gaaaactctc aaggatctta ccgctgttga | 8520 |
| gatccagttc gatgtaaccc actcgtgcac ccaactgatc ttcagcatct tttactttca | 8580 |
| ccagcgtttc tgggtgagca aaaacaggaa ggcaaaatgc cgcaaaaaag gaataagggg | 8640 |
| cgacacggaa atgttgaata ctcatactct tccttttca atattattga agcatttatc | 8700 |
| agggttattg tctcatgagc ggatacatat ttgaatgtat ttagaaaaat aaacaaatag | 8760 |
| gggttccgcg cacatttccc cgaaaagtgc cacctgacgt | 8800 |

<210> SEQ ID NO 5
<211> LENGTH: 1677
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

| | |
|---|---|
| gtcgacatgt ctgagaaaca atttggggcg aacttggttg tcgatagttt gattaaccat | 60 |
| aaagtgaagt atgtatttgg gattccagga gcaaaaattg accgggtttt tgatttatta | 120 |
| gaaaatgaag aaggccctca aatggtcgtg actcgtcatg agcaaggagc tgctttcatg | 180 |
| gctcaagctg ttggtcgttt gactggcgaa cctggtgtag tagttgttac gagtgggcct | 240 |
| ggtgtatcaa accttgcgac tccgcttttg accgcgactt cagaaggtga tgctattttg | 300 |
| gctatcggtg gacaagttaa acgaagtgac cgtcttaaac gtgcgcacca atcaatggat | 360 |
| aatgctggaa tgatgcaatc agcaacaaaa tattcagcag aagttcttga ccctgataca | 420 |
| ctttctgaat caattgccaa cgcttatcgt attgcaaaat caggacatcc aggtgcaact | 480 |
| ttcttatcaa tcccccaaga tgtaacggat gccgaagtat caatcaaggc cattcaacca | 540 |
| ctttcagacc ctaaaatggg gaatgcctct attgatgaca ttaattattt agcacaagca | 600 |
| attaaaaatg ctgtattgcc agtaattttg gttggagctg gtgcttcaga tgctaaagtc | 660 |
| gcttcatcat tgcgtaatct attaactcat gttaatattc ctgtcgttga acattccaa | 720 |
| ggtgcagggg ttattcaca tgatttagaa catactttt atggacgtat cggtctttc | 780 |
| cgcaatcaac caggagatat gcttctgaaa cgttctgacc ttgttattgc tgttggttat | 840 |
| gacccaattg aatatgaagc tcgtaactgg aatgcagaaa ttgatagtcg aattatcgtt | 900 |
| attgataatg ccattgctga aattgatact tactaccaac cagaacgtga attaattggt | 960 |
| gatatcgcag caacattgga taatctttta ccagctgttc gtggatacaa aattccaaaa | 1020 |
| ggaacaaaag attatctcga tggccttcat gaagttgctg agcaacacga atttgatact | 1080 |
| gaaaatactg aagaaggtag aatgcaccct cttgatttgg tcagcacttt ccaagaaatc | 1140 |
| gttaaagatg atgaaacagt aaccgttgac gtaggttcac tctacatttg gatggcacgt | 1200 |
| catttcaaat catacgaacc acgtcatctc ctcttctcaa acggaatgca aacacttgga | 1260 |
| gttgcacttc cttgggcaat tacagccgca ttgttgcgcc caggtaaaaa agtttattca | 1320 |
| cactctggtg atggaggctt ccttttcaca gggcaagagt tggaaacagc tgtacgtttg | 1380 |
| aatcttccaa tcgttcaaat tatctggaat gacggccatt atgatatggt taaattccaa | 1440 |
| gaagaaatga aatatggtcg ttcagcagcc gttgattttg ctatgttga ttacgtaaaa | 1500 |
| tatgctgaag caatgggagc aaaaggttac cgtgcacaca gcaaagaaga acttgctgaa | 1560 |
| attcttaaat caatcccaga tactactgga ccagtagtaa ttgacgttcc tttggactat | 1620 |
| tctgataaca ttaaattagc agaaaaatta ttgcctgaag agttttattg aggatcc | 1677 |

<210> SEQ ID NO 6
<211> LENGTH: 1488
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
gtcgacatgg ctaactactt caatacactg aatctgcgcc agcagctggc acagctgggc        60
aaatgtcgct ttatgggccg cgatgaattc gccgatggcg cgagctacct tcagggtaaa       120
aaagtagtca tcgtcggctg tggcgcacag ggtctgaacc agggcctgaa catgcgtgat       180
tctggtctcg atatctccta cgctctgcgt aaagaagcga ttgccgagaa gcgcgcgtcc       240
tggcgtaaag cgaccgaaaa tggttttaaa gtgggtactt acgaagaact gatcccacag       300
gcggatctgg tgattaacct gacgccggac aagcagcact ctgatgtagt gcgcaccgta       360
cagccactga tgaaagacgg cgcggcgctg ggctactcgc acggtttcaa catcgtcgaa       420
gtgggcgagc agatccgtaa agatatcacc gtagtgatgg ttgcgccgaa atgcccaggc       480
accgaagtgc gtgaagagta caaacgtggg ttcggcgtac cgacgctgat tgccgttcac       540
ccggaaaacg atccgaaagg cgaaggcatg gcgattgcca aagcctgggc ggctgcaacc       600
ggtggtcacc gtgcgggtgt gctggaatcg tccttcgttg cggaagtgaa atctgacctg       660
atgggcgagc aaaccatcct gtgcggtatg ttgcaggctg gctctctgct gtgcttcgac       720
aagctggtgg aagaaggtac cgatccagca tacgcagaaa aactgattca gttcggttgg       780
gaaaccatca ccgaagcact gaaacagggc ggcatcaccc tgatgatgga ccgtctctct       840
aacccggcga aactgcgtgc ttatgcgctt tctgaacagc tgaaagagat catggcaccc       900
ctgttccaga acatatgga cgacatcatc tccggcgaat tctcttccgg tatgatggcg       960
gactgggcca acgatgataa gaaactgctg acctggcgtg aagagaccgg caaaaccgcg      1020
tttgaaaccg cgccgcagta tgaaggcaaa atcggcgagc aggagtactt cgataaaggc      1080
gtactgatga ttgcgatggt gaaagcgggc gttgaactgg cgttcgaaac catggtcgat      1140
tccggcatca ttgaagagtc tgcatattat gaatcactgc acgagctgcc gctgattgcc      1200
aacaccatcg cccgtaagcg tctgtacgaa atgaacgtgg ttatctctga taccgctgag      1260
tacggtaact atctgttctc ttacgcttgt gtgccgttgc tgaaaccgtt tatggcagag      1320
ctgcaaccgg cgacctggg taaagctatt ccggaaggcg cggtagataa cgggcaactg      1380
cgtgatgtga acgaagcgat tcgcagccat gcgattgagc aggtaggtaa gaaactgcgc      1440
ggctatatga cagatatgaa acgtattgct gttgcgggtt aaggatcc                   1488
```

<210> SEQ ID NO 7
<211> LENGTH: 1863
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 7

```
gtcgacatgc ctaagtaccg ttccgccacc accactcatg gtcgtaatat ggcgggtgct        60
cgtgcgctgt ggcgcgccac cggaatgacc gacgccgatt tcggtaagcc gattatcgcg       120
gttgtgaact cgttcaccca atttgtaccg ggtcacgtcc atctgcgcga tctcggtaaa       180
ctggtcgccg aacaaattga agcggctggc ggcgttgcca aagagttcaa caccattgcg       240
```

```
gtggatgatg ggattgccat gggccacggg gggatgcttt attcactgcc atctcgcgaa      300
ctgatcgctg attccgttga gtatatggtc aacgcccact gcgccgacgc catggtctgc      360
atctctaact gcgacaaaat caccccgggg atgctgatgg cttccctgcg cctgaatatt      420
ccggtgatct ttgtttccgg cggcccgatg gaggccggga aaaccaaact ttccgatcag      480
atcatcaagc tcgatctggt tgatgcgatg atccagggcg cagacccgaa agtatctgac      540
tcccagagcg atcaggttga acgttccgcg tgtccgacct gcggttcctg ctccgggatg      600
tttaccgcta actcaatgaa ctgcctgacc gaagcgctgg gcctgtcgca gccgggcaac      660
ggctcgctgc tggcaaccca cgccgaccgt aagcagctgt ccttaatgc tggtaaacgc       720 attgttgaat tgaccaaacg ttattacgag caaaacgacg aaagtgcact gccgcgtaat      780
atcgccagta aggcggcgtt tgaaaacgcc atgacgctga tatcgcgat gggtggatcg       840 actaacaccg tacttcacct gctggcggcg gcgcaggaag cggaaatcga cttcaccatg      900
agtgatatcg ataagctttc ccgcaaggtt ccacagctgt gtaaagttgc gccgagcacc      960
cagaaatacc atatggaaga tgttcaccgt gctggtggtg ttatcggtat tctcggcgaa     1020
ctggatcgcg cggggttact gaaccgtgat gtgaaaaacg tacttggcct gacgttgccg     1080
caaacgctgg aacaatacga cgttatgctg acccaggatg acgcggtaaa aaatatgttc     1140
cgcgcaggtc ctgcaggcat tcgtaccaca caggcattct cgcaagattg ccgttgggat     1200
acgctggacg acgatcgcgc caatggctgt atccgctcgc tggaacacgc ctacagcaaa     1260
gacggcggcc tggcggtgct ctacggtaac tttgcggaaa acggctgcat cgtgaaaacg     1320
gcaggcgtcg atgacagcat cctcaaattc accggcccgg cgaaagtgta cgaaagccag     1380
gacgatgcgc tagaagcgat tctcggcggt aaagttgtcg ccggagatgt ggtagtaatt     1440
cgctatgaag gcccgaaagg cggtccgggg atgcaggaaa tgctctaccc aaccagcttc     1500
ctgaaatcaa tgggtctcgg caaagccgt gcgctgatca ccgacggtcg tttctctggt      1560
ggcacctctg gtctttccat cggccacgtc tcaccggaag cggcaagcgg cggcagcatt     1620
ggcctgattg aagatggtga cctgatcgct atcgacatcc gaaccgtgg cattcagtta      1680 caggtaagcg atgccgaact ggcggcgcgt cgtgaagcgc aggacgctcg aggtgacaaa     1740
gcctggacgc cgaaaaatcg tgaacgtcag gtctccttg ccctgcgtgc ttatgccagc      1800
ctggcaacca gcgccgacaa aggcgcggtg cgcgataaat cgaaactggg gggttaagga     1860
tcc                                                                   1863
```

<210> SEQ ID NO 8
<211> LENGTH: 1659
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8

```
gtcgacatgt atactgttgg tgattatctg ctggaccgtc tgcatgaact gggtatcgaa       60
gaaatcttcg gcgttccggg tgattacaat ctgcagttcc tggatcagat catctctcat      120
aaagacatga atgggtggg taacgctaac gaactgaacg caagctacat ggcagatggt      180
tatgcacgta ccaagaaagc cgcggcattt ctgaccactt tcggtgttgg cgaactgagc      240
gccgtcaacg gtctgcgggg ctcctacgcc gaaaacctgc cggtggtgga tcgtaggc       300 agcccaacga gcaaagttca gaacgaaggt aaattcgtcc accacactct ggctgacggc      360
```

```
gatttcaaac acttcatgaa aatgcatgaa cctgtgactg cggcacgtac gctgctgact    420
gcagagaacg ctactgtgga aatcgaccgc gttctgtctg cgctgctgaa agaacgcaaa    480
ccagtttaca tcaacctgcc tgtggatgtt gcggcagcta agcggaaaa accgagcctg     540 ccgctgaaga aagaaaactc cacttctaac actagcgacc aggaaatcct gaacaaaatc    600
caggagtctc tgaaaaacgc aaagaaacca atcgtgatca ccggccacga atcatttct    660 tttggtctgg agaagaccgt gacccaattc atcagcaaaa ccaaactgcc gattaccacc    720
ctgaacttcg gcaagtcctc tgttgacgag gctctgccgt cttcctggg catctacaac     780 ggtactctga gcgaaccgaa cctgaaagaa tttgttgaat ctgcggactt catcctgatg    840
ctgggcgtta aactgaccga ctcttctacc ggtgcattca ctcaccatct gaacgaaaac    900
aaaatgatta gcctgaacat cgacgagggt aaaatcttca cgagcgtat ccagaacttc     960 gacttcgaaa gcctgatcag ctctctgctg gacctgtccg aaatcgagta taaaggcaaa   1020
tacattgaca aaaagcaaga agatttcgta ccatctaacg cactgctgtc ccaggatcgc   1080
ctgtggcagg ccgtggagaa cctgacccag agcaatgaaa ccatcgtggc ggaacaaggt   1140
acgagctttt tcggcgcgtc ttctatcttt ctgaaatcca aaagccattt tatcggtcag   1200
ccgctgtggg gtagcattgg ctatactttc ccggcagcgc tgggctctca gatcgctgat   1260
aaagaatctc gtcatctgct gttcatcggt gacggttccc tgcagctgac cgtacaggaa   1320
ctgggtctgg caattcgtga aaagatcaac ccgatttgct tcattattaa caatgacggc   1380
tacaccgttg agcgtgagat ccacggtccg aaccagtctt acaacgatat ccctatgtgg   1440
aactactcta aactgccgga gtccttcggc gcaactgagg accgtgttgt gtctaaaatt   1500
gtgcgtaccg aaaacgaatt tgtgagcgtg atgaaagagg cccaggccga tccgaaccgt   1560
atgtactgga tcgaactgat cctggcgaaa gaaggcgcac cgaaggtact gaagaaaatg   1620
ggcaagctgt ttgctgaaca gaataaatcc taaggatcc                          1659
```

<210> SEQ ID NO 9
<211> LENGTH: 1059
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

```
gtcgacatgt ctattccaga aactcaaaaa gccattatct tctacgaatc caacggcaag    60
ttggagcata aggatatccc agttccaaag ccaaagccca acgaattgtt aatcaacgtc   120
aagtactctg gtgtctgcca caccgatttg cacgcttggc atggtgactg gccattgcca   180
actaagttac cattagttgg tggtcacgaa ggtgccggtg tcgttgtcgg catgggtgaa   240
aacgttaagg ctggaagat cggtgactac gccggtatca aatggttgaa cggttcttgt   300
atggcctgtg aatactgtga attgggtaac gaatccaact gtcctcacgc tgacttgtct   360
ggttacaccc acgacggttc ttttcaagaa tacgctaccg ctgacgctgt tcaagccgct   420
cacattcctc aaggtactga cttggctgaa gtcgcgccaa tcttgtgtgc tggtatcacc   480
gtatacaagg cttttgaagtc tgccaacttg agagcaggcc actgggcggc catttctggt   540
gctgctggtg gtctaggttc tttggctgtt caatatgcta aggcgatggg ttacagagtc   600
ttaggtattg atggtggtcc aggaaaggaa gaattgttta cctcgctcgg tggtgaagta   660
ttcatcgact tcaccaaaga gaaggacatt gttagcgcag tcgttaaggc taccaacggc   720
ggtgcccacg gtatcatcaa tgtttccgtt tccgaagccg ctatcgaagc ttctaccaga   780
```

```
tactgtaggg cgaacggtac tgttgtcttg gttggtttgc cagccggtgc aaagtgctcc    840
tctgatgtct tcaaccacgt tgtcaagtct atctccattg tcggctctta cgtggggaac    900
agagctgata ccagagaagc cttagatttc tttgccagag gtctagtcaa gtctccaata    960
aaggtagttg gcttatccag tttaccagaa atttacgaaa agatggagaa gggccaaatt   1020
gctggtagat acgttgttga cacttctaaa taaggatcc                          1059
```

<210> SEQ ID NO 10
<211> LENGTH: 9761
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataccac agcttttcaa ttcaattcat cattttttttt ttattctttt ttttgatttc    240
ggtttctttg aaattttttt gattcggtaa tctccgaaca aaggaagaa cgaaggaagg    300 agcacagact tagattggta tatatacgca tatgtagtgt tgaagaaaca tgaaattgcc    360
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa ttttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca agagacatg gtgaagag atgaaggta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattaccccta tgcggtgtga ataccgcac   1320 agatgcgtaa ggagaaaata ccgcatcagg aaattgtaaa cgttaatatt tgttaaaat   1380 tcgcgttaaa ttttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt ttgggtcg aggtgccgta   1620 aagcactaaa tcggaaccct aaagggagcc ccgatttag agcttgacgg ggaaagccgg   1680
cgaacgtggc gagaaaggaa gggaagaaag cgaaaggagc gggcgctagg gcgctggcaa   1740
```

```
gtgtagcggt cacgctgcgc gtaaccacca cacccgccgc gcttaatgcg ccgctacagg    1800
gcgcgtcgcg ccattcgcca ttcaggctgc gcaactgttg ggaagggcga tcggtgcggg    1860
cctcttcgct attacgccag ctggcgaaag ggggatgtgc tgcaaggcga ttaagttggg    1920
taacgccagg gttttcccag tcacgacgtt gtaaaacgac ggccagtgag cgcgcgtaat    1980
acgactcact atagggcgaa ttgggtaccg gccgcaaatt aaagccttcg agcgtcccaa    2040
aaccttctca agcaaggttt tcagtataat gttacatgcg tacacgcgtc tgtacagaaa    2100
aaaagaaaaa atttgaaata taaataacgt tcttaatact aacataacta taaaaaaata    2160
aatagggacc tagacttcag gttgtctaac tccttccttt tcggttagag cggatgtggg    2220
gggagggcgt gaatgtaagc gtgacataac taattacatg actcgagcgg ccgcggatcc    2280
ttatttagaa gtgtcaacaa cgtatctacc agcaatttgg cccttctcca tcttttcgta    2340
aatttctggt aaactggata agccaactac ctttattgga gacttgacta gacctctggc    2400
aaagaaatct aaggcttctc tggtatcagc tctgttcccc acgtaagagc cgacaatgga    2460
gatagacttg acaacgtggt tgaagacatc agaggagcac tttgcaccgg ctggcaaacc    2520
aaccaagaca acagtaccgt tcgccctaca gtatctggta gaagcttcga tagcggcttc    2580
ggaaacggaa acattgatga taccgtgggc accgccgttg gtagccttaa cgactgcgct    2640
aacaatgtcc ttctctttgg tgaagtcgat gaatacttca ccaccgagcg aggtaaacaa    2700
ttcttccttt cctggaccac catcaatacc taagactctg taacccatcg ccttagcata    2760
ttgaacagcc aaagaaccta gaccaccagc agcaccagaa atggccgccc agtggcctgc    2820
tctcaagttg gcagacttca aagccttgta tacggtgata ccagcacaca agattggcgc    2880
gacttcagcc aagtcagtac cttgaggaat gtgagcggct tgaacagcgt cagcggtagc    2940
gtattcttgg aaagaaccgt cgtgggtgta accagacaag tcagcgtgag gacagttgga    3000
ttcgttaccc aattcacagt attcacaggc catacaagaa ccgttcaacc atttgatacc    3060
ggcgtagtca ccgatcttcc agcccttaac gttttcaccc atgccgacaa cgacaccggc    3120
accttcgtga ccaccaacta atggtaactt agttggcaat ggccagtcac catgccaagc    3180
gtgcaaatcg gtgtggcaga caccagagta cttgacgttg attaacaatt cgttgggctt    3240
tggcttggga actgggatat ccttatgctc caacttgccg ttggattcgt agaagataat    3300 ggcttttga gtttctggaa tagacatgtc gacaccatct tcttctgaga tgagtttttg    3360
ttccatgcta gttctagaat ccgtcgaaac taagttctgg tgttttaaaa ctaaaaaaaa    3420
gactaactat aaaagtagaa tttaagaagt ttaagaaata gatttacaga attcaatca    3480 ataccctaccg tctttatata cttattagtc aagtagggga ataatttcag ggaactggtt    3540
tcaacctttt ttttcagctt tttccaaatc agagagagca gaaggtaata gaaggtgtaa    3600
gaaaatgaga tagatacatg cgtgggtcaa ttgccttgtg tcatcattta ctccaggcag    3660
gttgcatcac tccattgagg ttgtgcccgt tttttgcctg tttgtgcccc tgttctctgt    3720
agttgcgcta agagaatgga cctatgaact gatggttggt gaagaaaaca atattttggt    3780
gctgggattc ttttttttttc tggatgccag cttaaaaagc gggctccatt atatttagtg    3840
gatgccagga ataaactgtt cacccagaca cctacgatgt tatatattct gtgtaacccg    3900
cccctatttt gggcatgtta cggggttacag cagaattaaa aggctaattt tttgactaaa    3960
taaagttagg aaaatcacta ctattaatta tttacgtatt ctttgaaatg gcgagtattg    4020
ataatgataa actgaggatc cttaggattt attctgttca gcaaacagct tgcccatttt    4080
cttcagtacc ttcggtgcgc cttctttcgc caggatcagt tcgatccagt acatacggtt    4140
```

```
cggatcggcc tgggcctctt tcatcacgct cacaaattcg ttttcggtac gcacaatttt    4200
agacacaaca cggtcctcag ttgcgccgaa ggactccggc agtttagagt agttccacat    4260
agggatatcg ttgtaagact ggttcggacc gtggatctca cgctcaacgg tgtagccgtc    4320
attgttaata atgaagcaaa tcgggttgat cttttcacga attgccagac ccagttcctg    4380
tacggtcagc tgcagggaac cgtcaccgat gaacagcaga tgacgagatt ctttatcagc    4440
gatctgagag cccagcgctg ccgggaaagt atagccaatg ctaccccaca gcggctgacc    4500
gataaaatgg cttttggatt tcagaaagat agaagacgcg ccgaaaaagc tcgtaccttg    4560
ttccgccacg atggtttcat tgctctgggt caggttctcc acggcctgcc acaggcgatc    4620
ctgggacagc agtgcgttag atggtacgaa atcttcttgc tttttgtcaa tgtatttgcc    4680
tttatactcg atttcggaca ggtccagcag agagctgatc aggctttcga agtcgaagtt    4740
ctggatacgc tcgttgaaga ttttaccctc gtcgatgttc aggctaatca ttttgttttc    4800
gttcagatgg tgagtgaatg caccggtaga agagtcggtc agtttaacgc ccagcatcag    4860
gatgaagtcc gcagattcaa caaattcttt caggttcggt tcgctcagag taccgttgta    4920
gatgcccagg aaagacggca gagcctcgta acagaggac ttgccgaagt tcagggtggt    4980
aatcggcagt ttggttttgc tgatgaattg ggtcacggtc ttctccagac caaaagaaat    5040
gatttcgtgg ccggtgatca cgattggttt ctttgcgttt ttcagagact cctggatttt    5100
gttcaggatt tcctggtcgc tagtgttaga agtggagttt ctttcttca gcggcaggct    5160
cggttttttcc gctttagctg ccgcaacatc cacaggcagg ttgatgtaaa ctggtttgcg    5220
ttctttcagc agcgcagaca gaacgcggtc gatttccaca gtagcgttct ctgcagtcag    5280
cagcgtacgt gccgcagtca caggttcatg cattttcatg aagtgtttga atcgccgtc    5340
agccagagtg tggtggacga atttaccttc gttctgaact ttgctcgttg ggctgcctac    5400
gatctccacc accggcaggt tttcggcgta ggagcccgcc agaccgttga cggcgctcag    5460
ttcgccaaca ccgaaagtgg tcagaaatgc cgcggctttc ttggtacgtg cataaccatc    5520
tgccatgtag cttgcgttca gttcgttagc gttaccacc catttcatgt ctttatgaga    5580
gatgatctga tccaggaact gcagattgta atcacccgga acgccgaaga tttcttcgat    5640
acccagttca tgcagacggt ccagcagata atcaccaaca gtatacatgt cgacacccgc    5700
atagtcagga acatcgtatg ggtacatgct agttctagaa aacttagatt agattgctat    5760
gctttctttc taatgagcaa gaagtaaaaa aagttgtaat agaacaagaa aaatgaaact    5820
gaaacttgag aaattgaaga ccgtttatta acttaaatat caatgggagg tcatcgaaag    5880
agaaaaaaat caaaaaaaaa attttcaaga aaaagaaacg tgataaaaat ttttattgcc    5940
ttttcgacg aagaaaaga acgaggcgg tctcttttt cttttccaaa cctttagtac    6000
gggtaattaa cgacacccta gaggaagaaa gaggggaaat ttagtatgct gtgcttgggt    6060
gttttgaagt ggtacggcga tgcgcggagt ccgagaaaat ctggaagagt aaaaaaggag    6120
tagaaacatt ttgaagctat gagctccagc ttttgttccc tttagtgagg gttaattgcg    6180
cgcttggcgt aatcatggtc atagctgttt cctgtgtgaa attgttatcc gctcacaatt    6240
ccacacaaca taggagccgg aagcataaag tgtaaagcct ggggtgccta atgagtgagg    6300
taactcacat taattgcgtt gcgctcactg cccgctttcc agtcgggaaa cctgtcgtgc    6360
cagctgcatt aatgaatcgg ccaacgcgcg gggagaggcg gtttgcgtat tgggcgctct    6420
tccgcttcct cgctcactga ctcgctgcgc tcggtcgttc ggctgcggcg agcggtatca    6480
gctcactcaa aggcggtaat acggttatcc acagaatcag gggataacgc aggaaagaac    6540
```

```
atgtgagcaa aaggccagca aaaggccagg aaccgtaaaa aggccgcgtt gctggcgttt    6600
ttccataggc tccgcccccc tgacgagcat cacaaaaatc gacgctcaag tcagaggtgg    6660
cgaaacccga caggactata aagataccag gcgtttcccc ctggaagctc cctcgtgcgc    6720
tctcctgttc cgaccctgcc gcttaccgga tacctgtccg cctttctccc ttcgggaagc    6780
gtggcgcttt ctcatagctc acgctgtagg tatctcagtt cggtgtaggt cgttcgctcc    6840
aagctgggct gtgtgcacga accccccgtt cagcccgacc gctgcgcctt atccggtaac    6900
tatcgtcttg agtccaaccc ggtaagacac gacttatcgc cactggcagc agccactggt    6960
aacaggatta gcagagcgag gtatgtaggc ggtgctacag agttcttgaa gtggtggcct    7020
aactacggct acactagaag gacagtattt ggtatctgcg ctctgctgaa gccagttacc    7080
ttcggaaaaa gagttggtag ctcttgatcc ggcaaacaaa ccaccgctgg tagcggtggt    7140
ttttttgttt gcaagcagca gattacgcgc agaaaaaaag gatctcaaga agatcctttg    7200
atcttttcta cggggtctga cgctcagtgg aacgaaaact cacgttaagg gattttggtc    7260
atgagattat caaaaaggat cttcacctag atccttttaa attaaaaatg aagttttaaa    7320
tcaatctaaa gtatatatga gtaaacttgg tctgacagtt accaatgctt aatcagtgag    7380
gcacctatct cagcgatctg tctatttcgt tcatccatag ttgcctgact ccccgtcgtg    7440
tagataacta cgatacggga gggcttacca tctggcccca gtgctgcaat gataccgcga    7500
gacccacgct caccggctcc agatttatca gcaataaacc agccagccgg aagggccgag    7560
cgcagaagtg gtcctgcaac tttatccgcc tccatccagt ctattaattg ttgccgggaa    7620
gctagagtaa gtagttcgcc agttaatagt ttgcgcaacg ttgttgccat tgctacaggc    7680
atcgtggtgt cacgctcgtc gtttggtatg gcttcattca gctccggttc ccaacgatca    7740
aggcgagtta catgatcccc catgttgtgc aaaaaagcgg ttagctcctt cggtcctccg    7800
atcgttgtca gaagtaagtt ggccgcagtg ttatcactca tggttatggc agcactgcat    7860
aattctctta ctgtcatgcc atccgtaaga tgcttttctg tgactggtga gtactcaacc    7920
aagtcattct gagaatagtg tatgcggcga ccgagttgct cttgcccggc gtcaatacgg    7980
gataataccg cgccacatag cagaacttta aaagtgctca tcattggaaa acgttcttcg    8040
gggcgaaaac tctcaaggat cttaccgctg ttgagatcca gttcgatgta acccactcgt    8100
gcacccaact gatcttcagc atcttttact ttcaccagcg tttctgggtg agcaaaaaca    8160
ggaaggcaaa atgccgcaaa aaagggaata agggcgacac ggaaatgttg aatactcata    8220
ctcttccttt ttcaatatta ttgaagcatt tatcagggtt attgtctcat gagcggatac    8280
atatttgaat gtatttagaa aaataaacaa ataggggttc cgcgcacatt tccccgaaaa    8340
gtgccacctg aacgaagcat ctgtgcttca ttttgtagaa caaaaatgca acgcgagagc    8400
gctaattttt caaacaaaga atctgagctg cattttttaca gaacagaaat gcaacgcgaa    8460
agcgctattt taccaacgaa gaatctgtgc ttcattttg taaacaaaa atgcaacgcg    8520 agagcgctaa ttttttcaaac aaagaatctg agctgcattt ttacagaaca gaaatgcaac    8580
gcgagagcgc tattttacca acaaagaatc tatacttctt ttttgttcta caaaaatgca    8640
tcccgagagc gctatttttc taacaaagca tcttagatta cttttttttct cctttgtgcg    8700 ctctataatg cagtctcttg ataactttt gcactgtagg tccgttaagg ttagaagaag    8760
gctactttgg tgtctatttt ctcttccata aaaaaagcct gactccactt cccgcgttta    8820
ctgattacta gcgaagctgc gggtgcattt tttcaagata aaggcatccc cgattatatt    8880
ctataccgat gtggattgcg catactttgt gaacagaaag tgatagcgtt gatgattctt    8940
```

| | | | | |
|---|---|---|---|---|
| cattggtcag | aaaattatga | acggtttctt | ctattttgtc | tctatatact acgtatagga | 9000 |
| aatgtttaca | ttttcgtatt | gttttcgatt | cactctatga | atagttctta ctacaatttt | 9060 |
| tttgtctaaa | gagtaatact | agagataaac | ataaaaaatg | tagaggtcga gtttagatgc | 9120 |
| aagttcaagg | agcgaaaggt | ggatgggtag | gttatatagg | gatatagcac agagatatat | 9180 |
| agcaaagaga | tacttttgag | caatgtttgt | ggaagcggta | ttcgcaatat tttagtagct | 9240 |
| cgttacagtc | cggtgcgttt | ttggtttttt | gaaagtgcgt | cttcagagcg cttttggttt | 9300 |
| tcaaaagcgc | tctgaagttc | ctatactttc | tagagaatag | gaacttcgga ataggaactt | 9360 |
| caaagcgttt | ccgaaaacga | gcgcttccga | aaatgcaacg | cgagctgcgc acatacagct | 9420 |
| cactgttcac | gtcgcaccta | tatctgcgtg | ttgcctgtat | atatatatac atgagaagaa | 9480 |
| cggcatagtg | cgtgtttatg | cttaaatgcg | tacttatatg | cgtctattta tgtaggatga | 9540 |
| aaggtagtct | agtacctcct | gtgatattat | cccattccat | gcggggtatc gtatgcttcc | 9600 |
| ttcagcacta | ccctttagct | gttctatatg | ctgccactcc | tcaattggat tagtctcatc | 9660 |
| cttcaatgct | atcatttcct | ttgatattgg | atcatactaa | gaaaccatta ttatcatgac | 9720 |
| attaacctat | aaaaataggc | gtatcacgag | gccctttcgt | c | 9761 |

```
<210> SEQ ID NO 11
<211> LENGTH: 7990
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
```

| | | | | |
|---|---|---|---|---|
| tcgcgcgttt | cggtgatgac | ggtgaaaacc | tctgacacat | gcagctcccg gagacggtca | 60 |
| cagcttgtct | gtaagcggat | gccggagca | gacaagcccg | tcagggcgcg tcagcgggtg | 120 |
| ttggcgggtg | tcggggctgg | cttaactatg | cggcatcaga | gcagattgta ctgagagtgc | 180 |
| accataaacg | acattactat | atatataata | taggaagcat | ttaatagaca gcatcgtaat | 240 |
| atatgtgtac | tttgcagtta | tgacgccaga | tggcagtagt | ggaagatatt ctttattgaa | 300 |
| aaatagcttg | tcaccttacg | tacaatcttg | atccggagct | tttctttttt tgccgattaa | 360 |
| gaattaattc | ggtcgaaaaa | agaaaaggag | agggccaaga | gggagggcat tggtgactat | 420 |
| tgagcacgtg | agtatacgtg | attaagcaca | caaaggcagc | ttggagtatg tctgttatta | 480 |
| atttcacagg | tagttctggt | ccattggtga | agtttgcgg | cttgcagagc acagaggccg | 540 |
| cagaatgtgc | tctagattcc | gatgctgact | tgctgggtat | tatatgtgtg cccaatagaa | 600 |
| agagaacaat | tgacccggtt | attgcaagga | aaatttcaag | tcttgtaaaa gcatataaaa | 660 |
| atagttcagg | cactccgaaa | tacttggttg | gcgtgtttcg | taatcaacct aaggaggatg | 720 |
| ttttggctct | ggtcaatgat | tacggcattg | atatcgtcca | actgcatgga gatgagtcgt | 780 |
| ggcaagaata | ccaagagttc | ctcggttttgc | cagttattaa | aagactcgta tttccaaaag | 840 |
| actgcaacat | actactcagt | gcagcttcac | agaaacctca | ttcgtttatt cccttgtttg | 900 |
| attcagaagc | aggtgggaca | ggtgaacttt | tggattggaa | ctcgatttct gactgggttg | 960 |
| gaaggcaaga | gagccccgaa | agcttacatt | ttatgttagc | tggtggactg acgccagaaa | 1020 |
| atgttggtga | tgcgcttaga | ttaaatgcg | ttattggtgt | tgatgtaagc ggaggtgtgg | 1080 |
| agacaaatgg | tgtaaaagac | tctaacaaaa | tagcaaattt | cgtcaaaaat gctaagaaat | 1140 |
| aggttattac | tgagtagtat | ttatttaagt | attgttgtg | cacttgccta tgcggtgtga | 1200 |
| aataccgcac | agatgcgtaa | ggagaaaata | ccgcatcagg | aaattgtaaa cgttaatatt | 1260 |

```
ttgttaaaat tcgcgttaaa tttttgttaa atcagctcat tttttaacca ataggccgaa      1320
atcggcaaaa tcccttataa atcaaaagaa tagaccgaga tagggttgag tgttgttcca      1380
gtttggaaca agagtccact attaaagaac gtggactcca acgtcaaagg gcgaaaaacc      1440
gtctatcagg gcgatggccc actacgtgaa ccatcaccct aatcaagttt tttggggtcg      1500
aggtgccgta aagcactaaa tcggaaccct aaagggagcc cccgatttag agcttgacgg      1560
ggaaagccgg cgaacgtggc gagaaaggaa gggaagaaag cgaaaggagc gggcgctagg      1620
gcgctggcaa gtgtagcggt cacgctgcgc gtaaccacca cacccgccgc gcttaatgcg      1680
ccgctacagg gcgcgtcgcg ccattcgcca ttcaggctgc gcaactgttg ggaagggcga      1740
tcggtgcggg cctcttcgct attacgccag ctggcgaaag ggggatgtgc tgcaaggcga      1800
ttaagttggg taacgccagg gttttcccag tcacgacgtt gtaaaacgac ggccagtgag      1860
cgcgcgtaat acgactcact ataggggcgaa ttgggtaccg gccgcaaatt aaagccttcg      1920
agcgtcccaa aaccttctca agcaaggttt tcagtataat gttacatgcg tacacgcgtc      1980
tgtacagaaa aaaagaaaa atttgaaata taaataacgt tcttaatact aacataacta      2040
taaaaaaata aatagggacc tagacttcag gttgtctaac tccttccttt tcggttagag      2100
cggatgtggg gggagggcgt gaatgtaagc gtgacataac taattacatg actcgagcgg      2160
ccgcggatcc ttaacccgca acagcaatac gtttcatatc tgtcatatag ccgcgcagtt      2220
tcttacctac ctgctcaatc gcatggctgc gaatcgcttc gttcacatca gcagttgcc      2280 cgttatctac cgcgccttcc ggaatagctt acccaggtc gcccggttgc agctctgcca      2340
taaacggttt cagcaacggc acacaagcgt aagagaacag atagttaccg tactcagcgg      2400
tatcagagat aaccacgttc atttcgtaca gacgcttacg ggcgatggtg ttggcaatca      2460
gcggcagctc gtgcagtgat tcataatatg cagactcttc aatgatgccg gaatcgacca      2520
tggtttcgaa cgccagttca acgcccgctt tcaccatcgc aatcatcagt acgcctttat      2580
cgaagtactc ctgctcgccg attttgcctt catactgcgg cgcggtttca aacgcggttt      2640
tgccggtctc ttcacgccag gtcagcagtt tcttatcatc gttggcccag tccgccatca      2700
taccggaaga gaattcgccg gagatgatgt cgtccatatg tttctggaac aggggtgcca      2760
tgatctcttt cagctgttca gaaagcgcat aagcacgcag tttcgccggg ttagagagac      2820
ggtccatcat cagggtgatg ccgccctgtt tcagtgcttc ggtgatggtt tcccaaccga      2880
actgaatcag tttttctgcg tatgctggat cggtaccttc ttccaccagc ttgtcgaagc      2940
acagcagaga gccagcctgc aacataccgc acaggatggt ttgctcgccc atcaggtcag      3000
atttcacttc cgcaacgaag gacgattcca gcacacccgc acggtgacca ccggttgcag      3060
ccgcccaggc tttggcaatc gccatgcctt cgcctttcgg atcgttttcc gggtgaacgg      3120
caatcagcgt cggtacgccg aacccacgtt tgtactcttc acgcacttcg gtgcctgggc      3180
atttcggcgc aaccatcact acggtgatat ctttacggat ctgctcgccc acttcgacga      3240
tgttgaaacc gtgcgagtag cccagcgccg cgccgtcttt catcagtggc tgtacggtgc      3300
gcactacatc agagtgctgc ttgtccggcg tcaggttaat caccagatcc gctgtggga      3360 tcagttcttc gtaagtaccc actttaaaac cattttcggt cgctttacgc aggacgcgc      3420 gcttctcggc aatcgcttct ttacgcagag cgtaggagat atcgagacca gaatcacgca      3480
tgttcaggcc ctggttcaga ccctgtgcgc cacagccgac gatgactact ttttaccct      3540 gaaggtagct cgcgccatcg gcgaattcat cgcggcccat aaagcgacat tgcccagct      3600 gtgccagctg ctggcgcaga ttcagtgtat tgaagtagtt agccatgtcg acaccatctt      3660
```

```
cttctgagat gagtttttgt tccatgctag ttctagaatc cgtcgaaact aagttctggt    3720
gttttaaaac taaaaaaaag actaactata aagtagaat  ttaagaagtt taagaaatag    3780
atttacagaa ttacaatcaa tacctaccgt ctttatatac ttattagtca agtagggaa     3840 taatttcagg gaactggttt caacctttt  tttcagcttt ttccaaatca gagagagcag    3900
aaggtaatag aaggtgtaag aaaatgagat agatacatgc gtgggtcaat tgccttgtgt    3960
catcatttac tccaggcagg ttgcatcact ccattgaggt tgtgcccgtt ttttgcctgt    4020
ttgtgcccct gttctctgta gttgcgctaa gagaatggac ctatgaactg atggttggtg    4080
aagaaaacaa tattttggtg ctgggattct ttttttttct ggatgccagc ttaaaaagcg    4140
ggctccatta tatttagtgg atgccaggaa taaactgttc acccagacac ctacgatgtt    4200
atatattctg tgtaacccgc cccctatttt gggcatgtac gggttacagc agaattaaaa    4260
ggctaatttt ttgactaaat aaagttagga aaatcactac tattaattat ttacgtattc    4320
tttgaaatgg cgagtattga taatgataaa ctgagctaga tctgggcccg agctccagct    4380
tttgttccct ttagtgaggg ttaattgcgc gcttggcgta atcatggtca tagctgtttc    4440
ctgtgtgaaa ttgttatccg ctcacaattc cacacaacat aggagccgga agcataaagt    4500
gtaaagcctg gggtgcctaa tgagtgaggt aactcacatt aattgcgttg cgctcactgc    4560
ccgctttcca gtcgggaaac ctgtcgtgcc agctgcatta tgaatcggc  caacgcgcgg    4620 ggagaggcgg tttgcgtatt gggcgctctt ccgcttcctc gctcactgac tcgctgcgct    4680
cggtcgttcg gctgcggcga gcggtatcag ctcactcaaa ggcggtaata cggttatcca    4740
cagaatcagg ggataacgca ggaaagaaca tgtgagcaaa aggccagcaa aaggccagga    4800
accgtaaaaa ggccgcgttg ctggcgtttt tccataggct ccgcccccct gacgagcatc    4860
acaaaaatcg acgctcaagt cagaggtggc gaaacccgac aggactataa agataccagg    4920
cgtttccccc tggaagctcc ctcgtgcgct ctcctgttcc gaccctgccg cttaccggat    4980
acctgtccgc ctttctccct tcgggaagcg tggcgctttc tcatagctca cgctgtaggt    5040
atctcagttc ggtgtaggtc gttcgctcca agctgggctg tgtgcacgaa ccccccgttc    5100
agcccgaccg ctgcgcctta tccggtaact atcgtcttga gtccaacccg gtaagacacg    5160
acttatcgcc actggcagca gccactggta acaggattag cagagcgagg tatgtaggcg    5220
gtgctacaga gttcttgaag tggtggccta actacggcta cactagaagg acagtatttg    5280
gtatctgcgc tctgctgaag ccagttacct tcggaaaaag agttggtagc tcttgatccg    5340
gcaaacaaac caccgctggt agcggtggtt tttttgtttg caagcagcag attacgcgca    5400
gaaaaaaagg atctcaagaa gatcctttga tcttttctac ggggtctgac gctcagtgga    5460
acgaaaactc acgttaaggg attttggtca tgagattatc aaaaaggatc ttcacctaga    5520
tccttttaaa ttaaaaatga agttttaaat caatctaaag tatatatgag taaacttggt    5580
ctgacagtta ccaatgctta atcagtgagg cacctatctc agcgatctgt ctatttcgtt    5640
catccatagt tgcctgactc cccgtcgtgt agataactac gatacgggag gcttaccat     5700 ctggccccag tgctgcaatg ataccgcgag acccacgctc accggctcca gatttatcag    5760
caataaacca gccagccgga agggccgagc gcagaagtgg tcctgcaact ttatccgcct    5820
ccatccagtc tattaattgt tgccgggaag ctagagtaag tagttcgcca gttaatagtt    5880
tgcgcaacgt tgttgccatt gctacaggca tcgtggtgtc acgctcgtcg tttggtatgg    5940
cttcattcag ctccggttcc caacgatcaa ggcgagttac atgatccccc atgttgtgca    6000
aaaaagcggt tagctccttc ggtcctccga tcgttgtcag aagtaagttg gccgcagtgt    6060
```

```
tatcactcat ggttatggca gcactgcata attctcttac tgtcatgcca tccgtaagat    6120
gcttttctgt gactggtgag tactcaacca agtcattctg agaatagtgt atgcggcgac    6180
cgagttgctc ttgcccggcg tcaatacggg ataataccgc gccacatagc agaactttaa    6240
aagtgctcat cattggaaaa cgttcttcgg ggcgaaaact ctcaaggatc ttaccgctgt    6300
tgagatccag ttcgatgtaa cccactcgtg cacccaactg atcttcagca tcttttactt    6360
tcaccagcgt ttctgggtga gcaaaaacag gaaggcaaaa tgccgcaaaa aagggaataa    6420
gggcgacacg gaaatgttga atactcatac tcttcctttt tcaatattat tgaagcattt    6480
atcagggtta ttgtctcatg agcggataca tatttgaatg tatttagaaa aataaacaaa    6540
taggggttcc gcgcacattt ccccgaaaag tgccacctga acgaagcatc tgtgcttcat    6600
tttgtagaac aaaaatgcaa cgcgagagcg ctaattttc aaacaaagaa tctgagctgc     6660 attttacag aacagaaatg caacgcgaaa gcgctatttt accaacgaag aatctgtgct     6720 tcattttgt aaaacaaaaa tgcaacgcga gagcgctaat ttttcaaaca agaatctga     6780 gctgcatttt tacagaacag aaatgcaacg cgagagcgct attttaccaa caaagaatct    6840
atacttcttt tttgttctac aaaaatgcat cccgagagcg ctattttttct aacaaagcat   6900 cttagattac ttttttttctc ctttgtgcgc tctataatgc agtctcttga taactttttg   6960
cactgtaggt ccgttaaggt tagaagaagg ctactttggt gtctattttc tcttccataa    7020
aaaaagcctg actccacttc ccgcgtttac tgattactag cgaagctgcg ggtgcatttt    7080
ttcaagataa aggcatcccc gattatattc tataccgatg tggattgcgc atactttgtg    7140
aacagaaagt gatagcgttg atgattcttc attggtcaga aaattatgaa cggtttcttc    7200
tattttgtct ctatatacta cgtataggaa atgtttacat tttcgtattg ttttcgattc    7260
actctatgaa tagttcttac tacaattttt ttgtctaaag agtaatacta gagataaaca    7320
taaaaaatgt agaggtcgag tttagatgca agttcaagga gcgaaaggtg gatgggtagg    7380
ttatataggg atatagcaca gagatatata gcaaagagat acttttgagc aatgtttgtg    7440
gaagcggtat tcgcaatatt ttagtagctc gttacagtcc ggtgcgtttt tggttttttg    7500
aaagtgcgtc ttcagagcgc ttttggtttt caaaagcgct ctgaagttcc tatactttct    7560
agagaatagg aacttcggaa taggaacttc aaagcgtttc cgaaaacgag cgcttccgaa    7620
aatgcaacgc gagctgcgca catacagctc actgttcacg tcgcacctat atctgcgtgt    7680
tgcctgtata tatatataca tgagaagaac ggcatagtgc gtgtttatgc ttaaatgcgt    7740
acttatatgc gtctatttat gtaggatgaa aggtagtcta gtacctcctg tgatattatc    7800
ccattccatg cggggtatcg tatgcttcct tcagcactac cctttagctg ttctatatgc    7860
tgccactcct caattggatt agtctcatcc ttcaatgcta tcatttcctt tgatattgga    7920
tcatattaag aaaccattat tatcatgaca ttaacctata aaaataggcg tatcacgagg    7980
ccctttcgtc                                                          7990

<210> SEQ ID NO 12
<211> LENGTH: 8167
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
tcgcgcgttt cggtgatgac ggtgaaaacc tctgacacat gcagctcccg gagacggtca     60
```

-continued

```
cagcttgtct gtaagcggat gccgggagca gacaagcccg tcagggcgcg tcagcgggtg      120
ttggcgggtg tcgggctgg  cttaactatg cggcatcaga gcagattgta ctgagagtgc      180
accataaatt cccgttttaa gagcttggtg agcgctagga gtcactgcca ggtatcgttt      240
gaacacggca ttagtcaggg aagtcataac acagtccttt cccgcaattt tcttttcta       300 ttactcttgg cctcctctag tacactctat attttttat  gcctcggtaa tgattttcat      360
tttttttttt ccctagcgg  atgactcttt tttttttctta gcgattggca ttatcacata     420
atgaattata cattatataa agtaatgtga tttcttcgaa gaatatacta aaaaatgagc      480
aggcaagata aacgaaggca aagatgacag agcagaaagc cctagtaaag cgtattacaa      540
atgaaaccaa gattcagatt gcgatctctt taaagggtgg tccctagcg  atagagcact      600 cgatcttccc agaaaaagag gcagaagcag tagcagaaca ggccacacaa tcgcaagtga      660
ttaacgtcca cacaggtata gggtttctgg accatatgat acatgctctg ccaagcatt       720 ccggctggtc gctaatcgtt gagtgcattg gtgacttaca catagacgac catcacacca      780
ctgaagactg cgggattgct ctcggtcaag cttttaaaga ggccctaggg gccgtgcgtg      840
gagtaaaaag gtttggatca ggatttgcgc ctttggatga ggcactttcc agagcggtgg      900
tagatctttc gaacaggccg tacgcagttg tcgaacttgg tttgcaaagg gagaaagtag      960
gagatctctc ttgcgagatg atcccgcatt tccttgaaag ctttgcagag gctagcagaa     1020
ttaccctcca cgttgattgt ctgcgaggca agaatgatca tcaccgtagt gagagtgcgt     1080
tcaaggctct tgcggttgcc ataagagaag ccacctcgcc caatggtacc aacgatgttc     1140
cctccaccaa aggtgttctt atgtagtgac accgattatt taaagctgca gcatacgata     1200
tatatacatg tgtatatatg tatacctatg aatgtcagta agtatgtata cgaacagtat     1260
gatactgaag atgacaaggt aatgcatcat tctatacgtg tcattctgaa cgaggcgcgc     1320 tttcctttt  tcttttgct  ttttctttt  ttttctcttg aactcgacgg atctatgcgg     1380
tgtgaaatac cgcacagatg cgtaaggaga aaataccgca tcaggaaatt gtaaacgtta     1440
atattttgtt aaaattcgcg ttaaatttt  gttaaatcag ctcatttttt aaccaatagg     1500
ccgaaatcgg caaaatccct tataaatcaa agaatatagac cgagataggg ttgagtgttg    1560
ttccagtttg gaacaagagt ccactattaa agaacgtgga ctccaacgtc aaagggcgaa     1620
aaaccgtcta tcagggcgat ggcccactac gtgaaccatc accctaatca agttttttgg     1680
ggtcgaggtg ccgtaaagca ctaaatcgga accctaaagg gagcccccga tttagagctt     1740
gacggggaaa gccggcgaac gtggcgagaa aggaagggaa gaaagcgaaa ggagcgggcg     1800
ctagggcgct ggcaagtgta gcggtcacgc tgcgcgtaac caccacaccc gccgcgctta     1860
atgcgccgct acagggcgcg tcgcgccatt cgccattcag gctgcgcaac tgttgggaag     1920
ggcgatcggt gcgggcctct tcgctattac gccagctggc gaaggggga  tgtgctgcaa     1980 ggcgattaag ttgggtaacg ccagggtttt cccagtcacg acgttgtaaa acgacggcca     2040
gtgagcgcgc gtaatacgac tcactatagg gcgaattggg taccggccgc aaattaaagc     2100
cttcgagcgt cccaaaacct tctcaagcaa ggttttcagt ataatgttac atgcgtacac     2160
gcgtctgtac agaaaaaaaa gaaaaatttg aaatataaat aacgttctta atactaacat     2220
aactataaaa aaataaatag ggacctagac ttcaggttgt ctaactcctt ccttttcggt     2280
tagagcggat gtgggggag  ggcgtgaatg taagcgtgac ataactaatt acatgactcg     2340
agcggccgcg gatcctcaat aaaactcttc aggcaataat ttttctgcta atttaatgtt     2400
atcagaatag tccaaaggaa cgtcaattac tactggtcca gtagtatctg ggattgattt     2460
```

```
aagaatttca gcaagttctt cttttgctgtg tgcacggtaa cctttttgctc ccattgcttc    2520 agcatatttt acgtaatcaa catagccaaa atcaacggct gctgaacgac catatttcat    2580
ttcttcttgg aatttaacca tatcataatg gccgtcattc cagataattt gaacgattgg    2640
aagattcaaa cgtacagctg tttccaactc ttgccctgtg aaaaggaagc ctccatcacc    2700
agagtgtgaa taaactttt tacctgggcg caacaatgcg gctgtaattg cccaaggaag    2760
tgcaactcca agtgtttgca ttccgtttga agagaggaga tgacgtggtt cgtatgattt    2820
gaaatgacgt gccatccaaa tgtagagtga acctacgtca acggttactg tttcatcatc    2880
tttaacgatt tcttggaaag tgctgaccaa atcaagaggg tgcattctac cttcttcagt    2940
attttcagta tcaaattcgt gttgctcagc aacttcatga aggccatcga gataatcttt    3000
tgttcctttt ggaattttgt atccacgaac agctggtaaa agattatcca atgttgctgc    3060
gatatcacca attaattcac gttctggttg gtagtaagta tcaatttcag caatggcatt    3120
atcaataacg ataattcgac tatcaatttc tgcattccag ttacgagctt catattcaat    3180
tgggtcataa ccaacagcaa taacaaggtc agaacgtttc agaagcatat ctcctggttg    3240
attgcggaaa agaccgatac gtccataaaa agtatgttct aaatcatgtg aaataacccc    3300
tgcaccttgg aatgtttcaa cgacaggaat attaacatga gttaatagat tacgcaatga    3360
tgaagcgact ttagcatctg aagcaccagc tccaaccaaa attactggca atacagcatt    3420
tttaattgct tgtgctaaat aattaatgtc atcaatagag gcattcccca ttttagggtc    3480
tgaaagtggt tgaatggcct tgattgatac ttcggcatcc gttacatctt gggggattga    3540
taagaaagtt gcacctggat gtcctgattt tgcaatacga taagcgttgg caattgattc    3600
agaaagtgta tcagggtcaa gaacttctgc tgaatatttt gttgctgatt gcatcattcc    3660
agcattatcc attgattggt gcgcacgttt aagacggtca cttcgtttaa cttgtccacc    3720
gatagccaaa atagcatcac cttctgaagt cgcggtcaaa agcggagtcg caaggtttga    3780
tacaccaggc ccactcgtaa caactactac accaggttcg ccagtcaaac gaccaacagc    3840
ttgagccatg aaagcagctc cttgctcatg acgagtcacg accatttgag ggccttcttc    3900
attttctaat aaatcaaaaa cccggtcaat ttttgctcct ggaatcccaa atacatactt    3960
cactttatgg ttaatcaaac tatcgacaac caagttcgcc ccaaattgtt tctcagacat    4020
gtcgacaccg atatacctgt atgtgtcacc accaatgtat ctataagtat ccatgctagc    4080
cctaggttta tgtgatgatt gattgattga ttgtacagtt tgttttttctt aatatctatt    4140 tcgatgactc ctatatgata ttgcactaac aagaagatat tataatgcaa ttgatacaag    4200
acaaggagtt atttgcttct ctttatatg attctgacaa tccatattgc gttggtagtc    4260 tttttttgctg gaacggttca gcggaaaaga cgcatcgctc tttttgcttc tagaagaaat    4320
gccagcaaaa gaatctcttg acagtgactg acagcaaaaa tgtcttttc taactagtaa    4380 caaggctaag atatcagcct gaaataaagg gtggtgaagt aataattaaa tcatccgtat    4440
aaacctatac acatatatga ggaaaaataa tacaaaagtg ttttaaatac agatacatac    4500
atgaacatat gcacgtatag cgcccaaatg tcggtaatgg gatcggcgag ctccagcttt    4560
tgttcccttt agtgagggt aattgcgcgc ttggcgtaat catggtcata gctgtttcct    4620
gtgtgaaatt gttatccgct cacaattcca cacaacatag gagccggaag cataaagtgt    4680
aaagcctggg gtgcctaatg agtgaggtaa ctcacattaa ttgcgttgcg ctcactgccc    4740
gctttccagt cgggaaacct gtcgtgccag ctgcattaat gaatcggcca acgcgcgggg    4800
agaggcggtt tgcgtattgg gcgctcttcc gcttcctcgc tcactgactc gctgcgctcg    4860
```

```
gtcgttcggc tgcggcgagc ggtatcagct cactcaaagg cggtaatacg gttatccaca   4920
gaatcagggg ataacgcagg aaagaacatg tgagcaaaag gccagcaaaa ggccaggaac   4980
cgtaaaaagg ccgcgttgct ggcgtttttc cataggctcc gcccccctga cgagcatcac   5040
aaaaatcgac gctcaagtca gaggtggcga acccgacag gactataaag ataccaggcg    5100
tttccccctg gaagctccct cgtgcgctct cctgttccga ccctgccgct taccggatac   5160
ctgtccgcct ttctcccttc gggaagcgtg gcgctttctc atagctcacg ctgtaggtat   5220
ctcagttcgg tgtaggtcgt tcgctccaag ctgggctgtg tgcacgaacc ccccgttcag   5280
cccgaccgct gcgccttatc cggtaactat cgtcttgagt ccaacccggt aagacacgac   5340
ttatcgccac tggcagcagc cactggtaac aggattagca gagcgaggta tgtaggcggt   5400
gctacagagt tcttgaagtg gtggcctaac tacggctaca ctagaaggac agtatttggt   5460
atctgcgctc tgctgaagcc agttaccttc ggaaaaagag ttggtagctc ttgatccggc   5520
aaacaaacca ccgctggtag cggtggtttt tttgtttgca agcagcagat tacgcgcaga   5580
aaaaaaggat ctcaagaaga tcctttgatc ttttctacgg ggtctgacgc tcagtggaac   5640
gaaaactcac gttaagggat tttggtcatg agattatcaa aaaggatctt cacctagatc   5700
cttttaaatt aaaaatgaag ttttaaatca atctaaagta tatatgagta aacttggtct   5760
gacagttacc aatgcttaat cagtgaggca cctatctcag cgatctgtct atttcgttca   5820
tccatagttg cctgactccc cgtcgtgtag ataactacga tacgggaggg cttaccatct   5880
ggccccagtg ctgcaatgat accgcgagac ccacgctcac cggctccaga tttatcagca   5940
ataaaccagc cagccggaag ggccgagcgc agaagtggtc ctgcaacttt atccgcctcc   6000
atccagtcta ttaattgttg ccgggaagct agagtaagta gttcgccagt taatagtttg   6060
cgcaacgttg ttgccattgc tacaggcatc gtggtgtcac gctcgtcgtt tggtatggct   6120
tcattcagct ccggttccca acgatcaagg cgagttacat gatcccccat gttgtgcaaa   6180
aaagcggtta gctccttcgg tcctccgatc gttgtcagaa gtaagttggc cgcagtgtta   6240
tcactcatgg ttatggcagc actgcataat tctcttactg tcatgccatc cgtaagatgc   6300
ttttctgtga ctggtgagta ctcaaccaag tcattctgag aatagtgtat gcggcgaccg   6360
agttgctctt gcccggcgtc aatacgggat aataccgcgc cacatagcag aactttaaaa   6420
gtgctcatca ttggaaaacg ttcttcgggg cgaaaactct caaggatctt accgctgttg   6480
agatccagtt cgatgtaacc cactcgtgca cccaactgat cttcagcatc ttttactttc   6540
accagcgttt ctgggtgagc aaaaacagga aggcaaaatg ccgcaaaaaa gggaataagg   6600
gcgacacgga aatgttgaat actcatactc ttcctttttc aatattattg aagcatttat   6660
cagggttatt gtctcatgag cggatacata tttgaatgta tttagaaaaa taaacaaata   6720
ggggttccgc gcacatttcc ccgaaaagtg ccacctgaac gaagcatctg tcttcatttt   6780
tgtagaacaa aaatgcaacg cgagagcgct aattttcaa acaaagaatc tgagctgcat   6840
ttttacagaa cagaaatgca acgcgaaagc gctatttac caacgaagaa tctgtgcttc   6900
atttttgtaa aacaaaaatg caacgcgaga gcgctaattt ttcaaacaaa gaatctgagc   6960
tgcattttta cagaacagaa atgcaacgcg agagcgctat tttaccaaca aagaatctat   7020
acttcttttt tgttctacaa aaatgcatcc cgagagcgct attttttctaa caaagcatct   7080 tagattactt ttttttctcct tgtgcgctc tataatgcag tctcttgata actttttgca   7140
ctgtaggtcc gttaaggtta gaagaaggct actttggtgt ctatttttctc ttccataaaa   7200 aaagcctgac tccacttccc gcgtttactg attactagcg aagctgcggg tgcattttttt   7260
```

-continued

| | |
|---|---|
| caagataaag gcatccccga ttatattcta taccgatgtg gattgcgcat actttgtgaa | 7320 |
| cagaaagtga tagcgttgat gattcttcat tggtcagaaa attatgaacg gtttcttcta | 7380 |
| ttttgtctct atatactacg tataggaaat gtttacattt tcgtattgtt ttcgattcac | 7440 |
| tctatgaata gttcttacta caatttttt gtctaaagag taatactaga gataaacata | 7500 |
| aaaaatgtag aggtcgagtt tagatgcaag ttcaaggagc gaaaggtgga tgggtaggtt | 7560 |
| atataggggat atagcacaga gatatatagc aaagagatac ttttgagcaa tgtttgtgga | 7620 |
| agcggtattc gcaatatttt agtagctcgt tacagtccgg tgcgttttg gttttttgaa | 7680 |
| agtgcgtctt cagagcgctt ttggttttca aaagcgctct gaagttccta tactttctag | 7740 |
| agaataggaa cttcggaata ggaacttcaa agcgtttccg aaaacgagcg cttccgaaaa | 7800 |
| tgcaacgcga gctgcgcaca tacagctcac tgttcacgtc gcacctatat ctgcgtgttg | 7860 |
| cctgtatata tatatacatg agaagaacgg catagtgcgt gtttatgctt aaatgcgtac | 7920 |
| ttatatgcgt ctatttatgt aggatgaaag gtagtctagt acctcctgtg atattatccc | 7980 |
| attccatgcg gggtatcgta tgcttccttc agcactaccc tttagctgtt ctatatgctg | 8040 |
| ccactcctca attggattag tctcatcctt caatgctatc atttcctttg atattggatc | 8100 |
| atctaagaaa ccattattat catgacatta acctataaaa ataggcgtat cacgaggccc | 8160 |
| tttcgtc | 8167 |

<210> SEQ ID NO 13
<211> LENGTH: 9598
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatcga ctacgtcgta aggccgtttc tgacagagta aaattcttga gggaactttc | 240 |
| accattatgg gaaatgcttc aagaaggtat tgacttaaac tccatcaaat ggtcaggtca | 300 |
| ttgagtgttt tttatttgtt gtattttttt tttttagag aaaatcctcc aatatcaaat | 360 |
| taggaatcgt agtttcatga ttttctgtta cacctaactt tttgtgtggt gccctcctcc | 420 |
| ttgtcaatat taatgttaaa gtgcaattct ttttccttat cacgttgagc cattagtatc | 480 |
| aatttgctta cctgtattcc tttactatcc tccttttct ccttcttgat aaatgtatgt | 540 |
| agattgcgta tatagtttcg tctaccctat gaacatattc cattttgtaa tttcgtgtcg | 600 |
| tttctattat gaatttcatt tataaagttt atgtacaaat atcataaaaa aagagaatct | 660 |
| ttttaagcaa ggatttctt aacttcttcg gcgacagcat caccgacttc ggtggtactg | 720 |
| ttggaaccac ctaaatcacc agttctgata cctgcatcca aaacctttt aactgcatct | 780 |
| tcaatggcct taccttcttc aggcaagttc aatgacaatt tcaacatcat tgcagcagac | 840 |
| aagatagtgg cgatagggtc aaccttattc tttggcaaat ctggagcaga accgtggcat | 900 |
| ggttcgtaca aaccaaatgc ggtgttcttg tctggcaaag aggccaagga cgcagatggc | 960 |
| aacaaaccca aggaacctgg gataacggag gcttcatcgg agatgatatc accaaacatg | 1020 |
| ttgctggtga ttaataccc atttaggtgg gttgggttct taactaggat catggcggca | 1080 |
| gaatcaatca attgatgttg aaccttcaat gtagggaatt cgttcttgat ggtttcctcc | 1140 |

```
acagtttttc tccataatct tgaagaggcc aaaagattag ctttatccaa ggaccaaata    1200
ggcaatggtg gctcatgttg tagggccatg aaagcggcca ttcttgtgat tctttgcact    1260
tctggaacgg tgtattgttc actatcccaa gcgacaccat caccatcgtc ttcctttctc    1320
ttaccaaagt aaatacctcc cactaattct ctgacaacaa cgaagtcagt acctttagca    1380
aattgtggct tgattggaga taagtctaaa agagagtcgg atgcaaagtt acatggtctt    1440
aagttggcgt acaattgaag ttcttttacgg atttttagta aaccttgttc aggtctaaca    1500
ctaccggtac cccatttagg accagccaca gcacctaaca aaacggcatc aaccttcttg    1560
gaggcttcca gcgcctcatc tggaagtggg acacctgtag catcgatagc agcaccacca    1620
attaaatgat tttcgaaatc gaacttgaca ttggaacgaa catcagaaat agctttaaga    1680
accttaatgg cttcggctgt gatttcttga ccaacgtggt cacctggcaa aacgacgatc    1740
ttcttagggg cagacatagg ggcagacatt agaatggtat atccttgaaa tatatatata    1800
tattgctgaa atgtaaaagg taagaaaagt tagaaagtaa gacgattgct aaccacctat    1860
tggaaaaaac aataggtcct taaataatat tgtcaacttc aagtattgtg atgcaagcat    1920
ttagtcatga acgcttctct attctatatg aaaagccggt tccggcctct cacctttcct    1980
ttttctccca attttttcagt tgaaaaaggt atatgcgtca ggcgacctct gaaattaaca    2040
aaaaatttcc agtcatcgaa tttgattctg tgcgatagcg ccctgtgtg ttctcgttat     2100
gttgaggaaa aaaataatgg ttgctaagag attcgaactc ttgcatctta cgatacctga    2160
gtattcccac agttaactgc ggtcaagata tttcttgaat caggcgcctt agaccgctcg    2220
gccaaacaac caattacttg ttgagaaata gagtataatt atcctataaa tataacgttt    2280
ttgaacacac atgaacaagg aagtacagga caattgattt tgaagagaat gtggattttg    2340
atgtaattgt tgggattcca ttttttaataa ggcaataata ttaggtatgt ggatatacta    2400
gaagttctcc tcgaccgtcg atatgcggtg tgaaataccg cacagatgcg taaggagaaa    2460
ataccgcatc aggaaattgt aaacgttaat attttgttaa aattcgcgtt aaattttttgt    2520
taaatcagct cattttttaa ccaataggcc gaaatcggca aaatccctta taaatcaaaa    2580
gaatagaccg agataggggtt gagtgttgtt ccagtttgga acaagagtcc actattaaag    2640
aacgtggact ccaacgtcaa agggcgaaaa accgtctatc agggcgatgg cccactacgt    2700
gaaccatcac cctaatcaag ttttttgggg tcgaggtgcc gtaaagcact aaatcggaac    2760
cctaaaggga gcccccgatt tagagcttga cggggaaagc cggcgaacgt ggcgagaaag    2820
gaagggaaga aagcgaaagg agcgggcgct agggcgctgg caagtgtagc ggtcacgctg    2880
cgcgtaacca ccacacccgc cgcgcttaat gcgccgctac agggcgcgtc gcgccattcg    2940
ccattcaggc tgcgcaactg ttgggaaggg cgatcggtgc gggcctcttc gctattacgc    3000
cagctggcga aaggggatg tgctgcaagg cgattaagtt gggtaacgcc agggttttcc      3060
cagtcacgac gttgtaaaac gacggccagt gagcgcgcgt aatacgactc actatagggc    3120
gaattgggta ccggccgcaa attaaagcct tcgagcgtcc caaaaccttc tcaagcaagg    3180
ttttcagtat aatgttacat gcgtacacgc gtctgtacag aaaaaaaaga aaatttgaa     3240
atataaataa cgttcttaat actaacataa ctataaaaaa ataaatagggg acctagactt    3300
caggttgtct aactccttcc ttttcggtta gagcggatgt ggggggaggg cgtgaatgta    3360
agcgtgacat aactaattac atgactcgag cggccgcgga tccttaaccc ccagtttcg     3420
atttatcgcg caccgcgcct tgtcggcgc tggttgccag gctggcataa gcacgcaggg     3480
caaaggagac ctgacgttca cgattttcg gcgtccaggc tttgtcacct cgagcgtcct    3540
```

```
gcgcttcacg acgcgccgcc agttcggcat cgcttacctg taactgaatg ccacggttcg    3600
ggatgtcgat agcgatcagg tcaccatctt caatcaggcc aatgctgccg ccgcttgccg    3660
cttccggtga gacgtggccg atggaaagac cagaggtgcc accagagaaa cgaccgtcgg    3720
tgatcagcgc acaggctttg ccgagaccca ttgatttcag gaagctggtt gggtagagca    3780
tttcctgcat ccccggaccg cctttcgggc cttcatagcg aattactacc acatctccgg    3840
cgacaacttt accgccgaga atcgcttcta ccgcatcgtc ctggctttcg tacactttcg    3900
ccgggccggt gaatttgagg atgctgtcat cgacgcctgc cgttttcacg atgcagccgt    3960
tttccgcaaa gttaccgtag agcaccgcca ggccgccgtc tttgctgtag gcgtgttcca    4020
gcgagcggat acagccattg gcgcgatcgt cgtccagcgt atcccaacgg caatcttgcg    4080
agaatgcctg tgtggtacga atgcctgcag gacctgcgcg aacatatttt tttaccgcgt    4140
catcctgggt cagcataacg tcgtattgtt ccagcgtttg cggcaacgtc aggccaagta    4200
cgttttcac atcacggttc agtaaccccg cgcgatccag ttcgccgaga ataccgataa    4260
caccaccagc acggtgaaca tcttccatat ggtatttctg ggtgctcggc gcaactttac    4320
acagctgtgg aaccttgcgg gaaagcttat cgatatcact catggtgaag tcgatttccg    4380
cttcctgcgc cgccgccagc aggtgaagta cggtgttagt cgatccaccc atcgcgatat    4440
ccagcgtcat ggcgttttca aacgccgcct tactggcgat attacgcggc agtgcacttt    4500
cgtcgttttg ctcgtaataa cgtttggtca attcaacaat gcgtttacca gcattaagga    4560
acagctgctt acgtcggcg tgggttgcca gcagcgagcc gttgcccggc tgcgacaggc    4620
ccagcgcttc ggtcaggcag ttcattgagt tagcggtaaa catcccggag caggaaccgc    4680
aggtcggaca cgcggaacgt tcaacctgat cgctctggga gtcagatact ttcgggtctg    4740
cgccctggat catcgcatca accagatcga gcttgatgat ctgatcggaa gtttggttt    4800
tcccggcctc catcgggccg ccggaaacaa agatcaccgg aatattcagg cgcagggaag    4860
ccatcagcat ccccggggtg attttgtcgc agttagagat gcagaccatg cgtcggcgc    4920
agtgggcgtt gaccatatac tcaacggaat cagcgatcag ttcgcgagat ggcagtgaat    4980
aaagcatccc cccgtggccc atggcaatcc catcatccac cgcaatggtg ttgaactctt    5040
tggcaacgcc gccagccgct tcaatttgtt cggcgaccag tttaccgaga tcgcgcagat    5100
ggacgtgacc cggtacaaat tgggtgaacg agttcacaac cgcgataatc ggcttaccga    5160
aatcggcgtc ggtcattccg gtggcgcgcc acagcgcacg agcacccgcc atattacgac    5220
catgagtggt ggtggcggaa cggtacttag gcatgtcgac accatcttct tctgagatga    5280
gttttttgttc catgctagtt ctagaatccg tcgaaactaa gttctggtgt tttaaaacta    5340
aaaaaaagac taactataaa agtagaattt aagaagttta agaaatagat ttacagaatt    5400
acaatcaata cctaccgtct ttatatactt attagtcaag tagggaata atttcaggga    5460
actggtttca accttttttt tcagcttttt ccaaatcaga gagagcagaa ggtaatagaa    5520
ggtgtaagaa aatgagatag atacatgcgt gggtcaattg ccttgtgtca tcatttactc    5580
caggcaggtt gcatcactcc attgaggttg tgcccgtttt ttgcctgttt gtgccctgt    5640
tctctgtagt tgcgctaaga gaatggacct atgaactgat ggttggtgaa gaaaacaata    5700
ttttggtgct gggattcttt tttttttctgg atgccagctt aaaaagcggg ctccattata    5760
tttagtggat gccaggaata aactgttcac ccagacacct acgatgttat atattctgtg    5820
taacccgccc cctatttttgg gcatgtacgg gttacagcag aattaaaagg ctaattttt    5880
gactaaataa agttaggaaa atcactacta ttaattattt acgtattctt tgaaatggcg    5940
```

```
agtattgata atgataaact gagctagatc tgggcccgag ctccagcttt tgttcccttt     6000
agtgagggtt aattgcgcgc ttggcgtaat catggtcata gctgtttcct gtgtgaaatt     6060
gttatccgct cacaattcca cacaacatag gagccggaag cataaagtgt aaagcctggg     6120
gtgcctaatg agtgaggtaa ctcacattaa ttgcgttgcg ctcactgccc gctttccagt     6180
cgggaaacct gtcgtgccag ctgcattaat gaatcggcca acgcgcgggg agaggcggtt     6240
tgcgtattgg gcgctcttcc gcttcctcgc tcactgactc gctgcgctcg tcgttcggc      6300 tgcggcgagc ggtatcagct cactcaaagg cggtaatacg gttatccaca gaatcagggg     6360
ataacgcagg aaagaacatg tgagcaaaag gccagcaaaa ggccaggaac cgtaaaaagg     6420
ccgcgttgct ggcgtttttc cataggctcc gcccccctga cgagcatcac aaaaatcgac     6480
gctcaagtca gaggtggcga aacccgacag gactataaag ataccaggcg tttccccctg     6540
gaagctccct cgtgcgctct cctgttccga ccctgccgct taccggatac ctgtccgcct     6600
ttctcccttc gggaagcgtg gcgctttctc atagctcacg ctgtaggtat ctcagttcgg     6660
tgtaggtcgt tcgctccaag ctgggctgtg tgcacgaacc ccccgttcag cccgaccgct     6720
gcgccttatc cggtaactat cgtcttgagt ccaacccggt aagacacgac ttatcgccac     6780
tggcagcagc cactggtaac aggattagca gagcgaggta tgtaggcggt gctacagagt     6840
tcttgaagtg gtgcctaac tacgctaca ctagaaggac agtatttggt atctgcgctc      6900
tgctgaagcc agttaccttc ggaaaaagag ttggtagctc ttgatccggc aaacaaacca     6960
ccgctggtag cggtggtttt tttgtttgca agcagcagat tacgcgcaga aaaaaaggat     7020
ctcaagaaga tcctttgatc ttttctacgg ggtctgacgc tcagtggaac gaaaactcac     7080
gttaagggat tttggtcatg agattatcaa aaaggatctt cacctagatc cttttaaatt     7140
aaaaatgaag ttttaaatca atctaaagta tatatgagta aacttggtct gacagttacc     7200
aatgcttaat cagtgaggca cctatctcag cgatctgtct atttcgttca tccatagttg     7260
cctgactccc cgtcgtgtag ataactacga tacgggaggg cttaccatct ggccccagtg     7320
ctgcaatgat accgcgagac ccacgctcac cggctccaga tttatcagca ataaaccagc     7380
cagccggaag ggccgagcgc agaagtggtc ctgcaacttt atccgcctcc atccagtcta     7440
ttaattgttg ccgggaagct agagtaagta gttcgccagt taatagtttg cgcaacgttg     7500
ttgccattgc tacaggcatc gtggtgtcac gctcgtcgtt tggtatggct tcattcagct     7560
ccggttccca acgatcaagg cgagttacat gatcccccat gttgtgcaaa aaagcggtta     7620
gctccttcgg tcctccgatc gttgtcagaa gtaagttggc cgcagtgtta tcactcatgg     7680
ttatggcagc actgcataat tctcttactg tcatgccatc cgtaagatgc ttttctgtga     7740
ctggtgagta ctcaaccaag tcattctgag aatagtgtat gcggcgaccg agttgctctt     7800
gcccggcgtc aatacgggat aataccgcgc cacatagcag aactttaaaa gtgctcatca     7860
ttggaaaacg ttcttcgggg cgaaaactct caaggatctt accgctgttg agatccagtt     7920
cgatgtaacc cactcgtgca cccaactgat cttcagcatc ttttactttc accagcgttt     7980
ctgggtgagc aaaaacagga aggcaaaatg ccgcaaaaaa gggaataagg gcgacacgga     8040
aatgttgaat actcatactc ttcctttttc aatattattg aagcatttat cagggttatt     8100
gtctcatgag cggatacata tttgaatgta tttagaaaaa taaacaaata ggggttccgc     8160
gcacatttcc ccgaaaagtg ccacctgaac gaagcatctg tgcttcattt tgtagaacaa     8220
aaatgcaacg cgagagcgct aattttcaa acaaagaatc tgagctgcat ttttacagaa      8280
cagaaatgca acgcgaaagc gctattttac caacgaagaa tctgtgcttc attttgtaa      8340
```

```
aacaaaaatg caacgcgaga gcgctaattt ttcaaacaaa gaatctgagc tgcattttta    8400
cagaacagaa atgcaacgcg agagcgctat tttaccaaca aagaatctat acttcttttt    8460
tgttctacaa aaatgcatcc cgagagcgct atttttctaa caaagcatct tagattactt    8520
tttttctcct ttgtgcgctc tataatgcag tctcttgata acttttttgca ctgtaggtcc    8580 gttaaggtta aagaaggct actttggtgt ctatttttctc ttccataaaa aaagcctgac    8640
tccacttccc gcgtttactg attactagcg aagctgcggg tgcattttttt caagataaag    8700 gcatccccga ttatattcta taccgatgtg gattgcgcat actttgtgaa cagaaagtga    8760
tagcgttgat gattcttcat tggtcagaaa attatgaacg gtttcttcta ttttgtctct    8820
atatactacg tataggaaat gtttacattt tcgtattgtt ttcgattcac tctatgaata    8880
gttcttacta caattttttt gtctaaagag taatactaga gataaacata aaaaatgtag    8940
aggtcgagtt tagatgcaag ttcaaggagc gaaaggtgga tgggtaggtt atatagggat    9000
atagcacaga gatatatagc aaagagatac ttttgagcaa tgtttgtgga agcggtattc    9060
gcaatatttt agtagctcgt tacagtccgg tgcgttttttg gttttttgaa agtgcgtctt    9120
cagagcgctt ttggttttca aaagcgctct gaagttccta tactttctag aaataggaa    9180 cttcggaata ggaacttcaa agcgtttccg aaaacgagcg cttccgaaaa tgcaacgcga    9240
gctgcgcaca tacagctcac tgttcacgtc gcacctatat ctgcgtgttg cctgtatata    9300
tatatacatg agaagaacgg catagtgcgt gtttatgctt aaatgcgtac ttatatgcgt    9360
ctatttatgt aggatgaaag gtagtctagt acctcctgtg atattatccc attccatgcg    9420
gggtatcgta tgcttccttc agcactaccc tttagctgtt ctatatgctg ccactcctca    9480
attggattag tctcatcctt caatgctatc atttcctttg atattggatc atactaagaa    9540
accattatta tcatgacatt aacctataaa aataggcgta tcacgaggcc ctttcgtc      9598

<210> SEQ ID NO 14
<211> LENGTH: 8698
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
ctgattggaa agaccattct gctttacttt tagagcatct tggtcttctg agctcattat      60
acctcaatca aaactgaaat taggtgcctg tcacggctct tttttactg tacctgtgac     120 ttcctttctt atttccaagg atgctcatca caatacgctt ctagatctat tatgcattat     180
aattaatagt tgtagctaca aaaggtaaaa gaaagtccgg ggcaggcaac aatagaaatc     240
ggcaaaaaaa actacagaaa tactaagagc ttcttcccca ttcagtcatc gcatttcgaa     300
acaagagggg aatggctctg gctagggaac taaccaccat cgcctgactc tatgcactaa     360
ccacgtgact acatatatgt gatcgttttt aacattttc aaaggctgtg tgtctggctg     420
tttccattaa ttttcactga ttaagcagtc atattgaatc tgagctcatc accaacaaga     480
aatactaccg taaaagtgta aaagttcgtt taaatcattt gtaaactgga acagcaagag     540
gaagtatcat cagctagccc cataaactaa tcaaggagg atgtctacta agagttactc     600
ggaaagagca gctgctcata gaagtccagt tgctgccaag cttttaaact tgatggaaga     660
gaagaagtca aacttatgtg cttctcttga tgttcgtaaa acagcagagt tgttaagatt     720
agttgaggtt ttgggtccat atatctgtct attgaagaca catgtagata tcttggagga     780
```

```
tttcagcttt gagaatacca ttgtgccgtt gaagcaatta gcagagaaac acaagttttt    840
gatatttgaa gacaggaagt tgccgacat tgggaacact gttaaattac aatacacgtc    900
tggtgtatac cgtatcgccg aatggtctga tatcaccaat gcacacggtg tgactggtgc   960
gggcattgtt gctggtttga agcaaggtgc cgaggaagtt acgaaagaac ctagagggtt  1020
gttaatgctt gccgagttat cgtccaaggg gtctctagcg cacggtgaat acactcgtgg  1080
gaccgtggaa attgccaaga gtgataagga ctttgttatt ggatttattg ctcaaaacga  1140
tatgggtgga agagaagagg gctacgattg gttgatcatg acgccaggtg ttggtcttga  1200
tgacaaaggt gatgctttgg gacaacaata cagaactgtg gatgaagttg ttgccggtgg  1260
atcagacatc attattgttg gtagaggtct tttcgcaaag ggaagagatc ctgtagtgga  1320
aggtgagaga tacagaaagg cgggatggga cgcttacttg aagagagtag gcagatccgc  1380
ttaagagttc tccgagaaca agcagaggtt cgagtgtact cggatcagaa gttacaagtt  1440
gatcgtttat atataaacta tacagagatg ttagagtgta atggcattgc gtgccggcga  1500
tcacagcgga cggtggtggc atgatggggc ttgcgatgct atgtttgttt gttttgtgat  1560
gatgtatatt attattgaaa aacgatatca gacatttgtc tgataatgct tcattatcag  1620
acaaatgtct gatatcgttt ggagaaaaag aaaaggaaaa caaactaaat atctactata  1680
taccactgta ttttatacta atgactttct acgcctagtg tcaccctctc gtgtacccat  1740
tgaccctgta tcggcgcgtt gcctcgcgtt cctgtaccat atattttgt ttatttaggt  1800
attaaaattt actttcctca tacaaatatt aaattcacca aacttctcaa aaactaatta  1860
ttcgtagtta caaactctat tttacaatca cgtttattca accattctac atccaataac  1920
caaaatgccc atgtacctct cagcgaagtc caacggtact gtccaatatt ctcattaaat  1980
agtctttcat ctatatatca gaaggtaatt ataattagag atttcgaatc attaccgtgc  2040
cgattcgcac gctgcaacgg catgcatcac taatgaaaag catacgacgc ctgcgtctga  2100
catgcactca ttctgaagaa gattctgggc gcgtttcgtt ctcgtttttcc tctgtatatt  2160
gtactctggt ggacaatttg aacataacgt cttttcacctc gccattctca ataatgggtt  2220
ccaattctat ccaggtagcg gttaattgac ggtgcttaag ccgtatgctc actctaacgc  2280
taccgttgtc caaacaacgg accccttttgt gacgggtgta agacccatca tgaagtaaaa  2340
catctctaac ggtatggaaa agagtggtac ggtcaagttt cctggcacga gtcaattttc  2400
cctcttcgtg tagatcggta ccggccgcaa attaaagcct tcgagcgtcc caaaaccttc  2460
tcaagcaagg ttttcagtat aatgttacat gcgtacacgc gtctgtacag aaaaaaaaga  2520
aaaatttgaa atataaataa cgttcttaat actaacataa ctataaaaaa ataaataggg  2580
acctagactt caggttgtct aactccttcc ttttcggtta gagcggatgt ggggggaggg  2640
cgtgaatgta agcgtgacat aactaattac atgagcggcc gcctatttat ggaattttctt  2700
atcataatcg accaaagtaa atctgtattt gacgtctccg cttttccatcc ttgtaaaggc  2760
atggctgacg ccttcttcgc tgatcggaag ttttttccacc catattttga cattctttctc  2820
ggaaactaat ttcaatagtt gttcgatttc cttcctagat ccgatagcac tgcttgagat  2880
tgatactccc attaggccca acggttttaa acaagctttt tcattaactt caggagcagc  2940
aattgaaacg atgagcctc caatcttcat aatcttaacg atactgtcaa aattaacttt  3000
cgacaaagat gatgagcaaa cgacaagaag gtccaaagcg ttagagtatt gttctgtcca  3060
gcctttatcc tccaacatag caatatagtg atcagcaccg agtttcatag aatcctcccg  3120
cttggagtgg cctcgcgaaa acgcataaac ctcggctccc atagctttag ccaacagaat  3180
```

```
ccccatatgc caataccac cgatgccaac aatacctacc ctcttacctg gaccacagcc    3240
atttcttagt agtggagaga aaactgtaat accaccacac aataatggag cggctagcgg    3300
acttggaata ttttctggta tttgaatagc aaagtgttca tgaagcctca cgtgggaggc    3360
aaagcctcct tgtgaaatgt agccgtcctt gtaaggagtc cacatagtca aaacgtggtc    3420
attggtacag tattgctcgt tgtcactttt gcaacgttca cactcaaaac acgccaaggc    3480
ttgggcacca acaccaacac ggtcaccgat ttttaccccca gtgtggcact tggatccaac    3540
cttcaccacg cggccaatta tttcatgtcc aaggatttga ttttctggga ctggacccca    3600
attaccaacg gctatatgaa aatcagatcc gcagatacca caggcttcaa tttcaacatc    3660
aacgtcatga tcgccaaagg gttttgggtc aaaactcact aatttaggat gcttccaatc    3720
ctttgcgttg gaaataccga tgccctgaaa tttttctggg taaagcatgt cgagtcgaaa    3780
ctaagttctg gtgttttaaa actaaaaaaa agactaacta taaaagtaga atttaagaag    3840
tttaagaaat agatttacag aattacaatc aatacctacc gtctttatat acttattagt    3900
caagtagggg aataatttca gggaactggt ttcaaccttt tttttcagct ttttccaaat    3960
cagagagagc agaaggtaat agaaggtgta agaaaatgag atagatacat gcgtgggtca    4020
attgccttgt gtcatcattt actccaggca ggttgcatca ctccattgag gttgtgcccg    4080
tttttttgcct gtttgtgccc ctgttctctg tagttgcgct aagagaatgg acctatgaac    4140
tgatggttgg tgaagaaaac aatattttgg tgctgggatt cttttttttt ctggatgcca    4200
gcttaaaaag cgggctccat tatatttagt ggatgccagg aataaactgt tcacccagac    4260
acctacgatg ttatatattc tgtgtaaccc gccccctatt ttgggcatgt acgggttaca    4320
gcagaattaa aaggctaatt ttttgactaa ataaagttag gaaaatcact actattaatt    4380
atttacgtat tctttgaaat ggcgagtatt gataatgata aactggatcc ttaggattta    4440
ttctgttcag caaacagctt gcccattttc ttcagtacct tcggtgcgcc ttctttcgcc    4500
aggatcagtt cgatccagta catacggttc ggatcggcct gggcctcttt catcacgctc    4560
acaaattcgt tttcggtacg cacaatttta gacacaacac ggtcctcagt tgcgccgaag    4620
gactccggca gtttagagta gttccacata gggatatcgt tgtaagactg gttcggaccg    4680
tggatctcac gctcaacggt gtagccgtca ttgttaataa tgaagcaaat cgggttgatc    4740
ttttcacgaa ttgccagacc cagttcctgt acggtcagct gcagggaacc gtcaccgatg    4800
aacagcagat gacgagattc tttatcagcg atctgagagc ccagcgctgc cgggaaagta    4860
tagccaatgc taccccacag cggctgaccg ataaaatggc ttttggattt cagaaagata    4920
gaagacgcgc cgaaaaagct cgtaccttgt tccgccacga tggtttcatt gctctgggtc    4980
aggttctcca cggcctgcca caggcgatcc tgggacagca gtgcgttaga tggtacgaaa    5040
tcttcttgct ttttgtcaat gtatttgcct ttatactcga tttcggacag gtccagcaga    5100
gagctgatca ggctttcgaa gtcgaagttc tggatacgct cgttgaagat tttaccctcg    5160
tcgatgttca ggctaatcat tttgttttcg ttcagatggt gagtgaatgc accggtagaa    5220
gagtcggtca gttaacgcc cagcatcagg atgaagtccg cagattcaac aaattctttc    5280
aggttcggtt cgctcagagt accgttgtag atgcccagga aagacggcag agcctcgtca    5340
acagaggact tgccgaagtt cagggtggta atcggcagtt tggttttgct gatgaattgg    5400
gtcacggtct tctccagacc aaaagaaatg atttcgtggc cggtgatcac gattggtttc    5460
tttgcgtttt tcagagactc ctggattttg ttcaggattt cctggtcgct agtgttagaa    5520
gtggagtttt ctttcttcag cggcaggctc ggttttttccg ctttagctgc cgcaacatcc    5580
```

```
acaggcaggt tgatgtaaac tggtttgcgt tctttcagca gcgcagacag aacgcggtcg    5640
atttccacag tagcgttctc tgcagtcagc agcgtacgtg ccgcagtcac aggttcatgc    5700
attttcatga agtgtttgaa atcgccgtca gccagagtgt ggtggacgaa tttaccttcg    5760
ttctgaactt tgctcgttgg gctgcctacg atctccacca ccggcaggtt ttcggcgtag    5820
gagcccgcca gaccgttgac ggcgctcagt tcgccaacac cgaaagtggt cagaaatgcc    5880
gcggctttct tggtacgtgc ataaccatct gccatgtagc ttgcgttcag ttcgttagcg    5940
ttacccaccc atttcatgtc tttatgagag atgatctgat ccaggaactg cagattgtaa    6000
tcacccggaa cgccgaagat ttcttcgata cccagttcat gcagacggtc cagcagataa    6060
tcaccaacag tatacatgtc gacaaactta gattagattg ctatgctttc tttctaatga    6120
gcaagaagta aaaaaagttg taatagaaca agaaaaatga aactgaaact tgagaaattg    6180
aagaccgttt attaacttaa atatcaatgg gaggtcatcg aaagagaaaa aaatcaaaaa    6240
aaaaattttc aagaaaaaga aacgtgataa aaatttttat tgccttttc gacgaagaaa    6300 aagaaacgag gcggtctctt ttttcttttc caaacctta gtacgggtaa ttaacgacac    6360
cctagaggaa gaaagagggg aaatttagta tgctgtgctt gggtgttttg aagtggtacg    6420
gcgatgcgcg gagtccgaga aaatctggaa gagtaaaaaa ggagtagaaa cattttgaag    6480
ctatgagctc cagcttttgt tccctttagt gagggttaat tgcgcgcttg gcgtaatcat    6540
ggtcatagct gtttcctgtg tgaaattgtt atccgctcac aattccacac aacataggag    6600
ccggaagcat aaagtgtaaa gcctggggtg cctaatgagt gaggtaactc acattaattg    6660
cgttgcgctc actgcccgct ttccagtcgg gaaacctgtc gtgccagctg cattaatgaa    6720
tcggccaacg cgcggggaga ggcggtttgc gtattgggcg ctcttccgct tcctcgctca    6780
ctgactcgct gcgctcggtc gttcggctgc ggcgagcgg atcagctcac tcaaaggcgg    6840
taatacggtt atccacagaa tcaggggata acgcaggaaa gaacatgtga gcaaaaggcc    6900
agcaaaaggc caggaaccgt aaaaaggccg cgttgctggc gtttttccat aggctccgcc    6960
cccctgacga gcatcacaaa aatcgacgct caagtcagag gtggcgaaac ccgacaggac    7020
tataaagata ccaggcgttt cccctggaa gctccctcgt gcgctctcct gttccgaccc    7080
tgccgcttac cggatacctg tccgcctttc tcccttcggg aagcgtggcg ctttctcata    7140
gctcacgctg taggtatctc agttcggtgt aggtcgttcg ctccaagctg ggctgtgtgc    7200
acgaaccccc cgttcagccc gaccgctgcg ccttatccgg taactatcgt cttgagtcca    7260
acccggtaag acacgactta tcgccactgg cagcagccac tggtaacagg attagcagag    7320
cgaggtatgt aggcggtgct acagagttct tgaagtggtg gcctaactac ggctacacta    7380
gaaggacagt atttggtatc tgcgctctgc tgaagccagt taccttcgga aaagagttg    7440 gtagctcttg atccggcaaa caaaccaccg ctggtagcgg tggttttttt gtttgcaagc    7500
agcagattac gcgcagaaaa aaaggatctc aagaagatcc tttgatcttt tctacggggt    7560
ctgacgctca gtggaacgaa aactcacgtt aagggatttt ggtcatgaga ttatcaaaaa    7620
ggatcttcac ctagatcctt ttaaattaaa aatgaagttt taaatcaatc taagtatat    7680 atgagtaaac ttggtctgac agttaccaat gcttaatcag tgaggcacct atctcagcga    7740
tctgtctatt tcgttcatcc atagttgcct gactccccgt cgtgtagata actacgatac    7800
gggagggctt accatctggc cccagtgctg caatgatacc gcgagaccca cgctcaccgg    7860
ctccagattt atcagcaata aaccagccag ccggaagggc cgagcgcaga agtggtcctg    7920
caactttatc cgcctccatc cagtctatta attgttgccg gaagctaga gtaagtagtt    7980
```

```
cgccagttaa tagtttgcgc aacgttgttg ccattgctac aggcatcgtg gtgtcacgct    8040
cgtcgtttgg tatggcttca ttcagctccg gttcccaacg atcaaggcga gttacatgat    8100
cccccatgtt gtgcaaaaaa gcggttagct ccttcggtcc tccgatcgtt gtcagaagta    8160
agttggccgc agtgttatca ctcatggtta tggcagcact gcataattct cttactgtca    8220
tgccatccgt aagatgcttt tctgtgactg gtgagtactc aaccaagtca ttctgagaat    8280
agtgtatgcg gcgaccgagt tgctcttgcc cggcgtcaat acgggataat accgcgccac    8340
atagcagaac tttaaaagtg ctcatcattg gaaaacgttc ttcggggcga aaactctcaa    8400
ggatcttacc gctgttgaga tccagttcga tgtaacccac tcgtgcaccc aactgatctt    8460
cagcatcttt tactttcacc agcgtttctg ggtgagcaaa aacaggaagg caaaatgccg    8520
caaaaaaggg aataagggcg acacggaaat gttgaatact catactcttc ctttttcaat    8580
attattgaag catttatcag ggttattgtc tcatgagcgg atacatattt gaatgtattt    8640
agaaaaataa acaaataggg gttccgcgca catttccccg aaaagtgcca cctgacgt     8698
```

<210> SEQ ID NO 15
<211> LENGTH: 6012
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
caggcaagtg cacaaacaat acttaaataa atactactca gtaataacct atttcttagc      60
atttttgacg aaatttgcta ttttgttaga gtcttttaca ccatttgtct ccacacctcc     120
gcttacatca acaccaataa cgccatttaa tctaagcgca tcaccaacat tttctggcgt     180
cagtccacca gctaacataa aatgtaagct ttcggggctc tcttgccttc caacccagtc     240
agaaatcgag ttccaatcca aaagttcacc tgtcccacct gcttctgaat caaacaaggg     300
aataaacgaa tgaggtttct gtgaagctgc actgagtagt atgttgcagt cttttggaaa     360
tacgagtctt ttaataactg gcaaaccgag gaactcttgg tattcttgcc acgactcatc     420
tccatgcagt tggacgatat caatgccgta atcattgacc agagccaaaa catcctcctt     480
aggttgatta cgaaacacgc caaccaagta tttcggagtg cctgaactat ttttatatgc     540
ttttacaaga cttgaaattt ccttgcaat aaccgggtca attgttctct ttctattggg     600
cacacatata atacccagca agtcagcatc ggaatctaga gcacattctg cggcctctgt     660
gctctgcaag ccgcaaactt tcaccaatgg accagaacta cctgtgaaat taataacaga     720
catactccaa gctgcctttg tgtgcttaat cacgtatact cacgtgctca atagtcacca     780
atgccctccc tcttggccct ctcctttttct tttttcgacc gaattaattc ttaatcggca     840 aaaaagaaa agctccggat caagattgta cgtaaggtga caagctattt ttcaataaag     900
aatatcttcc actactgcca tctggcgtca taactgcaaa gtacacatat attacgatgc     960
tgtctattaa atgcttccta tattatatat atagtaatgt cgttgacgtc gccggcgaac    1020
gtggcgagaa aggaagggaa gaaagcgaaa ggagcgggcg ctagggcgct ggcaagtgta    1080
gcggtcacgc tgcgcgtaac caccacaccc gccgcgctta atgcgccgct acagggcgcg    1140
tcgcgccatt cgccattcag gctgcgcaac tgttgggaag ggcgatcggt gcgggcctct    1200
tcgctattac gccagctggc gaaagggggga tgtgctgcaa ggcgattaag ttgggtaacg    1260
ccagggtttt cccagtcacg acgttgtaaa acgacggcca gtgagcgcgc gtaatacgac    1320
tcactatagg gcgaattggg taccggccgc aaattaaagc cttcgagcgt cccaaaacct    1380
```

```
tctcaagcaa ggttttcagt ataatgttac atgcgtacac gcgtctgtac agaaaaaaaa    1440
gaaaaatttg aaatataaat aacgttctta atactaacat aactataaaa aaataaatag    1500
ggacctagac ttcaggttgt ctaactcctt ccttttcggt tagagcggat gtgggggggag   1560 ggcgtgaatg taagcgtgac ataactaatt acatgactcg agcggccgcg gatccctaga    1620
gagctttcgt tttcatgagt tccccgaatt ctttcggaag cttgtcactt gctaaattaa    1680
cgttatcact gtagtcaacc gggacatcaa tgatgacagg cccctcagcg ttcatgcctt    1740
gacgcagaac atctgccagc tggtctggtg attctacgcg taagccagtt gctccgaagc    1800
tttccgcgta tttcacgata tcgatatttc cgaaatcgac cgcagatgta cgattatatt    1860
ttttcaattg ctggaatgca accatgtcat atgtgctgtc gttccataca atgtgtacaa    1920
ttggtgcttt taaacgaact gctgtctcta attccatagc tgagaataag aaaccgccat    1980
caccggagac tgatactact ttttctcccg gtttcaccaa tgaagcgccg attgcccaag    2040
gaagcgcaac gccgagtgtt tgcataccgt tactaatcat taatgttaac ggctcgtagc    2100
tgcggaaata acgtgacatc caaatcgcgt gtgaaccgat atcgcaagtc actgtaacat    2160
gatcatcgac tgcgtttcgc aattcttaa cgatttcaag aggatgcact ctgtctgatt     2220
tccaatctgc aggcacctgc tcaccctcat gcatatattg ttttaaatca gaaaggatct    2280
tctgctcacg ttccgcaaag tctactttca cagcatcgtg ttcgtatga ttgatcgtag     2340 atggaatatc accgatcagt tcaagatccg gctggtaagc atgatcaatg tcagccagaa    2400
tctcgtctaa atggatgatc gtccggtctc cattgacatt ccagaatttc ggatcatatt    2460
caattgggtc atagccgatt gtcagaacaa catcagcctg ctcaagcagc agatcgccag    2520
gctggttgcg gaataaaccg atccggccaa aatactgatc ctctaaatct ctcgtaagag    2580
taccggcagc ttgatatgtt tcaacgaatg gaagctgcac ttttttcaat agcttgcgaa    2640
ccgctttaat cgcttccggt cttccgccct tcatgccgac taaaacgaca ggaagttttg    2700
ctgtttgaat ttttgcaatg gccatactga ttgcgtcatc tgctgcggga ccaagttttg    2760
gcgctgcgac agcacgtacg tttttttgtat ttgtgacttc attcacaaca tcttgcggaa    2820
aactcacaaa agcggcccca gcctgccctg ctgacgctat cctaaacgca tttgtaacag    2880
cttccggtat attttttaca tcttgaactt ctacactgta ttttgtaatc ggctggaata    2940
gcgccgcatt atccaaagat tgatgtgtcc gttttaaacg atctgcacgg atcacgttcc    3000
cagcaagcgc aacgacaggg tcaccttcag tgtttgctgt cagcagtcct gttgccaagt    3060
tcgaagcacc tggtcctgat gtgactaaca cgactcccgg ttttccagtt aaacggccga    3120
ctgcttgcgc cataaatgct gcattttgtt catgccgggc aacgataatt tcaggccctt    3180
tatcttgtaa agcgtcaaat accgcatcaa ttttgcacc tggaatgcca aatacatgtg      3240
tgacaccttg ctccgctaag caatcaacaa caagctccgc ccctctgctt ttcacaaggg    3300 attttttgttc ttttgttgct tttgtcaaca tgtcgacttt atgtgatgat tgattgattg    3360
attgtacagt ttgttttttct taatatctat ttcgatgact tctatatgat attgcactaa    3420
caagaagata ttataatgca attgatacaa gacaaggagt tatttgcttc tcttttatat    3480
gattctgaca atccatattg cgttggtagt cttttttgct ggaacggttc agcggaaaag    3540
acgcatcgct cttttgctt ctagaagaaa tgccagcaaa agaatctctt gacagtgact     3600
gacagcaaaa atgtctttt ctaactagta acaaggctaa gatatcagcc tgaaataaag     3660
ggtggtgaag taataattaa atcatccgta taaacctata cacatatatg aggaaaaata    3720
atacaaaagt gttttaaata cagatacata catgaacata tgcacgtata gcgcccaaat    3780
```

-continued

```
gtcggtaatg ggatcggcga gctccagctt tgttcccctt tagtgagggt taattgcgcg      3840
cttggcgtaa tcatggtcat agctgttttc ctgtgtgaaa tgttatccgc tcacaattcc      3900
acacaacata ggagccggaa gcataaagtg taaagcctgg ggtgcctaat gagtgaggta      3960
actcacatta attgcgttgc gctcactgcc cgctttccag tcgggaaacc tgtcgtgcca      4020
gctgcattaa tgaatcggcc aacgcgcggg gagaggcggt ttgcgtattg ggcgctcttc      4080
cgcttcctcg ctcactgact cgctgcgctc ggtcgttcgg ctgcggcgag cggtatcagc      4140
tcactcaaag gcggtaatac ggttatccac agaatcaggg gataacgcag gaaagaacat      4200
gtgagcaaaa ggccagcaaa aggccaggaa ccgtaaaaag gccgcgttgc tggcgttttt      4260
ccataggctc cgcccccctg acgagcatca caaaaatcga cgctcaagtc agaggtggcg      4320
aaacccgaca ggactataaa gataccaggc gtttccccct ggaagctccc tcgtgcgctc      4380
tcctgttccg accctgccgc ttaccggata cctgtccgcc tttctccctt cgggaagcgt      4440
ggcgctttct catagctcac gctgtaggta tctcagttcg gtgtaggtcg ttcgctccaa      4500
gctgggctgt gtgcacgaac ccccgttca gcccgaccgc tgcgccttat ccggtaacta      4560
tcgtcttgag tccaacccgg taagacacga cttatcgcca ctggcagcag ccactggtaa      4620
caggattagc agagcgaggt atgtaggcgg tgctacagag ttcttgaagt ggtggcctaa      4680
ctacggctac actagaagga cagtatttgg tatctgcgct ctgctgaagc cagttacctt      4740
cggaaaaaga gttggtagct cttgatccgg caaacaaacc accgctggta gcggtggttt      4800
ttttgtttgc aagcagcaga ttacgcgcag aaaaaaagga tctcaagaag atcctttgat      4860
cttttctacg gggtctgacg ctcagtggaa cgaaaactca cgttaaggga ttttggtcat      4920
gagattatca aaaggatctt caccctagat ccttttaaat taaaaatgaa gttttaaatc      4980
aatctaaagt atatatgagt aaacttggtc tgacagttac caatgcttaa tcagtgaggc      5040
acctatctca gcgatctgtc tatttcgttc atccatagtt gcctgactcc ccgtcgtgta      5100
gataactacg atacgggagg gcttaccatc tggccccagt gctgcaatga taccgcgaga      5160
cccacgctca ccggctccag atttatcagc aataaaccag ccagccggaa gggccgagcg      5220
cagaagtggt cctgcaactt tatccgcctc catccagtct attaattgtt gccgggaagc      5280
tagagtaagt agttcgccag ttaatagttt cgcaacgtt gttgccattg ctacaggcat      5340
cgtggtgtca cgctcgtcgt ttggtatggc ttcattcagc tccggttccc aacgatcaag      5400
gcgagttaca tgatccccca tgttgtgcaa aaaagcggtt agctccttcg gtcctccgat      5460
cgttgtcaga agtaagttgg ccgcagtgtt atcactcatg gttatggcag cactgcataa      5520
ttctcttact gtcatgccat ccgtaagatg cttttctgtg actggtgagt actcaaccaa      5580
gtcattctga gaatagtgta tgcggcgacc gagttgctct tgcccggcgt caatacggga      5640
taataccgcg ccacatagca gaactttaaa agtgctcatc attggaaaac gttcttcggg      5700
gcgaaaactc tcaaggatct taccgctgtt gagatccagt tcgatgtaac ccactcgtgc      5760
acccaactga tcttcagcat cttttacttt caccagcgtt tctgggtgag caaaaacagg      5820
aaggcaaaat gccgcaaaaa agggaataag ggcgacacgg aaatgttgaa tactcatact      5880
cttcctttt caatattatt gaagcattta tcagggttat tgtctcatga gcggatacat      5940
atttgaatgt atttagaaaa ataaacaaat aggggttccg cgcacatttc cccgaaaagt      6000
gccacctgac gt                                                         6012
```

<210> SEQ ID NO 16
<211> LENGTH: 8969

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

```
ccagttaact gtgggaatac tcaggtatcg taagatgcaa gagttcgaat ctcttagcaa      60
ccattatttt tttcctcaac ataacgagaa cacacagggg cgctatcgca cagaatcaaa     120
ttcgatgact ggaaattttt tgttaatttc agaggtcgcc tgacgcatat accttttca      180
actgaaaaat tgggagaaaa aggaaaggtg agagcgccgg aaccggcttt tcatatagaa     240
tagagaagcg ttcatgacta aatgcttgca tcacaatact tgaagttgac aatattattt     300
aaggacctat tgtttttcc aataggtggt tagcaatcgt cttactttct aacttttctt      360
accttttaca tttcagcaat atatatatat atatttcaag gatataccat tctaatgtct     420
gccctaaga agatcgtcgt tttgccaggt gaccacgttg gtcaagaaat cacagccgaa      480
gccattaagg ttcttaaagc tatttctgat gttcgttcca atgtcaagtt cgatttcgaa     540
aatcatttaa ttggtggtgc tgctatcgat gctacaggtg ttccacttcc agatgaggcg    600
ctggaagcct ccaagaaggc tgatgccgtt tgttaggtg ctgtgggtgg tcctaaatgg     660
ggtaccggta gtgttagacc tgaacaaggt ttactaaaaa tccgtaaaga acttcaattg    720
tacgccaact taagaccatg taactttgca tccgactctc ttttagactt atctccaatc     780
aagccacaat ttgctaaagg tactgacttc gttgttgtca gagaattagt gggaggtatt     840
tactttggta agagaaagga agacgatggt gatggtgtcg cttgggatag tgaacaatac     900
accgttccag aagtgcaaag aatcacaaga atggccgctt tcatggccct acaacatgag     960
ccaccattgc ctatttggtc cttggataaa gctaatgttt tggcctcttc aagattatgg    1020
agaaaaactg tggaggaaac catcaagaac gaattcccta cattgaaggt tcaacatcaa    1080
ttgattgatt ctgccgccat gatcctagtt aagaacccaa cccacctaaa tggtattata    1140
atcaccagca acatgtttgg tgatatcatc tccgatgaag cctccgttat cccaggttcc    1200
ttgggttgt tgccatctgc gtccttggcc tctttgccag acaagaacac cgcatttggt    1260
ttgtacgaac catgccacgg ttctgctcca gatttgccaa gaataaggt caaccctatc    1320
gccactatct tgtctgctgc aatgatgttg aaattgtcat tgaacttgcc tgaagaaggt    1380
aaggccattg aagatgcagt taaaaggtt ttggatgcag gtatcagaac tggtgattta    1440
ggtggttcca acagtaccac cgaagtcggt gatgctgtcg ccgaagaagt taagaaaatc    1500
cttgcttaaa aagattctct ttttttatga tatttgtaca taaactttat aaatgaaatt    1560
cataatagaa acgacacgaa attacaaaat ggaatatgtt cataggtag acgaaactat     1620
atacgcaatc tacatacatt tatcaagaag gagaaaaagg aggatgtaaa ggaatacagg    1680
taagcaaatt gatactaatg gctcaacgtg ataaggaaaa agaattgcac tttaacatta    1740
atattgacaa ggaggagggc accacacaaa aagttaggtg taacagaaaa tcatgaaact    1800
atgattccta atttatatat tggaggattt tctctaaaaa aaaaaaaata caacaaataa    1860
aaaacactca atgacctgac catttgatgg agttgccggc gaacgtggcg agaaaggaag    1920
ggaagaaagc gaaggagcg ggcgctaggg cgctggcaag tgtagcggtc acgctgcgcg    1980
taaccaccac acccgccgcg cttaatgcgc cgctacaggg cgcgtcgcgc cattcgccat    2040
tcaggctgcg caactgttgg gaagggcgat cggtgcgggc ctcttcgcta ttacgccagc    2100
tggcgaaagg gggatgtgct gcaaggcgat taagttgggt aacgccaggg ttttcccagt    2160
```

```
cacgacgttg taaaacgacg gccagtgagc gcgcgtaata cgactcacta tagggcgaat    2220
tgggtaccgg ccgcaaatta aagccttcga gcgtcccaaa accttctcaa gcaaggtttt    2280
cagtataatg ttacatgcgt acacgcgtct gtacagaaaa aaagaaaaa tttgaaatat     2340 aaataacgtt cttaatacta acataactat aaaaaaataa ataggacct agacttcagg     2400 ttgtctaact ccttccttt cggttagagc ggatgtgggg ggagggcgtg aatgtaagcg     2460
tgacataact aattacatga gcggccgcag atctttaacc cgcaacagca atacgtttca    2520
tatctgtcat atagccgcgc agtttcttac ctacctgctc aatcgcatgg ctgcgaatcg    2580
cttcgttcac atcacgcagt tgcccgttat ctaccgcgcc ttccggaata gctttaccca    2640
ggtcgcccgg ttgcagctct gccataaacg gtttcagcaa cggcacacaa gcgtaagaga    2700
acagatagtt accgtactca gcggtatcag agataaccac gttcatttcg tacagacgct    2760
tacgggcgat ggtgttggca atcagcggca gctcgtgcag tgattcataa tatgcagact    2820
cttcaatgat gccggaatcg accatggttt cgaacgccag ttcaacgccc gctttcacca    2880
tcgcaatcat cagtacgcct ttatcgaagt actcctgctc gccgattttg ccttcatact    2940
gcggcgcggt ttcaaacgcg gttttgccgg tctcttcacg ccaggtcagc agttcttat    3000 catcgttggc ccagtccgcc atcataccgg aagagaattc gccggagatg atgtcgtcca    3060
tatgtttctg gaacaggggt gccatgatct ctttcagctg ttcagaaagc gcataagcac    3120
gcagtttcgc cgggttagag agacggtcca tcatcagggt gatgccgccc tgtttcagtg    3180
cttcggtgat ggtttcccaa ccgaactgaa tcagtttttc tgcgtatgct ggatcggtac    3240
cttcttccac cagcttgtcg aagcacagca gagagccagc ctgcaacata ccgcacagga    3300
tggtttgctc gcccatcagg tcagatttca cttccgcaac gaaggacgat tccagcacac    3360
ccgcacggtg accaccggtt gcagccgccc aggctttggc aatcgccatg ccttcgcctt    3420
tcggatcgtt ttccgggtga acggcaatca gcgtcggtac gccgaaccca cgtttgtact    3480
cttcacgcac ttcggtgcct gggcatttcg gcgcaaccat cactacggtg atatctttac    3540
ggatctgctc gcccacttcg acgatgttga aaccgtgcga gtagcccagc gccgcgccgt    3600 cttttcatcag tggctgtacg gtgcgcacta catcagagtg ctgcttgtcc ggcgtcaggt    3660
taatcaccag atccgcctgt gggatcagtt cttcgtaagt acccacttta aaaccatttt    3720
cggtcgcttt acgccaggac gcgcgcttct cggcaatcgc ttcttacgc agagcgtagg     3780 agatatcgag accagaatca cgcatgttca ggccctggtt cagaccctgt gcgccacagc    3840
cgacgatgac tactttttta ccctgaaggt agctcgcgcc atcggcgaat tcatcgcggc    3900
ccatctcgag tcgaaactaa gttctggtgt tttaaaacta aaaaaaagac taactataaa    3960
agtagaattt aagaagttta agaaatagat ttacagaatt acaatcaata cctaccgtct    4020
ttatatactt attagtcaag taggggaata atttcaggga actggtttca acctttttt    4080 tcagcttttt ccaaatcaga gagagcagaa ggtaatagaa ggtgtaagaa atgagatag    4140 atacatgcgt gggtcaattg ccttgtgtca tcatttactc caggcaggtt gcatcactcc    4200
attgaggttg tgcccgtttt ttgcctgttt gtgcccctgt tctctgtagt tgcgctaaga    4260
gaatggacct atgaactgat ggttggtgaa gaaaacaata ttttggtgct gggattcttt    4320
ttttttctgg atgccagctt aaaaagcggg ctccattata tttagtggat gccaggaata    4380
aactgttcac ccagacacct acgatgttat atattctgtg taacccgccc cctatttgg    4440 gcatgtacgg gttacagcag aattaaaagg ctaattttt gactaaataa agttaggaaa    4500
atcactacta ttaattattt acgtattctt tgaaatggcg agtattgata atgataaact    4560
```

```
ggatcctcat ccacccaact tcgatttgtc tcttactgcc cccttatcgg ctgaagtagc    4620
caatgaagca taagccctaa gggcgaaact tacttgacgt tctctatttt taggagtcca    4680
agccttatct cctctggcat cttgtgcttc tcttcttgca gccaattcag cgtctgagac    4740
ttgtaattgg atacctctat ttgggatatc tatggcgatc aaatctccat cttcaatcaa    4800
tccaatcgaa ccaccagaag ctgcctctgg tgatacgtga ccgatactta aacccgaagt    4860
gccaccagag aatctaccgt cagtgataag ggcacaagct tttcctagtc ccatggactt    4920
caaaaatgaa gttgggtaaa gcatttcctg catacctggt cctcccttg gtccctcata     4980 tcttatcact accacgtctc ctgctaccac ctttccgcca agtatagcct caacagcatc    5040
gtcttgactt tcgtaaactt tagcgggtcc agtaaatttc aaaatactat catctacacc    5100
agcagttttc acaatgcaac cattttcagc gaagtttcca tataatactg ctaaaccacc    5160
atccttacta taagcatgct caagcgatct tatacatcca tttgctctat catcgtccaa    5220
agtgtcccac ctacagtctt gcgagaatgc ttgggtggtt ctgatccctg ctggacctgc    5280
cctgaacatg ttttcacgg catcatcttg agttaacatg acatcgtatt gctctaatgt     5340
ctgtggaagt gttaaaccca atacattctt cacatccctg tttaaaagac cggctctgtc    5400
caactcccct aaaataccaa taacccctcc tgcacgatga acgtcttcca tgtgatactt    5460
ttgagttgat ggtgcaacct tacataactg tggaacctta cgtgaaagct tgtcgatatc    5520
agacatggtg aaatctatct cagcttcttg ggctgcagct agaagatgta agaccgtgtt    5580
tgtactacca cccattgcaa tatccaatgt catggcattt tcgaatgcag cctttgaagc    5640
tatattcctc ggtaatgctg attcatcatt ttgttcgtaa tacctttcg ttagttccac     5700 aattcttttt ccggcattta agaacaattg ctttctgtct gcatgggtcg ctaataatga    5760
accatttcct ggttgagata aacctagagc ttcagtcaag caattcatag agttagccgt    5820
gaacattcca ctgcaagaac cacaagttgg acatgcactt ctttcaactt ggtctgactg    5880
cgagtctgaa acttttggat ctgcaccttg aatcattgca tccacaagat caagtttgat    5940
gatctgatca cttaacttag ttttaccagc ctccattggg ccgccagata cgaagattac    6000
tgggatgttc aatctcaagg acgccatcaa cataccaggc gttatcttat cacaattaga    6060
gatacaaacc attgcatcgg cacaatgagc attaaccata tattcgactg agtctgcaat    6120
taattctctc gatggtaaag agtataacat accgccatgc cccatagcta ccgtcgtc     6180 cacagcaata gtattaaact cttttgcgac accacctgca gcttcaattt gttcggcaac    6240
aagcttacct agatcacgca aatggacatg acccggaacg aattgtgtaa aagagttgac    6300
gacggcaatg attggctttc cgaaatctgc atcagtcatg ccagtcatgt cgacaaactt    6360
agattagatt gctatgcttt cttttctaatg agcaagaagt aaaaaaagtt gtaatagaac    6420
aagaaaaatg aaactgaaac ttgagaaatt gaagaccgtt tattaactta aatatcaatg    6480
ggaggtcatc gaaagagaaa aaaatcaaaa aaaaatttt caagaaaaag aaacgtgata     6540 aaaatttta ttgcctttt cgacgaagaa aaagaaacga ggcggtctct tttttctttt      6600
ccaaaccttt agtacgggta attaacgaca ccctagagga agaaagaggg gaaatttagt    6660
atgctgtgct tgggtgtttt gaagtggtac ggcgatgcgc ggagtccgag aaaatctgga    6720
agagtaaaaa aggagtagaa acattttgaa gctatgagct ccagcttttg ttcccttag     6780 tgagggttaa ttgcgcgctt ggcgtaatca tggtcatagc tgtttcctgt gtgaaattgt    6840
tatccgctca caattccaca caacatagga gccggaagca taagtgtaa agcctggggt     6900 gcctaatgag tgaggtaact cacattaatt gcgttgcgct cactgcccgc tttccagtcg    6960
```

```
ggaaacctgt cgtgccagct gcattaatga atcggccaac gcgcgggag aggcggtttg    7020 cgtattgggc gctcttccgc ttcctcgctc actgactcgc tgcgctcggt cgttcggctg    7080
cggcgagcgg tatcagctca ctcaaaggcg gtaatacggt tatccacaga atcaggggat    7140
aacgcaggaa agaacatgtg agcaaaaggc cagcaaaagg ccaggaaccg taaaaaggcc    7200
gcgttgctgg cgtttttcca taggctccgc cccctgacg agcatcacaa aaatcgacgc    7260
tcaagtcaga ggtggcgaaa cccgacagga ctataaagat accaggcgtt ccccctgga    7320 agctccctcg tgcgctctcc tgttccgacc ctgccgctta ccggatacct gtccgccttt    7380
ctcccttcgg gaagcgtggc gctttctcat agctcacgct gtaggtatct cagttcggtg    7440
taggtcgttc gctccaagct gggctgtgtg cacgaacccc ccgttcagcc cgaccgctgc    7500
gccttatccg gtaactatcg tcttgagtcc aacccggtaa gacacgactt atcgccactg    7560
gcagcagcca ctggtaacag gattagcaga gcgaggtatg taggcggtgc tacagagttc    7620
ttgaagtggt ggcctaacta cggctacact agaaggacag tatttggtat ctgcgctctg    7680
ctgaagccag ttaccttcgg aaaaagagtt ggtagctctt gatccggcaa acaaaccacc    7740
gctggtagcg gtggtttttt tgtttgcaag cagcagatta cgcgcagaaa aaaggatct    7800 caagaagatc ctttgatctt ttctacgggg tctgacgctc agtggaacga aaactcacgt    7860
taagggattt tggtcatgag attatcaaaa aggatcttca cctagatcct tttaaattaa    7920
aaatgaagtt ttaaatcaat ctaaagtata tatgagtaaa cttggtctga cagttaccaa    7980
tgcttaatca gtgaggcacc tatctcagcg atctgtctat ttcgttcatc catagttgcc    8040
tgactccccg tcgtgtagat aactacgata cgggagggct taccatctgg ccccagtgct    8100
gcaatgatac cgcgagaccc acgctcaccg gctccagatt tatcagcaat aaaccagcca    8160
gccggaaggg ccgagcgcag aagtggtcct gcaactttat ccgcctccat ccagtctatt    8220
aattgttgcc gggaagctag agtaagtagt tcgccagtta atagtttgcg caacgttgtt    8280
gccattgcta caggcatcgt ggtgtcacgc tcgtcgtttg gtatggcttc attcagctcc    8340
ggttcccaac gatcaaggcg agttacatga tcccccatgt tgtgcaaaaa agcggttagc    8400
tccttcggtc ctccgatcgt tgtcagaagt aagttggccg cagtgttatc actcatggtt    8460
atggcagcac tgcataattc tcttactgtc atgccatccg taagatgctt ttctgtgact    8520
ggtgagtact caaccaagtc attctgagaa tagtgtatgc ggcgaccgag ttgctcttgc    8580
ccggcgtcaa tacgggataa taccgcgcca catagcagaa ctttaaaagt gctcatcatt    8640
ggaaaacgtt cttcggggcg aaaactctca aggatcttac cgctgttgag atccagttcg    8700
atgtaaccca ctcgtgcacc caactgatct tcagcatctt ttactttcac cagcgtttct    8760
gggtgagcaa aaacaggaag gcaaaatgcc gcaaaaaagg gaataagggc gacacggaaa    8820
tgttgaatac tcatactctt cctttttcaa tattattgaa gcatttatca gggttattgt    8880
ctcatgagcg gatacatatt tgaatgtatt tagaaaaata aacaaatagg ggttccgcgc    8940
acatttcccc gaaaagtgcc acctgacgt                                      8969
```

<210> SEQ ID NO 17
<211> LENGTH: 5853
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
tcgcgcgttt cggtgatgac ggtgaaaacc tctgacacat gcagctcccg gagacggtca    60
```

```
cagcttgtct gtaagcggat gccgggagca gacaagcccg tcaggcgcg tcagcgcgtg      120 ttggcgggtg tcgggctgg cttaactatg cggcatcaga gcagattgta ctgagagtgc      180
accataaatt cccgttttaa gagcttggtg agcgctagga gtcactgcca ggtatcgttt      240
gaacacggca ttagtcaggg aagtcataac acagtccttt cccgcaattt tcttttttcta    300 ttactcttgg cctcctctag tacactctat atttttttat gcctcggtaa tgattttcat     360
tttttttttt cccctagcgg atgactcttt ttttttctta gcgattggca ttatcacata     420
atgaattata cattatataa agtaatgtga tttcttcgaa gaatatacta aaaaatgagc     480
aggcaagata aacgaaggca aagatgacag agcagaaagc cctagtaaag cgtattacaa     540
atgaaaccaa gattcagatt gcgatctctt taaagggtgg tccctagcg atagagcact      600 cgatcttccc agaaaaagag gcagaagcag tagcagaaca ggccacacaa tcgcaagtga     660
ttaacgtcca cacaggtata gggtttctgg accatatgat acatgctctg ccaagcatt      720 ccggctggtc gctaatcgtt gagtgcattg gtgacttaca catagacgac catcacacca    780
ctgaagactg cgggattgct ctcggtcaag ctttttaaaga ggccctaggg gccgtgcgtg    840
gagtaaaaag gtttggatca ggatttgcgc ctttggatga ggcactttcc agagcggtgg     900
tagatctttc gaacaggccg tacgcagttg tcgaacttgg tttgcaaagg gagaaagtag     960
gagatctctc ttgcgagatg atcccgcatt ttcttgaaag ctttgcagag gctagcagaa     1020
ttaccctcca cgttgattgt ctgcgaggca agaatgatca tcaccgtagt gagagtgcgt    1080
tcaaggctct tgcggttgcc ataagagaag ccacctcgcc caatggtacc aacgatgttc    1140
cctccaccaa aggtgttctt atgtagtgac accgattatt taaagctgca gcatacgata    1200
tatatacatg tgtatatatg tatacctatg aatgtcagta agtatgtata cgaacagtat    1260
gatactgaag atgacaaggt aatgcatcat tctatacgtg tcattctgaa cgaggcgcgc    1320 tttcctttt tctttttgct ttttcttttt ttttctcttg aactcgacgg atctatgcgg     1380
tgtgaaatac cgcacagatg cgtaaggaga aaataccgca tcaggaaatt gtaaacgtta    1440
atattttgtt aaaattcgcg ttaaattttt gttaaatcag ctcatttttt aaccaatagg    1500
ccgaaatcgg caaaatccct tataaatcaa aagaatagac cgagataggg ttgagtgttg    1560
ttccagtttg gaacaagagt ccactattaa agaacgtgga ctccaacgtc aaagggcgaa    1620
aaaccgtcta tcagggcgat ggcccactac gtgaaccatc accctaatca agttttttgg    1680
ggtcgaggtg ccgtaaagca ctaaatcgga accctaaagg gagcccccga tttagagctt    1740
gacggggaaa gccggcgaac gtggcgagaa aggaaggaa gaaagcgaaa ggagcgggcg     1800
ctagggcgct ggcaagtgta gcggtcacgc tgcgcgtaac caccacaccc gccgcgctta    1860
atgcgccgct acagggcgcg tcgcgccatt cgccattcag gctgcgcaac tgttgggaag    1920
ggcgatcggt gcgggcctct tcgctattac gccagctggc gaaaggggga tgtgctgcaa    1980
ggcgattaag ttgggtaacg ccagggtttt cccagtcacg acgttgtaaa acgacggcca    2040
gtgagcgcgc gtaatacgac tcactatagg gcgaattggg taccggccgc aaattaaagc    2100
cttcgagcgt cccaaaacct tctcaagcaa ggttttcagt ataatgttac atgcgtacac    2160
gcgtctgtac agaaaaaaaa gaaaaatttg aaatataaat aacgttctta atactaacat    2220
aactataaaa aaataaatag ggacctagac ttcaggttgt ctaactcctt ccttttcggt    2280
tagagcggat gtgggggag ggcgtgaatg taagcgtgac ataactaatt acatgactcg     2340
aggtcgacgt tatcgataag cttgatatcg aattcctgca gcccggggga tccactagtt   2400
ctagaatccg tcgaaactaa gttctggtgt tttaaaacta aaaaaaagac taactataaa    2460
```

```
agtagaattt aagaagttta agaaatagat ttacagaatt acaatcaata cctaccgtct   2520
ttatatactt attagtcaag tagggaata atttcaggga actggtttca acctttttt    2580 tcagcttttt ccaaatcaga gagagcagaa ggtaatagaa ggtgtaagaa aatgagatag   2640
atacatgcgt gggtcaattg ccttgtgtca tcatttactc caggcaggtt gcatcactcc   2700
attgaggttg tgcccgtttt ttgcctgttt gtgccctgt  tctctgtagt tgcgctaaga   2760
gaatggacct atgaactgat ggttggtgaa gaaaacaata ttttggtgct gggattcttt   2820 tttttctgg  atgccagctt aaaaagcggg ctccattata tttagtggat gccaggaata   2880
aactgttcac ccagacacct acgatgttat atattctgtg taacccgccc cctattttgg   2940
gcatgtacgg gttacagcag aattaaaagg ctaattttt  gactaaataa agttaggaaa   3000
atcactacta ttaattattt acgtattctt tgaaatggcg agtattgata atgataaact   3060
gagctccagc ttttgttccc tttagtgagg gttaattgcg cgcttggcgt aatcatggtc   3120
atagctgttt cctgtgtgaa attgttatcc gctcacaatt ccacacaaca taggagccgg   3180
aagcataaag tgtaaagcct ggggtgccta atgagtgagg taactcacat taattgcgtt   3240
gcgctcactg cccgctttcc agtcgggaaa cctgtcgtgc cagctgcatt aatgaatcgg   3300
ccaacgcgcg gggagaggcg gtttgcgtat gggcgctct  tccgcttcct cgctcactga   3360
ctcgctgcgc tcggtcgttc ggctgcggcg agcggtatca gctcactcaa aggcggtaat   3420
acggttatcc acagaatcag gggataacgc aggaaagaac atgtgagcaa aaggccagca   3480
aaaggccagg aaccgtaaaa aggccgcgtt gctggcgttt ttccataggc tccgccccc    3540 tgacgagcat cacaaaaatc gacgctcaag tcagaggtgg cgaaacccga caggactata   3600
aagataccag gcgtttcccc ctggaagctc cctcgtgcgc tctcctgttc cgaccctgcc   3660
gcttaccgga tacctgtccg cctttctccc ttcgggaagc gtggcgcttt ctcatagctc   3720
acgctgtagg tatctcagtt cggtgtaggt cgttcgctcc aagctgggct gtgtgcacga   3780 acccccgtt  cagcccgacc gctgcgcctt atccggtaac tatcgtcttg agtccaaccc   3840
ggtaagacac gacttatcgc cactggcagc agccactggt aacaggatta gcagagcgag   3900
gtatgtaggc ggtgctacag agttcttgaa gtggtggcct aactacggct acactagaag   3960
gacagtattt ggtatctgcg ctctgctgaa gccagttacc ttcggaaaaa gagttggtag   4020
ctcttgatcc ggcaaacaaa ccaccgctgg tagcggtggt ttttttgttt gcaagcagca   4080
gattacgcgc agaaaaaaag gatctcaaga agatcctttg atcttttcta cggggtctga   4140
cgctcagtgg aacgaaaact cacgttaagg gattttggtc atgagattat caaaaaggat   4200
cttcacctag atccttttaa attaaaaatg aagttttaaa tcaatctaaa gtatatatga   4260
gtaaacttgg tctgacagtt accaatgctt aatcagtgag gcacctatct cagcgatctg   4320
tctatttcgt tcatccatag ttgcctgact ccccgtcgtg tagataacta cgatacggga   4380
gggcttacca tctggcccca gtgctgcaat gataccgcga cccacgct  caccggctcc   4440 agatttatca gcaataaacc agccagccgg aagggccgag cgcagaagtg gtcctgcaac   4500
tttatccgcc tccatccagt ctattaattg ttgccgggaa gctagagtaa gtagttcgcc   4560
agttaatagt ttgcgcaacg ttgttgccat tgctacaggc atcgtggtgt cacgctcgtc   4620
gtttggtatg gcttcattca gctccggttc ccaacgatca aggcgagtta catgatcccc   4680
catgttgtgc aaaaaagcgg ttagctcctt cggtcctccg atcgttgtca gaagtaagtt   4740
ggccgcagtg ttatcactca tggttatggc agcactgcat aattctctta ctgtcatgcc   4800
atccgtaaga tgcttttctg tgactggtga gtactcaacc aagtcattct gagaatagtg   4860
```

-continued

```
tatgcggcga ccgagttgct cttgcccggc gtcaataccgg gataataccg cgccacatag    4920
cagaacttta aaagtgctca tcattggaaa acgttcttcg gggcgaaaac tctcaaggat    4980
cttaccgctg ttgagatcca gttcgatgta acccactcgt gcacccaact gatcttcagc    5040 atctttact ttcaccagcg tttctgggtg agcaaaaaca ggaaggcaaa atgccgcaaa     5100
aaagggaata agggcgacac ggaaatgttg aatactcata ctcttccttt ttcaatatta    5160
ttgaagcatt tatcagggtt attgtctcat gagcggatac atatttgaat gtatttagaa    5220
aaataaacaa ataggggttc cgcgcacatt tccccgaaaa gtgccacctg gtccttttc     5280 atcacgtgct ataaaaataa ttataattta aattttttaa tataaatata taaattaaaa    5340
atagaaagta aaaaaagaaa ttaaagaaaa aatagttttt gttttccgaa gatgtaaaag    5400
actctagggg gatcgccaac aaatactacc ttttatcttg ctcttcctgc tctcaggtat    5460
taatgccgaa ttgtttcatc ttgtctgtgt agaagaccac acacgaaaat cctgtgattt    5520
tacattttac ttatcgttaa tcgaatgtat atctatttaa tctgcttttc ttgtctaata    5580
aatatatatg taaagtacgc ttttgttga aattttttaa acctttgttt atttttttt      5640 cttcattccg taactcttct accttcttta tttactttct aaaatccaaa tacaaaacat    5700
aaaaataaat aaacacagag taaattccca aattattcca tcattaaaag atacgaggcg    5760
cgtgtaagtt acaggcaagc gatccgtcct aagaaaccat tattatcatg acattaacct    5820
ataaaaatag gcgtatcacg aggccctttc gtc                                 5853
```

<210> SEQ ID NO 18
<211> LENGTH: 5778
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc    180
accataccac agcttttcaa ttcaattcat catttttttt ttattctttt ttttgatttc    240
ggtttctttg aaatttttt gattcggtaa tctccgaaca gaaggaagaa cgaaggaagg    300
agcacagact tagattggta tatatacgca tatgtagtgt tgaagaaaca tgaaattgcc    360
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa ttttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac    1020
```

```
ccggtgtggg tttagatgac aagggagacg cattgggtca acagtataga accgtggatg    1080
atgtggtctc tacaggatct gacattatta ttgttggaag aggactattt gcaaagggaa    1140
gggatgctaa ggtagagggt gaacgttaca gaaaagcagg ctgggaagca tatttgagaa    1200
gatgcggcca gcaaaactaa aaaactgtat tataagtaaa tgcatgtata ctaaactcac    1260
aaattagagc ttcaatttaa ttatatcagt tattacccta tgcggtgtga ataccgcac    1320 agatgcgtaa ggagaaaata ccgcatcagg aaattgtaaa cgttaatatt ttgttaaaat    1380
tcgcgttaaa ttttttgttaa atcagctcat tttttaacca ataggccgaa atcggcaaaa    1440
tcccttataa atcaaaagaa tagaccgaga taggggttgag tgttgttcca gtttggaaca    1500
agagtccact attaaagaac gtggactcca acgtcaaagg gcgaaaaacc gtctatcagg    1560
gcgatggccc actacgtgaa ccatcaccct aatcaagttt tttggggtcg aggtgccgta    1620
aagcactaaa tcggaaccct aaagggagcc cccgatttag agcttgacgg ggaaagccgg    1680
cgaacgtggc gagaaaggaa gggaagaaag cgaaaggagc gggcgctagg gcgctggcaa    1740
gtgtagcggt cacgctgcgc gtaaccacca cacccgccgc gcttaatgcg ccgctacagg    1800
gcgcgtcgcg ccattcgcca ttcaggctgc gcaactgttg ggaagggcga tcggtgcggg    1860
cctcttcgct attacgccag ctggcgaaag ggggatgtgc tgcaaggcga ttaagttggg    1920
taacgccagg gttttcccag tcacgacgtt gtaaaacgac ggccagtgag cgcgcgtaat    1980
acgactcact atagggcgaa ttgggtaccg gccgcaaatt aaagccttcg agcgtcccaa    2040
aaccttctca gcaaggtttt tcagtataat gttacatgcg tacacgcgtc tgtacagaaa    2100
aaaaagaaaa atttgaaata taaataacgt tcttaatact aacataacta taaaaaaata    2160
aatagggacc tagacttcag gttgtctaac tccttccttt tcggttagag cggatgtggg    2220
gggagggcgt gaatgtaagc gtgacataac taattacatg actcgaggtc gacggtatcg    2280
ataagcttga tatcgaattc ctgcagcccg ggggatccac tagttctaga atccgtcgaa    2340
actaagttct ggtgttttaa aactaaaaaa aagactaact ataaaagtag aatttaagaa    2400
gtttaagaaa tagatttaca gaattacaat caatacctac cgtctttata tacttattag    2460
tcaagtaggg gaataatttc agggaactgg tttcaacctt ttttttcagc ttttttccaaa    2520 tcagagagag cagaaggtaa tagaaggtgt aagaaaatga gatagataca tgcgtgggtc    2580
aattgccttg tgtcatcatt tactccaggc aggttgcatc actccattga ggttgtgccc    2640
gttttttgcc tgtttgtgcc cctgttctct gtagttgcgc taagagaatg gacctatgaa    2700
ctgatggttg gtgaagaaaa caatattttg gtgctgggat tctttttttt tctggatgcc    2760
agcttaaaaa gcgggctcca ttatatttag tggatgccag gaataaactg ttcacccaga    2820
cacctacgat gttatatatt ctgtgtaacc cgccccctat tttgggcatg tacgggttac    2880
agcagaatta aaaggctaat ttttttgacta aataaagtta ggaaaatcac tactattaat    2940
tatttacgta ttctttgaaa tggcgagtat tgataatgat aaactgagct ccagcttttg    3000
ttccctttag tgagggttaa ttgcgcgctt ggcgtaatca tggtcatagc tgtttcctgt    3060
gtgaaattgt tatccgctca caattccaca acataggag gccggaagca taagtgtaa    3120 agcctggggt gcctaatgag tgaggtaact cacattaatt gcgttgcgct cactgcccgc    3180
tttccagtcg ggaaacctgt cgtgccagct gcattaatga atcggccaac gcgcggggag    3240
aggcggtttg cgtattgggc gctcttccgc ttcctcgctc actgactcgc tgcgctcggt    3300
cgttcggctg cggcgagcgg tatcagctca ctcaaaggcg gtaatacggt tatccacaga    3360
atcaggggat aacgcaggaa agaacatgtg agcaaaaggc cagcaaaagg ccaggaaccg    3420
```

```
taaaaaggcc gcgttgctgg cgttttttcca taggctccgc ccccctgacg agcatcacaa    3480
aaatcgacgc tcaagtcaga ggtggcgaaa cccgacagga ctataaagat accaggcgtt    3540 tcccctgga agctccctcg tgcgctctcc tgttccgacc ctgccgctta ccggatacct    3600
gtccgccttt ctcccttcgg gaagcgtggc gctttctcat agctcacgct gtaggtatct    3660
cagttcggtg taggtcgttc gctccaagct gggctgtgtg cacgaacccc ccgttcagcc    3720
cgaccgctgc gccttatccg gtaactatcg tcttgagtcc aacccggtaa gacacgactt    3780
atcgccactg gcagcagcca ctggtaacag gattagcaga gcgaggtatg taggcggtgc    3840
tacagagttc ttgaagtggt ggcctaacta cggctacact agaaggacag tatttggtat    3900
ctgcgctctg ctgaagccag ttaccttcgg aaaaagagtt ggtagctctt gatccggcaa    3960
acaaaccacc gctggtagcg gtggtttttt tgtttgcaag cagcagatta cgcgcagaaa    4020
aaaaggatct caagaagatc ctttgatctt ttctacgggg tctgacgctc agtggaacga    4080
aaactcacgt taagggattt tggtcatgag attatcaaaa aggatcttca cctagatcct    4140
tttaaattaa aaatgaagtt ttaaatcaat ctaaagtata tatgagtaaa cttggtctga    4200
cagttaccaa tgcttaatca gtgaggcacc tatctcagcg atctgtctat ttcgttcatc    4260
catagttgcc tgactccccg tcgtgtagat aactacgata cgggagggct taccatctgg    4320
ccccagtgct gcaatgatac cgcgagaccc acgctcaccg gctccagatt tatcagcaat    4380
aaaccagcca gccggaaggg ccgagcgcag aagtggtcct gcaactttat ccgcctccat    4440
ccagtctatt aattgttgcc gggaagctag agtaagtagt tcgccagtta atagtttgcg    4500
caacgttgtt gccattgcta caggcatcgt ggtgtcacgc tcgtcgtttg gtatggcttc    4560
attcagctcc ggttcccaac gatcaaggcg agttacatga tcccccatgt tgtgcaaaaa    4620
agcggttagc tccttcggtc ctccgatcgt tgtcagaagt aagttggccg cagtgttatc    4680
actcatggtt atggcagcac tgcataattc tcttactgtc atgccatccg taagatgctt    4740
ttctgtgact ggtgagtact caaccaagtc attctgagaa tagtgtatgc ggcgaccgag    4800
ttgctcttgc ccggcgtcaa tacgggataa taccgcgcca catagcagaa ctttaaaagt    4860
gctcatcatt ggaaaacgtt cttcggggcg aaaactctca aggatcttac cgctgttgag    4920
atccagttcg atgtaaccca ctcgtgcacc caactgatct tcagcatctt ttactttcac    4980
cagcgtttct gggtgagcaa aaacaggaag gcaaaatgcc gcaaaaaagg gaataagggc    5040
gacacggaaa tgttgaatac tcatactctt cctttttcaa tattattgaa gcatttatca    5100
gggttattgt ctcatgagcg gatacatatt tgaatgtatt tagaaaaata aacaaatagg    5160
ggttccgcgc acatttcccc gaaaagtgcc acctgggtcc ttttcatcac gtgctataaa    5220
aataattata atttaaattt tttaatataa atatataaat taaaaataga aagtaaaaaa    5280
agaaattaaa gaaaaaatag ttttttgtttt ccgaagatgt aaaagactct aggggatcg    5340 ccaacaaata ctacctttta tcttgctctt cctgctctca ggtattaatg ccgaattgtt    5400
tcatcttgtc tgtgtagaag accacacacg aaaatcctgt gattttacat tttacttatc    5460
gttaatcgaa tgtatatcta tttaatctgc ttttcttgtc taataaatat atatgtaaag    5520
tacgcttttt gttgaaattt tttaaacctt tgtttatttt tttttcttca ttccgtaact    5580
cttctacctt ctttatttac tttctaaaat ccaaatacaa aacataaaaa taaataaaca    5640
cagagtaaat tcccaaatta ttccatcatt aaaagatacg aggcgcgtgt aagttacagg    5700
caagcgatcc gtcctaagaa accattatta tcatgacatt aacctataaa aataggcgta    5760
tcacgaggcc ctttcgtc                                                   5778
```

<210> SEQ ID NO 19
<211> LENGTH: 6362
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcaggcgcg | tcagcgggtg | 120 |
| ttggcgggtg | tcggggctgg | cttaactatg | cggcatcaga | gcagattgta | ctgagagtgc | 180 |
| accataccac | agcttttcaa | ttcaattcat | catttttttt | ttattcttt | ttttgatttc | 240 |
| ggtttctttg | aaattttttt | gattcggtaa | tctccgaaca | aaggaagaa | cgaaggaagg | 300 |
| agcacagact | tagattggta | tatatacgca | tatgtagtgt | tgaagaaaca | tgaaattgcc | 360 |
| cagtattctt | aacccaactg | cacagaacaa | aaacctgcag | gaaacgaaga | taaatcatgt | 420 |
| cgaaagctac | atataaggaa | cgtgctgcta | ctcatcctag | tcctgttgct | gccaagctat | 480 |
| ttaatatcat | gcacgaaaag | caaacaaact | tgtgtgcttc | attggatgtt | cgtaccacca | 540 |
| aggaattact | ggagttagtt | gaagcattag | gtcccaaaat | ttgtttacta | aaaacacatg | 600 |
| tggatatctt | gactgatttt | tccatggagg | gcacagttaa | gccgctaaag | gcattatccg | 660 |
| ccaagtacaa | ttttttactc | ttcgaagaca | gaaaatttgc | tgacattggt | aatacagtca | 720 |
| aattgcagta | ctctgcgggt | gtatacgaa | tagcagaatg | gcagacatt | acgaatgcac | 780 |
| acggtgtggt | gggcccaggt | attgttagcg | gtttgaagca | ggcggcagaa | gaagtaacaa | 840 |
| aggaacctag | aggcctttg | atgttagcag | aattgtcatg | caagggctcc | ctatctactg | 900 |
| gagaatatac | taagggtact | gttgacattg | cgaagagcga | caaagatttt | gttatcggct | 960 |
| ttattgctca | aagagacatg | ggtggaagag | atgaaggtta | cgattggttg | attatgacac | 1020 |
| ccggtgtggg | tttagatgac | aagggagacg | cattgggtca | acagtataga | accgtggatg | 1080 |
| atgtggtctc | tacaggatct | gacattatta | ttgttggaag | aggactattt | gcaaagggaa | 1140 |
| gggatgctaa | ggtagagggt | gaacgttaca | gaaaagcagg | ctgggaagca | tatttgagaa | 1200 |
| gatgcggcca | gcaaaactaa | aaaactgtat | tataagtaaa | tgcatgtata | ctaaactcac | 1260 |
| aaattagagc | ttcaatttaa | ttatatcagt | tattacccta | tgcggtgtga | aataccgcac | 1320 |
| agatgcgtaa | ggagaaaata | ccgcatcagg | aaattgtaaa | cgttaatatt | tgttaaaat | 1380 |
| tcgcgttaaa | ttttttgttaa | atcagctcat | ttttttaacca | ataggccgaa | atcggcaaaa | 1440 |
| tcccttataa | atcaaaagaa | tagaccgaga | tagggttgag | tgttgttcca | gtttggaaca | 1500 |
| agagtccact | attaaagaac | gtggactcca | acgtcaaagg | gcgaaaaacc | gtctatcagg | 1560 |
| gcgatggccc | actacgtgaa | ccatcaccct | aatcaagttt | tttggggtcg | aggtgccgta | 1620 |
| aagcactaaa | tcggaaccct | aaagggagcc | cccgatttag | agcttgacgg | ggaaagccgg | 1680 |
| cgaacgtggc | gagaaaggaa | gggaagaaag | cgaaaggagc | gggcgctagg | gcgctggcaa | 1740 |
| gtgtagcggt | cacgctgcgc | gtaaccacca | cacccgccgc | gcttaatgcg | ccgctacagg | 1800 |
| gcgcgtcgcg | ccattcgcca | ttcaggctgc | gcaactgttg | ggaagggcga | tcggtgcggg | 1860 |
| cctcttcgct | attacgccag | ctggcgaaag | gggatgtgc | tgcaaggcga | ttaagttggg | 1920 |
| taacgccagg | gttttcccag | tcacgacgtt | gtaaaacgac | ggccagtgag | cgcgcgtaat | 1980 |
| acgactcact | atagggcgaa | ttgggtaccg | gccgcaaatt | aaagccttcg | agcgtcccaa | 2040 |
| aaccttctca | agcaaggttt | tcagtataat | gttacatgcg | tacacgcgtc | tgtacagaaa | 2100 |

```
aaaaagaaaa atttgaaata taaataacgt tcttaatact aacataacta taaaaaaata   2160
aatagggacc tagacttcag gttgtctaac tccttccttt tcggttagag cggatgtggg   2220
gggagggcgt gaatgtaagc gtgacataac taattacatg actcgagcgg ccgcggatcc   2280
cgggaattcg tcgacacccg catagtcagg aacatcgtat gggtacatgc tagttctaga   2340
aaacttagat tagattgcta tgcttttcttt ctaatgagca agaagtaaaa aaagttgtaa   2400
tagaacaaga aaaatgaaac tgaaacttga gaaattgaag accgtttatt aacttaaata   2460
tcaatgggag gtcatcgaaa gagaaaaaaa tcaaaaaaaa aattttcaag aaaaagaaac   2520
gtgataaaaa ttttttattgc ctttttcgac gaagaaaaag aaacgaggcg gtctcttttt   2580
tcttttccaa acctttagta cgggtaatta acgacaccct agaggaagaa agagggaaa    2640 tttagtatgc tgtgcttggg tgttttgaag tggtacggcg atgcgcggag tccgagaaaa   2700
tctggaagag taaaaaagga gtagaaacat tttgaagcta tgagctccag cttttgttcc   2760
ctttagtgag ggttaattgc gcgcttggcg taatcatggt catagctgtt tcctgtgtga   2820
aattgttatc cgctcacaat tccacacaac ataggagccg gaagcataaa gtgtaaagcc   2880
tggggtgcct aatgagtgag gtaactcaca ttaattgcgt tgcgctcact gcccgctttc   2940
cagtcgggaa acctgtcgtg ccagctgcat taatgaatcg gccaacgcgc ggggagaggc   3000
ggtttgcgta ttgggcgctc ttccgcttcc tcgctcactg actcgctgcg ctcggtcgtt   3060
cggctgcggc gagcggtatc agctcactca aaggcggtaa tacggttatc cacagaatca   3120
ggggataacg caggaaagaa catgtgagca aaaggccagc aaaaggccag gaaccgtaaa   3180
aaggccgcgt tgctggcgtt tttccatagg ctccgccccc ctgacgagca tcacaaaaat   3240
cgacgctcaa gtcagaggtg gcgaaacccg acaggactat aaagatacca ggcgtttccc   3300
cctggaagct ccctcgtgcg ctctcctgtt ccgaccctgc cgcttaccgg atacctgtcc   3360
gcctttctcc cttcgggaag cgtggcgctt tctcatagct cacgctgtag gtatctcagt   3420
tcggtgtagg tcgttcgctc caagctgggc tgtgtgcacg aaccccccgt tcagcccgac   3480
cgctgcgcct tatccggtaa ctatcgtctt gagtccaacc cggtaagaca cgacttatcg   3540
ccactggcag cagccactgg taacaggatt agcagagcga ggtatgtagg cggtgctaca   3600
gagttcttga agtggtggcc taactacggc tacactagaa ggacagtatt tggtatctgc   3660
gctctgctga agccagttac cttcggaaaa agagttggta gctcttgatc cggcaaacaa   3720
accaccgctg gtagcggtgg tttttttgtt tgcaagcagc agattacgcg cagaaaaaaa   3780
ggatctcaag aagatccttt gatcttttct acggggtctg acgctcagtg gaacgaaaac   3840
tcacgttaag ggattttggt catgagatta tcaaaaagga tcttcaccta gatccttta   3900 aattaaaaat gaagttttaa atcaatctaa agtatatatg agtaaacttg gtctgacagt   3960
taccaatgct taatcagtga ggcacctatc tcagcgatct gtctatttcg ttcatccata   4020
gttgcctgac tccccgtcgt gtagataact acgatacggg agggcttacc atctggcccc   4080
agtgctgcaa tgataccgcg agacccacgc tcaccggctc cagatttatc agcaataaac   4140
cagccagccg gaagggccga gcgcagaagt ggtcctgcaa ctttatccgc ctccatccag   4200
tctattaatt gttgccggga agctagagta agtagttcgc cagttaatag tttgcgcaac   4260
gttgttgcca ttgctacagg catcgtggtg tcacgctcgt cgtttggtat ggcttcattc   4320
agctccggtt cccaacgatc aaggcgagtt acatgatccc ccatgttgtg caaaaaagcg   4380
gttagctcct tcggtcctcc gatcgttgtc agaagtaagt tggccgcagt gttatcactc   4440
atggttatgg cagcactgca taattctctt actgtcatgc catccgtaag atgcttttct   4500
```

```
gtgactggtg agtactcaac caagtcattc tgagaatagt gtatgcggcg accgagttgc   4560
tcttgcccgg cgtcaatacg ggataatacc gcgccacata gcagaacttt aaaagtgctc   4620
atcattggaa aacgttcttc ggggcgaaaa ctctcaagga tcttaccgct gttgagatcc   4680
agttcgatgt aacccactcg tgcacccaac tgatcttcag catcttttac tttcaccagc   4740
gtttctgggt gagcaaaaac aggaaggcaa aatgccgcaa aaagggaat aagggcgaca   4800 cggaaatgtt gaatactcat actcttcctt tttcaatatt attgaagcat ttatcagggt   4860
tattgtctca tgagcggata catatttgaa tgtatttaga aaaataaaca aatagggggtt  4920 ccgcgcacat ttccccgaaa agtgccacct gaacgaagca tctgtgcttc attttgtaga   4980
acaaaaatgc aacgcgagag cgctaatttt caaacaaag aatctgagct gcatttttac    5040
agaacagaaa tgcaacgcga aagcgctatt ttaccaacga agaatctgtg cttcattttt   5100
gtaaaacaaa aatgcaacgc gagagcgcta attttcaaa caagaatctc gagctgcatt   5160
tttacagaac agaaatgcaa cgcgagagcg ctattttacc aacaaagaat ctatacttct   5220
tttttgttct acaaaaatgc atcccgagag cgctattttt ctaacaaagc atcttagatt   5280 acttttttc tcctttgtgc gctctataat gcagtctctt gataactttt tgcactgtag    5340
gtccgttaag gttagaagaa ggctactttg gtgtctattt tctcttccat aaaaaaagcc   5400
tgactccact tcccgcgttt actgattact agcgaagctg cgggtgcatt ttttcaagat   5460
aaaggcatcc ccgattatat tctataccga tgtggattgc gcatactttg tgaacagaaa   5520
gtgatagcgt tgatgattct tcattggtca gaaaattatg aacggtttct tctattttgt   5580
ctctatatac tacgtatagg aaatgtttac attttcgtat tgttttcgat tcactctatg   5640
aatagttctt actacaattt ttttgtctaa agagtaatac tagagataaa cataaaaaat   5700
gtagaggtcg agtttagatg caagttcaag gagcgaaagg tggatgggta ggttatatag   5760
ggatatagca cagagatata tagcaaagag atacttttga gcaatgtttg tggaagcggt   5820
attcgcaata ttttagtagc tcgttacagt ccggtgcgtt tttggttttt tgaaagtgcg   5880
tcttcagagc gcttttggtt ttcaaaagcg ctctgaagtt cctatacttt ctagagaata   5940
ggaacttcgg aataggaact tcaaagcgtt tccgaaaacg agcgcttccg aaaatgcaac   6000
gcgagctgcg cacatacagc tcactgttca cgtcgcacct atatctgcgt gttgcctgta   6060
tatatatata catgagaaga acggcatagt gcgtgtttat gcttaaatgc gtacttatat   6120
gcgtctattt atgtaggatg aaaggtagtc tagtacctcc tgtgatatta tcccattcca   6180
tgcggggtat cgtatgcttc cttcagcact acccttagc tgttctatat gctgccactc     6240
ctcaattgga ttagtctcat ccttcaatgc tatcatttcc tttgatattg gatcatacta   6300
agaaaccatt attatcatga cattaaccta taaaaatagg cgtatcacga ggccctttcg   6360
tc                                                                 6362
```

<210> SEQ ID NO 20
<211> LENGTH: 6690
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
```

```
ttggcgggtg tcggggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tcttttcta    300 ttactcttgg cctcctctag tacactctat attttttat gcctcggtaa tgattttcat    360
tttttttttt cccctagcgg atgactcttt tttttcctta gcgattggca ttatcacata    420
atgaattata cattatataa agtaatgtga tttcttcgaa gaatatacta aaaatgagc    480 aggcaagata aacgaaggca aagatgacag agcagaaagc cctagtaaag cgtattacaa    540
atgaaaccaa gattcagatt gcgatctctt taaagggtgg tcccctagcg atagagcact    600
cgatcttccc agaaaaagag gcagaagcag tagcagaaca ggccacacaa tcgcaagtga    660
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctaggg gccgtgcgtg    840
gagtaaaaag gtttggatca ggatttgcgc cttttggatga ggcactttcc agagcggtgg    900
tagatctttc gaacaggccg tacgcagttg tcgaacttgg tttgcaaagg gagaaagtag    960
gagatctctc ttgcgagatg atcccgcatt ttcttgaaag ctttgcagag gctagcagaa    1020
ttaccctcca cgttgattgt ctgcgaggca agaatgatca tcaccgtagt gagagtgcgt    1080
tcaaggctct tgcggttgcc ataagagaag ccacctcgcc caatggtacc aacgatgttc    1140
cctccaccaa aggtgttctt atgtagtgac accgattatt taaagctgca gcatacgata    1200
tatatacatg tgtatatatg tatacctatg aatgtcagta agtatgtata cgaacagtat    1260
gatactgaag atgacaaggt aatgcatcat tctatacgtg tcattctgaa cgaggcgcgc    1320
tttccttttt tcttttgct ttttcttttt ttttctcttg aactcgacgg atctatgcgg    1380
tgtgaaatac cgcacagatg cgtaaggaga aaataccgca tcaggaaatt gtaaacgtta    1440
atattttgtt aaaattcgcg ttaaattttt gttaaatcag ctcattttt aaccaatagg    1500 ccgaaatcgg caaaatccct tataaatcaa aagaatagac cgagataggg ttgagtgttg    1560 ttccagttg gaacaagagt ccactattaa agaacgtgga ctccaacgtc aaagggcgaa    1620
aaaccgtcta tcagggcgat ggcccactac gtgaaccatc accctaatca agttttttgg    1680
ggtcgaggtg ccgtaaagca ctaaatcgga accctaaagg gagcccccga tttagagctt    1740
gacggggaaa gccggcgaac gtggcgagaa aggaagggaa gaaagcgaaa ggagcgggcg    1800
ctagggcgct ggcaagtgta gcggtcacgc tgcgcgtaac caccacaccc gccgcgctta    1860
atgcgccgct acagggcgcg tcgcgccatt cgccattcag gctgcgcaac tgttgggaag    1920
ggcgatcggt gcgggcctct tcgctattac gccagctggc gaaagggggga tgtgctgcaa    1980 ggcgattaag ttgggtaacg ccagggtttt cccagtcacg acgttgtaaa acgacggcca    2040
gtgagcgcgc gtaatacgac tcactatagg gcgaattggg taccggccgc aaattaaagc    2100
cttcgagcgt cccaaaacct tctcaagcaa ggttttcagt ataatgttac atgcgtacac    2160
gcgtctgtac agaaaaaaaa gaaaaatttg aaatataaat aacgttctta atactaacat    2220
aactataaaa aaataaatag ggacctagac ttcaggttgt ctaactcctt ccttttcggt    2280
tagagcggat gtgggggag ggcgtgaatg taagcgtgac ataactaatt acatgactcg    2340
agcggccgcg gatcccggga attcgtcgac accatcttct tctgagatga gttttgttc    2400 catgctagtt ctagaatccg tcgaaactaa gttctggtgt tttaaaacta aaaaaagac    2460 taactataaa agtagaattt aagaagttta agaaatagat ttacagaatt acaatcaata    2520
```

```
cctaccgtct ttatatactt attagtcaag tagggaata atttcaggga actggtttca  2580
accttttttt tcagcttttt ccaaatcaga gagagcagaa ggtaatagaa ggtgtaagaa  2640
aatgagatag atacatgcgt gggtcaattg ccttgtgtca tcatttactc caggcaggtt  2700
gcatcactcc attgaggttg tgcccgtttt ttgcctgttt gtgcccctgt tctctgtagt  2760
tgcgctaaga gaatggacct atgaactgat ggttggtgaa gaaaacaata ttttggtgct  2820
gggattcttt ttttttctgg atgccagctt aaaaagcggg ctccattata tttagtggat  2880
gccaggaata aactgttcac ccagacacct acgatgttat atattctgtg taacccgccc  2940
cctattttgg gcatgtacgg gttacagcag aattaaaagg ctaattttt gactaaataa  3000
agttaggaaa atcactacta ttaattattt acgtattctt tgaaatggcg agtattgata  3060
atgataaact gagctccagc ttttgttccc tttagtgagg gttaattgcg cgcttggcgt  3120
aatcatggtc atagctgttt cctgtgtgaa attgttatcc gctcacaatt ccacacaaca  3180
taggagccgg aagcataaag tgtaaagcct ggggtgccta atgagtgagg taactcacat  3240
taattgcgtt gcgctcactg cccgctttcc agtcgggaaa cctgtcgtgc cagctgcatt  3300
aatgaatcgg ccaacgcgcg gggagaggcg gtttgcgtat tgggcgctct tccgcttcct  3360
cgctcactga ctcgctgcgc tcggtcgttc ggctgcggcg agcggtatca gctcactcaa  3420
aggcggtaat acggttatcc acagaatcag gggataacgc aggaaagaac atgtgagcaa  3480
aaggccagca aaaggccagg aaccgtaaaa aggccgcgtt gctggcgttt ttccataggc  3540
tccgcccccc tgacgagcat cacaaaaatc gacgctcaag tcagaggtgg cgaaacccga  3600
caggactata aagataccag gcgtttcccc ctggaagctc cctcgtgcgc tctcctgttc  3660
cgaccctgcc gcttaccgga tacctgtccg ccttttctcc cttcgggaagc gtggcgcttt  3720
ctcatagctc acgctgtagg tatctcagtt cggtgtaggt cgttcgctcc aagctgggct  3780
gtgtgcacga accccccgtt cagcccgacc gctgcgcctt atccggtaac tatcgtcttg  3840
agtccaaccc ggtaagacac gacttatcgc cactggcagc agccactggt aacaggatta  3900
gcagagcgag gtatgtaggc ggtgctacag agttcttgaa gtggtggcct aactacggct  3960
acactagaag gacagtattt ggtatctgcg ctctgctgaa gccagttacc ttcggaaaaa  4020
gagttggtag ctcttgatcc ggcaaacaaa ccaccgctgg tagcggtggt ttttttgttt  4080
gcaagcagca gattacgcgc agaaaaaaag gatctcaaga agatcctttg atcttttcta  4140
cggggtctga cgctcagtgg aacgaaaact cacgttaagg gattttggtc atgagattat  4200
caaaaaggat cttcacctag atccttttaa attaaaaatg aagttttaaa tcaatctaaa  4260
gtatatatga gtaaacttgg tctgacagtt accaatgctt aatcagtgag gcacctatct  4320
cagcgatctg tctatttcgt tcatccatag ttgcctgact ccccgtcgtg tagataacta  4380
cgatacggga gggcttacca tctggcccca gtgctgcaat gataccgcga gacccacgct  4440
caccggctcc agatttatca gcaataaacc agccagccgg aagggccgag cgcagaagtg  4500
gtcctgcaac tttatccgcc tccatccagt ctattaattg ttgccgggaa gctagagtaa  4560
gtagttcgcc agttaatagt ttgcgcaacg ttgttgccat tgctacaggc atcgtggtgt  4620
cacgctcgtc gtttggtatg gcttcattca gctccggttc ccaacgatca aggcgagtta  4680
catgatcccc catgttgtgc aaaaaagcgg ttagctcctt cggtcctccg atcgttgtca  4740
gaagtaagtt ggccgcagtg ttatcactca tggttatggc agcactgcat aattctctta  4800
ctgtcatgcc atccgtaaga tgcttttctg tgactggtga gtactcaacc aagtcattct  4860
gagaatagtg tatgcggcga ccgagttgct cttgcccggc gtcaatacgg gataataccg  4920
```

```
cgccacatag cagaactttq aaagtgctca tcattggaaa acgttcttcg gggcgaaaac    4980
tctcaaggat cttaccgctg ttgagatcca gttcgatgta acccactcgt gcacccaact    5040
gatcttcagc atctttfact ttccaccagcg tttctgggtg agcaaaaaca ggaaggcaaa    5100
atgccgcaaa aaagggaata agggcgacac ggaaatgttg aatactcata ctcttccttt    5160
ttcaatatta ttgaagcatt tatcagggtt attgtctcat gagcggatac atatttgaat    5220
gtatttagaa aaataaacaa ataggggttc cgcgcacatt tccccgaaaa gtgccacctg    5280
aacgaagcat ctgtgcttca ttttgtagaa caaaaatgca acgcgagagc gctaattttt    5340
caaacaaaga atctgagctg cattttacta gaacagaaat gcaacgcgaa agcgctatgt    5400
taccaacgaa gaatctgtgc ttcattttttg taaaacaaaa atgcaacgcg agagcgctaa    5460 ttttttcaaac aaagaatctg agctgcattt ttacagaaca gaaatgcaac gcgagagcgc    5520
tattttacca acaaagaatc tatacttctt ttttgttcta caaaaatgca tcccgagagc    5580 gctattttc taacaaagca tcttagatta cttttttttct cctttgtgcg ctctataatg    5640
cagtctcttg ataactttt gcactgtagg tccgttaagg ttagaagaag ctactttgg    5700 tgtctatttt ctcttccata aaaaaagcct gactccactt cccgcgttta ctgattacta    5760
gcgaagctgc gggtgcattt tttcaagata aaggcatccc cgattatatt ctataccgat    5820
gtggattgcg catactttgt gaacagaaag tgatagcgtt gatgattctt cattggtcag    5880
aaaattatga acgtttcttt ctatttttgtc tctataract acgtatagga aatgttaca    5940 ttttcgtatt gttttcgatt cactctatga atagttctta ctacaatttt tttgtctaaa    6000
gagtaatact agagataaac ataaaaaatg tagaggtcga gtttagatgc aagttcaagg    6060
agcgaaaggt ggatgggtag gttatatagg gatatagcac agagatatat agcaaagaga    6120 tactttgag caatgtttgt ggaagcggta ttcgcaatat tttagtagct cgttacagtc    6180
cggtgcgttt ttggtttttt gaaagtgcgt cttcagagcg cttttggttt tcaaaagcgc    6240
tctgaagttc ctatactttc tagagaatag gaacttcgga ataggaactt caaagcgttt    6300
ccgaaaacga cgcttccga aaatgcaacg cgagctgcgc acatacagct cactgttcac    6360
gtcgcaccta tatctgcgtg ttgcctgtat atatataac atgagaagaa cggcatagtg    6420
cgtgtttatg cttaaatgcg tacttatatg cgtctattta tgtaggatga aaggtagtct    6480
agtacctcct gtgatattat cccattccat gcgggggtatc gtatgcttcc ttcagcacta    6540
ccctttagct gttctatatg ctgccactcc tcaattggat tagtctcatc cttcaatgct    6600
atcatttcct ttgatattgg atcatctaag aaaccattat tatcatgaca ttaacctata    6660
aaaataggcg tatcacgagg ccctttcgtc                                      6690
```

<210> SEQ ID NO 21
<211> LENGTH: 6506
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accataaacg acattactat atatataata taggaagcat ttaatagaca gcatcgtaat    240
atatgtgtac tttgcagtta tgacgccaga tggcagtagt ggaagatatt ctttattgaa    300
```

-continued

```
aaatagcttg tcaccttacg tacaatcttg atccggagct tttctttttt tgccgattaa    360
gaattaattc ggtcgaaaaa agaaaaggag agggccaaga gggagggcat tggtgactat    420
tgagcacgtg agtatacgtg attaagcaca caaaggcagc ttggagtatg tctgttatta    480
atttcacagg tagttctggt ccattggtga agtttgcgg cttgcagagc acagaggccg     540
cagaatgtgc tctagattcc gatgctgact tgctgggtat tatatgtgtg cccaatagaa    600
agagaacaat tgacccggtt attgcaagga aaatttcaag tcttgtaaaa gcatataaaa    660
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa ttttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt ttggggtcg    1500 aggtgccgta aagcactaaa tcggaaccct aaagggagcc ccgatttag agcttgacgg    1560 ggaaagccgg cgaacgtggc gagaaaggaa gggaagaaag cgaaaggagc gggcgctagg    1620
gcgctggcaa gtgtagcggt cacgctgcgc gtaaccacca caccgccgc gcttaatgcg    1680 ccgctacagg gcgcgtcgcg ccattcgcca ttcaggctgc gcaactgttg ggaagggcga    1740
tcggtgcggg cctcttcgct attacgccag ctggcgaaag ggggatgtgc tgcaaggcga    1800
ttaagttggg taacgccagg ttttcccag tcacgacgtt gtaaaacgac ggccagtgag    1860
cgcgcgtaat acgactcact ataggcgaa ttgggtaccg gccgcaaatt aaagccttcg    1920
agcgtcccaa aaccttctca agcaaggttt tcagtataat gttacatgcg tacacgcgtc   1980
tgtacagaaa aaaagaaaa atttgaaata taaataacgt tcttaatact aacataacta   2040
taaaaaaata aataggggacc tagacttcag gttgtctaac tccttccttt tcggttagag   2100
cggatgtggg gggagggcgt gaatgtaagc gtgacataac taattacatg actcgagcgg   2160
ccgcggatcc cgggaattcg tcgacaccat cttcttctga gatgagtttt tgttccatgc   2220
tagttctaga atccgtcgaa actaagttct ggtgttttaa aactaaaaaa aagactaact   2280 ataaagtag aatttaagaa gtttaagaaa tagatttaca gaattacaat caataacctac   2340 cgtctttata tacttattag tcaagtaggg gaataatttc agggaactgg tttcaacctt   2400
ttttttcagc ttttttccaaa tcagagagag cagaaggtaa tagaaggtgt aagaaaatga   2460
gatagataca tgcgtgggtc aattgccttg tgtcatcatt tactccaggc aggttgcatc   2520
actccattga ggttgtgccc gttttttgcc tgtttgtgcc cctgttctct gtagttgcgc    2580
taagagaatg gacctatgaa ctgatggttg gtgaagaaaa caatattttg gtgctgggat    2640
tctttttttt tctggatgcc agcttaaaaa gcgggctcca ttatatttag tggatgccag    2700
```

```
gaataaactg ttcacccaga cacctacgat gttatatatt ctgtgtaacc cgccccctat    2760
tttgggcatg tacgggttac agcagaatta aaaggctaat tttttgacta aataaagtta    2820
ggaaaatcac tactattaat tatttacgta ttctttgaaa tggcgagtat tgataatgat    2880
aaactgagct ccagcttttg ttcccttag tgagggttaa ttgcgcgctt ggcgtaatca    2940
tggtcatagc tgtttcctgt gtgaaattgt tatccgctca caattccaca caacatagga    3000
gccggaagca taaagtgtaa agcctggggt gcctaatgag tgaggtaact cacattaatt    3060
gcgttgcgct cactgcccgc tttccagtcg ggaaacctgt cgtgccagct gcattaatga    3120
atcggccaac gcgcgggag aggcggtttg cgtattgggc gctcttccgc ttcctcgctc    3180
actgactcgc tgcgctcggt cgttcggctg cggcgagcgg tatcagctca ctcaaaggcg    3240
gtaatacggt tatccacaga atcaggggat aacgcaggaa agaacatgtg agcaaaaggc    3300
cagcaaaagg ccaggaaccg taaaaaggcc gcgttgctgg cgtttttcca taggctccgc    3360 cccccctgacg agcatcacaa aaatcgacgc tcaagtcaga ggtggcgaaa cccgacagga    3420
ctataaagat accaggcgtt ccccctgga agctccctcg tgcgctctcc tgttccgacc    3480
ctgccgctta ccggatacct gtccgccttt ctcccttcgg gaagcgtggc gctttctcat    3540
agctcacgct gtaggtatct cagttcggtg taggtcgttc gctccaagct gggctgtgtg    3600 cacgaaccc cgttcagcc cgaccgctgc gccttatccg gtaactatcg tcttgagtcc    3660
aacccggtaa gacacgactt atcgccactg gcagcagcca ctggtaacag gattagcaga    3720
gcgaggtatg taggcggtgc tacagagttc ttgaagtggt ggcctaacta cggctacact    3780
agaaggacag tatttggtat ctgcgctctg ctgaagccag ttaccttcgg aaaaagagtt    3840
ggtagctctt gatccggcaa acaaaccacc gctggtagcg tggtttttt tgtttgcaag    3900 cagcagatta cgcgcagaaa aaaggatct caagaagatc ctttgatctt ttctacgggg    3960
tctgacgctc agtggaacga aaactcacgt taagggattt tggtcatgag attatcaaaa    4020
aggatcttca cctagatcct tttaaattaa aatgaagtt ttaaatcaat ctaaagtata    4080
tatgagtaaa cttggtctga cagttaccaa tgcttaatca gtgaggcacc tatctcagcg    4140
atctgtctat ttcgttcatc catagttgcc tgactccccg tcgtgtagat aactacgata    4200
cgggagggct taccatctgg ccccagtgct gcaatgatac cgcgagaccc acgctcaccg    4260
gctccagatt tatcagcaat aaaccagcca gccggaaggg ccgagcgcag aagtggtcct    4320
gcaactttat ccgcctccat ccagtctatt aattgttgcc gggaagctag agtaagtagt    4380
tcgccagtta atagtttgcg caacgttgtt gccattgcta caggcatcgt ggtgtcacgc    4440
tcgtcgtttg gtatggcttc attcagctcc ggttcccaac gatcaaggcg agttacatga    4500
tcccccatgt tgtgcaaaaa agcggttagc tccttcggtc ctccgatcgt tgtcagaagt    4560
aagttggccg cagtgttatc actcatggtt atggcagcac tgcataattc tcttactgtc    4620
atgccatccg taagatgctt ttctgtgact ggtgagtact caaccaagtc attctgagaa    4680
tagtgtatgc ggcgaccgag ttgctcttgc ccggcgtcaa tacgggataa taccgcgcca    4740
catagcagaa ctttaaaagt gctcatcatt ggaaaacgtt cttcggggcg aaaactctca    4800
aggatcttac cgctgttgag atccagttcg atgtaaccca ctcgtgcacc caactgatct    4860
tcagcatctt ttactttcac cagcgtttct gggtgagcaa aaacaggaag gcaaaatgcc    4920
gcaaaaaagg gaataagggc gacacggaaa tgttgaatac tcatactctt ccttttttcaa    4980 tattattgaa gcatttatca gggttattgt ctcatgagcg gatacatatt tgaatgtatt    5040
tagaaaaata aacaaatagg ggttccgcgc acatttcccc gaaaagtgcc acctgaacga    5100
```

```
agcatctgtg cttcattttg tagaacaaaa atgcaacgcg agagcgctaa tttttcaaac    5160
aaagaatctg agctgcattt ttacagaaca gaaatgcaac gcgaaagcgc tattttacca    5220
acgaagaatc tgtgcttcat ttttgtaaaa caaaaatgca acgcgagagc gctaattttt    5280
caaacaaaga atctgagctg cattttaca gaacagaaat gcaacgcgag agcgctattt    5340
taccaacaaa gaatctatac ttcttttttg ttctacaaaa atgcatcccg agagcgctat    5400
ttttctaaca aagcatctta gattactttt tttctccttt gtgcgctcta taatgcagtc    5460
tcttgataac tttttgcact gtaggtccgt taaggttaga agaaggctac tttggtgtct    5520 atttctctt ccataaaaaa agcctgactc cacttcccgc gtttactgat tactagcgaa    5580
gctgcgggtg catttttca agataaaggc atccccgatt atattctata ccgatgtgga    5640
ttgcgcatac tttgtgaaca gaaagtgata gcgttgatga ttcttcattg gtcagaaaat    5700
tatgaacggt ttcttctatt ttgtctctat atactacgta taggaaatgt ttacattttc    5760
gtattgtttt cgattcactc tatgaatagt tcttactaca attttttttgt ctaaagagta    5820 atactagaga taaacataaa aaatgtagag gtcgagttta gatgcaagtt caaggagcga    5880
aaggtggatg ggtaggttat atagggatat agcacagaga tatatagcaa agagatactt    5940
ttgagcaatg tttgtggaag cggtattcgc aatatttag tagctcgtta cagtccggtg    6000 cgttttggt tttttgaaag tgcgtcttca gagcgctttt ggttttcaaa agcgctctga    6060
agttcctata ctttctagag aataggaact tcggaatagg aacttcaaag cgtttccgaa    6120
aacgagcgct tccgaaaatg caacgcgagc tgcgcacata cagctcactg ttcacgtcgc    6180
acctatatct gcgtgttgcc tgtatatata tatacatgag aagaacggca tagtgcgtgt    6240
ttatgcttaa atgcgtactt tatgcgtct atttatgtag gatgaaaggt agtctagtac    6300
ctcctgtgat attatcccat tccatgcggg gtatcgtatg cttccttcag cactacccctt    6360 tagctgttct atatgctgcc actcctcaat tggattagtc tcatccttca atgctatcat    6420
ttcctttgat attggatcat attaagaaac cattattatc atgacattaa cctataaaaa    6480
taggcgtatc acgaggcccct ttcgtc                                        6506
```

<210> SEQ ID NO 22
<211> LENGTH: 6616
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accataccac agcttttcaa ttcaattcat cattttttt ttattctttt ttttgatttc     240
ggtttctttg aaattttttt gattcggtaa tctccgaaca gaaggaagaa cgaaggaagg    300
agcacagact tagattggta tatatacgca tatgtagtgt tgaagaaaca tgaaattgcc    360
cagtattctt aacccaactg cacagaacaa aaacctgcag gaaacgaaga taatcatgt     420 cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
```

```
tggatatctt gactgatttt tccatggagg gcacagttaa gccgctaaag gcattatccg    660
ccaagtacaa ttttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattaccctg tgcggtgtga ataccgcac    1320 agatgcgtaa ggagaaaata ccgcatcagg aaattgtaaa cgttaatatt tgttaaaat    1380 tcgcgttaaa ttttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt ttggggtcg aggtgccgta    1620 aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740 gtgtagcgt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag gggatgtgc tgcaaggcga ttaagttggg    1920
taacgccagg gttttcccag tcacgacgtt gtaaaacgac ggccagtgag cgcgcgtaat   1980
acgactcact ataggcgaa ttgggtaccg gccgcaaatt aaagccttcg agcgtcccaa    2040
aaccttctca agcaaggttt tcagtataat gttacatgcg tacacgcgtc tgtacagaaa   2100 aaaagaaaa atttgaaata taaataacgt tcttaatact aacataacta taaaaaaata   2160
aatagggacc tagacttcag gttgtctaac tccttccttt tcggttagag cggatgtggg   2220
gggagggcgt gaatgtaagc gtgacataac taattacatg actcgagcgg ccgcggatcc   2280
cgggaattcg tcgacaccat cttcttctga gatgagtttt tgttccatgc tagttctaga   2340
atccgtcgaa actaagttct ggtgttttaa aactaaaaaa aagactaact ataaaagtag   2400
aatttaagaa gttaagaaa tagatttaca gaattacaat caatacctac cgtctttata    2460
tacttattag tcaagtaggg gaataatttc agggaactgg tttcaacctt ttttttcagc   2520
tttttccaaa tcagagagag cagaaggtaa tagaaggtgt aagaaaatga gatagataca   2580
tgcgtgggtc aattgccttg tgtcatcatt tactccaggc aggttgcatc actccattga   2640
ggttgtgccc gttttttgcc tgtttgtgcc cctgttctct gtagttgcgc taagagaatg   2700
gacctatgaa ctgatggttg gtgaagaaaa caatattttg gtgctgggat tctttttttt   2760
tctggatgcc agcttaaaaa gcgggctcca ttatatttag tggatgccag gaataaactg   2820
ttcacccaga cacctacgat gttatatatt ctgtgtaacc cgcccctat tttgggcatg    2880 tacgggttac agcagaatta aaaggctaat tttttgacta aataaagtta ggaaaatcac   2940
tactattaat tatttacgta ttcctttgaaa tggcgagtat tgataatgat aaactgagct   3000
```

```
ccagcttttg ttcccttag tgagggttaa ttgcgcgctt ggcgtaatca tggtcatagc    3060
tgtttcctgt gtgaaattgt tatccgctca caattccaca caacatagga gccggaagca    3120
taaagtgtaa agcctggggt gcctaatgag tgaggtaact cacattaatt gcgttgcgct    3180
cactgcccgc tttccagtcg ggaaacctgt cgtgccagct gcattaatga atcggccaac    3240
gcgcggggag aggcggtttg cgtattgggc gctcttccgc ttcctcgctc actgactcgc    3300
tgcgctcggt cgttcggctg cggcgagcgg tatcagctca ctcaaaggcg gtaatacggt    3360
tatccacaga atcaggggat aacgcaggaa agaacatgtg agcaaaaggc cagcaaaagg    3420
ccaggaaccg taaaaaggcc gcgttgctgg cgttttttcca taggctccgc cccctgacg    3480 agcatcacaa aaatcgacgc tcaagtcaga ggtggcgaaa cccgacagga ctataaagat    3540
accaggcgtt tccccctgga agctccctcg tgcgctctcc tgttccgacc ctgccgctta    3600
ccggatacct gtccgccttt ctcccttcgg gaagcgtggc gctttctcat agctcacgct    3660
gtaggtatct cagttcggtg taggtcgttc gctccaagct gggctgtgtg cacgaaccc    3720 ccgttcagcc cgaccgctgc gccttatccg gtaactatcg tcttgagtcc aacccggtaa    3780
gacacgactt atcgccactg gcagcagcca ctggtaacag gattagcaga gcgaggtatg    3840
taggcggtgc tacagagttc ttgaagtggt ggcctaacta cggctacact agaaggacag    3900
tatttggtat ctgcgctctg ctgaagccag ttaccttcgg aaaaagagtt ggtagctctt    3960
gatccggcaa acaaaccacc gctggtagcg gtggtttttt tgtttgcaag cagcagatta    4020
cgcgcagaaa aaaaggatct caagaagatc ctttgatctt ttctacgggg tctgacgctc    4080
agtggaacga aaactcacgt taagggattt tggtcatgag attatcaaaa aggatcttca    4140
cctagatcct tttaaattaa aaatgaagtt ttaaatcaat ctaaagtata tatgagtaaa    4200
cttggtctga cagttaccaa tgcttaatca gtgaggcacc tatctcagcg atctgtctat    4260
ttcgttcatc catagttgcc tgactccccg tcgtgtagat aactacgata cgggagggct    4320
taccatctgg ccccagtgct gcaatgatac cgcgagaccc acgctcaccg gctccagatt    4380
tatcagcaat aaaccagcca gccggaaggg ccgagcgcag aagtggtcct gcaactttat    4440
ccgcctccat ccagtctatt aattgttgcc gggaagctag agtaagtagt tcgccagtta    4500
atagtttgcg caacgttgtt gccattgcta caggcatcgt ggtgtcacgc tcgtcgtttg    4560
gtatggcttc attcagctcc ggttcccaac gatcaaggcg agttacatga tcccccatgt    4620
tgtgcaaaaa agcggttagc tccttcggtc ctccgatcgt tgtcagaagt aagttggccg    4680
cagtgttatc actcatggtt atggcagcac tgcataattc tcttactgtc atgccatccg    4740
taagatgctt ttctgtgact ggtgagtact caaccaagtc attctgagaa tagtgtatgc    4800
ggcgaccgag ttgctcttgc ccggcgtcaa tacgggataa taccgcgcca catagcagaa    4860
ctttaaaagt gctcatcatt ggaaaacgtt cttcggggcg aaaactctca aggatcttac    4920
cgctgttgag atccagttcg atgtaaccca ctcgtgcacc caactgatct tcagcatctt    4980
ttactttcac cagcgtttct gggtgagcaa aaacaggaag gcaaaatgcc gcaaaaaagg    5040
gaataagggc gacacggaaa tgttaatac tcatactctt cctttttcaa tattattgaa    5100
gcatttatca gggttattgt ctcatgagcg gatacatatt tgaatgtatt tagaaaaata    5160
aacaaatagg ggttccgcgc acatttcccc gaaaagtgcc acctgaacga agcatctgtg    5220
cttcattttg tagaacaaaa atgcaacgcg agagcgctaa ttttcaaac aaagaatctg    5280 agctgcattt ttacagaaca gaaatgcaac gcgaaagcgc tattttacca acgaagaatc    5340
tgtgcttcat ttttgtaaaa caaaaatgca acgcgagagc gctaattttt caaacaaaga    5400
```

-continued

```
atctgagctg cattttttaca gaacagaaat gcaacgcgag agcgctattt taccaacaaa      5460
gaatctatac ttcttttttg ttctacaaaa atgcatcccg agagcgctat ttttctaaca      5520
aagcatctta gattacttTT tttctccttt gtgcgctcta taatgcagtc tcttgataac      5580 ttttttgcact gtaggtccgt taaggttaga agaaggctac tttggtgtct attttctctt      5640
ccataaaaaa agcctgactc cacttcccgc gtttactgat tactagcgaa gctgcgggtg      5700
cattttttca agataaaggc atccccgatt atattctata ccgatgtgga ttgcgcatac      5760
tttgtgaaca gaaagtgata gcgttgatga ttcttcattg gtcagaaaat tatgaacggt      5820
ttcttctatt ttgtctctat atactacgta taggaaatgt ttacatTTTC gtattgtttt      5880
cgattcactc tatgaatagt tcttactaca atttttttgt ctaaagagta atactagaga      5940
taaacataaa aaatgtagag gtcgagttta gatgcaagtt caaggagcga aggtggatg      6000 ggtaggttat atagggatat agcacagaga tatatagcaa agagatactt tgagcaatg      6060 tttgtggaag cggtattcgc aatatttag tagctcgtta cagtccggtg cgttttTGGT      6120
tttttgaaag tgcgtcttca gagcgctttt ggttttcaaa agcgctctga agttcctata      6180
ctttctagag aataggaact tcggaatagg aacttcaaag cgtttccgaa aacgagcgct      6240
tccgaaaatg caacgcgagc tgcgcacata cagctcactg ttcacgtcgc acctatatct      6300
gcgtgttgcc tgtatatata tatacatgag aagaacggca tagtgcgtgt ttatgcttaa      6360
atgcgtactt atatgcgtct atttatgtag gatgaaaggt agtctagtac ctcctgtgat      6420
attatcccat tccatgcggg gtatcgtatg cttccttcag cactacccTT tagctgttct      6480
atatgctgcc actcctcaat tggattagtc tcatccttca atgctatcat ttcctttgat      6540
attggatcat actaagaaac cattattatc atgacattaa cctataaaaa taggcgtatc      6600
acgaggccct ttcgtc                                                      6616
```

<210> SEQ ID NO 23
<211> LENGTH: 7974
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accataaacg acattactat atatataata taggaagcat ttaatagaca gcatcgtaat      240
atatgtgtac tttgcagtta tgacgccaga tggcagtagt ggaagatatt ctttattgaa      300
aaatagcttg tcaccttacg tacaatcttg atccggagct tttctttttt tgccgattaa      360
gaattaattc ggtcgaaaaa agaaaaggag agggccaaga gggagggcat tggtgactat      420
tgagcacgtg agtatacgtg attaagcaca caaaggcagc ttggagtatg tctgttatta      480
atttcacagg tagttctggt ccattggtga agtttgcgg cttgcagagc acagaggccg      540
cagaatgtgc tctagattcc gatgctgact tgctgggtat tatatgtgtg cccaatagaa      600
agagaacaat tgacccggtt attgcaagga aatttcaag tcttgtaaaa gcatataaaa      660
atagttcagg cactccgaaa tacttggttg gcgtgtttcg taatcaacct aaggaggatg      720
ttttggctct ggtcaatgat tacggcattg atatcgtcca actgcatgga gatgagtcgt      780
ggcaagaata ccaagagttc ctcggtttgc cagttattaa aagactcgta tttccaaaag      840
```

```
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa tttttgttaa atcagctcat tttttaacca ataggccgaa   1320
atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca tcaggctgc gcaactgttg ggaagggcga   1740
tcggtgcggg cctcttcgct attacgccag ctggcgaaag ggggatgtgc tgcaaggcga   1800
ttaagttggg taacgccagg gttttcccag tcacgacgtt gtaaaacgac ggccagtgag   1860
cgcgcgtaat acgactcact ataggcgaa ttgggtaccg gccgcaaatt aaagccttcg   1920
agcgtcccaa aaccttctca agcaaggttt tcagtataat gttacatgcg tacacgcgtc   1980
tgtacagaaa aaaagaaaa atttgaaata taaataacgt tcttaatact aacataacta   2040
taaaaaaata aatagggacc tagacttcag gttgtctaac tccttccttt tcggttagag   2100
cggatgtggg gggagggcgt gaatgtaagc gtgacataac taattacatg actcgagcgg   2160
ccgcggatcc ctagagagct ttcgttttca tgagttcccc gaattctttc ggaagcttgt   2220
cacttgctaa attaacgtta tcactgtagt caaccgggac atcaatgatg acaggcccct   2280
cagcgttcat gccttgacgc agaacatctg ccagctggtc tggtgattct acgcgtaagc   2340
cagttgctcc gaagctttcc gcgtatttca cgatatcgat atttccgaaa tcgaccgcag   2400
atgtacgatt atatttttc aattgctgga atgcaaccat gtcatatgtg ctgtcgttcc   2460
atacaatgtg tacaattggt gcttttaaac gaactgctgt ctctaattcc atagctgaga   2520
ataagaaacc gccatcaccg gagactgata ctacttttc tcccggtttc accaatgaag   2580
cgccgattgc ccaaggaagc gcaacgccga gtgtttgcat accgttacta atcattaatg   2640
ttaacggctc gtagctgcgg aaataacgtg acatccaaat cgcgtgtgaa ccgatatcgc   2700
aagtcactgt aacatgatca tcgactgcgt ttcgcaattc tttaacgatt tcaagaggat   2760
gcactctgtc tgatttccaa tctgcaggca cctgctcacc ctcatgcata tattgtttta   2820
aatcagaaag gatcttctgc tcacgttccg caaagtctac tttcacagca tcgtgttcga   2880
tatgattgat cgtagatgga atatcaccga tcagttcaag atccggctgg taagcatgat   2940
caatgtcagc cagaatctcg tctaaatgga tgatcgtccg gtctccattg acattccaga   3000
atttcggatc atattcaatt gggtcatagc cgattgtcag acaacatca gcctgctcaa   3060
gcagcagatc gccaggctgg ttgcggaata aaccgatccg gccaaaatac tgatcctcta   3120
aatctctcgt aagagtaccg gcagcttgat atgtttcaac gaatggaagc tgcacttttt   3180
tcaatagctt gcgaaccgct ttaatcgctt ccggtcttcc gcccttcatg ccgactaaaa   3240
```

```
cgacaggaag ttttgctgtt tgaattttg  caatggccat actgattgcg tcatctgctg  3300
cgggaccaag ttttggcgct gcgacagcac gtacgttttt tgtatttgtg acttcattca  3360
caacatcttg cggaaaactc acaaaagcgg ccccagcctg ccctgctgac gctatcctaa  3420
acgcatttgt aacagcttcc ggtatatttt ttacatcttg aacttctaca ctgtattttg  3480
taatcggctg gaatagcgcc gcattatcca aagattgatg tgtccgtttt aaacgatctg  3540
cacggatcac gttcccagca agcgcaacga cagggtcacc ttcagtgttt gctgtcagca  3600
gtcctgttgc caagttcgaa gcacctggtc ctgatgtgac taacacgact cccggttttc  3660
cagttaaacg gccgactgct tgcgccataa atgctgcatt ttgttcatgc cgggcaacga  3720
taatttcagg cccttatct  tgtaaagcgt caaataccgc atcaattttt gcacctggaa  3780
tgccaaatac atgtgtgaca ccttgctccg ctaagcaatc aacaacaagc tccgcccctc  3840
tgcttttcac aagggatttt tgttcttttg ttgcttttgt caacatgtcg actttatgtg  3900
atgattgatt gattgattgt acagtttgtt tttcttaata tctatttcga tgacttctat  3960
atgatattgc actaacaaga agatattata atgcaattga tacaagacaa ggagttattt  4020
gcttctcttt tatatgattc tgacaatcca tattgcgttg gtagtctttt ttgctggaac  4080
ggttcagcgg aaaagacgca tcgctctttt tgcttctaga agaaatgcca gcaaaagaat  4140
ctcttgacag tgactgacag caaaaatgtc tttttctaac tagtaacaag gctaagatat  4200
cagcctgaaa taagggtgg  tgaagtaata attaaatcat ccgtataaac ctatacacat  4260
atatgaggaa aaataataca aaagtgtttt aaatacagat acatcatga  acatatgcac  4320 gtatagcgcc caaatgtcgg taatgggatc ggcgagctcc agcttttgtt cccttagtg  4380 agggttaatt gcgcgcttgg cgtaatcatg gtcatagctg tttcctgtgt gaaattgtta  4440
tccgctcaca attccacaca ataggagc  cggaagcata aagtgtaaag cctggggtgc  4500
ctaatgagtg aggtaactca cattaattgc gttgcgctca ctgcccgctt tccagtcggg  4560
aaacctgtcg tgccagctgc attaatgaat cggccaacgc gcggggagag gcggtttgcg  4620
tattgggcgc tcttccgctt cctcgctcac tgactcgctg cgctcggtcg ttcggctgcg  4680
gcgagcggta tcagctcact caaaggcggt aatacggtta ccacagaat  caggggataa  4740 cgcaggaaag aacatgtgag caaaaggcca gcaaaaggcc aggaaccgta aaaaggccgc  4800
gttgctggcg ttttccata  ggctccgccc ccctgacgag catcacaaaa atcgacgctc  4860
aagtcagagg tggcgaaacc cgacaggact ataaagatac caggcgtttc ccctggaag   4920 ctccctcgtg cgctctcctg ttccgaccct gccgcttacc ggatacctgt ccgcctttct  4980
cccttcggga agcgtggcgc tttctcatag ctcacgctgt aggtatctca gttcggtgta  5040
ggtcgttcgc tccaagctgg gctgtgtgca cgaaccccc  gttcagcccg accgctgcgc  5100
cttatccggt aactatcgtc ttgagtccaa cccggtaaga cacgacttat cgccactggc  5160
agcagccact ggtaacagga ttagcagagc gaggtatgta ggcggtgcta cagagttctt  5220
gaagtggtgg cctaactacg gctacactag aaggacagta tttggtatct gcgctctgct  5280
gaagccagtt accttcggaa aaagagttgg tagctcttga tccggcaaac aaaccaccgc  5340
tggtagcggt ggtttttttg tttgcaagca gcagattacg cgcagaaaaa aaggatctca  5400
agaagatcct ttgatctttt ctacgggtc  tgacgctcag tggaacgaaa actcacgtta  5460
agggattttg gtcatgagat tatcaaaaag gatcttcacc tagatccttt taaattaaaa  5520
atgaagtttt aaatcaatct aaagtatata tgagtaaact tggtctgaca gttaccaatg  5580
cttaatcagt gaggcaccta tctcagcgat ctgtctattt cgttcatcca tagttgcctg  5640
```

```
actcccgtc gtgtagataa ctacgatacg ggagggctta ccatctggcc ccagtgctgc    5700
aatgataccg cgagacccac gctcaccggc tccagattta tcagcaataa accagccagc    5760
cggaagggcc gagcgcagaa gtggtcctgc aactttatcc gcctccatcc agtctattaa    5820
ttgttgccgg gaagctagag taagtagttc gccagttaat agtttgcgca acgttgttgc    5880
cattgctaca ggcatcgtgg tgtcacgctc gtcgtttggt atggcttcat tcagctccgg    5940
ttcccaacga tcaaggcgag ttacatgatc ccccatgttg tgcaaaaaag cggttagctc    6000
cttcggtcct ccgatcgttg tcagaagtaa gttggccgca gtgttatcac tcatggttat    6060
ggcagcactg cataattctc ttactgtcat gccatccgta agatgctttt ctgtgactgg    6120
tgagtactca accaagtcat tctgagaata gtgtatgcgg cgaccgagtt gctcttgccc    6180
ggcgtcaata cgggataata ccgcgccaca tagcagaact ttaaaagtgc tcatcattgg    6240
aaaacgttct cggggcgaaa actctcaag gatcttaccg ctgttgagat ccagttcgat    6300
gtaacccact cgtgcaccca actgatcttc agcatctttt actttcacca gcgtttctgg    6360
gtgagcaaaa acaggaaggc aaaatgccgc aaaaaaggga ataagggcga cacggaaatg    6420
ttgaatactc atactcttcc ttttcaata ttattgaagc atttatcagg gttattgtct    6480
catgagcgga tacatatttg aatgtattta gaaaaataaa caatagggg ttccgcgcac    6540 atttcccga aaagtgccac ctgaacgaag catctgtgct tcattttgta gaacaaaaat    6600
gcaacgcgag agcgctaatt tttcaaacaa agaatctgag ctgcattttt acagaacaga    6660
aatgcaacgc gaaagcgcta ttttaccaac gaagaatctg tgcttcattt ttgtaaaaca    6720
aaaatgcaac gcgagagcgc taattttttca aacaaagaat ctgagctgca ttttacaga    6780 acagaaatgc aacgcgagag cgctatttta ccaacaaaga atctatactt cttttttgtt    6840
ctacaaaaat gcatcccgag agcgctattt ttctaacaaa gcatcttaga ttactttttt    6900
tctcctttgt gcgctctata atgcagtctc ttgataactt tttgcactgt aggtccgtta    6960
aggttagaag aaggctactt tggtgtctat tttctcttcc ataaaaaaag cctgactcca    7020
cttcccgcgt ttactgatta ctagcgaagc tgcgggtgca ttttttcaag ataaaggcat    7080
ccccgattat attctatacc gatgtggatt gcgcatactt tgtgaacaga aagtgatagc    7140
gttgatgatt cttcattggt cagaaaatta tgaacggttt cttctatttt gtctctatat    7200
actacgtata ggaaatgttt acattttcgt attgttttcg attcactcta tgaatagttc    7260
ttactacaat tttttttgtct aaagagtaat actagagata aacataaaaa atgtagaggt    7320
cgagtttaga tgcaagttca aggagcgaaa ggtggatggg taggttatat agggatatag    7380
cacagagata tatagcaaag agatactttt gagcaatgtt tgtggaagcg gtattcgcaa    7440
tattttagta gctcgttaca gtccggtgcg ttttttggttt tttgaaagtg cgtcttcaga    7500
gcgcttttgg ttttcaaaag cgctctgaag ttcctatact ttctagagaa taggaacttc    7560
ggaataggaa cttcaaagcg tttccgaaaa cgagcgcttc cgaaaatgca acgcgagctg    7620
cgcacataca gctcactgtt cacgtcgcac ctatatctgc gtgttgcctg tatatatata    7680
tacatgagaa gaacggcata gtgcgtgttt atgcttaaat gcgtacttat atgcgtctat    7740
ttatgtagga tgaaaggtag tctagtacct cctgtgatat tatcccattc catgcgggt    7800 atcgtatgct tccttcagca ctacccttta gctgttctat atgctgccac tcctcaattg    7860
gattagtctc atccttcaat gctatcattt cctttgatat tggatcatat taagaaacca    7920
ttattatcat gacattaacc tataaaaata ggcgtatcac gaggcccttt cgtc           7974
```

<210> SEQ ID NO 24
<211> LENGTH: 9692
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

| | | | | | |
|---|---|---|---|---|---|
| ttggatcata | ctaagaaacc | attattatca | tgacattaac | ctataaaaat | aggcgtatca | 60 |
| cgaggccctt | tcgtctcgcg | cgtttcggtg | atgacggtga | aaacctctga | cacatgcagc | 120 |
| tcccggagac | ggtcacagct | tgtctgtaag | cggatgccgg | gagcagacaa | gcccgtcagg | 180 |
| gcgcgtcagc | gggtgttggc | gggtgtcggg | gctggcttaa | ctatgcggca | tcagagcaga | 240 |
| ttgtactgag | agtgcaccat | accacagctt | tcaattcaa | ttcatcattt | tttttttatt | 300 |
| cttttttttg | atttcggttt | ctttgaaatt | tttttgattc | ggtaatctcc | gaacagaagg | 360 |
| aagaacgaag | gaaggagcac | agacttagat | tggtatatat | acgcatatgt | agtgttgaag | 420 |
| aaacatgaaa | ttgcccagta | ttcttaaccc | aactgcacag | aacaaaaacc | tgcaggaaac | 480 |
| gaagataaat | catgtcgaaa | gctacatata | aggaacgtgc | tgctactcat | cctagtcctg | 540 |
| ttgctgccaa | gctatttaat | atcatgcacg | aaaagcaaac | aaacttgtgt | gcttcattgg | 600 |
| atgttcgtac | caccaaggaa | ttactggagt | tagttgaagc | attaggtccc | aaaatttgtt | 660 |
| tactaaaaac | acatgtggat | atcttgactg | attttttccat | ggagggcaca | gttaagccgc | 720 |
| taaaggcatt | atccgccaag | tacaattttt | tactcttcga | agacagaaaa | tttgctgaca | 780 |
| ttggtaatac | agtcaaattg | cagtactctg | cgggtgtata | cagaatagca | gaatgggcag | 840 |
| acattacgaa | tgcacacggt | gtggtgggcc | caggtattgt | tagcggtttg | aagcaggcgg | 900 |
| cagaagaagt | aacaaaggaa | cctagaggcc | ttttgatgtt | agcagaattg | tcatgcaagg | 960 |
| gctccctatc | tactgagaa | tatactaagg | gtactgttga | cattgcgaag | agcgacaaag | 1020 |
| attttgttat | cggctttatt | gctcaaagag | acatgggtgg | aagagatgaa | ggttacgatt | 1080 |
| ggttgattat | gacacccggt | gtgggtttag | atgacaaggg | agacgcattg | ggtcaacagt | 1140 |
| atagaaccgt | ggatgatgtg | gtctctacag | gatctgacat | tattattgtt | ggaagaggac | 1200 |
| tatttgcaaa | gggaagggat | gctaaggtag | agggtgaacg | ttacagaaaa | gcaggctggg | 1260 |
| aagcatattt | gagaagatgc | ggccagcaaa | actaaaaaac | tgtattataa | gtaaatgcat | 1320 |
| gtatactaaa | ctcacaaatt | agagcttcaa | tttaattata | tcagttatta | ccctatgcgg | 1380 |
| tgtgaaatac | cgcacagatg | cgtaaggaga | aaataccgca | tcaggaaatt | gtaaacgtta | 1440 |
| atattttgtt | aaaattcgcg | ttaaattttt | gttaaatcag | ctcattttttt | aaccaatagg | 1500 |
| ccgaaatcgg | caaaatccct | tataaatcaa | agaatagac | cgagataggg | ttgagtgttg | 1560 |
| ttccagtttg | gaacaagagt | ccactattaa | agaacgtgga | ctccaacgtc | aaagggcgaa | 1620 |
| aaaccgtcta | tcagggcgat | ggcccactac | gtgaaccatc | accctaatca | agttttttgg | 1680 |
| ggtcgaggtg | ccgtaaagca | ctaaatcgga | accctaaagg | gagcccccga | tttagagctt | 1740 |
| gacggggaaa | gccggcgaac | gtggcgagaa | aggaagggaa | gaaagcgaaa | ggagcgggcg | 1800 |
| ctagggcgct | ggcaagtgta | gcggtcacgc | tgcgcgtaac | caccacaccc | gccgcgctta | 1860 |
| atgcgccgct | acagggcgcg | tcgcgccatt | cgccattcag | gctgcgcaac | tgttgggaag | 1920 |
| ggcgatcggt | gcgggcctct | tcgctattac | gccagctggc | gaaagggga | tgtgctgcaa | 1980 |
| ggcgattaag | ttgggtaacg | ccagggtttt | cccagtcacg | acgttgtaaa | acgacggcca | 2040 |
| gtgagcgcgc | gtaatacgac | tcactatagg | gcgaattggg | taccggccgc | aaattaaagc | 2100 |

```
cttcgagcgt cccaaaacct tctcaagcaa ggttttcagt ataatgttac atgcgtacac   2160
gcgtctgtac agaaaaaaaa gaaaaatttg aaatataaat aacgttctta atactaacat   2220
aactataaaa aaataaatag ggacctagac ttcaggttgt ctaactcctt ccttttcggt   2280
tagagcggat gtggggggag ggcgtgaatg taagcgtgac ataactaatt acatgagcgg   2340
ccgcctattt atggaatttc ttatcataat cgaccaaagt aaatctgtat ttgacgtctc   2400
cgctttccat ccttgtaaag gcatggctga cgccttcttc gctgatcgga agttttcca   2460 cccatatttt gacattcttt tcggaaacta atttcaatag ttgttcgatt tccttcctag   2520
atccgatagc actgcttgag attgatactc ccattaggcc caacggtttt aaaacaagct   2580
tttcattaac ttcaggagca gcaattgaaa cgatggagcc tccaatcttc ataatcttaa   2640
cgatactgtc aaaattaact ttcgacaaag atgatgagca aacgacaaga aggtccaaag   2700
cgttagagta ttgttctgtc cagcctttat cctccaacat agcaatatag tgatcagcac   2760
cgagtttcat agaatcctcc cgcttggagt ggcctcgcga aaacgcataa acctcggctc   2820
ccatagcttt agccaacaga atccccatat gcccaatacc accgatgcca acaataccta   2880
ccctcttacc tggaccacag ccatttctta gtagtggaga gaaaactgta ataccaccac   2940
acaataatgg agcggctagc ggacttggaa tattttctgg tatttgaata gcaaagtgtt   3000
catgaagcct cacgtgggag gcaaagcctc cttgtgaaat gtagccgtcc ttgtaaggag   3060
tccacatagt caaaacgtgg tcattggtac agtattgctc gttgtcactt ttgcaacgtt   3120
cacactcaaa acacgccaag gcttgggcac caacaccaac acggtcaccg attttacccc   3180
cagtgtggca cttggatcca accttcacca cgcggccaat tatttcatgt ccaaggattt   3240
gattttctgg gactggaccc caattaccaa cggctatatg aaaatcagat ccgcagatac   3300
cacaggcttc aatttcaaca tcaacgtcat gatcgccaaa gggttttggg tcaaaactca   3360
ctaatttagg atgcttccaa tcctttgcgt tggaaatacc gatgccctga aattttctg   3420 ggtaaagcat gtcgagtcga aactaagttc tggtgtttta aaactaaaaa aaagactaac   3480
tataaaagta gaatttaaga agtttaagaa atagatttac agaattacaa tcaatcccta   3540
ccgtctttat atacttatta gtcaagtagg ggaataattt cagggaactg gtttcaacct   3600
tttttttcag cttttttccaa atcagagaga gcagaaggta atagaaggtg taagaaaatg   3660
agatagatac atgcgtgggt caattgcctt gtgtcatcat ttactccagg caggttgcat   3720
cactccattg aggttgtgcc cgttttttgc ctgtttgtgc ccctgttctc tgtagttgcg   3780
ctaagagaat ggacctatga actgatggtt ggtgaagaaa acaatatttt ggtgctggga   3840 ttctttttt ttctggatgc cagcttaaaa agcgggctcc attatattta gtggatgcca   3900
ggaataaact gttcacccag acacctacga tgttatatat tctgtgtaac ccgcccccta   3960
ttttgggcat gtacgggtta cagcagaatt aaaaggctaa ttttttgact aaataaagtt   4020
aggaaaatca ctactattaa ttatttacgt attctttgaa atggcgagta ttgataatga   4080
taaactggat ccttaggatt tattctgttc agcaaacagc ttgcccattt tcttcagtac   4140
cttcggtgcg ccttctttcg ccaggatcag ttcgatccag tacatacggt tcggatcggc   4200
ctgggcctct ttcatcacgc tcacaaattc gttttcggta cgcacaattt tagacacaac   4260
acggtcctca gttgcgccga aggactccgg cagtttagag tagttccaca tagggatatc   4320
gttgtaagac tggttcggac cgtggatctc acgctcaacg gtgtagccgt cattgttaat   4380
aatgaagcaa atcggggttga tcttttcacg aattgccaga cccagttcct gtacggtcag   4440
ctgcagggaa ccgtcaccga tgaacagcag atgacgagat tctttatcag cgatctgaga   4500
```

```
gcccagcgct gccgggaaag tatagccaat gctaccccac agcggctgac cgataaaatg    4560
gcttttggat ttcagaaaga tagaagacgc gccgaaaaag ctcgtacctt gttccgccac    4620
gatggtttca ttgctctggg tcaggttctc cacggcctgc cacaggcgat cctgggacag    4680
cagtgcgtta gatggtacga aatcttcttg cttttgtca atgtatttgc ctttatactc    4740
gatttcggac aggtccagca gagagctgat caggctttcg aagtcgaagt tctggatacg    4800
ctcgttgaag attttacccct cgtcgatgtt caggctaatc attttgtttt cgttcagatg    4860
gtgagtgaat gcaccggtag aagagtcggt cagtttaacg cccagcatca ggatgaagtc    4920
cgcagattca acaaattctt tcaggttcgg ttcgctcaga gtaccgttgt agatgcccag    4980
gaaagacggc agagcctcgt caacagagga cttgccgaag ttcagggtgg taatcggcag    5040
tttggttttg ctgatgaatt gggtcacggt cttctccaga ccaaaagaaa tgatttcgtg    5100
gccggtgatc acgattggtt tctttgcgtt tttcagagac tcctggattt tgttcaggat    5160
ttcctggtcg ctagtgttag aagtggagtt ttctttcttc agcggcaggc tcggttttttc    5220 cgctttagct gccgcaacat ccacaggcag gttgatgtaa actggtttgc gttctttcag    5280
cagcgcagac agaacgcggt cgatttccac agtagcgttc tctgcagtca gcagcgtacg    5340
tgccgcagtc acaggttcat gcattttcat gaagtgtttg aaatcgccgt cagccagagt    5400
gtggtggacg aatttacctt cgttctgaac tttgctcgtt gggctgccta cgatctccac    5460
caccggcagg ttttcggcgt aggagcccgc cagaccgttg acggcgctca gttcgccaac    5520
accgaaagtg gtcagaaatg ccgcggcttt cttggtacgt gcataaccat ctgccatgta    5580
gcttgcgttc agttcgttag cgttacccac ccatttcatg tctttatgag agatgatctg    5640
atccaggaac tgcagattgt aatcaccccgg aacgccgaag attttcttcga tacccagttc    5700 atgcagacgg tccagcagat aatcaccaac agtatacatg tcgacaaact tagattagat    5760
tgctatgctt tctttctaat gagcaagaag taaaaaaagt tgtaatagaa caagaaaaat    5820
gaaactgaaa cttgagaaat tgaagaccgt ttattaactt aaatatcaat gggaggtcat    5880
cgaaagagaa aaaatcaaa aaaaaaattt tcaagaaaaa gaaacgtgat aaaaattttt    5940
attgcctttt tcgacgaaga aaaagaaacg aggcggtctc ttttttctttt tccaaacctt    6000 tagtacgggt aattaacgac accctagagg aagaagagg ggaaatttag tatgctgtgc    6060
ttgggtgttt tgaagtggta cggcgatgcg cggagtccga aaaatctgg aagagtaaaa    6120 aaggagtaga aacattttga agctatgagc tccagctttt gttcccttta gtgagggtta    6180
attgcgcgct tggcgtaatc atggtcatag ctgtttcctg tgtgaaattg ttatccgctc    6240
acaattccac acaacatagg agccggaagc ataaagtgta aagcctgggg tgcctaatga    6300
gtgaggtaac tcacattaat tgcgttcgc tcactgcccg ctttccagtc gggaaacctg    6360
tcgtgccagc tgcattaatg aatcggccaa cgcgcgggga gaggcggttt gcgtattggg    6420
cgctcttccg cttcctcgct cactgactcg ctgcgctcgg tcgttcggct gcggcgagcg    6480
gtatcagctc actcaaaggc ggtaatacgg ttatccacag aatcagggga taacgcagga    6540
aagaacatgt gagcaaaagg ccagcaaaag gccaggaacc gtaaaaaggc cgcgttgctg    6600 gcgttttttcc ataggctccg ccccctgac gagcatcaca aaaatcgacg ctcaagtcag    6660
aggtggcgaa acccgacagg actataaaga taccaggcgt tttcccctgg aagctccctc    6720
gtgcgctctc ctgttccgac cctgccgctt accggatacc tgtccgcctt tctcccttcg    6780
ggaagcgtgg cgctttctca tagctcacgc tgtaggtatc tcagttcggt gtaggtcgtt    6840
cgctccaagc tgggctgtgt gcacgaaccc cccgttcagc ccgaccgctg cgccttatcc    6900
```

```
ggtaactatc gtcttgagtc caacccggta agacacgact tatcgccact ggcagcagcc   6960
actggtaaca ggattagcag agcgaggtat gtaggcggtg ctacagagtt cttgaagtgg   7020
tggcctaact acggctacac tagaaggaca gtatttggta tctgcgctct gctgaagcca   7080
gttaccttcg gaaaaagagt tggtagctct tgatccggca acaaaccac cgctggtagc    7140
ggtggttttt ttgtttgcaa gcagcagatt acgcgcagaa aaaaggatc tcaagaagat    7200
cctttgatct tttctacggg gtctgacgct cagtggaacg aaaactcacg ttaagggatt   7260
ttggtcatga gattatcaaa aaggatcttc acctagatcc ttttaaatta aaaatgaagt   7320
tttaaatcaa tctaaagtat atatgagtaa acttggtctg acagttacca atgcttaatc   7380
agtgaggcac ctatctcagc gatctgtcta tttcgttcat ccatagttgc ctgactcccc   7440
gtcgtgtaga taactacgat acgggagggc ttaccatctg gccccagtgc tgcaatgata   7500
ccgcgagacc cacgctcacc ggctccagat ttatcagcaa taaaccagcc agccggaagg   7560
gccgagcgca gaagtggtcc tgcaacttta tccgcctcca tccagtctat taattgttgc   7620
cgggaagcta gagtaagtag ttcgccagtt aatagtttgc gcaacgttgt tgccattgct   7680
acaggcatcg tggtgtcacg ctcgtcgttt ggtatggctt cattcagctc cggttcccaa   7740
cgatcaaggc gagttacatg atcccccatg ttgtgcaaaa aagcggttag ctccttcggt   7800
cctccgatcg ttgtcagaag taagttggcc gcagtgttat cactcatggt tatggcagca   7860
ctgcataatt ctcttactgt catgccatcc gtaagatgct tttctgtgac tggtgagtac   7920
tcaaccaagt cattctgaga atagtgtatg cggcgaccga gttgctcttg cccggcgtca   7980
atacgggata ataccgcgcc acatagcaga actttaaaag tgctcatcat tggaaaacgt   8040
tcttcgggc gaaaactctc aaggatctta ccgctgttga gatccagttc gatgtaaccc    8100
actcgtgcac ccaactgatc ttcagcatct tttactttca ccagcgtttc tgggtgagca   8160
aaaacaggaa ggcaaaatgc cgcaaaaaag ggaataaggg cgacacggaa atgttgaata   8220
ctcatactct tcctttttca atattattga agcatttatc agggttattg tctcatgagc   8280
ggatacatat ttgaatgtat ttagaaaaat aaacaaatag gggttccgcg cacatttccc   8340
cgaaaagtgc cacctgaacg aagcatctgt gcttcatttt gtagaacaaa aatgcaacgc   8400
gagagcgcta ttttttcaaa caaagaatct gagctgcatt tttacagaac agaaatgcaa   8460
cgcgaaagcg ctattttacc aacgaagaat ctgtgcttca ttttttgtaaa acaaaaatgc   8520
aacgcgagag cgctaatttt tcaaacaaag aatctgagct gcattttac agaacagaaa    8580
tgcaacgcga gagcgctatt ttaccaacaa agaatctata cttcttttttt gttctacaaa   8640
aatgcatccc gagagcgcta ttttctaac aaagcatctt agattacttt ttttctcctt    8700
tgtgcgctct ataatgcagt ctcttgataa cttttttgcac tgtaggtccg ttaaggttag   8760
aagaaggcta ctttggtgtc tattttctct tccataaaaa aagcctgact ccacttcccg   8820
cgttactga ttactagcga agctgcgggt gcatttttc aagataaagg catcccgat      8880
tatattctat accgatgtgg attgcgcata ctttgtgaac agaaagtgat agcgttgatg   8940
attcttcatt ggtcagaaaa ttatgaacgg tttcttctat tttgtctcta tatactacgt   9000
ataggaaatg tttacatttt cgtattgttt tcgattcact ctatgaatag ttcttactac   9060
aattttttg tctaaagagt aatactagag ataaacataa aaaatgtaga ggtcgagttt    9120
agatgcaagt tcaaggagcg aaaggtggat gggtaggtta tatagggata tagcacagag   9180
atatatagca aagagatact tttgagcaat gtttgtggaa gcggtattcg caatatttta   9240
gtagctcgtt acagtccggt gcgttttggt ttttttgaaa gtgcgtcttc agagcgcttt   9300
```

```
tggttttcaa aagcgctctg aagttcctat actttctaga gaataggaac ttcggaatag    9360
gaacttcaaa gcgtttccga aaacgagcgc ttccgaaaat gcaacgcgag ctgcgcacat    9420
acagctcact gttcacgtcg cacctatatc tgcgtgttgc ctgtatatat atatacatga    9480
gaagaacggc atagtgcgtg tttatgctta aatgcgtact tatatgcgtc tatttatgta    9540
ggatgaaagg tagtctagta cctcctgtga tattatccca ttccatgcgg ggtatcgtat    9600
gcttccttca gcactaccct ttagctgttc tatatgctgc cactcctcaa ttggattagt    9660
ctcatccttc aatgctatca tttcctttga ta                                  9692

<210> SEQ ID NO 25
<211> LENGTH: 5439
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accataaacg acattactat atatataata taggaagcat ttaatagaca gcatcgtaat     240
atatgtgtac tttgcagtta tgacgccaga tggcagtagt ggaagatatt ctttattgaa     300
aaatagcttg tcaccttacg tacaatcttg atccggagct tttcttttt tgccgattaa     360 gaattaattc ggtcgaaaaa agaaaaggag agggccaaga gggagggcat tggtgactat     420
tgagcacgtg agtatacgtg attaagcaca caaaggcagc ttggagtatg tctgttatta     480
atttcacagg tagttctggt ccattggtga agtttgcgg cttgcagagc acagaggccg     540
cagaatgtgc tctagattcc gatgctgact tgctgggtat tatatgtgtg cccaatagaa     600
agagaacaat tgacccggtt attgcaagga aaatttcaag tcttgtaaaa gcatataaaa     660
atagttcagg cactccgaaa tacttggttg gcgtgtttcg taatcaacct aaggaggatg     720
ttttggctct ggtcaatgat tacggcattg atatcgtcca actgcatgga gatgagtcgt     780
ggcaagaata ccaagagttc ctcggttttgc cagttattaa aagactcgta tttccaaaag     840
actgcaacat actactcagt gcagcttcac agaaacctca ttcgtttatt cccttgtttg     900
attcagaagc aggtgggaca ggtgaacttt tggattggaa ctcgatttct gactgggttg     960
gaaggcaaga gagccccgaa agcttacatt ttatgttagc tggtggactg acgccagaaa    1020
atgttggtga tgcgcttaga ttaaatggcg ttattggtgt tgatgtaagc ggaggtgtgg    1080
agacaaatgg tgtaaaagac tctaacaaaa tagcaaattt cgtcaaaaat gctaagaaat    1140
aggttattac tgagtagtat ttatttaagt attgtttgtg cacttgccta tgcggtgtga    1200
aataccgcac agatgcgtaa ggagaaaata ccgcatcagg aaattgtaaa cgttaatatt    1260
ttgttaaaat tcgcgttaaa ttttttgttaa atcagctcat ttttttaacca ataggccgaa    1320 atcggcaaaa tcccttataa atcaaaagaa tagaccgaga tagggttgag tgttgttcca    1380
gtttggaaca agagtccact attaaagaac gtggactcca acgtcaaagg gcgaaaaacc    1440
gtctatcagg gcgatggccc actacgtgaa ccatcaccct aatcaagttt ttgggtcg    1500 aggtgccgta aagcactaaa tcggaaccct aaagggagcc ccgatttag agcttgacgg    1560 ggaaagccgg cgaacgtggc gagaaaggaa gggaagaaag cgaaaggagc gggcgctagg    1620
gcgctggcaa gtgtagcggt cacgctgcgc gtaaccacca cacccgccgc gcttaatgcg    1680
```

```
ccgctacagg gcgcgtcgcg ccattcgcca ttcaggctgc gcaactgttg ggaagggcga    1740
tcggtgcggg cctcttcgct attacgccag ctggcgaaag ggggatgtgc tgcaaggcga    1800
ttaagttggg taacgccagg gttttcccag tcacgacgtt gtaaaacgac ggccagtgag    1860
cgcgcgtaat acgactcact ataggcgaa ttgggtaccg gccgcaaatt aaagccttcg    1920
agcgtcccaa aaccttctca agcaaggttt tcagtataat gttacatgcg tacacgcgtc    1980
tgtacagaaa aaaagaaaa atttgaaata taaataacgt tcttaatact aacataacta    2040
taaaaaaata aatagggacc tagacttcag gttgtctaac tccttccttt tcggttagag    2100
cggatgtggg gggagggcgt gaatgtaagc gtgacataac taattacatg actcgagcgg    2160
ccgcggatcc cgggaattcg tcgactttat gtgatgattg attgattgat tgtacagttt    2220 gttttctta atatctattt cgatgacttc tatatgatat tgcactaaca agaagatatt    2280
ataatgcaat tgatacaaga caaggagtta tttgcttctc ttttatatga ttctgacaat    2340
ccatattgcg ttggtagtct tttttgctgg aacggttcag cggaaaagac gcatcgctct    2400
ttttgcttct agaagaaatg ccagcaaaag aatctcttga cagtgactga cagcaaaaat    2460 gtcttttct aactagtaac aaggctaaga tatcagcctg aaataaaggg tggtgaagta    2520
ataattaaat catccgtata aacctataca catatatgag gaaaataat acaaagtgt    2580 tttaaataca gatacataca tgaacatatg cacgtatagc gcccaaatgt cggtaatggg    2640
atcggcgagc tccagcttt gttcccttta gtgagggtta attgcgcgct tggcgtaatc    2700
atggtcatag ctgtttcctg tgtgaaattg ttatccgctc acaattccac acaacatagg    2760
agccggaagc ataaagtgta aagcctgggg tgcctaatga gtgaggtaac tcacattaat    2820 tgcgttcgc tcactgcccg ctttccagtc gggaaacctg tcgtgccagc tgcattaatg    2880
aatcggccaa cgcgcgggga gaggcggttt gcgtattggg cgctcttccg cttcctcgct    2940
cactgactcg ctgcgctcgg tcgttcggct gcggcgagcg gtatcagctc actcaaaggc    3000
ggtaatacgg ttatccacag aatcagggga taacgcagga agaacatgt gagcaaaagg    3060 ccagcaaaag gccaggaacc gtaaaaaggc cgcgttgctg gcgttttcc ataggctccg    3120 cccccctgac gagcatcaca aaaatcgacg ctcaagtcag aggtggcgaa acccgacagg    3180
actataaaga taccaggcgt ttccccctgg aagctccctc gtgcgctctc ctgttccgac    3240
cctgccgctt accggatacc tgtccgcctt tctcccttcg ggaagcgtgg cgctttctca    3300
tagctcacgc tgtaggtatc tcagttcggt gtaggtcgtt cgctccaagc tgggctgtgt    3360
gcacgaaccc cccgttcagc ccgaccgctg cgccttatcc ggtaactatc gtcttgagtc    3420
caacccggta agacacgact tatcgccact ggcagcagcc actggtaaca ggattagcag    3480
agcgaggtat gtaggcggtg ctacagagtt cttgaagtgg tggcctaact acggctacac    3540
tagaaggaca gtatttggta tctgcgctct gctgaagcca gttaccttcg gaaaagagt    3600 tggtagctct tgatccggca aacaaaccac cgctggtagc ggtggttttt tgtttgcaa    3660 gcagcagatt acgcgcagaa aaaaggatc tcaagaagat cctttgatct tttctacggg    3720
gtctgacgct cagtggaacg aaaactcacg ttaagggatt ttggtcatga gattatcaaa    3780
aaggatcttc acctagatcc ttttaaatta aaaatgaagt tttaaatcaa tctaaagtat    3840
atatgagtaa acttggtctg acagttacca atgcttaatc agtgaggcac ctatctcagc    3900
gatctgtcta tttcgttcat ccatagttgc ctgactcccc gtcgtgtaga taactacgat    3960
acgggagggc ttaccatctg gccccagtgc tgcaatgata ccgcgagacc cacgctcacc    4020
ggctccagat ttatcagcaa taaaccagcc agccggaagg gccgagcgca gaagtggtcc    4080
```

```
tgcaacttta tccgcctcca tccagtctat taattgttgc cgggaagcta gagtaagtag    4140
ttcgccagtt aatagtttgc gcaacgttgt tgccattgct acaggcatcg tggtgtcacg    4200
ctcgtcgttt ggtatggctt cattcagctc cggttcccaa cgatcaaggc gagttacatg    4260
atcccccatg ttgtgcaaaa aagcggttag ctccttcggt cctccgatcg ttgtcagaag    4320
taagttggcc gcagtgttat cactcatggt tatggcagca ctgcataatt ctcttactgt    4380
catgccatcc gtaagatgct tttctgtgac tggtgagtac tcaaccaagt cattctgaga    4440
atagtgtatg cggcgaccga gttgctcttg cccggcgtca atacgggata ataccgcgcc    4500
acatagcaga actttaaaag tgctcatcat tggaaaacgt tcttcggggc gaaaactctc    4560
aaggatctta ccgctgttga gatccagttc gatgtaaccc actcgtgcac ccaactgatc    4620
ttcagcatct tttactttca ccagcgtttc tgggtgagca aaaacaggaa ggcaaaatgc    4680
cgcaaaaaag ggaataaggg cgacacggaa atgttgaata ctcatactct tcctttttca    4740
atattattga agcatttatc agggttattg tctcatgagc ggatacatat ttgaatgtat    4800
ttagaaaaat aaacaaatag gggttccgcg cacatttccc cgaaaagtgc cacctgggtc    4860
cttttcatca cgtgctataa aaataattat aatttaaatt ttttaatata aatatataaa    4920
ttaaaaatag aaagtaaaaa agaaattaa agaaaaaata gttttgtttt ccgaagatg     4980 taaaagactc tagggggatc gccaacaaat actaccttt atcttgctct tcctgctctc    5040
aggtattaat gccgaattgt ttcatcttgt ctgtgtagaa gaccacacac gaaaatcctg    5100
tgattttaca ttttacttat cgttaatcga atgtatatct atttaatctg cttttcttgt    5160
ctaataaata tatatgtaaa gtacgctttt tgttgaaatt ttttaaacct tgtttatttt    5220
ttttttcttc attccgtaac tcttctacct tctttattta cttctaaaa tccaaataca    5280 aaacataaaa ataaataaac acagagtaaa ttcccaaatt attccatcat taaaagatac    5340
gaggcgcgtg taagttacag gcaagcgatc cgtcctaaga aaccattatt atcatgacat    5400
taacctataa aaataggcgt atcacgaggc cctttcgtc                          5439

<210> SEQ ID NO 26
<211> LENGTH: 7146
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accataaacg acattactat atatataata taggaagcat taatagaca gcatcgtaat     240 atatgtgtac tttgcagtta tgacgccaga tggcagtagt ggaagatatt ctttattgaa     300
aaatagcttg tcaccttacg tacaatcttg atccggagct ttttcttttt tgccgattaa     360
gaattaattc ggtcgaaaaa agaaaaggag agggccaaga gggagggcat tggtgactat     420
tgagcacgtg agtatacgtg attaagcaca caaaggcagc ttggagtatg tctgttatta     480
atttcacagg tagttctggt ccattggtga agtttgcgg cttgcagagc acagaggccg     540
cagaatgtgc tctagattcc gatgctgact tgctgggtat tatatgtgtg cccaatagaa     600
agagaacaat tgacccggtt attgcaagga aaatttcaag tcttgtaaaa gcatataaaa     660
```

```
atagttcagg cactccgaaa tacttggttg gcgtgtttcg taatcaacct aaggaggatg    720
ttttggctct ggtcaatgat tacggcattg atatcgtcca actgcatgga gatgagtcgt    780
ggcaagaata ccaagagttc ctcggtttgc cagttattaa aagactcgta tttccaaaag    840
actgcaacat actactcagt gcagcttcac agaaacctca ttcgtttatt cccttgtttg    900
attcagaagc aggtgggaca ggtgaacttt tggattggaa ctcgatttct gactgggttg    960
gaaggcaaga gagccccgaa agcttacatt ttatgttagc tggtggactg acgccagaaa   1020
atgttggtga tgcgcttaga ttaaatggcg ttattggtgt tgatgtaagc ggaggtgtgg   1080
agacaaatgg tgtaaaagac tctaacaaaa tagcaaattt cgtcaaaaat gctaagaaat   1140
aggttattac tgagtagtat ttatttaagt attgtttgtg cacttgccta tgcggtgtga   1200
aataccgcac agatgcgtaa ggagaaaata ccgcatcagg aaattgtaaa cgttaatatt   1260
ttgttaaaat tcgcgttaaa ttttttgttaa atcagctcat ttttttaacca ataggccgaa   1320 atcggcaaaa tcccttataa atcaaaagaa tagaccgaga tagggttgag tgttgttcca   1380
gtttggaaca agagtccact attaaagaac gtggactcca acgtcaaagg gcgaaaaacc   1440
gtctatcagg gcgatggccc actacgtgaa ccatcaccct aatcaagttt tttggggtcg   1500
aggtgccgta aagcactaaa tcggaaccct aaagggagcc cccgatttag agcttgacgg   1560
ggaaagccgg cgaacgtggc gagaaaggaa gggaagaaag cgaaaggagc gggcgctagg   1620
gcgctggcaa gtgtagcggt cacgctgcgc gtaaccacca cacccgccgc gcttaatgcg   1680
ccgctacagg gcgcgtcgcg ccattcgcca ttcaggctgc gcaactgttg gaagggcga   1740 tcggtgcggg cctcttcgct attacgccag ctggcgaaag ggggatgtgc tgcaaggcga   1800
ttaagttggg taacgccagg gttttcccag tcacgacgtt gtaaaacgac ggccagtgag   1860
cgcgcgtaat acgactcact atagggcgaa ttgggtaccg gccgcaaatt aaagccttcg   1920
agcgtcccaa aaccttctca agcaaggttt tcagtataat gttacatgcg tacacgcgtc   1980
tgtacagaaa aaaagaaaa atttgaaata taaataacgt tcttaatact aacataacta   2040
taaaaaaata aatagggacc tagacttcag gttgtctaac tccttccttt tcggttagag   2100
cggatgtggg ggagggcgt gaatgtaagc gtgacataac taattacatg actcgagcgg   2160
ccgcggatcc ctagagagct ttcgttttca tgagttcccc gaattctttc ggaagcttgt   2220
cacttgctaa attaacgtta tcactgtagt caaccgggac atcaatgatg acaggcccct   2280
cagcgttcat gccttgacgc agaacatctg ccagctggtc tggtgattct acgcgtaagc   2340
cagttgctcc gaagctttcc gcgtatttca cgatatcgat atttccgaaa tcgaccgcag   2400
atgtacgatt atattttttc aattgctgga atgcaaccat gtcatatgtg ctgtcgttcc   2460
atacaatgtg tacaattggt gcttttaaac gaactgctgt ctctaattcc atagctgaga   2520
ataagaaacc gccatcaccg gagactgata ctacttttc tcccggtttc accaatgaag   2580
cgccgattgc ccaaggaagc gcaacgccga gtgtttgcat accgttacta atcattaatg   2640
ttaacggctc gtagctgcgg aaataacgtg acatccaaat cgcgtgtgaa ccgatatcgc   2700
aagtcactgt aacatgatca tcgactgcgt ttcgcaattc tttaacgatt tcaagaggat   2760
gcactctgtc tgatttccaa tctgcaggca cctgctcacc ctcatgcata tattgtttta   2820
aatcagaaag gatcttctgc tcacgttccg caaagtctac tttcacagca tcgtgttcga   2880
tatgattgat cgtagatgga atatcaccga tcagttcaag atccggctgg taagcatgat   2940
caatgtcagc cagaatctcg tctaaatgga tgatcgtccg gtctccattg acattccaga   3000
atttcggatc atattcaatt gggtcatagc cgattgtcag aacaacatca gcctgctcaa   3060
```

```
gcagcagatc gccaggctgg ttgcggaata aaccgatccg gccaaaatac tgatcctcta    3120
aatctctcgt aagagtaccg gcagcttgat atgtttcaac gaatggaagc tgcactttt     3180 tcaatagctt gcgaaccgct ttaatcgctt ccggtcttcc gcccttcatg ccgactaaaa    3240
cgacaggaag ttttgctgtt tgaattttg  caatggccat actgattgcg tcatctgctg    3300
cgggaccaag ttttggcgct gcgacagcac gtacgttttt tgtatttgtg acttcattca    3360
caacatcttg cggaaaactc acaaaagcgg ccccagcctg ccctgctgac gctatcctaa    3420
acgcatttgt aacagcttcc ggtatatttt ttacatcttg aacttctaca ctgtattttg    3480
taatcggctg gaatagcgcc gcattatcca aagattgatg tgtccgtttt aaacgatctg    3540
cacggatcac gttcccagca agcgcaacga cagggtcacc ttcagtgttt gctgtcagca    3600
gtcctgttgc caagttcgaa gcacctggtc ctgatgtgac taacacgact cccgttttc     3660 cagttaaacg gccgactgct tgcgccataa atgctgcatt ttgttcatgc cgggcaacga    3720
taatttcagg ccctttatct tgtaaagcgt caaataccgc atcaatttt  gcacctggaa    3780 tgccaaatac atgtgtgaca ccttgctccg ctaagcaatc aacaacaagc tccgcccctc    3840
tgcttttcac aagggatttt tgttcttttg ttgcttttgt caacatgtcg actttatgtg    3900
atgattgatt gattgattgt acagtttgtt tttcttaata tctatttcga tgacttctat    3960
atgatattgc actaacaaga agatattata atgcaattga tacaagacaa ggagttattt    4020
gcttctcttt tatatgattc tgacaatcca tattgcgttg gtagtctttt ttgctggaac    4080
ggttcagcgg aaaagacgca tcgctctttt tgcttctaga agaaatgcca gcaaagaat    4140 ctcttgacag tgactgacag caaaaatgtc tttttctaac tagtaacaag gctaagatat    4200
cagcctgaaa taagggtgg  tgaagtaata attaaatcat ccgtataaac ctatacacat    4260
atatgaggaa aaataataca aaagtgtttt aaatacagat acatacatga acatatgcac    4320
gtatagcgcc caaatgtcgg taatgggatc ggcgagctcc agcttttgtt ccctttagtg    4380
agggttaatt gcgcgcttgg cgtaatcatg gtcatagctg tttcctgtgt gaaattgtta    4440
tccgctcaca attccacaca acataggagc cggaagcata aagtgtaaag cctggggtgc    4500
ctaatgagtg aggtaactca cattaattgc gttgcgctca ctgcccgctt tccagtcggg    4560
aaacctgtcg tgccagctgc attaatgaat cggccaacgc gcggggagag cggtttgcg     4620 tattgggcgc tcttccgctt cctcgctcac tgactcgctg cgctcggtcg ttcggctgcg    4680
gcgagcggta tcagctcact caaaggcggt aatacggtta tccacagaat caggggataa    4740
cgcaggaaag aacatgtgag caaaaggcca gcaaaaggcc aggaaccgta aaaaggccgc    4800
gttgctggcg ttttccata  ggctccgccc cctgacgag  catcacaaaa atcgacgctc    4860
aagtcagagg tggcgaaacc cgacaggact ataaagatac caggcgtttc ccctggaag    4920 ctccctcgtg cgctctcctg ttccgaccct gccgcttacc ggatacctgt ccgcctttct    4980
cccttcggga agcgtggcgc tttctcatag ctcacgctgt aggtatctca gttcggtgta    5040
ggtcgttcgc tccaagctgg gctgtgtgca cgaaccccc  gttcagcccg accgctgcgc    5100
cttatccggt aactatcgtc ttgagtccaa cccggtaaga cacgacttat cgccactggc    5160
agcagccact ggtaacagga ttagcagagc gaggtatgta ggcggtgcta cagagttctt    5220
gaagtggtgg cctaactacg gctacactag aaggacagta tttggtatct gcgctctgct    5280
gaagccagtt accttcggaa aaagagttgg tagctcttga tccggcaaac aaaccaccgc    5340
tggtagcggt ggtttttttg tttgcaagca gcagattacg cgcagaaaaa aaggatctca    5400
agaagatcct ttgatctttt ctacggggtc tgacgctcag tggaacgaaa actcacgtta    5460
```

```
agggattttg gtcatgagat tatcaaaaag gatcttcacc tagatccttt taaattaaaa      5520
atgaagtttt aaatcaatct aaagtatata tgagtaaact tggtctgaca gttaccaatg      5580
cttaatcagt gaggcaccta tctcagcgat ctgtctattt cgttcatcca tagttgcctg      5640
actccccgtc gtgtagataa ctacgatacg ggagggctta ccatctggcc ccagtgctgc      5700
aatgataccg cgagacccac gctcaccggc tccagattta tcagcaataa accagccagc      5760
cggaagggcc gagcgcagaa gtggtcctgc aactttatcc gcctccatcc agtctattaa      5820
ttgttgccgg gaagctagag taagtagttc gccagttaat agtttgcgca acgttgttgc      5880
cattgctaca ggcatcgtgg tgtcacgctc gtcgtttggt atggcttcat tcagctccgg      5940
ttcccaacga tcaaggcgag ttacatgatc ccccatgttg tgcaaaaaag cggttagctc      6000
cttcggtcct ccgatcgttg tcagaagtaa gttggccgca gtgttatcac tcatggttat      6060
ggcagcactg cataattctc ttactgtcat gccatccgta agatgctttt ctgtgactgg      6120
tgagtactca accaagtcat tctgagaata gtgtatgcgg cgaccgagtt gctcttgccc      6180
ggcgtcaata cgggataata ccgcgccaca tagcagaact ttaaaagtgc tcatcattgg      6240
aaaacgttct cggggcgaaa actctcaag gatcttaccg ctgttgagat ccagttcgat      6300
gtaacccact cgtgcaccca actgatcttc agcatctttt actttcacca gcgtttctgg      6360
gtgagcaaaa acaggaaggc aaaatgccgc aaaaaaggga ataagggcga cacggaaatg      6420
ttgaatactc atactcttcc ttttccaata ttattgaagc atttatcagg gttattgtct      6480
catgagcgga tacatatttg aatgtattta gaaaaataaa caaatagggg ttccgcgcac      6540
atttccccga aaagtgccac ctgggtcctt ttcatcacgt gctataaaaa taattataat      6600
ttaaattttt taatataaat atataaatta aaaatagaaa gtaaaaaag aattaaaga      6660 aaaaatagtt tttgttttcc gaagatgtaa aagactctag ggggatcgcc aacaaatact      6720 acctttatc ttgctcttcc tgctctcagg tattaatgcc gaattgtttc atcttgtctg      6780
tgtagaagac cacacacgaa aatcctgtga ttttacattt tacttatcgt taatcgaatg      6840
tatatctatt taatctgctt ttcttgtcta ataaatatat atgtaaagta cgcttttgt      6900 tgaaattttt taacctttg tttattttt tttcttcatt ccgtaactct tctaccttct      6960
ttatttactt tctaaaatcc aaatacaaaa cataaaaata aataaacaca gagtaaattc      7020
ccaaattatt ccatcattaa aagatacgag gcgcgtgtaa gttacaggca agcgatccgt      7080
cctaagaaac cattattatc atgacattaa cctataaaaa taggcgtatc acgaggccct      7140
ttcgtc                                                                 7146

<210> SEQ ID NO 27
<211> LENGTH: 10231
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcgggctgg cttaactatg cggcatcaga gcagattgta ctgagagtgc      180
accataaatt cccgttttaa gagcttggtg agcgctagga gtcactgcca ggtatcgttt      240
gaacacggca ttagtcaggg aagtcataac acagtccttt cccgcaattt tctttttcta      300
ttactcttgg cctcctctag tacactctat attttttat gcctcggtaa tgattttcat      360
```

```
ttttttttttt cccctagcgg atgactcttt ttttttctta gcgattggca ttatcacata    420
atgaattata cattatataa agtaatgtga tttcttcgaa gaatatacta aaaaatgagc    480
aggcaagata aacgaaggca aagatgacag agcagaaagc cctagtaaag cgtattacaa    540
atgaaaccaa gattcagatt gcgatctctt taaagggtgg tccctagcg atagagcact     600 cgatcttccc agaaaagag gcagaagcag tagcagaaca ggccacacaa tcgcaagtga     660
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctaggg gccgtgcgtg    840
gagtaaaaag gtttggatca ggatttgcgc ctttggatga ggcactttcc agagcggtgg    900
tagatctttc gaacaggccg tacgcagttg tcgaacttgg tttgcaaagg gagaaagtag    960
gagatctctc ttgcgagatg atcccgcatt ttcttgaaag ctttgcagag gctagcagaa    1020
ttaccctcca cgttgattgt ctgcgaggca agaatgatca tcaccgtagt gagagtgcgt    1080
tcaaggctct tgcggttgcc ataagagaag ccacctcgcc caatggtacc aacgatgttc    1140
cctccaccaa aggtgttctt atgtagtgac accgattatt taaagctgca gcatacgata    1200
tatatacatg tgtatatatg tatacctatg aatgtcagta agtatgtata cgaacagtat    1260
gatactgaag atgacaaggt aatgcatcat tctatacgtg tcattctgaa cgaggcgcgc    1320
tttccttttt tctttttgct tttttctttt ttttctcttg aactcgacgg atctatgcgg    1380
tgtgaaatac cgcacagatg cgtaaggaga aaataccgca tcaggaaatt gtaaacgtta    1440
atattttgtt aaaattcgcg ttaaattttt gttaaatcag ctcattttt aaccaatagg     1500 ccgaaatcgg caaaatccct tataaatcaa aagaatagac cgagatagg ttgagtgttg     1560 ttccagtttg gaacaagagt ccactattaa agaacgtgga ctccaacgtc aaagggcgaa    1620
aaaccgtcta tcagggcgat ggcccactac gtgaaccatc accctaatca agttttttgg    1680
ggtcgaggtg ccgtaaagca ctaaatcgga accctaaagg gagcccccga tttagagctt    1740
gacggggaaa gccggcgaac gtggcgagaa aggaagggaa gaaagcgaaa ggagcgggcg    1800
ctagggcgct ggcaagtgta gcggtcacgc tgcgcgtaac caccacaccc gccgcgctta    1860
atgcgccgct acagggcgcg tcgcgccatt cgccattcag gctgcgcaac tgttgggaag    1920
ggcgatcggt gcgggcctct tcgctattac gccagctggc gaaagggga tgtgctgcaa     1980 ggcgattaag ttgggtaacg ccagggtttt cccagtcacg acgttgtaaa acgacggcca    2040
gtgagcgcgc gtaatacgac tcactatagg gcgaattggg taccggccgc aaattaaagc    2100
cttcgagcgt cccaaaacct tctcaagcaa ggttttcagt ataatgttac atgcgtacac    2160
gcgtctgtac agaaaaaaa gaaaaatttg aaatataaat aacgttctta atactaacat     2220
aactataaaa aaataaatag ggacctagac ttcaggttgt ctaactcctt ccttttcggt    2280
tagagcggat gtggggggag ggcgtgaatg taagcgtgac ataactaatt acatgagcgg    2340
ccgcagatct ttaacccgca acagcaatac gtttcatatc tgtcatatag ccgcgcagtt    2400
tcttacctac ctgctcaatc gcatggctgc gaatcgcttc gttcacatca cgcagttgcc    2460
cgttatctac cgcgccttcc ggaatagctt tacccaggtc gcccggttgc agctctgcca    2520
taaacggttt cagcaacggc acacaagcgt aagagaacag atagttaccg tactcagcgg    2580
tatcagagat aaccacgttc atttcgtaca gacgcttacg ggcgatggtg ttggcaatca    2640
gcggcagctc gtgcagtgat tcataatatg cagactcttc aatgatgccg gaatcgacca    2700
tggtttcgaa cgccagttca acgcccgctt tcaccatcgc aatcatcagt acgcctttat    2760
```

```
cgaagtactc ctgctcgccg attttgcctt catactgcgg cgcggtttca aacgcggttt    2820
tgccggtctc ttcacgccag gtcagcagtt tcttatcatc gttggcccag tccgccatca    2880
taccggaaga gaattcgccg gagatgatgt cgtccatatg tttctggaac agggtgcca    2940 tgatctcttt cagctgttca gaaagcgcat aagcacgcag tttcgccggg ttagagagac    3000
ggtccatcat cagggtgatg ccgccctgtt tcagtgcttc ggtgatggtt cccaaccga    3060 actgaatcag ttttctgcg tatgctggat cggtaccttc ttccaccagc ttgtcgaagc    3120
acagcagaga gccagcctgc aacataccgc acaggatggt ttgctcgccc atcaggtcag    3180
atttcacttc cgcaacgaag gacgattcca gcacacccgc acggtgacca ccggttgcag    3240
ccgcccaggc tttggcaatc gccatgcctt cgcctttcgg atcgttttcc gggtgaacgg    3300
caatcagcgt cggtacgccg aacccacgtt tgtactcttc acgcacttcg gtgcctgggc    3360
atttcggcgc aaccatcact acggtgatat ctttacggat ctgctcgccc acttcgacga    3420
tgttgaaacc gtgcgagtag cccagcgccg cgccgtcttt catcagtggc gtacggtgc    3480 gcactacatc agagtgctgc ttgtccggcg tcaggttaat caccagatcc gcctgtggga    3540
tcagttcttc gtaagtaccc actttaaaac cattttcggt cgcttacgc caggacgcgc    3600 gcttctcggc aatcgcttct ttacgcagag cgtaggagat atcgagacca gaatcacgca    3660
tgttcaggcc ctggttcaga ccctgtgcgc cacagccgac gatgactact ttttaccct    3720 gaaggtagct cgcgccatcg gcgaattcat cgcggcccat ctcgagtcga aactaagttc    3780
tggtgtttta aaactaaaaa aaagactaac tataaaagta gaatttaaga agtttaagaa    3840
atagatttac agaattacaa tcaataccta ccgtctttat atacttatta gtcaagtagg    3900
ggaataattt cagggaactg gtttcaacct ttttttttcag cttttttccaa atcagagaga    3960 gcagaaggta atagaaggtg taagaaaatg agatagatac atgcgtgggt caattgcctt    4020
gtgtcatcat ttactccagg caggttgcat cactccattg aggttgtgcc cgttttttgc    4080
ctgtttgtgc ccctgttctc tgtagttgcg ctaagagaat ggacctatga actgatggtt    4140
ggtgaagaaa acaatatttt ggtgctggga ttcttttttt ttctggatgc cagcttaaaa    4200
agcgggctcc attatattta gtggatgcca ggaataaact gttcacccag acacctacga    4260
tgttatatat tctgtgtaac ccgcccccta ttttgggcat gtacgggtta cagcagaatt    4320
aaaaggctaa ttttttgact aaataaagtt aggaaaatca ctactattaa ttatttacgt    4380
attctttgaa atggcgagta ttgataatga taaactggat cctcatccac ccaacttcga    4440
tttgtctctt actgccccct tatcggctga agtagccaat gaagcataag ccctaagggc    4500
gaaacttact tgacgttctc tattttttagg agtccaagcc ttatctcctc tggcatcttg    4560
tgcttctctt cttgcagcca attcagcgtc tgagacttgt aattggatac ctctatttgg    4620
gatatctatg gcgatcaaat ctccatcttc aatcaatcca atcgaaccac cagaagctgc    4680
ctctggtgat acgtgaccga tacttaaacc cgaagtgcca ccagagaatc taccgtcagt    4740
gataagggca caagctttc ctagtcccat ggacttcaaa aatgaagttg ggtaaagcat    4800
ttcctgcata cctggtcctc cctttggtcc ctcatatctt atcactacca cgtctcctgc    4860
taccaccttt ccgccaagta tagcctcaac agcatcgtct tgactttcgt aaactttagc    4920
gggtccagta aatttcaaaa tactatcatc tacaccagca gttttcacaa tgcaaccatt    4980
ttcagcgaag tttccatata atactgctaa accaccatcc ttactataag catgctcaag    5040
cgatcttata catccatttg ctctatcatc gtccaaagtg tcccacctac agtcttgcga    5100
gaatgcttgg gtggttctga tccctgctgg acctgccctg aacatgttt tcacggcatc    5160
```

```
atcttgagtt aacatgacat cgtattgctc taatgtctgt ggaagtgtta aacccaatac    5220
attcttcaca tccctgttta aaagaccggc tctgtccaac tcccctaaaa taccaataac    5280
ccctcctgca cgatgaacgt cttccatgtg atacttttga gttgatggtg caaccttaca    5340
taactgtgga accttacgtg aaagcttgtc gatatcagac atggtgaaat ctatctcagc    5400
ttcttgggct gcagctagaa gatgtaagac cgtgtttgta ctaccaccca ttgcaatatc    5460
caatgtcatg gcattttcga atgcagcctt tgaagctata ttcctcggta atgctgattc    5520
atcattttgt tcgtaatacc ttttcgttag ttccacaatt cttttccgg catttaagaa     5580 caattgcttt ctgtctgcat gggtcgctaa taatgaacca tttcctggtt gagataaacc    5640
tagagcttca gtcaagcaat tcatagagtt agccgtgaac attccactgc aagaaccaca    5700
agttggacat gcacttcttt caacttggtc tgactgcgag tctgaaactt ttggatctgc    5760
accttgaatc attgcatcca caagatcaag tttgatgatc tgatcactta acttagtttt    5820
accagcctcc attgggccgc cagatacgaa gattactggg atgttcaatc tcaaggacgc    5880
catcaacata ccaggcgtta tcttatcaca attagagata caaaccattg catcggcaca    5940
atgagcatta accatatatt cgactgagtc tgcaattaat tctctcgatg gtaaagagta    6000
taacataccg ccatgcccca tagctatacc gtcgtccaca gcaatagtat taaactcttt    6060
tgcgacacca cctgcagctt caatttgttc ggcaacaagc ttacctagat cacgcaaatg    6120
gacatgaccc ggaacgaatt gtgtaaaaga gttgacgacg gcaatgattg gctttccgaa    6180
atctgcatca gtcatgccag tcatgtcgac aaacttagat tagattgcta tgctttcttt    6240
ctaatgagca agaagtaaaa aaagttgtaa tagaacaaga aaaatgaaac tgaaacttga    6300
gaaattgaag accgtttatt aacttaaata tcaatgggag gtcatcgaaa gagaaaaaaa    6360
tcaaaaaaaa aattttcaag aaaaagaaac gtgataaaaa tttttattgc cttttcgac     6420 gaagaaaaag aaacgaggcg gtctcttttt tcttttccaa acctttagta cgggtaatta    6480
acgacaccct agaggaagaa agagggaaa tttagtatgc tgtgcttggg tgttttgaag     6540
tggtacggcg atgcgcggag tccgagaaaa tctggaagga taaaaaagga gtagaaacat    6600
tttgaagcta tgagctccag cttttgttcc ctttagtgag ggttaattgc gcgcttggcg    6660
taatcatggt catagctgtt tcctgtgtga aattgttatc cgctcacaat tccacacaac    6720
ataggagccg gaagcataaa gtgtaaagcc tggggtgcct aatgagtgag gtaactcaca    6780
ttaattgcgt tgcgctcact gcccgctttc cagtcgggaa acctgtcgtg ccagctgcat    6840
taatgaatcg gccaacgcgc ggggagaggc ggtttgcgta ttgggcgctc ttccgcttcc    6900
tcgctcactg actcgctgcg ctcggtcgtt cggctgcggc gagcggtatc agctcactca    6960
aaggcggtaa tacggttatc cacagaatca ggggataacg caggaaagaa catgtgagca    7020
aaaggccagc aaaaggccag gaaccgtaaa aaggccgcgt tgctggcgtt tttccatagg    7080
ctccgccccc ctgacgagca tcacaaaaat cgacgctcaa gtcagaggtg gcgaaacccg    7140
acaggactat aaagatacca ggcgtttccc cctggaagct ccctcgtgcg ctctcctgtt    7200
ccgaccctgc cgcttaccgg atacctgtcc gcctttctcc cttcgggaag cgtggcgctt    7260
tctcatagct cacgctgtag gtatctcagt tcggtgtagg tcgttcgctc caagctgggc    7320
tgtgtgcacg aaccccccgt tcagcccgac cgctgcgcct tatccggtaa ctatcgtctt    7380
gagtccaacc cggtaagaca cgacttatcg ccactggcag cagccactgg taacaggatt    7440
agcagagcga ggtatgtagg cggtgctaca gagttcttga agtggtggcc taactacggc    7500
tacactagaa ggacagtatt tggtatctgc gctctgctga agccagttac cttcggaaaa    7560
```

```
agagttggta gctcttgatc cggcaaacaa accaccgctg gtagcggtgg ttttttttgtt    7620
tgcaagcagc agattacgcg cagaaaaaaa ggatctcaag aagatccttt gatcttttct    7680
acggggtctg acgctcagtg gaacgaaaac tcacgttaag ggattttggt catgagatta    7740
tcaaaaagga tcttcaccta gatcctttta aattaaaaat gaagttttaa atcaatctaa    7800
agtatatatg agtaaacttg gtctgacagt taccaatgct taatcagtga ggcacctatc    7860
tcagcgatct gtctatttcg ttcatccata gttgcctgac tccccgtcgt gtagataact    7920
acgatacggg agggcttacc atctggcccc agtgctgcaa tgataccgcg agacccacgc    7980
tcaccggctc cagatttatc agcaataaac cagccagccg aagggccga gcgcagaagt     8040
ggtcctgcaa ctttatccgc ctccatccag tctattaatt gttgccggga agctagagta    8100
agtagttcgc cagttaatag tttgcgcaac gttgttgcca ttgctacagg catcgtggtg    8160
tcacgctcgt cgtttggtat ggcttcattc agctccggtt cccaacgatc aaggcgagtt    8220
acatgatccc ccatgttgtg caaaaaagcg gttagctcct tcggtcctcc gatcgttgtc    8280
agaagtaagt tggccgcagt gttatcactc atggttatgg cagcactgca taattctctt    8340
actgtcatgc catccgtaag atgcttttct gtgactggtg agtactcaac caagtcattc    8400
tgagaatagt gtatgcggcg accgagttgc tcttgcccgg cgtcaatacg ggataatacc    8460
gcgccacata gcagaacttt aaaagtgctc atcattggaa aacgttcttc ggggcgaaaa    8520
ctctcaagga tcttaccgct gttgagatcc agttcgatgt aacccactcg tgcacccaac    8580
tgatcttcag catcttttac tttcaccagc gtttctgggt gagcaaaaac aggaaggcaa    8640
aatgccgcaa aaaagggaat aagggcgaca cggaaatgtt gaatactcat actcttcctt    8700
tttcaatatt attgaagcat ttatcagggt tattgtctca tgagcggata catatttgaa    8760
tgtatttaga aaaataaaca ataggggtt ccgcgcacat ttccccgaaa agtgccacct     8820
gaacgaagca tctgtgcttc attttgtaga acaaaaatgc aacgcgagag cgctaatttt    8880
tcaaacaaag aatctgagct gcatttttac agaacagaaa tgcaacgcga agcgctatt     8940
ttaccaacga agaatctgtg cttcatttt gtaaaacaaa aatgcaacgc gagagcgcta    9000
attttttcaaa caagaatct gagctgcatt tttacagaac agaaatgcaa cgcgagagcg    9060
ctattttacc aacaaagaat ctatacttct tttttgttct acaaaaatgc atccgagag     9120
cgctattttt ctaacaaagc atcttagatt acttttttc tcctttgtgc gctctataat     9180
gcagtctctt gataactttt tgcactgtag gtccgttaag gttagaagaa ggctactttg    9240
gtgtctattt tctcttccat aaaaaaagcc tgactccact tcccgcgttt actgattact    9300
agcgaagctg cgggtgcatt ttttcaagat aaaggcatcc ccgattatat tctataccga    9360
tgtggattgc gcatactttg tgaacagaaa gtgatagcgt tgatgattct tcattggtca    9420
gaaaattatg aacggtttct tctatttttgt ctctatatac tacgtatagg aaatgtttac    9480
attttcgtat tgttttcgat tcactctatg aatagttctt actacaattt ttttgtctaa    9540
agagtaatac tagagataaa cataaaaaat gtagaggtcg agtttagatg caagttcaag    9600
gagcgaaagg tggatgggta ggttatatag ggatatagca cagagatata tagcaaagag    9660
atacttttga gcaatgtttg tggaagcggt attcgcaata ttttagtagc tcgttacagt    9720
ccggtgcgtt tttggttttt tgaaagtgcg tcttcagagc gcttttggtt ttcaaaagcg    9780
ctctgaagtt cctatacttt ctagagaata ggaacttcgg aataggaact tcaaagcgtt    9840
tccgaaaacg agcgcttccg aaaatgcaac gcgagctgcg cacatacagc tcactgttca    9900
cgtcgcacct atatctgcgt gttgcctgta tatatatata catgagaaga acggcatagt    9960
```

```
gcgtgtttat gcttaaatgc gtacttatat gcgtctattt atgtaggatg aaaggtagtc    10020
tagtacctcc tgtgatatta tcccattcca tgcggggtat cgtatgcttc cttcagcact    10080 acccttttagc tgttctatat gctgccactc ctcaattgga ttagtctcat ccttcaatgc   10140
tatcatttcc tttgatattg gatcatctaa gaaaccatta ttatcatgac attaacctat    10200
aaaaataggc gtatcacgag gcccttttcgt c                                  10231
```

<210> SEQ ID NO 28
<211> LENGTH: 9404
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgcgtg     120
ttggcgggtg tcggggctgg cttaactatg cggcatcaga gcagattgta ctgagagtgc     180
accataaatt cccgttttaa gagcttggtg agcgctagga gtcactgcca ggtatcgttt     240
gaacacggca ttagtcaggg aagtcataac acagtccttt cccgcaattt tcttttttcta    300 ttactcttgg cctcctctag tacactctat atttttttat gcctcggtaa tgattttcat     360
tttttttttt cccctagcgg atgactcttt ttttttctta gcgattggca ttatcacata     420
atgaattata cattatataa agtaatgtga tttcttcgaa gaatatacta aaaaatgagc     480
aggcaagata aacgaaggca agatgacag agcagaaagc cctagtaaag cgtattacaa     540
atgaaaccaa gattcagatt gcgatctctt taaagggtgg tcccctagcg atagagcact     600
cgatcttccc agaaaaagag gcagaagcag tagcagaaca ggccacacaa tcgcaagtga    660
ttaacgtcca cacaggtata gggtttctgg accatatgat acatgctctg gccaagcatt    720
ccggctggtc gctaatcgtt gagtgcattg gtgacttaca catagacgac catcacacca    780
ctgaagactg cgggattgct ctcggtcaag cttttaaaga ggccctaggg gccgtgcgtg    840
gagtaaaaag gtttggatca ggatttgcgc ctttggatga ggcactttcc agagcggtgg    900
tagatctttc gaacaggccg tacgcagttg tcgaacttgg tttgcaaagg gagaaagtag     960
gagatctctc ttgcgagatg atcccgcatt tcttgaaag ctttgcagag gctagcagaa    1020
ttaccctcca cgttgattgt ctgcgaggca agaatgatca tcaccgtagt gagagtgcgt    1080
tcaaggctct gcggttgcc ataagagaag ccacctcgcc caatggtacc aacgatgttc     1140
cctccaccaa aggtgttctt atgtagtgac accgattatt taaagctgca gcatacgata   1200
tatatacatg tgtatatatg tataacctatg aatgtcagta agtatgtata cgaacagtat   1260
gatactgaag atgacaaggt aatgcatcat tctatacgtg tcattctgaa cgaggcgcgc   1320
tttccttttt tcttttttgct ttttcttttt ttttctcttg aactcgacgg atctatgcgg   1380
tgtgaaatac cgcacagatg cgtaaggaga aaataccgca tcaggaaatt gtaaacgtta    1440
atattttgtt aaaattcgcg ttaaatttttt gttaaatcag ctcattttttt aaccaatagg   1500 ccgaaatcgg caaaatccct tataaatcaa agaatagac cgagataggg ttgagtgttg    1560
ttccagtttg gaacaagagt ccactattaa agaacgtgga ctccaacgtc aaagggcgaa    1620
aaaccgtcta tcagggcgat ggcccactac gtgaaccatc accctaatca agttttttgg    1680
ggtcgaggtg ccgtaaagca ctaaatcgga acccctaagg gagcccccga tttagagctt    1740
```

```
gacggggaaa gccggcgaac gtggcgagaa aggaagggaa gaaagcgaaa ggagcgggcg    1800
ctagggcgct ggcaagtgta gcggtcacgc tgcgcgtaac caccacaccc gccgcgctta    1860
atgcgccgct acagggcgcg tcgcgccatt cgccattcag gctgcgcaac tgttgggaag    1920
ggcgatcggt gcgggcctct tcgctattac gccagctggc gaaagggga tgtgctgcaa    1980 ggcgattaag ttgggtaacg ccagggtttt cccagtcacg acgttgtaaa acgacggcca    2040
gtgagcgcgc gtaatacgac tcactatagg gcgaattggg taccggccgc aaattaaagc    2100
cttcgagcgt cccaaaacct tctcaagcaa ggttttcagt ataatgttac atgcgtacac    2160
gcgtctgtac agaaaaaaaa gaaaaatttg aaatataaat aacgttctta atactaacat    2220
aactataaaa aaataaatag ggacctagac ttcaggttgt ctaactcctt ccttttcggt    2280
tagagcggat gtgggggag ggcgtgaatg taagcgtgac ataactaatt acatgagcgg    2340
ccgcagatct ttaacccgca acagcaatac gtttcatatc tgtcatatag ccgcgcagtt    2400
tcttacctac ctgctcaatc gcatggctgc gaatcgcttc gttcacatca cgcagttgcc    2460
cgttatctac cgcgccttcc ggaatagctt tacccaggtc gcccggttgc agctctgcca    2520
taaacggttt cagcaacggc acacaagcgt aagagaacag atagttaccg tactcagcgg    2580
tatcagagat aaccacgttc atttcgtaca gacgcttacg ggcgatggtg ttggcaatca    2640
gcggcagctc gtgcagtgat tcataatatg cagactcttc aatgatgccg gaatcgacca    2700
tggtttcgaa cgccagttca acgcccgctt tcaccatcgc aatcatcagt acgcctttat    2760
cgaagtactc ctgctcgccg attttgcctt catactgcgg cgcggtttca aacgcggttt    2820
tgccggtctc ttcacgccag gtcagcagtt tcttatcatc gttggcccag tccgccatca    2880
taccggaaga gaattcgccg gagatgatgt cgtccatatg tttctggaac aggggtgcca    2940
tgatctcttt cagctgttca gaaagcgcat aagcacgcag tttcgccggg ttagagagac    3000
ggtccatcat cagggtgatg ccgccctgtt tcagtgcttc ggtgatggtt tcccaaccga    3060
actgaatcag tttttctgcg tatgctggat cggtaccttc ttccaccagc ttgtcgaagc    3120
acagcagaga gccagcctgc aacataccgc acaggatggt ttgctcgccc atcaggtcag    3180
atttcacttc cgcaacgaag gacgattcca gcacacccgc acggtgacca ccggttgcag    3240
ccgcccaggc tttggcaatc gccatgcctt cgcctttcgg atcgttttcc gggtgaacgg    3300
caatcagcgt cggtacgccg aacccacgtt tgtactcttc acgcacttcg gtgcctgggc    3360
atttcggcgc aaccatcact acggtgatat ctttacggat ctgctcgccc acttcgacga    3420
tgttgaaacc gtgcgagtag cccagcgccg cgccgtcttt catcagtggc tgtacggtgc    3480
gcactacatc agagtgctgc ttgtccggcg tcaggttaat caccagatcc gcctgtggga    3540
tcagttcttc gtaagtaccc actttaaaac catttttcggt cgcttacgc caggacgcgc    3600 gcttctcggc aatcgcttct ttacgcagag cgtaggagat atcgagacca gaatcacgca    3660
tgttcaggcc ctggttcaga ccctgtgcgc cacagccgac gatgactact ttttacccct    3720
gaaggtagct cgcgccatcg gcgaattcat cgcggcccat ctcgagtcga aactaagttc    3780
tggtgtttta aaactaaaaa aaagactaac tataaaagta gaatttaaga agtttaagaa    3840
atagatttac agaattacaa tcaataccta ccgtctttat atacttatta gtcaagtagg    3900
ggaataattt cagggaactg gtttcaacct tttttttcag cttttttccaa atcagagaga    3960 gcagaaggta atagaaggtg taagaaaatg agatagatac atgcgtgggt caattgcctt    4020
gtgtcatcat ttactccagg caggttgcat cactccattg aggttgtgcc cgttttttgc    4080
ctgtttgtgc ccctgttctc tgtagttgcg ctaagagaat ggacctatga actgatggtt    4140
```

```
ggtgaagaaa acaatatttt ggtgctggga ttctttttt  ttctggatgc cagcttaaaa   4200
agcgggctcc attatattta gtggatgcca ggaataaact gttcacccag acacctacga   4260
tgttatatat tctgtgtaac ccgcccccta ttttgggcat gtacgggtta cagcagaatt   4320
aaaaggctaa ttttttgact aaataaagtt aggaaaatca ctactattaa ttatttacgt   4380
attctttgaa atggcgagta ttgataatga taaactggat cctcatccac ccaacttcga   4440
tttgtctctt actgcccct  tatcggctga agtagccaat gaagcataag ccctaagggc   4500
gaaacttact tgacgttctc tattttagg  agtccaagcc ttatctcctc tggcatcttg   4560
tgcttctctt cttgcagcca attcagcgtc tgagacttgt aattggatac ctctatttgg   4620
gatatctatg gcgatcaaat ctccatcttc aatcaatcca atcgaaccac cagaagctgc   4680
ctctggtgat acgtgaccga tacttaaacc cgaagtgcca ccagagaatc taccgtcagt   4740
gataagggca caagcttttc ctagtcccat ggacttcaaa aatgaagttg ggtaaagcat   4800
ttcctgcata cctggtcctc cctttggtcc ctcatatctt atcactacca cgtctcctgc   4860
taccaccttt ccgccaagta tagcctcaac agcatcgtct tgactttcgt aaactttagc   4920
gggtccagta aatttcaaaa tactatcatc tacaccagca gttttcacaa tgcaaccatt   4980
ttcagcgaag tttccatata atactgctaa accaccatcc ttactataag catgctcaag   5040
cgatcttata catccatttg ctctatcatc gtccaaagtg tcccacctac agtcttgcga   5100
gaatgcttgg gtggttctga tccctgctgg acctgccctg aacatgtttt tcacggcatc   5160
atcttgagtt aacatgacat cgtattgctc taatgtctgt ggaagtgtta aacccaatac   5220
attcttcaca tccctgttta aaagaccggc tctgtccaac tcccctaaaa taccaataac   5280
ccctcctgca cgatgaacgt cttccatgtg atactttga  gttgatggtg caaccttaca   5340
taactgtgga accttacgtg aaagcttgtc gatatcagac atggtgaaat ctatctcagc   5400
ttctgggct  gcagctagaa gatgtaagac cgtgtttgta ctaccaccca ttgcaatatc   5460
caatgtcatg gcattttcga atgcagcctt tgaagctata ttcctcggta atgctgattc   5520
atcattttgt tcgtaatacc ttttcgttag ttccacaatt ctttttccgg catttaagaa   5580
caattgcttt ctgtctgcat gggtcgctaa taatgaacca tttcctggtt gagataaacc   5640
tagagcttca gtcaagcaat tcatagagtt agccgtgaac attccactgc aagaaccaca   5700
agttggacat gcacttcttt caacttggtc tgactgcgag tctgaaactt ttggatctgc   5760
accttgaatc attgcatcca caagatcaag tttgatgatc tgatcactta acttagtttt   5820
accagcctcc attgggccgc cagatacgaa gattactggg atgttcaatc tcaaggacgc   5880
catcaacata ccaggcgtta tcttatcaca attagagata caaccattg  catcggcaca   5940
atgagcatta accatatatt cgactgagtc tgcaattaat tctctcgatg gtaaagagta   6000
taacataccg ccatgcccca tagctatacc gtcgtccaca gcaatagtat aaactctttt   6060
tgcgacacca cctgcagctt caatttgttc ggcaacaagc ttacctagat cacgcaaatg   6120
gacatgaccc ggaacgaatt gtgtaaaaga gttgacgacg gcaatgattg ctttccgaa   6180
atctgcatca gtcatgccag tcatgtcgac aaacttagat tagattgcta tgcttttcttt  6240
ctaatgagca agaagtaaaa aaagttgtaa tagaacaaga aaaatgaaac tgaaacttga   6300
gaaattgaag accgtttatt aacttaaata tcaatgggag gtcatcgaaa gagaaaaaaa   6360
tcaaaaaaaa aattttcaag aaaaagaaac gtgataaaaa tttttattgc ctttttcgac   6420
gaagaaaaag aaacgaggcg gtctctttt  tcttttccaa accttagta  cgggtaatta   6480
acgacaccct agaggaagaa agaggggaaa tttagtatgc tgtgcttggg tgttttgaag   6540
```

```
tggtacggcg atgcgcggag tccgagaaaa tctggaagag taaaaaagga gtagaaacat    6600
tttgaagcta tgagctccag cttttgttcc ctttagtgag ggttaattgc gcgcttggcg    6660
taatcatggt catagctgtt tcctgtgtga aattgttatc cgctcacaat tccacacaac    6720
ataggagccg gaagcataaa gtgtaaagcc tggggtgcct aatgagtgag gtaactcaca    6780
ttaattgcgt tgcgctcact gcccgctttc cagtcgggaa acctgtcgtg ccagctgcat    6840
taatgaatcg gccaacgcgc ggggagaggc ggtttgcgta ttgggcgctc ttccgcttcc    6900
tcgctcactg actcgctgcg ctcggtcgtt cggctgcggc gagcggtatc agctcactca    6960
aaggcggtaa tacggttatc cacagaatca ggggataacg caggaaagaa catgtgagca    7020
aaaggccagc aaaaggccag gaaccgtaaa aaggccgcgt tgctggcgtt tttccatagg    7080
ctccgccccc ctgacgagca tcacaaaaat cgacgctcaa gtcagaggtg gcgaaacccg    7140
acaggactat aaagatacca ggcgtttccc cctggaagct ccctcgtgcg ctctcctgtt    7200
ccgaccctgc cgcttaccgg atacctgtcc gcctttctcc cttcgggaag cgtggcgctt    7260
tctcatagct cacgctgtag gtatctcagt tcggtgtagg tcgttcgctc caagctgggc    7320
tgtgtgcacg aaccccccgt tcagcccgac cgctgcgcct tatccggtaa ctatcgtctt    7380
gagtccaacc cggtaagaca cgacttatcg ccactggcag cagccactgg taacaggatt    7440
agcagagcga ggtatgtagg cggtgctaca gagttcttga agtggtggcc taactacggc    7500
tacactagaa ggacagtatt tggtatctgc gctctgctga agccagttac cttcggaaaa    7560
agagttggta gctcttgatc cggcaaacaa accaccgctg gtagcggtgg ttttttttgtt    7620 tgcaagcagc agattacgcg cagaaaaaaa ggatctcaag aagatccttt gatcttttct    7680
acggggtctg acgctcagtg gaacgaaaac tcacgttaag ggattttggt catgagatta    7740
tcaaaaagga tcttcaccta gatcctttta aattaaaaat gaagttttaa atcaatctaa    7800
agtatatatg agtaaacttg gtctgacagt taccaatgct taatcagtga ggcacctatc    7860
tcagcgatct gtctatttcg ttcatccata gttgcctgac tccccgtcgt gtagataact    7920
acgatacggg agggcttacc atctggcccc agtgctgcaa tgataccgcg agacccacgc    7980
tcaccggctc cagatttatc agcaataaac cagccagccg aagggccga gcgcagaagt    8040 ggtcctgcaa ctttatccgc ctccatccag tctattaatt gttgccggga agctagagta    8100
agtagttcgc cagttaatag tttgcgcaac gttgttgcca ttgctacagg catcgtggtg    8160
tcacgctcgt cgtttggtat ggcttcattc agctccggtt cccaacgatc aaggcgagtt    8220
acatgatccc ccatgttgtg caaaaaagcg gttagctcct tcggtcctcc gatcgttgtc    8280
agaagtaagt tggccgcagt gttatcactc atggttatgg cagcactgca taattctctt    8340
actgtcatgc catccgtaag atgcttttct gtgactggtg agtactcaac caagtcattc    8400
tgagaatagt gtatgcggcg accgagttgc tcttgcccgg cgtcaatacg ggataatacc    8460
gcgccacata gcagaacttt aaaagtgctc atcattggaa aacgttcttc ggggcgaaaa    8520
ctctcaagga tcttaccgct gttgagatcc agttcgatgt aacccactcg tgcacccaac    8580
tgatcttcag catcttttac tttcaccagc gtttctgggt gagcaaaaac aggaaggcaa    8640
aatgccgcaa aaaagggaat aagggcgaca cggaaatgtt gaatactcat actcttcctt    8700
tttcaatatt attgaagcat ttatcagggt tattgtctca tgagcggata catatttgaa    8760
tgtatttaga aaaataaaca ataggggtt ccgcgcacat ttccccgaaa agtgccacct    8820
gggtcctttt catcacgtgc tataaaaata attataattt aaattttta atataaatat    8880 ataaattaaa aatagaaagt aaaaaaagaa attaagaaa aatagttttt tgttttccga    8940
```

-continued

| | | | | |
|---|---|---|---|---|
| agatgtaaaa | gactctaggg | ggatcgccaa | caaatactac | cttttatctt gctcttcctg | 9000 |
| ctctcaggta | ttaatgccga | attgtttcat | cttgtctgtg | tagaagacca cacacgaaaa | 9060 |
| tcctgtgatt | ttacatttta | cttatcgtta | atcgaatgta | tatctattta atctgctttt | 9120 |
| cttgtctaat | aaatatatat | gtaaagtacg | cttttttgttg | aaattttta aacctttgtt | 9180 |
| tatttttttt | tcttcattcc | gtaactcttc | taccttcttt | atttactttc taaaatccaa | 9240 |
| atacaaaaca | taaaaataaa | taaacacaga | gtaaattccc | aaattattcc atcattaaaa | 9300 |
| gatacgaggc | gcgtgtaagt | tacaggcaag | cgatccgtcc | taagaaacca ttattatcat | 9360 |
| gacattaacc | tataaaaata | ggcgtatcac | gaggcccttt | cgtc | 9404 |

<210> SEQ ID NO 29
<211> LENGTH: 9404
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

| | | | | |
|---|---|---|---|---|
| tcgcgcgttt | cggtgatgac | ggtgaaaacc | tctgacacat | gcagctcccg gagacggtca | 60 |
| cagcttgtct | gtaagcggat | gccgggagca | gacaagcccg | tcagggcgcg tcagcgcgtg | 120 |
| ttggcgggtg | tcgggctgg | cttaactatg | cggcatcaga | gcagattgta ctgagagtgc | 180 |
| accataaatt | cccgttttaa | gagcttggtg | agcgctagga | gtcactgcca ggtatcgttt | 240 |
| gaacacggca | ttagtcaggg | aagtcataac | acagtccttt | cccgcaattt tctttttcta | 300 |
| ttactcttgg | cctcctctag | tacactctat | atttttttat | gcctcggtaa tgattttcat | 360 |
| ttttttttt | cccctagcgg | atgactcttt | tttttctta | gcgattggca ttatcacata | 420 |
| atgaattata | cattatataa | agtaatgtga | tttcttcgaa | gaatatacta aaaatgagc | 480 |
| aggcaagata | aacgaaggca | aagatgacag | agcagaaagc | cctagtaaag cgtattacaa | 540 |
| atgaaaccaa | gattcagatt | gcgatctctt | taaagggtgg | tcccctagcg atagagcact | 600 |
| cgatcttccc | agaaaaagag | gcagaagcag | tagcagaaca | ggccacacaa tcgcaagtga | 660 |
| ttaacgtcca | cacaggtata | gggtttctgg | accatatgat | acatgctctg gccaagcatt | 720 |
| ccggctggtc | gctaatcgtt | gagtgcattg | gtgacttaca | catagacgac catcacacca | 780 |
| ctgaagactg | cgggattgct | ctcggtcaag | cttttaaaga | ggccctaggg gccgtgcgtg | 840 |
| gagtaaaaag | gtttggatca | ggatttgcgc | ctttggatga | ggcactttcc agagcggtgg | 900 |
| tagatctttc | gaacaggccg | tacgcagttg | tcgaacttgg | tttgcaaagg gagaaagtag | 960 |
| gagatctctc | ttgcgagatg | atcccgcatt | tccttgaaag | ctttgcagag gctagcagaa | 1020 |
| ttaccctcca | cgttgattgt | ctgcgaggca | agaatgatca | tcaccgtagt gagagtgcgt | 1080 |
| tcaaggctct | tgcggttgcc | ataagagaag | ccacctcgcc | caatggtacc aacgatgttc | 1140 |
| cctccaccaa | aggtgttctt | atgtagtgac | accgattatt | taaagctgca gcatacgata | 1200 |
| tatatacatg | tgtatatatg | tatacctatg | aatgtcagta | agtatgtata cgaacagtat | 1260 |
| gatactgaag | atgacaaggt | aatgcatcat | tctatacgtg | tcattctgaa cgaggcgcgc | 1320 |
| tttccttttt | tcttttttgct | ttttctttttt | ttttctcttg | aactcgacgg atctatgcgg | 1380 |
| tgtgaaatac | cgcacagatg | cgtaaggaga | aaataccgca | tcaggaaatt gtaaacgtta | 1440 |
| atattttgtt | aaaattcgcg | ttaaattttt | gttaaatcag | ctcatttttt aaccaatagg | 1500 |
| ccgaaatcgg | caaaatccct | tataaatcaa | agaatagac | cgagataggg ttgagtgttg | 1560 |
| ttccagtttg | gaacaagagt | ccactattaa | agaacgtgga | ctccaacgtc aaagggcgaa | 1620 |

```
aaaccgtcta tcagggcgat ggcccactac gtgaaccatc accctaatca agttttttgg   1680
ggtcgaggtg ccgtaaagca ctaaatcgga accctaaagg gagccccega tttagagctt   1740 gacggggaaa gccggcgaac gtggcgagaa aggaagggaa gaaagcgaaa ggagcgggcg   1800
ctagggcgct ggcaagtgta gcggtcacgc tgcgcgtaac caccacaccc gccgcgctta   1860
atgcgccgct acagggcgcg tcgcgccatt cgccattcag gctgcgcaac tgttgggaag   1920
ggcgatcggt gcgggcctct tcgctattac gccagctggc gaaaggggga tgtgctgcaa   1980
ggcgattaag ttgggtaacg ccagggtttt cccagtcacg acgttgtaaa acgacggcca   2040
gtgagcgcgc gtaatacgac tcactatagg gcgaattggg taccggccgc aaattaaagc   2100
cttcgagcgt cccaaaacct tctcaagcaa ggttttcagt ataatgttac atgcgtacac   2160
gcgtctgtac agaaaaaaaa gaaaaatttg aatataaat aacgttctta atactaacat   2220
aactataaaa aaataaatag ggacctagac ttcaggttgt ctaactcctt ccttttcggt   2280
tagagcggat gtggggggag ggcgtgaatg taagcgtgac ataactaatt acatgagcgg   2340
ccgcagatct ttaacccgca acagcaatac gtttcatatc tgtcatatag ccgcgcagtt   2400
tcttacctac ctgctcaatc gcatggctgc gaatcgcttc gttcacatca cgcagttgcc   2460
cgttatctac cgcgccttcc ggaatagctt tacccaggtc gcccggttgc agctctgcca   2520
taaacggttt cagcaacggc acacaagcgt aagagaacag atagttaccg tactcagcgg   2580
tatcagagat aaccacgttc atttcgtaca gacgcttacg ggcgatggtg ttggcaatca   2640
gcggcagctc gtgcagtgat tcataatatg cagactcttc aatgatgccg gaatcgacca   2700
tggtttcgaa cgccagttca acgcccgctt tcaccatcgc aatcatcagt acgcctttat   2760
cgaagtactc ctgctcgccg attttgcctt catactgcgg cgcggtttca aacgcggttt   2820
tgccggtctc ttcacgccag gtcagcagtt tcttatcatc gttggcccag tccgccatca   2880
taccggaaga gaattcgccg gagatgatgt cgtccatatg tttctggaac aggggtgcca   2940
tgatctcttt cagctgttca gaaagcgcat aagcacgcag tttcgccggg ttagagagac   3000
ggtccatcat cagggtgatg ccgccctgtt tcagtgcttc ggtgatggtt tcccaaccga   3060
actgaatcag ttttttctgcg tatgctggat cggtaccttc ttccaccagc ttgtcgaagc   3120
acagcagaga gccagcctgc aacataccgc acaggatggt ttgctcgccc atcaggtcag   3180
atttcacttc cgcaacgaag gacgattcca gcacacccgc acggtgacca ccggttgcag   3240
ccgcccaggc tttggcaatc gccatgcctt cgcctttcgg atcgttttcc gggtgaacgg   3300
caatcagcgt cggtacgccg aacccacgtt tgtactcttc acgcacttcg gtgcctgggc   3360
atttcggcgc aaccatcact acggtgatat ctttacggat ctgctcgccc acttcgacga   3420
tgttgaaacc gtgcgagtag cccagcgccg cgccgtcttt catcagtggc tgtacggtgc   3480
gcactacatc agagtgctgc ttgtccggcg tcaggttaat caccagatcc gcctgtggga   3540
tcagttcttc gtaagtaccc actttaaaac catttcggt cgctttacgc caggacgcgc   3600
gcttctcggc aatcgcttct ttacgcagag cgtaggagat atcgagacca gaatcacgca   3660
tgttcaggcc ctggttcaga ccctgtgcgc cacagccgac gatgactact ttttaccct   3720 gaaggtagct cgcgccatcg gcgaattcat cgcggcccat ctcgagtcga aactaagttc   3780
tggtgtttta aaactaaaaa aaagactaac tataaaagta gaatttaaga agtttaagaa   3840
atagatttac agaattacaa tcaataccta ccgtctttat atacttatta gtcaagtagg   3900
ggaataattt cagggaactg gtttcaacct ttttttttcag ctttttccaa atcagagaga   3960
gcagaaggta atagaaggtg taagaaaatg agatagatac atgcgtgggt caattgcctt   4020
```

```
gtgtcatcat ttactccagg caggttgcat cactccattg aggttgtgcc cgttttttgc   4080
ctgtttgtgc ccctgttctc tgtagttgcg ctaagagaat ggacctatga actgatggtt   4140
ggtgaagaaa acaatatttt ggtgctggga ttctttttttt ttctggatgc cagcttaaaa   4200
agcgggctcc attatattta gtggatgcca ggaataaact gttcacccag acacctacga   4260
tgttatatat tctgtgtaac ccgcccccta ttttgggcat gtacgggtta cagcagaatt   4320
aaaaggctaa ttttttgact aaataaagtt aggaaaatca ctactattaa ttatttacgt   4380
attctttgaa atggcgagta ttgataatga taaactggat cctcatccac ccaacttcga   4440
tttgtctctt actgcccct tatcggctga agtagccaat gaagcataag ccctaagggc     4500
gaaacttact tgacgttctc tattttagg agtccaagcc ttatctcctc tggcatcttg     4560
tgcttctctt cttgcagcca attcagcgtc tgagacttgt aattggatac ctctatttgg   4620
gatatctatg gcgatcaaat ctccatcttc aatcaatcca atcgaaccac cagaagctgc   4680
ctctggtgat acgtgaccga tacttaaacc cgaagtgcca ccagagaatc taccgtcagt   4740
gataagggca caagcttttc ctagtcccat ggacttcaaa aatgaagttg ggtaaagcat   4800
ttcctgcata cctggtcctc cctttggtcc ctcatatctt atcactacca cgtctcctgc   4860 taccacctt ccgccaagta tagcctcaac agcatcgtct tgactttcgt aaactttagc    4920
gggtccagta aatttcaaaa tactatcatc tacaccagca gttttcacaa tgcaaccatt   4980
ttcagcgaag tttccatata atactgctaa accaccatcc ttactataag catgctcaag   5040
cgatcttata catccatttg ctctatcatc gtccaaagtg tcccacctac agtcttgcga   5100
gaatgcttgg gtggttctga tccctgctgg acctgccctg aacatgtttt tcacggcatc   5160
atcttgagtt aacatgacat cgtattgctc taatgtctgt ggaagtgtta aacccaatac   5220
attcttcaca tccctgttta aaagaccggc tctgtccaac tccctaaaa taccaataac     5280 ccctcctgca cgatgaacgt cttccatgtg atactttga gttgatggtg caaccttaca    5340
taactgtgga accttacgtg aaagcttgtc gatatcagac atggtgaaat ctatctcagc   5400
ttcttgggct gcagctagaa gatgtaagac cgtgtttgta ctaccaccca ttgcaatatc    5460
caatgtcatg gcattttcga atgcagcctt tgaagctata ttcctcggta atgctgattc   5520
atcattttgt tcgtaatacc ttttcgttag ttccacaatt cttttccgg catttaagaa     5580 caattgcttt ctgtctgcat gggtcgctaa taatgaacca tttcctggtt gagataaacc   5640
tagagcttca gtcaagcaat tcatagagtt agccgtgaac attccactgc aagaaccaca   5700
agttggacat gcacttcttt caacttggtc tgactgcgag tctgaaactt ttggatctgc   5760
accttgaatc attgcatcca caagatcaag tttgatgatc tgatcactta acttagtttt   5820
accagcctcc attgggccgc cagatacgaa gattactggg atgttcaatc tcaaggacgc   5880
catcaacata ccaggcgtta tcttatcaca attagagata caaaccattg catcggcaca   5940
atgagcatta accatatatt cgactgagtc tgcaattaat tctctcgatg gtaaagagta   6000
taacataccg ccatgcccca tagctatacc gtcgtccaca gcaatagtat taaactcttt   6060
tgcgacacca cctgcagctt caatttgttc ggcaacaagc ttacctagat cacgcaaatg   6120
gacatgaccc ggaacgaatt gtgtaaaaga gttgacgacg gcaatgattg ctttccgaa    6180 atctgcatca gtcatgccag tcatgtcgac aaacttagat tagattgcta tgctttcttt   6240
ctaatgagca agaagtaaaa aaagttgtaa tagaacaaga aaaatgaaac tgaaacttga   6300
gaaattgaag accgtttatt aacttaaata tcaatgggag gtcatcgaaa gagaaaaaaa   6360
tcaaaaaaaa aattttcaag aaaaagaaac gtgataaaaa ttttttattgc cttttttcgac 6420
```

```
gaagaaaaag aaacgaggcg gtctctttt tcttttccaa acctttagta cgggtaatta    6480
acgacaccct agaggaagaa agagggaaa tttagtatgc tgtgcttggg tgttttgaag    6540
tggtacggcg atgcgcggag tccgagaaaa tctggaagag taaaaaagga gtagaaacat   6600
tttgaagcta tgagctccag cttttgttcc ctttagtgag ggttaattgc gcgcttggcg   6660
taatcatggt catagctgtt tcctgtgtga aattgttatc cgctcacaat tccacacaac   6720
ataggagccg gaagcataaa gtgtaaagcc tggggtgcct aatgagtgag gtaactcaca   6780
ttaattgcgt tgcgctcact gcccgctttc cagtcgggaa acctgtcgtg ccagctgcat   6840
taatgaatcg gccaacgcgc ggggagaggc ggtttgcgta ttgggcgctc ttccgcttcc   6900
tcgctcactg actcgctgcg ctcggtcgtt cggctgcggc gagcggtatc agctcactca   6960
aaggcggtaa tacggttatc cacagaatca ggggataacg caggaaagaa catgtgagca   7020
aaaggccagc aaaaggccag gaaccgtaaa aaggccgcgt tgctggcgtt tttccatagg   7080
ctccgccccc ctgacgagca tcacaaaaat cgacgctcaa gtcagaggtg gcgaaacccg   7140
acaggactat aaagatacca ggcgtttccc cctggaagct ccctcgtgcg ctctcctgtt   7200
ccgaccctgc cgcttaccgg atacctgtcc gcctttctcc cttcgggaag cgtggcgctt   7260
tctcatagct cacgctgtag gtatctcagt tcggtgtagg tcgttcgctc caagctgggc   7320
tgtgtgcacg aacccccgt tcagcccgac cgctgcgcct tatccggtaa ctatcgtctt    7380
gagtccaacc cggtaagaca cgacttatcg ccactggcag cagccactgg taacaggatt   7440
agcagagcga ggtatgtagg cggtgctaca gagttcttga agtggtggcc taactacggc   7500
tacactagaa ggacagtatt tggtatctgc gctctgctga agccagttac cttcggaaaa   7560
agagttggta gctcttgatc cggcaaacaa accaccgctg gtagcggtgg tttttttgtt   7620
tgcaagcagc agattacgcg cagaaaaaaa ggatctcaag aagatccttt gatcttttct   7680
acggggtctg acgctcagtg gaacgaaaac tcacgttaag ggattttggt catgagatta   7740
tcaaaaagga tcttcaccta gatccttta aattaaaaat gaagttttaa atcaatctaa   7800
agtatatatg agtaaacttg gtctgacagt taccaatgct taatcagtga ggcacctatc   7860
tcagcgatct gtctatttcg ttcatccata gttgcctgac tccccgtcgt gtagataact   7920
acgatacggg agggcttacc atctggcccc agtgctgcaa tgataccgcg agacccacgc   7980
tcaccggctc cagatttatc agcaataaac cagccagccg aagggccga gcgcagaagt    8040 ggtcctgcaa ctttatccgc ctccatccag tctattaatt gttgccggga agctagagta   8100
agtagttcgc cagttaatag tttgcgcaac gttgttgcca ttgctacagg catcgtggtg   8160
tcacgctcgt cgtttggtat ggcttcattc agctccggtt cccaacgatc aaggcgagtt   8220
acatgatccc ccatgttgtg caaaaaagcg gttagctcct tcggtcctcc gatcgttgtc   8280
agaagtaagt tggccgcagt gttatcactc atggttatgg cagcactgca taattctctt   8340
actgtcatgc catccgtaag atgcttttct gtgactggtg agtactcaac caagtcattc   8400
tgagaatagt gtatgcggcg accgagttgc tcttgcccgg cgtcaatacg ggataatacc   8460
gcgccacata gcagaacttt aaaagtgctc atcattggaa aacgttcttc ggggcgaaaa   8520
ctctcaagga tcttaccgct gttgagatcc agttcgatgt aacccactcg tgcacccaac   8580
tgatcttcag catcttttac tttcaccagc gtttctgggt gagcaaaaac aggaaggcaa   8640
aatgccgcaa aaagggaat aagggcgaca cggaaatgtt gaatactcat actcttcctt    8700
tttcaatatt attgaagcat ttatcagggt tattgtctca tgagcggata catatttgaa   8760
tgtatttaga aaaataaaca aataggggtt ccgcgcacat ttccccgaaa agtgccacct   8820
```

```
gggtccttt  catcacgtgc  tataaaaata  attataattt  aaatttttta  atataaatat    8880
ataaattaaa  aatagaaagt  aaaaaaagaa  attaaagaaa  aaatagtttt  tgttttccga    8940
agatgtaaaa  gactctaggg  ggatcgccaa  caaatactac  cttttatctt  gctcttcctg    9000
ctctcaggta  ttaatgccga  attgtttcat  cttgtctgtg  tagaagacca  cacacgaaaa    9060
tcctgtgatt  ttacatttta  cttatcgtta  atcgaatgta  tatctattta  atctgctttt    9120
cttgtctaat  aaatatatat  gtaaagtacg  cttttgttg   aaatttttta  aacctttgtt    9180 tattttttt   tcttcattcc  gtaactcttc  taccttcttt  atttactttc  taaaatccaa    9240
atacaaaaca  taaaaataaa  taaacacaga  gtaaattccc  aaattattcc  atcattaaaa    9300
gatacgaggc  gcgtgtaagt  tacaggcaag  cgatccgtcc  taagaaacca  ttattatcat    9360
gacattaacc  tataaaaata  ggcgtatcac  gaggcccttt  cgtc                      9404
```

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
agtcacatca agatcgttta tgg                                                 23

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gcacggaata tgggactact tcg                                                 23

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
actccacttc aagtaagagt ttg                                                 23

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tattgtctca tgagcggata c                                                   21

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
acaacgagtg tcatggggag aggaagagg                                    29

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gatcttcggc tgggtcatgt gaggcgg                                      27

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
acgctgaaca cgttggtgtc ttgc                                         24

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aacccttagc agcatcggca acc                                          23

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tattcatggg ccaatactac g                                            21

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gtagaagacg tcacctggta gaccaaagat g                                 31

<210> SEQ ID NO 40
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 40
catcgtgacg tcgctcaatt gactgctgct ac                                    32

<210> SEQ ID NO 41
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
actaagcgac acgtgcggtt tctgtggtat ag                                    32

<210> SEQ ID NO 42
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gaaaccgcac gtgtcgctta gtttacattt ctttcc                                36

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tttgaagtgg tacggcgatg                                                  20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aatcatatcg aacacgatgc                                                  20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
agctggtctg gtgattctac                                                  20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
```
tatcaccgta gtgatggttg                                              20

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gtcagcagtt tcttatcatc g                                            21

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gcgaaactta cttgacgttc                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
actttggacg atgatagagc                                              20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gcgttagatg gtacgaaatc                                              20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cttctaacac tagcgaccag                                              20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aaagatgatg agcaaacgac                                              20

```
<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cgagcaatac tgtaccaatg                                                  20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tcacggatga tttccagggt                                                  20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cacctgcgtt gttaccacaa                                                  20
```